US011499198B2

(12) United States Patent
Kawauchi et al.

(10) Patent No.: US 11,499,198 B2
(45) Date of Patent: Nov. 15, 2022

(54) BILIARY TRACT CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Junpei Kawauchi, Kamakura (JP); Hitoshi Nobumasa, Kamakura (JP); Satoko Kozono, Kamakura (JP); Satoshi Kondou, Kamakura (JP); Hiroko Sudo, Kamakura (JP); Atsushi Ochiai, Kashiwa (JP); Motohiro Kojima, Kashiwa (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 116 days.

(21) Appl. No.: 16/822,839

(22) Filed: Mar. 18, 2020

(65) Prior Publication Data

US 2020/0216914 A1 Jul. 9, 2020

Related U.S. Application Data

(62) Division of application No. 15/317,846, filed as application No. PCT/JP2015/066820 on Jun. 11, 2015, now Pat. No. 10,633,708.

(30) Foreign Application Priority Data

Jun. 11, 2014 (JP) ................................ 2014-120884
Sep. 11, 2014 (JP) ................................ 2014-185733

(51) Int. Cl.

| | |
|---|---|
| ***C12Q 1/68*** | (2018.01) |
| ***C12P 19/34*** | (2006.01) |
| ***C12Q 1/6886*** | (2018.01) |
| ***G01N 37/00*** | (2006.01) |
| ***G01N 33/566*** | (2006.01) |
| ***C12N 15/09*** | (2006.01) |
| ***G01N 33/53*** | (2006.01) |

(52) U.S. Cl.

CPC .......... *C12Q 1/6886* (2013.01); *C12N 15/09* (2013.01); *C12Q 1/68* (2013.01); *G01N 33/53* (2013.01); *G01N 33/566* (2013.01); *G01N 37/00* (2013.01); *C12Q 2600/158* (2013.01); *C12Q 2600/178* (2013.01)

(58) Field of Classification Search

CPC ........... C12Q 1/6886; C12Q 2600/158; C12Q 2600/178; C12Q 1/6813; C12Q 1/6837; C12Q 2600/16

See application file for complete search history.

(56) References Cited

U.S. PATENT DOCUMENTS

| | | | |
|---|---|---|---|
| 2011/0143360 A1 | 6/2011 | Kuroda et al. |
| 2012/0157341 A1 | 6/2012 | Kaneko et al. |

FOREIGN PATENT DOCUMENTS

| | | |
|---|---|---|
| EP | 2638912 A1 | 9/2013 |
| JP | 2012-237685 A | 12/2012 |
| JP | 2013-223520 A | 10/2013 |
| WO | WO 2009/133915 A1 | 11/2009 |
| WO | WO 2012/063894 A1 | 5/2012 |
| WO | WO 2013/107459 A2 | 7/2013 |

OTHER PUBLICATIONS

Qiagen Product description of "miScript™ miRNA PCR Array (384-well, 384HC) Human miRBase Profiler HC Plate 4", document 1073798, Aug. 2012, from https://b2b.qiagen.com/~/media/genetable/mi/hs/34/mihs-3404z (Year: 2012).*

P. Chang, et al., "Analysis of the correlation between the expression of miR-655 and esophageal cancer prognosis" Oncology Letters: 4691-4694, 2017 (Year: 2017).*

Yosuke Harazono, et al., "miR-655 is an EMT-Suppressive MicroRNA Targeting ZEB1 and TGFBR2"2. PLoS One 8(5): e62757, May 14, 2013 (Year: 2013).*

Hongxiang Li, et al., "miR-655: A promising regulator with therapeutic potential", Gene, 757 (2020) 144932. (Year: 2020).*

MiScript™ miRNA PCR Array (384-well, 384HC) Human miRBase Profiler HC Plate 6 from Qiagen, 2012.

Office Action dated Sep. 7, 2021, in Republic of Korea Patent Application No. 10-2017-7000779.

Zhong et al., "MicroRNA-421 functions as an oncogenic miRNA in biliary tract cancer through down-regulating famesoid X receptor expression," Gene (2012), vol. 493, pp. 44-51.

Communication Pursuant to Article 94(3) EPC dated May 27, 2021, in European Patent Application No. 15 806 290.1.

Liu et al., "MiR-6836-3p promotes proliferation of hypertrophic scar fibroblasts by targeting CTGF," European Review for Medical and Pharmacological Sciences (2018), vol. 22, No. 13, pp. 4069-4074.

Anonymous, "Mature sequence hsa-miR-6836-3p," miRBase, Accession No. MIMAT0027575, Sep. 2012, :http://www.mirbase.org/cgi-bin/mature.pl?mature_acc=MIMAT0027575, 1 page, XP055422997.

Chen et al., "The role of microRNA expression pattern in human intrahepatic cholangiocarcinoma," Journal of Hepatology, vol. 50, No. 2, Feb. 28, 2009 (available online Nov. 21, 2008), pp. 358-369, XP025949528.

Cheung et al., "Natural variation in human gene expression assessed in lymphoblastoid cells," Nature Genetics, vol. 33, 2003, 422-425.

(Continued)

*Primary Examiner* — Stephen T Kapushoc
(74) *Attorney, Agent, or Firm* — Birch, Stewart, Kolasch & Birch, LLP

(57) ABSTRACT

The present invention provides a kit or device for the detection of biliary tract cancer, and a method for detecting biliary tract cancer. The present invention relates to a kit or device for the detection of biliary tract cancer, comprising a nucleic acid capable of specifically binding to miRNA in a sample of a subject, and a method for detecting biliary tract cancer, comprising measuring the miRNA in vitro.

6 Claims, 4 Drawing Sheets

Specification includes a Sequence Listing.

(56) References Cited

OTHER PUBLICATIONS

Cobb et al., "Sepsis gene expression profiling: murine splenic compared with hepatic responses determined by using complementary DNA microarrays," Critical Care Medicine, vol. 30, 2002, pp. 2711-2721.
Eto et al., "Prospect of microRNA toward laboratory medicine Gastrointestinal Cancer and microRNA", Clinical Chemistry, vol. 43, No. 2, 2014, p. 99-105.
GenBank Locus NR_106895 (2013) obtained from https://www.ncbi.nlm.nih.gov/nuccore/563319728?sat=18&satkey=2746180 on Aug. 1, 2019. Two pages.
Hayes et al., "Hepatitis B Virus-Specific miRNAs and Argonaute2 Play a Role in the Viral Life Cycle", PLoS One, vol. 7, Issue 10, Oct. 2012, pp. 1-12.
Hoshikawa et al., "Hypoxia induces different genes in the lungs of rats compared with mice," Physiological Genomics, vol. 12, 2003, pp. 209-219.
International Search Report, issued in PCT/JP2015/066820, PCT/ISA/210, dated Aug. 25, 2015.
Kawahigashi et al., "MicroRNA Profiling of Human Intrahepatic Cholangiocarcinoma Cell Lines Reveals Biliary Epithelial Cell-specific MiroRNAs", J Nippon Med Sch, 2009, vol. 76, No. 4, p. 188-197.
Kishimoto et al., "Plasma miR-21 is a novel diagnostic biomarker for biliary tract cancer," Cancer Science, vol. 104, No. 12, Dec. 2013 (published online Nov. 12, 2013), pp. 1626-1631, XP055422944.
Kojima et al., "Micro RNA markers for the diagnosis of pancreatic and bile duct cancers," E-2020, Digital abstract for the 73rd Annual Meeting of the Japanese Cancer Association, published online Sep. 19, 2014, 3 pages.
Kojima et al., "Micro RNA markers for the diagnosis of pancreatic and bile duct cancers," E-2020, English oral session at the 73rd Annual Meeting of the Japanese Cancer Association, Sep. 26, 2014, 22 pages.
Kojima et al., "MicroRNA Markers for the Diagnosis of Pancreatic and Biliary-Tract Cancers," PLoS One, vol. 10, No. 2, Feb. 23, 2015, pp. 1-22.
Kurokawa et al., "Data Book for Clinical Examination", Lab Data, 2013-2014, p. 633, 636.
Ladewig et al., "Discovery of hundreds of mirtrons in mouse and human small RNA data," Genome Research, vol. 22, No. 9, Sep. 2012, pp. 1634-1645, XP055419072.
Ladewig et al., "Discovery of hundreds of mirtrons in mouse and human small RNA data," miRNAs associated with reference PubMed ID 22955976, miRBase, Sep. 2012, http://www.mirbase.org/cgi-bin/reference.pl?medline=22955976, pp. 1-11, XP055423044.
MiScript™ miRNA PCR Array (384-well, 384HC) Human miRBase Profiler HC Plate 5 from Qiagen, 2012.
NCBI Geo Accession Display for Platform GPL7766, public on May 14, 2009. Kyoto Univ. 3D-Gene Human miRNA Oligo chip v11.0. Obtained from https://www.ncbi.nlm.nih.gov/geo/query/acc.cgi?acc=GPL7766 on Aug. 22, 2018. Including full Data Table. 12 pages 2009.
Partial Supplementary European Search Report, dated Nov. 21, 2017, for European Application No. 15806290.1.
Shen et al., "Exploration of genome-wide circulating microRNA in hepatocellular carcinoma: MiR-483-5p as a potential biomarker," Cancer Epidemiology and Prevention Biomarkers, vol. 22, No 12, 2013, pp. 2364-2373.
Shigehara et al., "Real-time PCR-based analysis of the human bile microRNAome identifies miR-9 as a potential diagnostic biomarker for biliary tract cancer," PloS one, vol. 6, Issue 8, e23584, Aug. 17, 2011, pp. 1-9, XP055422939.
Tadahiro Takada, "Evidence-based clinical practice guidelines for the management of biliary tract cancers", Edited by the publishing committee of the evidence-based clinical practice guidelines for the management of biliary tract cancers, Igakutosho-shuppan Ltd., 2007, p. 38-39.
Written Opinion of the International Searching Authority, issued in PCT/JP2015/066820, PCT/ISA/237, dated Aug. 25, 2015.
Yan et al., "One-step real time RT-PCR for detection of microRNAs," Talanta, vol. 110, 2013, pp. 190-195.

* cited by examiner

Training cohort
Healthy subject
Biliary tract cancer patient
hsa-miR-4476 measurement value
hsa-miR-6893-5p measurement value
Validation cohort
Healthy subject
Biliary tract cancer patient
hsa-miR-4476 measurement value
hsa-miR-6893-5p measurement value

BILIARY TRACT CANCER DETECTION KIT OR DEVICE, AND DETECTION METHOD

CROSS-REFERENCE TO RELATED APPLICATIONS

This application is a Divisional of application Ser. No. 15/317,846, filed on Dec. 9, 2016, which is the National Phase under 35 U.S.C. § 371 of International Application No. PCT/JP2015/066820, filed on Jun. 11, 2015, and claims the benefit under 35 U.S.C. § 119(a) to Patent Application No. 2014-185733, filed in Japan on Sep. 11, 2014 and Patent Application No. 2014-120884, filed in Japan on Jun. 11, 2014. All of the above applications are hereby expressly incorporated by reference into the present application.

TECHNICAL FIELD

The present invention relates to a kit or a device for the detection of biliary tract cancer, comprising a nucleic acid capable of specifically binding to a particular miRNA, which is used for examining the presence or absence of biliary tract cancer in a subject, and a method for detecting biliary tract cancer, comprising measuring an expression level of the miRNA using the nucleic acid.

BACKGROUND ART

The biliary tract refers to the entire route of excretion of bile secreted from hepatic cells into the duodenum, and is broadly divided into the intrahepatic bile duct inside the liver and the extrahepatic biliary tree outside the liver. The extrahepatic biliary tree is broadly divided into 3 areas: the extrahepatic bile duct through which the bile is transported from the liver to the duodenum; the gallbladder which temporarily stores and enriches the bile; and the duodenal papilla or the papilla which is an opening site of the bile duct and the main pancreatic duct at the duodenal lumen.

A great majority of biliary tract cancer cases are caused by the malignant transformation of biliary epithelial cells that surround the lumen, and respond, merely weakly, to chemotherapy or radiotherapy. Thus, surgical resection based on early detection is only one radical cure for such biliary tract cancer. However, early biliary tract cancer lacks subjective symptoms. For example, this cancer manifests subjective symptoms such as jaundice or itch only after the bile duct is obstructed with the progression of the cancer so that the bile flows back into a blood vessel. Therefore, biliary tract cancer is often detected in an advanced cancer state. As for intrahepatic bile duct cancer, because the extrahepatic bile duct is rarely obstructed, the disease often progresses asymptomatically without symptoms of jaundice. According to the 2011 statistics of cancer type-specific mortality in Japan disclosed by the Center for Cancer Control and Information Services, National Cancer Center, the number of biliary tract cancer deaths climbed to 18,186 people, and 5-year relative survival rates by cancer type in 2003 to 2005 were in the second lowest position following pancreatic cancer with 22.5% for males and 19.9% for females. Since the biliary tract is closely related to important organs such as the liver and the pancreas, biliary tract cancer is responsible for poor prognosis resulting from its metastasis to these organs.

The biliary tract cancer is broadly divided into three types, extrahepatic bile duct cancer, gallbladder cancer, and papillary cancer, depending on sites of origin. The extrahepatic bile duct cancer is further divided into four types: a cancer that develops in the hepatic portal region which serves as the entrance of the liver (hilar cholangiocarcinoma); a cancer that develops in the upper region from the hepatic portal region to the gallbladder (upper bile duct cancer); a cancer that develops in the middle region from the gallbladder to the pancreas (middle bile duct cancer); and a cancer that develops in the distal region from the pancreas to the duodenal papilla (distal bile duct cancer). A bile duct cancer that develops closer to the liver is known to be more difficult to operate and to have poorer prognosis.

The UICC (Unio Internationalis Contra Cancrum) stages of progression of extrahepatic bile duct cancer, gallbladder cancer, and papillary cancer are defined in "Classification of Biliary Tract Cancer, the 5th edition" (edited by the Japanese Society of Hepato-Biliary-Pancreatic Surgery, KANEHARA & Co., LTD., 2003, p. 109) and classified into stages 0, IA, IB, IIA, IIB, III, IVa, and IVb according to lymph node metastasis, metastasis to extraperitoneal distant organs, macroscopic spread around the bile duct, etc. The UICC stages of progression of intrahepatic bile duct cancer are defined in "TNM Classification of Malignant Tumours, the 7th edition, Japanese version" (UICC Japan National Committee, translated by TNM Committee, KANEHARA & Co., LTD., 2012, p. 110) and classified into stages I, II, III, IVa. and IVb according to lymph node metastasis, metastasis to extraperitoneal distant organs, macroscopic spread around the bile duct, etc.

Limitedly invasive biochemical examination of blood, tumor marker tests, and abdominal ultrasonography are generally used in the initial diagnosis of biliary tract cancer (Non-patent Literature 1). The biochemical examination of blood for the detection of biliary tract cancer employs, for example, alkaline phosphatase, γ-GTP, or bilirubin, which is elevated due to hepatic dysfunction. For example, CEA, CA19-9, DUPAN-2, CA195, CA242, and IL-6 are known as the tumor markers for the detection of biliary tract cancer. As for how to use these tumor markers, a subject is suspected of having a cancer % when their concentrations in blood are higher or lower than predetermined reference values. For example, as described in Non-patent Literature 2, the reference value of CEA is set to 5 ng/mL, and the reference value of CA19-9 is set to 37 U/mL. A subject is suspected of having a cancer including biliary tract cancer when their concentrations exhibit these values or higher.

There are reports, albeit at a research stage, on the detection of biliary tract cancer using the expression levels of proteins or genes in biological samples including blood.

Patent Literature 1 describes a method for detecting biliary tract cancer using the expression levels of proteins in biliary tract tissues.

Patent Literature 2 describes a method for diagnosing digestive organ cancers including biliary tract cancer using mRNA genes extracted from cells (mononuclear cells, etc.) in blood.

CITATION LIST

Patent Literature

Patent Literature 1: JP Patent Publication (Kokai) No. 2012-237685 A (2012)

Patent Literature 2: JP Patent Publication (Kokai) No. 2013-223520 A (2013)

Non-Patent Literature

Non-patent Literature 1: "Evidence-based clinical practice guidelines for the management of biliary tract cancers", edited by the publishing committee of the evidence-based clinical practice guidelines for the management of biliary tract cancers, Igakutosho-shuppan Ltd., 2007, p. 38-39

Non-patent Literature 2: Kiyoshi Kurokawa, LAB DATA, 2013, p. 633, 636

SUMMARY OF INVENTION

Problem to be Solved by Invention

An object of the present invention is to find a novel tumor marker for biliary tract cancer and to provide a method that can effectively detect biliary tract cancer using a nucleic acid capable of specifically binding to the marker. As described in Non-patent Literature 1, limitedly invasive biochemical examination of blood, tumor marker tests, and abdominal ultrasonography are generally used in the initial diagnosis of biliary tract cancer. The rate of tumor visualization (probability at which cancer can be detected from images) for biliary tract cancer by the abdominal ultrasonography varies widely from 21 to 90% (Non-patent Literature 1) and is decreased, particularly, for sites of tumors that occupy the lower bile duct. The biochemical examination of blood for the detection of biliary tract cancer employs, for example, alkaline phosphatase, γ-GTP, or bilirubin, which is elevated due to hepatic dysfunction. However, such biochemical examination of blood does not specifically detect biliary tract cancer. For example, CEA, CA19-9, DUPAN-2, CA195, CA242, and IL-6 are known as the tumor markers for the detection of biliary tract cancer. Among them, CEA is known to be elevated by 40 to 70% in biliary tract cancer patients, while CA19-9 is known to be elevated by 50 to 79% in biliary tract cancer patients (Non-patent Literature 1). However, Non-patent Literature 1 states that these tumor markers are not specific for biliary tract cancer and are difficult to use in early diagnosis. Also, Non-patent Literature 1 states that the clinical usefulness of DUPAN-2, CA195, CA242, or IL-6 is not clear. Therefore, in the case of using the conventional tumor markers, there may be the possibility of false detection of other cancers and/or benign tumors and/or benign diseases of the biliary tract and/or peribiliary organs, etc.

As described below, there are reports, albeit at a research stage, on the detection of biliary tract cancer using the expression levels of proteins or genes in biological samples including blood, none of which, however, have yet been brought into practical use.

Patent Literature 1 describes a method for detecting biliary tract cancer using the expression levels of proteins in biliary tract tissues. In this detection method, however, tissue resection by surgical operation is essential for obtaining samples. This step places a great physical burden on patients. Therefore, this method is not favorable as an examination method. In addition, Patent Literature 1 does not describe the specific detection performance, such as accuracy, sensitivity, or specificity for discriminating biliary tract cancer, of this detection method and is thus poorly industrially practical.

Patent Literature 2 describes a method for diagnosing digestive organ cancers including biliary tract cancer using mRNA genes extracted from cells (mononuclear cells, etc.) in blood. This detection method, however, requires dozens to several hundreds of mRNAs to be used in combination and might thus cause increased examination cost and a complicated classification algorithm when actually developed for examination. In addition, the mRNAs are easily decomposable and unstable in blood and are therefore not favorable as analytes.

As mentioned above, the existing tumor markers exhibit low performance in the detection of biliary tract cancer, and neither performance nor detection methods are specifically shown as to the markers at a research stage. Therefore, use of these markers might impose an implementation of needless extra examination due to the false detection of healthy subjects as being biliary tract cancer patients, or might waste therapeutic opportunity because of overlooking biliary tract cancer patients. In addition, the measurement of dozens to several hundreds of genes increases examination cost and is therefore difficult to use in large-scale screening such as medical checkup. Furthermore, the collection of biliary tract tissues for measuring the tumor markers is highly invasive to patients and is not favorable. Hence, there is a demand for a highly accurate biliary tract cancer marker that is detectable from blood, which can be collected in a less invasive manner, and is capable of correctly determining a biliary tract cancer patient as a biliary tract cancer patient and a healthy subject as a healthy subject. Particularly, a highly sensitive biliary tract cancer marker is desired because tumor resection based on early detection is only radical cure for biliary tract cancer.

Means for Solution of Problem

The present inventors have conducted diligent studies to attain the object and consequently completed the present invention by finding several genes usable as markers for the detection of biliary tract cancer from blood, which can be collected with limited invasiveness, and finding that biliary tract cancer can be significantly detected by using nucleic acid(s) capable of specifically binding to any of these markers.

SUMMARY OF INVENTION

Specifically, the present invention has the following features:

(1) A kit for the detection of biliary tract cancer, comprising nucleic acid(s) capable of specifically binding to at least one or more polynucleotide(s) selected from the group consisting of biliary tract cancer markers miR-125a-3p, miR-6893-5p, miR-204-3p, miR-4476, miR-4294, miR-150-3p, miR-6729-5p, miR-7641, miR-6765-3p, miR-6820-5p, miR-575, miR-6836-3p, miR-1469, miR-663a, miR-6075, miR-4634, miR-423-5p, miR-4454, miR-7109-5p, miR-6789-5p, miR-6877-5p, miR-4792, miR-4530, miR-7975, miR-6724-5p, miR-8073, miR-7977, miR-1231, miR-6799-5p, miR-615-5p, miR-4450, miR-6726-5p, miR-6875-5p, miR-4734, miR-16-5p, miR-602, miR-4651, miR-8069, miR-1238-5p, miR-6880-5p, miR-8072, miR-4723-5p, miR-4732-5p, miR-6125, miR-6090, miR-7114-5p, miR-564, miR-451a, miR-3135b, miR-4497, miR-4665-5p, miR-3622a-5p, miR-6850-5p, miR-6821-5p, miR-5100, miR-6872-3p, miR-4433-3p, miR-1227-5p, miR-3188, miR-7704, miR-3185, miR-1908-3p, miR-6781-5p, miR-6805-5p, miR-8089, miR-665, miR-4486, miR-6722-3p, miR-1260a, miR-4707-5p, miR-6741-5p, miR-1260b, miR-1246, miR-6845-5p, miR-4638-5p, miR-6085, miR-1228-3p, miR-4534, miR-5585-3p, miR-4741, miR-4433b-3p, miR-197-5p, miR-718, miR-4513, miR-4446-3p, miR-619-5p, miR-6816-5p, miR-6778-5p, miR-24-3p, miR-1915-3p, miR-4665-3p, miR-4449, miR-6889-5p, miR-486-3p, miR-7113-3p, miR-642a-3p, miR-7847-3p, miR-6768-5p, miR- 1290, miR-7108-5p, miR-92b-5p, miR-663b, miR-3940-5p, miR-4467, miR-6858-5p, miR-4417, miR-3665, miR-4736, miR-4687-3p, miR-1908-5p, miR-5195-3p, miR-4286, miR-3679-3p, miR-6791-5p, miR-1202, miR-3656, miR-4746-3p, miR-3184-5p, miR-3937, miR-6515-3p, miR-6132, miR-187-5p, miR-7111-5p, miR-5787, miR-6779-5p, miR-4516, miR-4649-5p, miR-760, miR-3162-5p, miR-3178, miR-940, miR-4271, miR-6769b-5p, miR-4508, miR-6826-5p, miR-6757-5p, miR-3131, and miR-1343-3p.

(2) The kit according to (1), wherein miR-125a-3p is hsa-miR-125a-3p, miR-6893-5p is hsa-miR-6893-5p, miR-204-3p is hsa-miR-204-3p, miR-4476 is hsa-miR-4476, miR-4294 is hsa-miR-4294, miR-150-3p is hsa-miR-150-3p, miR-6729-5p is hsa-miR-6729-5p, miR-7641 is hsa-miR-7641, miR-6765-3p is hsa-miR-6765-3p, miR-6820-5p is hsa-miR-6820-5p, miR-575 is hsa-miR-575, miR-6836-3p is hsa-miR-6836-3p, miR-1469 is hsa-miR-1469, miR-663a is hsa-miR-663a, miR-6075 is hsa-miR-6075, miR-4634 is hsa-miR-4634, miR-423-5p is hsa-miR-423-5p, miR-4454 is hsa-miR-4454, miR-7109-5p is hsa-miR-7109-5p, miR-6789-5p is hsa-miR-6789-5p, miR-6877-5p is hsa-miR-6877-5p, miR-4792 is hsa-miR-4792, miR-4530 is hsa-miR-4530, miR-7975 is hsa-miR-7975, miR-6724-5p is hsa-miR-6724-5p, miR-8073 is hsa-miR-8073, miR-7977 is hsa-miR-7977, miR-1231 is hsa-miR-1231, miR-6799-5p is hsa-miR-6799-5p, miR-615-5p is hsa-miR-615-5p, miR-4450 is hsa-miR-4450, miR-6726-5p is hsa-miR-6726-5p, miR-6875-5p is hsa-miR-6875-5p, miR-4734 is hsa-miR-4734, miR-16-5p is hsa-miR-16-5p, miR-602 is hsa-miR-602, miR-4651 is hsa-miR-4651, miR-8069 is hsa-miR-8069, miR-1238-5p is hsa-miR-1238-5p, miR-6880-5p is hsa-miR-6880-5p, miR-8072 is hsa-miR-8072, miR-4723-5p is hsa-miR-4723-5p, miR-4732-5p is hsa-miR-4732-5p, miR-6125 is hsa-miR-6125, miR-6090 is hsa-miR-6090, miR-7114-5p is hsa-miR-7114-5p, miR-564 is hsa-miR-564, miR-451a is hsa-miR-451a, miR-3135b is hsa-miR-3135b, miR-4497 is hsa-miR-4497, miR-4665-5p is hsa-miR-4665-5p, miR-3622a-5p is hsa-miR-3622a-5p, miR-6850-5p is hsa-miR-6850-5p, miR-6821-5p is hsa-miR-6821-5p, miR-5100 is hsa-miR-5100, miR-6872-3p is hsa-miR-6872-3p, miR-4433-3p is hsa-miR-4433-3p, miR-1227-5p is hsa-miR-1227-5p, miR-3188 is hsa-miR-3188, miR-7704 is hsa-miR-7704, miR-3185 is hsa-miR-3185, miR-1908-3p is hsa-miR-1908-3p, miR-6781-5p is hsa-miR-6781-5p, miR-6805-5p is hsa-miR-6805-5p, miR-8089 is hsa-miR-8089, miR-665 is hsa-miR-665, miR-4486 is hsa-miR-4486, miR-6722-3p is hsa-miR-6722-3p, miR-1260a is hsa-miR-1260a, miR-4707-5p is hsa-miR-4707-5p, miR-6741-5p is hsa-miR-6741-5p, miR-1260b is hsa-miR-1260b, miR-1246 is hsa-miR-1246, miR-6845-5p is hsa-miR-6845-5p, miR-4638-5p is hsa-miR-4638-5p, miR-6085 is hsa-miR-6085, miR-1228-3p is hsa-miR-1228-3p, miR-4534 is hsa-miR-4534, miR-5585-3p is hsa-miR-5585-3p, miR-4741 is hsa-miR-4741, miR-4433b-3p is hsa-miR-4433b-3p, miR-197-5p is hsa-miR-197-5p, miR-718 is hsa-miR-718, miR-4513 is hsa-miR-4513, miR-4446-3p is hsa-miR-4446-3p, miR-619-5p is hsa-miR-619-5p, miR-6816-5p is hsa-miR-6816-5p, miR-6778-5p is hsa-miR-6778-5p, miR-24-3p is hsa-miR-24-3p, miR-1915-3p is hsa-miR-1915-3p, miR-4665-3p is hsa-miR-4665-3p, miR-4449 is hsa-miR-4449, miR-6889-5p is hsa-miR-6889-5p, miR-486-3p is hsa-miR-486-3p, miR-7113-3p is hsa-miR-7113-3p, miR-642a-3p is hsa-miR-642a-3p, miR-7847-3p is hsa-miR-7847-3p, miR-6768-5p is hsa-miR-6768-5p, miR-1290 is hsa-miR-1290, miR-7108-5p is hsa-miR-7108-5p, miR-92b-5p is hsa-miR-92b-5p, miR-663b is hsa-miR-663b, miR-3940-5p is hsa-miR-3940-5p, miR-4467 is hsa-miR-4467, miR-6858-5p is hsa-miR-6858-5p, miR-4417 is hsa-miR-4417, miR-3665 is hsa-miR-3665, miR-4736 is hsa-miR-4736, miR-4687-3p is hsa-miR-4687-3p, miR-1908-5p is hsa-miR-1908-5p, miR-5195-3p is hsa-miR-5195-3p, miR-4286 is hsa-miR-4286, miR-3679-3p is hsa-miR-3679-3p, miR-6791-5p is hsa-miR-6791-5p, miR-1202 is hsa-miR-1202, miR-3656 is hsa-miR-3656, miR-4746-3p is hsa-miR-4746-3p, miR-3184-5p is hsa-miR-3184-5p, miR-3937 is hsa-miR-3937, miR-6515-3p is hsa-miR-6515-3p, miR-6132 is hsa-miR-6132, miR-187-5p is hsa-miR-187-5p, miR-7111-5p is hsa-miR-7111-5p, miR-5787 is hsa-miR-5787, miR-6779-5p is hsa-miR-6779-5p, miR-4516 is hsa-miR-4516, miR-4649-5p is hsa-miR-4649-5p, miR-760 is hsa-miR-760, miR-3162-5p is hsa-miR-3162-5p, miR-3178 is hsa-miR-3178, miR-940 is hsa-miR-940, miR-4271 is hsa-miR-4271, miR-6769b-5p is hsa-miR-6769b-5p, miR-4508 is hsa-miR-4508, miR-6826-5p is hsa-miR-6826-5p, miR-6757-5p is hsa-miR-6757-5p, miR-3131 is hsa-miR-3131, and miR-1343-3p is hsa-miR-1343-3p.

(3) The kit according to (1) or (2), wherein the nucleic acid is a polynucleotide selected from the group consisting of the following polynucleotides (a) to (e):

(a) a polynucleotide consisting of a nucleotide sequence represented by any of SEQ ID NOs: 1 to 125 and 466 to 478 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 125 and 466 to 478, (c) a polynucleotide consisting of a nucleotide sequence complementary to a nucleotide sequence represented by any of SEQ ID NOs: 1 to 125 and 466 to 478 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 125 and 466 to 478 or a nucleotide sequence derived from the nucleotide sequence by the replacement of u with t, and (e) a polynucleotide hybridizing under stringent conditions to any of the polynucleotides (a) to (d).

(4) The kit according to any one of (1) to (3), wherein the kit further comprises nucleic acid(s) capable of specifically binding to at least one or more polynucleotide(s) selected from the group consisting of other biliary tract cancer markers: miR-6808-5p, miR-6774-5p, miR-4656, miR-6806-5p, miR-1233-5p, miR-328-5p, miR-4674, miR-2110, miR-6076, miR-3619-3p, miR-92a-2-5p, miR-128-1-5p, miR-638, miR-2861, miR-371a-5p, miR-211-3p, miR-1273g-3p, miR-1203, miR-122-5p, miR-4258, miR-4484, miR-4648 and miR-6780b-5p.

(5) The kit according to (4), wherein miR-6808-5p is hsa-miR-6808-5p, miR-6774-5p is hsa-miR-6774-5p, miR-4656 is hsa-miR-4656, miR-6806-5p is hsa-miR-6806-5p, miR-1233-5p is hsa-miR-1233-5p, miR-328-5p is hsa-miR-328-5p, miR-4674 is hsa-miR-4674, miR-2110 is hsa-miR-2110, miR-6076 is hsa-miR-6076, miR-3619-3p is hsa-miR-3619-3p, miR-92a-2-5p is hsa-miR-92a-2-5p, miR-128-1-5p is hsa-miR-128-1-5p, miR-638 is hsa-miR-638, miR-2861 is hsa-miR-2861, miR-371a-5p is hsa-miR-371a-5p, miR-211-3p is hsa-miR-211-3p, miR-1273g-3p is hsa-miR-1273g-3p, miR-1203 is hsa-miR-1203, miR-122-5p is hsamiR-122-5p, miR-4258 is hsa-miR-4258, miR-4484 is hsa-miR-4484, miR-4648 is hsa-miR-4648, and miR-6780b-5p is hsa-miR-6780b-5p.

(6) The kit according to (4) or (5), wherein the nucleic acid is a polynucleotide selected from the group consisting of the following polynucleotides (f) to (j):

(f) a polynucleotide consisting of a nucleotide sequence represented by any of SEQ ID NOs: 126 to 148 or a nucleotide sequence derived from the nucleotide sequence by the replacement of u with t, a variant thereof, a derivative thereof, or a fragment thereof comprising 15 or more consecutive nucleotides.

(g) a polynucleotide comprising a nucleotide sequence represented by any of SEQ ID NOs: 126 to 148, (h) a polynucleotide consisting of a nucleotide sequence complementary to a nucleotide sequence represented by any of SEQ ID NOs: 126 to 148 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 126 to 148 or a nucleotide sequence derived from the nucleotide sequence by the replacement of u with t, and (j) a polynucleotide hybridizing under stringent conditions to any of the polynucleotides (f) to (i).

(7) The kit according to any one of (1) to (6), wherein the kit comprises at least two or more nucleic acids capable of specifically binding to at least two or more polynucleotides, respectively, selected from all of the biliary tract cancer markers according to (1) or (2).

(8) A device for the detection of biliary tract cancer, comprising nucleic acid(s) capable of specifically binding to at least one or more polynucleotide(s) selected from the group consisting of biliary tract cancer markers miR-125a-3p, miR-6893-5p, miR-204-3p, miR-4476, miR-4294, miR-150-3p, miR-6729-5p, miR-7641, miR-6765-3p, miR-6820-5p, miR-575, miR-6836-3p, miR-1469, miR-663a, miR-6075, miR-4634, miR-423-5p, miR-4454, miR-7109-5p, miR-6789-5p, miR-6877-5p, miR-4792, miR-4530, miR-7975, miR-6724-5p, miR-8073, miR-7977, miR-1231, miR-6799-5p, miR-615-5p, miR-4450, miR-6726-5p, miR-6875-5p, miR-4734, miR-16-5p, miR-602, miR-4651, miR-8069, miR-1238-5p, miR-6880-5p, miR-8072, miR-4723-5p, miR-4732-5p, miR-6125, miR-6090, miR-7114-5p, miR-564, miR-451a, miR-3135b, miR-4497, miR-4665-5p, miR-3622a-5p, miR-6850-5p, miR-6821-5p, miR-5100, miR-6872-3p, miR-4433-3p, miR-1227-5p, miR-3188, miR-7704, miR-3185, miR-1908-3p, miR-6781-5p, miR-6805-5p, miR-8089, miR-665, miR-4486, miR-6722-3p, miR-1260a, miR-4707-5p, miR-6741-5p, miR-1260b, miR-1246, miR-6845-5p, miR-4638-5p, miR-6085, miR-1228-3p, miR-4534, miR-5585-3p, miR-4741, miR-4433b-3p, miR-197-5p, miR-718, miR-4513, miR-4446-3p, miR-619-5p, miR-6816-5p, miR-6778-5p, miR-24-3p, miR-1915-3p, miR-4665-3p, miR-4449, miR-6889-5p, miR-486-3p, miR-7113-3p, miR-642a-3p, miR-7847-3p, miR-6768-5p, miR-1290, miR-7108-5p, miR-92b-5p, miR-663b, miR-3940-5p, miR-4467, miR-6858-5p, miR-4417, miR-3665, miR-4736, miR-4687-3p, miR-1908-5p, miR-5195-3p, miR-4286, miR-3679-3p, miR-6791-5p, miR-1202, miR-3656, miR-4746-3p, miR-3184-5p, miR-3937, miR-6515-3p, miR-6132, miR-187-5p, miR-7111-5p, miR-5787, miR-6779-5p, miR-4516, miR-4649-5p, miR-760, miR-3162-5p, miR-3178, miR-940, miR-4271, miR-6769b-5p, miR-4508, miR-6826-5p, miR-6757-5p, miR-3131, and miR-1343-3p.

(9) The device according to (8), wherein miR-125a-3p is hsa-miR-125a-3p, miR-6893-5p is hsa-miR-6893-5p, miR-204-3p is hsa-miR-204-3p, miR-4476 is hsa-miR-4476, miR-4294 is hsa-miR-4294, miR-150-3p is hsa-miR-150-3p, miR-6729-5p is hsa-miR-6729-5p, miR-7641 is hsa-miR-7641, miR-6765-3p is hsa-miR-6765-3p, miR-6820-5p is hsa-miR-6820-5p, miR-575 is hsa-miR-575, miR-6836-3p is hsa-miR-6836-3p, miR-1469 is hsa-miR-1469, miR-663a is hsa-miR-663a, miR-6075 is hsa-miR-6075, miR-4634 is hsa-miR-4634, miR-423-5p is hsa-miR-423-5p, miR-4454 is hsa-miR-4454, miR-7109-5p is hsa-miR-7109-5p, miR-6789-5p is hsa-miR-6789-5p, miR-6877-5p is hsa-miR-6877-5p, miR-4792 is hsa-miR-4792, miR-4530 is hsa-miR-4530, miR-7975 is hsa-miR-7975, miR-6724-5p is hsa-miR-6724-5p, miR-8073 is hsa-miR-8073, miR-7977 is hsa-miR-7977, miR-1231 is hsa-miR-1231, miR-6799-5p is hsa-miR-6799-5p, miR-615-5p is hsa-miR-615-5p, miR-4450 is hsa-miR-4450, miR-6726-5p is hsa-miR-6726-5p, miR-6875-5p is hsa-miR-6875-5p, miR-4734 is hsa-miR-4734, miR-16-5p is hsa-miR-16-5p, miR-602 is hsa-miR-602, miR-4651 is hsa-miR-4651, miR-8069 is hsa-miR-8069, miR-1238-5p is hsa-miR-1238-5p, miR-6880-5p is hsa-miR-6880-5p, miR-8072 is hsa-miR-8072, miR-4723-5p is hsa-miR-4723-5p, miR-4732-5p is hsa-miR-4732-5p, miR-6125 is hsa-miR-6125, miR-6090 is hsa-miR-6090, miR-7114-5p is hsa-miR-7114-5p, miR-564 is hsa-miR-564, miR-451a is hsa-miR-451a, miR-3135b is hsa-miR-3135b, miR-4497 is hsa-miR-4497, miR-4665-5p is hsa-miR-4665-5p, miR-3622a-5p is hsa-miR-3622a-5p, miR-6850-5p is hsa-miR-6850-5p, miR-6821-5p is hsa-miR-6821-5p, miR-5100 is hsa-miR-5100, miR-6872-3p is hsa-miR-6872-3p, miR-4433-3p is hsa-miR-4433-3p, miR-1227-5p is hsa-miR-1227-5p, miR-3188 is hsa-miR-3188, miR-7704 is hsa-miR-7704, miR-3185 is hsa-miR-3185, miR-1908-3p is hsa-miR-1908-3p, miR-6781-5p is hsa-miR-6781-5p, miR-6805-5p is hsa-miR-6805-5p, miR-8089 is hsa-miR-8089, miR-665 is hsa-miR-665, miR-4486 is hsa-miR-4486, miR-6722-3p is hsa-miR-6722-3p, miR-1260a is hsa-miR-1260a, miR-4707-5p is hsa-miR-4707-5p, miR-6741-5p is hsa-miR-6741-5p, miR-1260b is hsa-miR-1260b, miR-1246 is hsa-miR-1246, miR-6845-5p is hsa-miR-6845-5p, miR-4638-5p is hsa-miR-4638-5p, miR-6085 is hsa-miR-6085, miR-1228-3p is hsa-miR-1228-3p, miR-4534 is hsa-miR-4534, miR-5585-3p is hsa-miR-5585-3p, miR-4741 is hsa-miR-4741, miR-4433b-3p is hsa-miR-4433b-3p, miR-197-5p is hsa-miR-197-5p, miR-718 is hsa-miR-718, miR-4513 is hsa-miR-4513, miR-4446-3p is hsa-miR-4446-3p, miR-619-5p is hsa-miR-619-5p, miR-6816-5p is hsa-miR-6816-5p, miR-6778-5p is hsa-miR-6778-5p, miR-24-3p is hsa-miR-24-3p, miR-1915-3p is hsa-miR-1915-3p, miR-4665-3p is hsa-miR-4665-3p, miR-4449 is hsa-miR-4449, miR-6889-5p is hsa-miR-6889-5p, miR-486-3p is hsa-miR-486-3p, miR-7113-3p is hsa-miR-7113-3p, miR-642a-3p is hsa-miR-642a-3p, miR-7847-3p is hsa-miR-7847-3p, miR-6768-5p is hsa-miR-6768-5p, miR-1290 is hsa-miR-1290, miR-7108-5p is hsa-miR-7108-5p, miR-92b-5p is hsa-miR-92b-5p, miR-663b is hsa-miR-663b, miR-3940-5p is hsa-miR-3940-5p, miR-4467 is hsa-miR-4467, miR-6858-5p is hsa-miR-6858-5p, miR-4417 is hsa-miR-4417, miR-3665 is hsa-miR-3665, miR-4736 is hsa-miR-4736, miR-4687-3p is hsa-miR-4687-3p, miR-1908-5p is hsa-miR-1908-5p, miR-5195-3p is hsa-miR-5195-3p, miR-4286 is hsa-miR-4286, miR-3679-3p is hsa-miR-3679-3p, miR-6791-5p is hsa-miR-6791-5p, miR-1202 is hsa-miR-1202, miR-3656 is hsa-miR-3656, miR-4746-3p is hsa-miR-4746-3p, miR-3184-5p is hsa-miR-3184-5p, miR-3937 is hsa-miR-3937, miR-6515-3p is hsa-miR-6515-3p, miR-6132 is hsa-miR- 6132, miR-187-5p is hsa-miR-187-5p, miR-7111-5p is hsa-miR-7111-5p, miR-5787 is hsa-miR-5787, miR-6779-5p is hsa-miR-6779-5p, miR-4516 is hsa-miR-4516, miR-4649-5p is hsa-miR-4649-5p, miR-760 is hsa-miR-760, miR-3162-5p is hsa-miR-3162-5p, miR-3178 is hsa-miR-3178, miR-940 is hsa-miR-940, miR-4271 is hsa-miR-4271, miR-6769b-5p is hsa-miR-6769b-5p, miR-4508 is hsa-miR-4508, miR-6826-5p is hsa-miR-6826-5p, miR-6757-5p is hsa-miR-6757-5p, miR-3131 is hsa-miR-3131, and miR-1343-3p is hsa-miR-1343-3p.

(10) The device according to (8) or (9), wherein the nucleic acid is a polynucleotide selected from the group consisting of the following polynucleotides (a) to (e):

(a) a polynucleotide consisting of a nucleotide sequence represented by any of SEQ ID NOs: 1 to 125 and 466 to 478 or a nucleotide sequence derived from the nucleotide sequence by the replacement of u with t, a variant thereof, a derivative thereof, or a fragment thereof comprising 15 or more consecutive nucleotides.

(b) a polynucleotide comprising a nucleotide sequence represented by any of SEQ ID NOs: 1 to 125 and 466 to 478, (c) a polynucleotide consisting of a nucleotide sequence complementary to a nucleotide sequence represented by any of SEQ ID NOs: 1 to 125 and 466 to 478 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 125 and 466 to 478 or a nucleotide sequence derived from the nucleotide sequence by the replacement of u with t, and (e) a polynucleotide hybridizing under stringent conditions to any of the polynucleotides (a) to (d).

(11) The device according to any one of (8) to (10), wherein the device further comprises nucleic acid(s) capable of specifically binding to at least one or more polynucleotide(s) selected from the group consisting of other biliary tract cancer markers miR-6808-5p, miR-6774-5p, miR-4656, miR-6806-5p, miR-1233-5p, miR-328-5p, miR-4674, miR-2110, miR-6076, miR-3619-3p, miR-92a-2-5p, miR-128-1-5p, miR-638, miR-2861, miR-371a-5p, miR-211-3p, miR-1273g-3p, miR-1203, miR-122-5p, miR-4258, miR-4484, miR-4648 and miR-6780b-5p.

(12) The device according to (11), wherein miR-6808-5p is hsa-miR-6808-5p, miR-6774-5p is hsa-miR-6774-5p, miR-4656 is hsa-miR-4656, miR-6806-5p is hsa-miR-6806-5p, miR-1233-5p is hsa-miR-1233-5p, miR-328-5p is hsa-miR-328-5p, miR-4674 is hsa-miR-4674, miR-2110 is hsa-miR-2110, miR-6076 is hsa-miR-6076, miR-3619-3p is hsa-miR-3619-3p, miR-92a-2-5p is hsa-miR-92a-2-5p, miR-128-1-5p is hsa-miR-128-1-5p, miR-638 is hsa-miR-638, miR-2861 is hsa-miR-2861, miR-371a-5p is hsa-miR-371a-5p, miR-211-3p is hsa-miR-211-3p, miR-1273g-3p is hsa-miR-1273g-3p, miR-1203 is hsa-miR-1203, miR-122-5p is hsa-miR-122-5p, miR-4258 is hsa-miR-4258, miR-4484 is hsa-miR-4484, miR-4648 is hsa-miR-4648, and miR-6780b-5p is hsa-miR-6780b-5p.

(13) The device according to (11) or (12), wherein the nucleic acid is a polynucleotide selected from the group consisting of the following polynucleotides (f) to (j):

(f) a polynucleotide consisting of a nucleotide sequence represented by any of SEQ ID NOs: 126 to 148 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 126 to 148.

(h) a polynucleotide consisting of a nucleotide sequence complementary to a nucleotide sequence represented by any of SEQ ID NOs: 126 to 148 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 126 to 148 or a nucleotide sequence derived from the nucleotide sequence by the replacement of u with t, and (j) a polynucleotide hybridizing under stringent conditions to any of the polynucleotides (f) to (i).

(14) The device according to any one of (8) to (13), wherein the device is for measurement based on a hybridization technique.

(15) The device according to (14), wherein the hybridization technique is a nucleic acid array technique.

(16) The device according to any one of (8) to (15), wherein the device comprises at least two or more nucleic acids capable of specifically binding to at least two or more polynucleotides, respectively, selected from all of the biliary tract cancer markers according to (8) or (9).

(17) A method for detecting biliary tract cancer, comprising measuring an expression level of a target nucleic acid in a sample of a subject using the kit according to any one of (1) to (7) or the device according to any one of (8) to (16); and evaluating in vitro whether or not the subject has biliary tract cancer using the measured expression level and a control expression level for a healthy subject measured in the same way.

(18) The method according to (17), wherein the subject is a human.

(19) The method according to (17) or (18), wherein the sample is blood, serum, or plasma.

Definition of Term

The terms used herein are defined as follows.

The term "biliary tract cancer" used herein refers to any malignant tumor formed in the biliary tract. Specifically, the "biliary tract cancer" includes extrahepatic bile duct cancer, gallbladder cancer, papillary cancer, duodenal papilla cancer, intrahepatic bile duct cancer, and the like.

The term "benign tumors and/or benign diseases of the biliary tract and/or peribiliary organs" used herein refers to diseases with nonmalignant tumors in the biliary tract, the liver, and the pancreas.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein refers to a nucleic acid, including any of RNA, DNA, and RNA/DNA (chimera). The DNA includes any of cDNA, genomic DNA, and synthetic DNA. The RNA includes all of total RNA, mRNA, rRNA, miRNA, siRNA, snoRNA, snRNA, non-coding RNA and synthetic RNA. The "synthetic DNA" and the "synthetic RNA" used herein refer to DNA and RNA artificially prepared using, for example, an automated nucleic acid synthesizer, on the basis of predetermined nucleotide sequences (which may be any of natural and non-natural sequences). The "non-natural sequence" used herein is intended to be used in a broad sense and includes, for example, a sequence containing substitution, deletion, insertion, and/or addition of one or more nucleotide(s) (i.e., a variant sequence) and a sequence containing one or more modified nucleotide(s) (i.e., a modified sequence), which are different from the natural sequence. As used herein, the term "polynucleotide" is used interchangeably with the term "nucleic acid."

The term "fragment" used herein is a polynucleotide having a nucleotide sequence having a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but also each single-stranded DNA such as a plus strand (or a sense strand) or a complementary strand (or an antisense strand) constituting the duplex. The gene is not particularly limited by its length.

Thus, the "gene" used herein includes all of double-stranded DNA including human genomic DNA, single-stranded DNA (plus strand), single-stranded DNA that has a sequence complementary to the plus strand (complementary strand) including cDNA, microRNA (miRNA), and their fragments, and transcripts, unless otherwise specified. The "gene" includes not only a "gene" represented by a particular nucleotide sequence (or SEQ ID NO) but "nucleic acids" that encode RNAs that have biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" that has a nucleotide sequence that hybridizes under stringent conditions described later to a complementary sequence of a nucleotide sequence represented by any of SEQ ID NOs: 1 to 509 or a nucleotide sequence derived from the nucleotide sequence by the replacement of u with t. The "gene" is not particularly limited by its functional region and can contain, for example, an expression regulatory region, a coding region, an exon, or an intron. The "gene" may be contained in a cell or may exist alone after being released into the outside of a cell. Alternatively, the "gene" may be in a state enclosed in a vesicle called exosome.

The term "exosome" used herein is a vesicle that is encapsulated by a lipid bilayer and secreted from a cell. The exosome is derived from a multivesicular endosome and may incorporate a biomaterial such as a "gene" (e.g., RNA or DNA) or a protein when released into an extracellular environment. The exosome is known to be contained in a body fluid such as blood, serum, plasma, serum, or lymph.

The term "transcript" used herein refers to RNA synthesized from the DNA sequence of a gene as a template. RNA polymerase binds to a site called a promoter located upstream of the gene and adds ribonucleotides complementary to the nucleotide sequence of the DNA to the 3' end to synthesize an RNA. This RNA contains not only the gene itself but also the whole sequence from a transcription initiation site to the end of a polyA sequence, including an expression regulatory region, a coding region, an exon, or an intron.

The term "microRNA (miRNA)" used herein is intended to mean a 15- to 25-nucleotide non-coding RNA that is transcribed as an RNA precursor having a hairpin-like structure, cleaved by a dsRNA-cleaving enzyme which has RNase III cleavage activity, integrated into a protein complex called RISC, and involved in the suppression of translation of mRNA, unless otherwise specified. The term "miRNA" used herein includes not only a "miRNA" represented by a particular nucleotide sequence (or SEQ ID NO) but a precursor of the "miRNA" (pre-miRNA or pri-miRNA), and miRNAs that have biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" that has a nucleotide sequence that hybridizes under stringent conditions described later to a complementary sequence of any particular nucleotide sequence represented by any of SEQ ID NOs: 1 to 509. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting an RNA that results from the expression of a gene, or a polynucleotide derived from the RNA, and/or a polynucleotide complementary thereto.

The term "primer" used herein includes a polynucleotide that specifically recognizes and amplifies an RNA that results from the expression of a gene or a polynucleotide derived from the RNA, and/or a polynucleotide complementary thereto.

In this context, the complementary polynucleotide (complementary strand or reverse strand) means a polynucleotide in a complementary relationship of A:T (U) and G:C base pairs with the full-length sequence of a polynucleotide consisting of a nucleotide sequence defined by any of SEQ ID NOs: 1 to 509 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a larger extent (e.g., a measurement value equal to or larger than a mean of background measurement values+a standard deviation of the background measurement values×2) than that for other sequences. The stringent conditions are dependent on a sequence and differ depending on an environment where hybridization is performed. A target sequence complementary 100% to the nucleic acid probe can be identified by controlling the stringency of hybridization and/or washing conditions. Specific examples of the "stringent conditions" are mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1 or 2 or more nucleotides in a nucleotide sequence represented by any of SEQ ID NOs: 1 to 509, or a nucleotide sequence derived from the nucleotide sequence by the replacement of u with t, or a partial sequence thereof; a variant that exhibits percent (%) identity of approximately 90% or higher, approximately 95% or higher, approximately 97% or higher, approximately 98% or higher, approximately 99% or higher to each of these nucleotide sequences or the partial sequences thereof; or a nucleic acid that hybridizes under the stringent conditions defined above to a polynucleotide or an oligonucleotide comprising each of these nucleotide sequences or the partial sequence thereof.

The term "several" used herein means an integer of approximately 10, 9, 8, 7, 6, 5, 4, 3, or 2.

The variant used herein can be prepared by use of a well-known technique such as site-directed mutagenesis or PCR-based mutagenesis.

The term "percent (%) identity" used herein can be determined with or without an introduced gap, using a protein or gene search system based on BLAST or FASTA described above (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A, Vol. 85, p. 2444-2448).

The term "derivative" used herein is meant to include a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404) without any limitation.

As used herein, the "nucleic acid" capable of specifically binding to a polynucleotide selected from the biliary tract cancer marker miRNA group described above is a synthesized or prepared nucleic acid and specifically includes a "nucleic acid probe" or a "primer". The "nucleic acid" is utilized directly or indirectly for detecting the presence or absence of biliary tract cancer in a subject, for diagnosing the presence or absence of biliary tract cancer, or the severity of biliary tract cancer, the presence or absence of amelioration or the degree of amelioration of biliary tract cancer, or the therapeutic sensitivity of biliary tract cancer, or for screening for a candidate substance useful in the prevention, amelioration, or treatment of biliary tract cancer. The "nucleic acid" includes a nucleotide, an oligonucleotide, and a polynucleotide capable of specifically recognizing and binding to a transcript represented by any of SEQ ID NOs: 1 to 509 or a synthetic cDNA nucleic acid thereof in vivo, particularly, in a sample such as a body fluid (e.g., blood or urine), in relation to the development of biliary tract cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "detection" or "decision support". The term "evaluation" used herein is meant to include diagnosis or evaluation support on the basis of examination results or measurement results.

The term "subject" used herein means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected.

The term "P" or "P value" used herein refers to a probability at which a more extreme statistic than that is actually calculated from data under a null hypothesis is observed in a statistical test. Thus, smaller "P" or "P value" is regarded as being more significant difference between subjects to be compared.

The term "sensitivity" used herein means a value of (the number of true positives)/(the number of true positives+the number of false negatives). High sensitivity allows biliary tract cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being biliary tract cancer patients, leading to reduction in burden on patients and reduction in medical expense.

The term "accuracy" used herein means a value of (the number of true positives+the number of true negatives)/(the total number of cases). The accuracy indicates the ratio of samples that are correctly identified in the discriminant results to all samples, and serves as a primary index for evaluating detection performance.

As used herein, the "sample" that is subject to determination, detection, or diagnosis refers to a tissue and a biological material in which the expression of the gene of the present invention varies as biliary tract cancer develops, as biliary tract cancer progresses, or as therapeutic effects on biliary tract cancer are exerted. Specifically, the "sample" refers to a biliary tract tissue, a peribiliary vascular channel, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-125a-3p gene" or "hsa-miR-125a-3p" used herein includes the hsa-miR-125a-3p gene (miRBase Accession No. MIMAT0004602) described in SEQ ID NO: 1, a homolog or an ortholog of a different organism species, and the like. The hsa-miR-125a-3p gene can be obtained by a method described in Lagos-Quintana M et al., 2002, Curr Biol, Vol. 12, p. 735-739. Also, "hsa-mir-125a" (miRBase Accession No. MI0000469. SEQ ID NO: 149) having a hairpin-like structure is known as a precursor of "hsa-miR-125a-3p".

The term "hsa-miR-6893-5p gene" or "hsa-miR-6893-5p" used herein includes the hsa-miR-6893-5p gene (miRBase Accession No. MIMAT0027686) described in SEQ ID NO: 2, a homolog or an ortholog of a different organism species, and the like. The hsa-miR-6893-5p gene can be obtained by a method described in Ladewig E et al., 2012, Genome Res, Vol. 22, p. 1634-1645. Also, "hsa-mir-6893" (miRBase Accession No. MI0022740, SEQ ID NO: 150) having a hairpin-like structure is known as a precursor of "hsa-miR-6893-5p".

The term "hsa-miR-204-3p gene" or "hsa-miR-204-3p" used herein includes the hsa-miR-204-3p gene (miRBase Accession No. MIMAT0022693) described in SEQ ID NO: 3, a homolog or an ortholog of a different organism species, and the like. The hsa-miR-204-3p gene can be obtained by a method described in Lim L P et al., 2003, Science, Vol. 299, p. 1540. Also, "hsa-mir-204" (miRBase Accession No. MI0000284, SEQ ID NO: 151) having a hairpin-like structure is known as a precursor of "hsa-miR-204-3p".

The term "hsa-miR-4476 gene" or "hsa-miR-4476" used herein includes the hsa-miR-4476 gene (miRBase Accession No. MIMAT0019003) described in SEQ ID NO: 4, a homolog or an ortholog of a different organism species, and the like. The hsa-miR-4476 gene can be obtained by a method described in Jima D D et al., 2010, Blood, Vol. 116, e118-e127. Also, "hsa-mir-4476" (miRBase Accession No. MI0016828, SEQ ID NO: 152) having a hairpin-like structure is known as a precursor of "hsa-miR-4476".

The term "hsa-miR-4294 gene" or "hsa-miR-4294" used herein includes the hsa-miR-4294 gene (miRBase Accession No. MIMAT0016849) described in SEQ ID NO: 5, a homolog or an ortholog of a different organism species, and the like. The hsa-miR-4294 gene can be obtained by a method described in Goff L A et al., 2009, PLoS One, Vol. 4, e7192. Also, "hsa-mir-4294" (miRBase Accession No. MI0015827. SEQ ID NO: 153) having a hairpin-like structure is known as a precursor of "hsa-miR-4294".

The term "hsa-miR-150-3p gene" or "hsa-miR-150-3p" used herein includes the hsa-miR-150-3p gene (miRBase Accession No. MIMAT0004610) described in SEQ ID NO: 6, a homolog or an ortholog of a different organism species, and the like. The hsa-miR-150-3p gene can be obtained by a method described in Lagos-Quintana M et al., 2002, Curr Biol, Vol. 12, p. 735-739. Also, "hsa-mir-150" (miRBase Accession No. MI0000479, SEQ ID NO: 154) having a hairpin-like structure is known as a precursor of "hsa-miR-150-3p".

The term "hsa-miR-6729-5p gene" or "hsa-miR-6729-5p" used herein includes the hsa-miR-6729-5p gene (miRBase Accession No. MIMAT0027359) described in SEQ ID NO: 7, a homolog or an ortholog of a different organism species, and the like. The hsa-miR-6729-5p gene can be obtained by a method described in Ladewig E et al., 2012, Genome Res, Vol. 22, p. 1634-1645. Also, "hsa-mir-6729" (miRBase Accession No. MI0022574, SEQ ID NO: 155) having a hairpin-like structure is known as a precursor of "hsa-miR-6729-5p".

The term "hsa-miR-7641 gene" or "hsa-miR-7641" used herein includes the hsa-miR-7641 gene (miRBase Accession No. MIMAT0029782) described in SEQ ID NO: 8, a homolog or an ortholog of a different organism species, and the like. The hsa-miR-7641 gene can be obtained by a method described in Yoo J K et al., 2013, Arch Pharm Res, Vol. 36, p. 353-358. Also, "hsa-mir-7641-1" and "hsa-mir-7641-2" (miRBase Accession Nos. M10024975 and MI0024976, SEQ ID NOs: 156 and 157) having a hairpin-like structure are known as a precursor of "hsa-miR-7641".

The term "hsa-miR-6765-3p gene" or "hsa-miR-6765-3p" used herein includes the hsa-miR-6765-3p gene (miRBase Accession No. MIMAT0027431) described in SEQ ID NO: 9, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 158) having a hairpin-like structure is known as a precursor of "hsa-miR-6765-3p".

The term "hsa-miR-6820-5p gene" or "hsa-miR-6820-5p" used herein includes the hsa-miR-6820-5p gene (miRBase Accession No. MIMAT0027540) described in SEQ ID NO: 10, a homolog or an ortholog of a different organism species, and the like. The hsa-miR-6820-5p gene can be obtained by a method described in Ladewig E et al., 2012, Genome Res, Vol. 22, p. 1634-1645. Also, "hsa-mir-6820" (miRBase Accession No. MI0022665, SEQ ID NO: 159) having a hairpin-like structure is known as a precursor of "hsa-miR-6820-5p".

The term "hsa-miR-575 gene" or "hsa-miR-575" used herein includes the hsa-miR-575 gene (miRBase Accession No. MIMAT0003240) described in SEQ ID NO: 11, a homolog or an ortholog of a different organism species, and the like. The hsa-miR-575 gene can be obtained by a method described in Cummins J M et al., 2006, Proc Natl Acad Sci USA, Vol. 103, p. 3687-3692. Also, "hsa-mir-575" (miRBase Accession No. MI0003582, SEQ ID NO: 160) having a hairpin-like structure is known as a precursor of "hsa-miR-575".

The term "hsa-miR-6836-3p gene" or "hsa-miR-6836-3p" used herein includes the hsa-miR-6836-3p gene (miRBase Accession No. MIMAT0027575) described in SEQ ID NO: 12, a homolog or an ortholog of a different organism species, and the like. The hsa-miR-6836-3p gene can be obtained by a method described in Ladewig E et al., 2012, Genome Res, Vol. 22, p. 1634-1645. Also, "hsa-mir-6836" (miRBase Accession No. MI0022682, SEQ ID NO: 161) having a hairpin-like structure is known as a precursor of "hsa-miR-6836-3p".

The term "hsa-miR-1469 gene" or "hsa-miR-1469" used herein includes the hsa-miR-1469 gene (miRBase Accession No. MIMAT0007347) described in SEQ ID NO: 13, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 162) having a hairpin-like structure is known as a precursor of "hsa-miR-1469".

The term "hsa-miR-663a gene" or "hsa-miR-663a" used herein includes the hsa-miR-663a gene (miRBase Accession No. MIMAT0003326) described in SEQ ID NO: 14, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 163) having a hairpin-like structure is known as a precursor of "hsa-miR-663a".

The term "hsa-miR-6075 gene" or "hsa-miR-6075" used herein includes the hsa-miR-6075 gene (miRBase Accession No. MIMAT0023700) described in SEQ ID NO: 15, a homolog or an ortholog of a different organism species, and the like. The hsa-miR-6075 gene can be obtained by a method described in Voellenkle C et al., 2012, RNA, Vol. 18, p. 472-484. Also, "hsa-mir-6075" (miRBase Accession No. MI0020352, SEQ ID NO: 164) having a hairpin-like structure is known as a precursor of "hsa-miR-6075".

The term "hsa-miR-4634 gene" or "hsa-miR-4634" used herein includes the hsa-miR-4634 gene (miRBase Accession No. MIMAT0019691) described in SEQ ID NO: 16, a homolog or an ortholog of a different organism species, and the like. The hsa-miR-4634 gene can be obtained by a method described in Persson H et al., 2011, Cancer Res, Vol. 71, p. 78-86. Also, "hsa-mir-4634" (miRBase Accession No. MI0017261, SEQ ID NO: 165) having a hairpin-like structure is known as a precursor of "hsa-miR-4634".

The term "hsa-miR-423-5p gene" or "hsa-miR-423-5p" used herein includes the hsa-miR-423-5p gene (miRBase Accession No. MIMAT0004748) described in SEQ ID NO: 17, a homolog or an ortholog of a different organism species, and the like. The hsa-miR-423-5p gene can be obtained by a method described in Kasashima K et al., 2004, Biochem Biophys Res Commun, Vol. 322, p. 403-410. Also, "hsa-mir-423" (miRBase Accession No. MI0001445, SEQ ID NO: 166) having a hairpin-like structure is known as a precursor of "hsa-miR-423-5p".

The term "hsa-miR-4454 gene" or "hsa-miR-4454" used herein includes the hsa-miR-4454 gene (miRBase Accession No. MIMAT0018976) described in SEQ ID NO: 18, a homolog or an ortholog of a different organism species, and the like. The hsa-miR-4454 gene can be obtained by a method described in Jima D D et al., 2010, Blood, Vol. 116, e118-e127. Also, "hsa-mir-4454" (miRBase Accession No. MI0016800, SEQ ID NO: 167) having a hairpin-like structure is known as a precursor of "hsa-miR-4454".

The term "hsa-miR-7109-5p gene" or "hsa-miR-7109-5p" used herein includes the hsa-miR-7109-5p gene (miRBase Accession No. MIMAT0028115) described in SEQ ID NO: 19, a homolog or an ortholog of a different organism species, and the like. The hsa-miR-7109-5p gene can be obtained by a method described in Ladewig E et al., 2012, Genome Res, Vol. 22, p. 1634-1645. Also, "hsa-mir-7109" (miRBase Accession No. MI0022960, SEQ ID NO: 168) having a hairpin-like structure is known as a precursor of "hsa-miR-7109-5p".

The term "hsa-miR-6789-5p gene" or "hsa-miR-6789-5p" used herein includes the hsa-miR-6789-5p gene (miRBase Accession No. MIMAT0027478) described in SEQ ID NO: 20, a homolog or an ortholog of a different organism species, and the like. The hsa-miR-6789-5p gene can be obtained by a method described in Ladewig E et al., 2012, Genome Res, Vol. 22, p. 1634-1645. Also, "hsa-mir-6789" (miRBase Accession No. MI0022634, SEQ ID NO: 169) having a hairpin-like structure is known as a precursor of "hsa-miR-6789-5p".

The term "hsa-miR-6877-5p gene" or "hsa-miR-6877-5p" used herein includes the hsa-miR-6877-5p gene (miRBase Accession No. MIMAT0027654) described in SEQ ID NO: 21, a homolog or an ortholog of a different organism species, and the like. The hsa-miR-6877-5p gene can be obtained by a method described in Ladewig E et al., 2012. Genome Res, Vol. 22, p. 1634-1645. Also, "hsa-mir-6877" (miRBase Accession No. MI0022724, SEQ ID NO: 170) having a hairpin-like structure is known as a precursor of "hsa-miR-6877-5p".

The term "hsa-miR-4792 gene" or "hsa-miR-4792" used herein includes the hsa-miR-4792 gene (miRBase Accession No. MIMAT0019964) described in SEQ ID NO: 22, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 171) having a hairpin-like structure is known as a precursor of "hsa-miR-4792".

The term "hsa-miR-4530 gene" or "hsa-miR-4530" used herein includes the hsa-miR-4530 gene (miRBase Accession No. MIMAT0019069) described in SEQ ID NO: 23, a homolog or an ortholog of a different organism species, and the like. The hsa-miR-4530 gene can be obtained by a method described in Jima D D et al., 2010, Blood, Vol. 116, e118-e127. Also, "hsa-mir-4530" (miRBase Accession No. MI0016897, SEQ ID NO: 172) having a hairpin-like structure is known as a precursor of "hsa-miR-4530".

The term "hsa-miR-7975 gene" or "hsa-miR-7975" used herein includes the hsa-miR-7975 gene (miRBase Accession No. MIMAT0031178) described in SEQ ID NO: 24, a homolog or an ortholog of a different organism species, and the like. The hsa-miR-7975 gene can be obtained by a method described in Velthut-Meikas A et al., 2013, Mol Endocrinol, online. Also, "hsa-mir-7975" (miRBase Accession No. MI0025751, SEQ ID NO: 173) having a hairpin-like structure is known as a precursor of "hsa-miR-7975".

The term "hsa-miR-6724-5p gene" or "hsa-miR-6724-5p" used herein includes the hsa-miR-6724-5p gene (miRBase Accession No. MIMAT0025856) described in SEQ ID NO: 25, a homolog or an ortholog of a different organism species, and the like. The hsa-miR-6724-5p gene can be obtained by a method described in Li Y et al., 2012, Gene, Vol. 497, p. 330-335. Also, "hsa-mir-6724" (miRBase Accession No. MI0022559, SEQ ID NO: 174) having a hairpin-like structure is known as a precursor of "hsa-miR-6724-5p".

The term "hsa-miR-8073 gene" or "hsa-miR-8073" used herein includes the hsa-miR-8073 gene (miRBase Accession No. MIMAT0031000) described in SEQ ID NO: 26, a homolog or an ortholog of a different organism species, and the like. The hsa-miR-8073 gene can be obtained by a method described in Wang H J et al., 2013, Shock, Vol. 39, p. 480-487. Also, "hsa-mir-8073" (miRBase Accession No. MI0025909, SEQ ID NO: 175) having a hairpin-like structure is known as a precursor of "hsa-miR-8073".

The term "hsa-miR-7977 gene" or "hsa-miR-7977" used herein includes the hsa-miR-7977 gene (miRBase Accession No. MIMAT0031180) described in SEQ ID NO: 27, a homolog or an ortholog of a different organism species, and the like. The hsa-miR-7977 gene can be obtained by a method described in Velthut-Meikas A et al., 2013, Mol Endocrinol, online. Also, "hsa-mir-7977" (miRBase Accession No. MI0025753, SEQ ID NO: 176) having a hairpin-like structure is known as a precursor of "hsa-miR-7977".

The term "hsa-miR-1231 gene" or "hsa-miR-1231" used herein includes the hsa-miR-1231 gene (miRBase Accession No. MIMAT0005586) described in SEQ ID NO: 28, a homolog or an ortholog of a different organism species, and the like. The hsa-miR-1231 gene can be obtained by a method described in Berezikov E et al., 2007, Mol Cell, Vol. 28, p. 328-336. Also, "hsa-mir-1231" (miRBase Accession No. MI0006321, SEQ ID NO: 177) having a hairpin-like structure is known as a precursor of "hsa-miR-1231".

The term "hsa-miR-6799-5p gene" or "hsa-miR-6799-5p" used herein includes the hsa-miR-6799-5p gene (miRBase Accession No. MIMAT0027498) described in SEQ ID NO: 29, a homolog or an ortholog of a different organism species, and the like. The hsa-miR-6799-5p gene can be obtained by a method described in Ladewig E et al., 2012, Genome Res, Vol. 22, p. 1634-1645. Also, "hsa-mir-6799" (miRBase Accession No. MI0022644, SEQ ID NO: 178) having a hairpin-like structure is known as a precursor of "hsa-miR-6799-5p".

The term "hsa-miR-615-5p gene" or "hsa-miR-615-5p" used herein includes the hsa-miR-615-5p gene (miRBase Accession No. MIMAT0004804) described in SEQ ID NO: 30, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. MI0003628, SEQ ID NO: 179) having a hairpin-like structure is known as a precursor of "hsa-miR-615-5p".

The term "hsa-miR-4450 gene" or "hsa-miR-4450" used herein includes the hsa-miR-4450 gene (miRBase Accession No. MIMAT0018971) described in SEQ ID NO: 31, a homolog or an ortholog of a different organism species, and the like. The hsa-miR-4450 gene can be obtained by a method described in Jima D D et al., 2010, Blood, Vol. 116, e118-e127. Also, "hsa-mir-4450" (miRBase Accession No. MI0016795, SEQ ID NO: 180) having a hairpin-like structure is known as a precursor of "hsa-miR-4450".

The term "hsa-miR-6726-5p gene" or "hsa-miR-6726-5p" used herein includes the hsa-miR-6726-5p gene (miRBase Accession No. MIMAT0027353) described in SEQ ID NO: 32, a homolog or an ortholog of a different organism species, and the like. The hsa-miR-6726-5p gene can be obtained by a method described in Ladewig E et al., 2012, Genome Res. Vol. 22, p. 1634-1645. Also, "hsa-mir-6726" (miRBase Accession No. MI0022571, SEQ ID NO: 181) having a hairpin-like structure is known as a precursor of "hsa-miR-6726-5p".

The term "hsa-miR-6875-5p gene" or "hsa-miR-6875-5p" used herein includes the hsa-miR-6875-5p gene (miRBase Accession No. MIMAT0027650) described in SEQ ID NO: 33, a homolog or an ortholog of a different organism species, and the like. The hsa-miR-6875-5p gene can be obtained by a method described in Ladewig E et al., 2012, Genome Res, Vol. 22, p. 1634-1645. Also, "hsa-mir-6875" (miRBase Accession No. MI0022722, SEQ ID NO: 182) having a hairpin-like structure is known as a precursor of "hsa-miR-6875-5p".

The term "hsa-miR-4734 gene" or "hsa-miR-4734" used herein includes the hsa-miR-4734 gene (miRBase Accession No. MIMAT0019859) described in SEQ ID NO: 34, a homolog or an ortholog of a different organism species, and the like. The hsa-miR-4734 gene can be obtained by a method described in Persson H et al., 2011, Cancer Res, Vol. 71, p. 78-86. Also, "hsa-mir-4734" (miRBase Accession No. MI0017371, SEQ ID NO: 183) having a hairpin-like structure is known as a precursor of "hsa-miR-4734".

The term "hsa-miR-16-5p gene" or "hsa-miR-16-5p" used herein includes the hsa-miR-16-5p gene (miRBase Accession No. MIMAT0000069) described in SEQ ID NO: 35, a homolog or an ortholog of a different organism species, and the like. The hsa-miR-16-5p gene can be obtained by a method described in Lagos-Quintana M et al., 2001, Science, Vol. 294, p. 853-858. Also, "hsa-mir-16-1" and "hsa-mir-16-2" (miRBase Accession Nos. MI0000070 and MI0000115, SEQ ID NOs: 184 and 185) having a hairpin-like structure are known as precursors of "hsa-miR-16-5p".

The term "hsa-miR-602 gene" or "hsa-miR-602" used herein includes the hsa-miR-602 gene (miRBase Accession No. MIMAT0003270) described in SEQ ID NO: 36, a homolog or an ortholog of a different organism species, and the like. The hsa-miR-602 gene can be obtained by a method described in Cummins J M et al., 2006, Proc Natl Acad Sci USA. Vol. 103, p. 3687-3692. Also, "hsa-mir-602" (miRBase Accession No. MI0003615, SEQ ID NO: 186) having a hairpin-like structure is known as a precursor of "hsa-miR-602".

The term "hsa-miR-4651 gene" or "hsa-miR-4651" used herein includes the hsa-miR-4651 gene (miRBase Accession No. MIMAT0019715) described in SEQ ID NO: 37, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 187) having a hairpin-like structure is known as a precursor of "hsa-miR-4651".

The term "hsa-miR-8069 gene" or "hsa-miR-8069" used herein includes the hsa-miR-8069 gene (miRBase Accession No. MIMAT0030996) described in SEQ ID NO: 38, a homolog or an ortholog of a different organism species, and the like. The hsa-miR-8069 gene can be obtained by a method described in Wang H J et al., 2013. Shock, Vol. 39, p. 480-487. Also, "hsa-mir-8069" (miRBase Accession No. MI0025905, SEQ ID NO: 188) having a hairpin-like structure is known as a precursor of "hsa-miR-8069".

The term "hsa-miR-1238-5p gene" or "hsa-miR-1238-5p" used herein includes the hsa-miR-1238-5p gene (miRBase Accession No. MIMAT0022947) described in SEQ ID NO: 39, a homolog or an ortholog of a different organism species, and the like. The hsa-miR-1238-5p gene can be obtained by a method described in Berezikov E et al., 2007, Mol Cell, Vol. 28, p. 328-336. Also, "hsa-mir-1238" (miRBase Accession No. MI0006328. SEQ ID NO: 189) having a hairpin-like structure is known as a precursor of "hsa-miR-1238-5p".

The term "hsa-miR-6880-5p gene" or "hsa-miR-6880-5p" used herein includes the hsa-miR-6880-5p gene (miRBase Accession No. MIMAT0027660) described in SEQ ID NO: 40, a homolog or an ortholog of a different organism species, and the like. The hsa-miR-6880-5p gene can be obtained by a method described in Ladewig E et al., 2012, Genome Res, Vol. 22, p. 1634-1645. Also, "hsa-mir-6880" (miRBase Accession No. MI0022727, SEQ ID NO: 190) having a hairpin-like structure is known as a precursor of "hsa-miR-6880-5p".

The term "hsa-miR-8072 gene" or "hsa-miR-8072" used herein includes the hsa-miR-8072 gene (miRBase Accession No. MIMAT0030999) described in SEQ ID NO: 41, a homolog or an ortholog of a different organism species, and the like. The hsa-miR-8072 gene can be obtained by a method described in Wang H J et al., 2013, Shock, Vol. 39, p. 480-487. Also, "hsa-mir-8072" (miRBase Accession No. MI0025908, SEQ ID NO: 191) having a hairpin-like structure is known as a precursor of "hsa-miR-8072".

The term "hsa-miR-4723-5p gene" or "hsa-miR-4723-5p" used herein includes the hsa-miR-4723-5p gene (miRBase Accession No. MIMAT0) 19838) described in SEQ ID NO: 42, a homolog or an ortholog of a different organism species, and the like. The hsa-miR-4723-5p gene can be obtained by a method described in Persson H et al., 2011, Cancer Res, Vol. 71, p. 78-86. Also, "hsa-mir-4723" (miRBase Accession No. MI0017359, SEQ ID NO: 192) having a hairpin-like structure is known as a precursor of "hsa-miR-4723-5p".

The term "hsa-miR-4732-5p gene" or "hsa-miR-4732-5p" used herein includes the hsa-miR-4732-5p gene (miRBase Accession No. MIMAT0019855) described in SEQ ID NO: 43, a homolog or an ortholog of a different organism species, and the like. The hsa-miR-4732-5p gene can be obtained by a method described in Persson H et al., 2011, Cancer Res, Vol. 71, p. 78-86. Also, "hsa-mir-4732" (miRBase Accession No. MI0017369, SEQ ID NO: 193) having a hairpin-like structure is known as a precursor of "hsa-miR-4732-5p".

The term "hsa-miR-6125 gene" or "hsa-miR-6125" used herein includes the hsa-miR-6125 gene (miRBase Accession No. MIMAT0024598) described in SEQ ID NO: 44, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 194) having a hairpin-like structure is known as a precursor of "hsa-miR-6125".

The term "hsa-miR-6090 gene" or "hsa-miR-6090" used herein includes the hsa-miR-6090 gene (miRBase Accession No. MIMAT0023715) described in SEQ ID NO: 45, a homolog or an ortholog of a different organism species, and the like. The hsa-miR-6090 gene can be obtained by a method described in Yoo J K et al., 2012, Stem Cells Dev, Vol. 21, p. 2049-2057. Also, "hsa-mir-6090" (miRBase Accession No. MI0020367, SEQ ID NO: 195) having a hairpin-like structure is known as a precursor of "hsa-miR-6090".

The term "hsa-miR-7114-5p gene" or "hsa-miR-7114-5p" used herein includes the hsa-miR-7114-5p gene (miRBase Accession No. MIMAT0028125) described in SEQ ID NO: 46, a homolog or an ortholog of a different organism species, and the like. The hsa-miR-7114-5p gene can be obtained by a method described in Ladewig E et al., 2012, Genome Res, Vol. 22, p. 1634-1645. Also, "hsa-mir-7114" (miRBase Accession No. MI0022965, SEQ ID NO: 196) having a hairpin-like structure is known as a precursor of "hsa-miR-7114-5p".

The term "hsa-miR-564 gene" or "hsa-miR-564" used herein includes the hsa-miR-564 gene (miRBase Accession No. MIMAT0003228) described in SEQ ID NO: 47, a homolog or an ortholog of a different organism species, and the like. The hsa-miR-564 gene can be obtained by a method described in Cummins J M et al., 2006, Proc Natl Acad Sci USA, Vol. 103, p. 3687-3692. Also, "hsa-mir-564" (miRBase Accession No. MI0003570, SEQ ID NO: 197) having a hairpin-like structure is known as a precursor of "hsa-miR-564".

The term "hsa-miR-451a gene" or "hsa-miR-451a" used herein includes the hsa-miR-451a gene (miRBase Accession No. MIMAT0001631) described in SEQ ID NO: 48, a homolog or an ortholog of a different organism species, and the like. The hsa-miR-451 a gene can be obtained by a method described in Altuvia Y et al., 2005, Nucleic Acids Res, Vol. 33, p. 2697-2706. Also, "hsa-mir-451a" (miRBase Accession No. MI0001729, SEQ ID NO: 198) having a hairpin-like structure is known as a precursor of "hsa-miR-451a".

The term "hsa-miR-3135b gene" or "hsa-miR-3135b" used herein includes the hsa-miR-3135b gene (miRBase Accession No. MIMAT0018985) described in SEQ ID NO: 49, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 199) having a hairpin-like structure is known as a precursor of "hsa-miR-3135b".

The term "hsa-miR-4497 gene" or "hsa-miR-4497" used herein includes the hsa-miR-4497 gene (miRBase Accession No. MIMAT0019032) described in SEQ ID NO: 50, a homolog or an ortholog of a different organism species, and the like. The hsa-miR-4497 gene can be obtained by a method described in Jima D D et al., 2010, Blood. Vol. 116, e118-e127. Also, "hsa-mir-4497" (miRBase Accession No. MI0016859, SEQ ID NO: 200) having a hairpin-like structure is known as a precursor of "hsa-miR-4497".

The term "hsa-miR-4665-5p gene" or "hsa-miR-4665-5p" used herein includes the hsa-miR-4665-5p gene (miRBase Accession No. MIMAT0019739) described in SEQ ID NO: 51, a homolog or an ortholog of a different organism species, and the like. The hsa-miR-4665-5p gene can be obtained by a method described in Persson H et al., 2011, Cancer Res, Vol. 71, p. 78-86. Also, "hsa-mir-4665" (miRBase Accession No. MI0017295, SEQ ID NO: 201) having a hairpin-like structure is known as a precursor of "hsa-miR-4665-5p".

The term "hsa-miR-3622a-5p gene" or "hsa-miR-3622a-5p" used herein includes the hsa-miR-3622a-5p gene (miRBase Accession No. MIMAT0018003) described in SEQ ID NO: 52, a homolog or an ortholog of a different organism species, and the like. The hsa-miR-3622a-5p gene can be obtained by a method described in Witten D et al., 2010, BMC Biol. Vol. 8, p. 58. Also, "hsa-mir-3622a" (miRBase Accession No. MI0016013, SEQ ID NO: 202) having a hairpin-like structure is known as a precursor of "hsa-miR-3622a-5p".

The term "hsa-miR-6850-5p gene" or "hsa-miR-6850-5p" used herein includes the hsa-miR-6850-5p gene (miRBase Accession No. MIMAT0027600) described in SEQ ID NO: 53, a homolog or an ortholog of a different organism species, and the like. The hsa-miR-6850-5p gene can be obtained by a method described in Ladewig E et al., 2012, Genome Res, Vol. 22, p. 1634-1645. Also, "hsa-mir-6850" (miRBase Accession No. MI0022696, SEQ ID NO: 203) having a hairpin-like structure is known as a precursor of "hsa-miR-6850-5p".

The term "hsa-miR-6821-5p gene" or "hsa-miR-6821-5p" used herein includes the hsa-miR-6821-5p gene (miRBase Accession No. MIMAT0027542) described in SEQ ID NO: 54, a homolog or an ortholog of a different organism species, and the like. The hsa-miR-6821-5p gene can be obtained by a method described in Ladewig E et al., 2012, Genome Res, Vol. 22, p. 1634-1645. Also, "hsa-mir-6821" (miRBase Accession No. MI0022666, SEQ ID NO: 204) having a hairpin-like structure is known as a precursor of "hsa-miR-6821-5p".

The term "hsa-miR-5100 gene" or "hsa-miR-5100" used herein includes the hsa-miR-5100 gene (miRBase Accession No. MIMAT0022259) described in SEQ ID NO: 55, a homolog or an ortholog of a different organism species, and the like. The hsa-miR-5100 gene can be obtained by a method described in Tandon M et al., 2012, Oral Dis, Vol. 18, p. 127-131. Also, "hsa-mir-5100" (miRBase Accession No. MI0019116, SEQ ID NO: 205) having a hairpin-like structure is known as a precursor of "hsa-miR-5 100".

The term "hsa-miR-6872-3p gene" or "hsa-miR-6872-3p" used herein includes the hsa-miR-6872-3p gene (miRBase Accession No. MIMAT0027645) described in SEQ ID NO: 56, a homolog or an ortholog of a different organism species, and the like. The hsa-miR-6872-3p gene can be obtained by a method described in Ladewig E et al., 2012, Genome Res, Vol. 22, p. 1634-1645. Also, "hsa-mir-6872" (miRBase Accession No. MI0022719, SEQ ID NO: 206) having a hairpin-like structure is known as a precursor of "hsa-miR-6872-3p".

The term "hsa-miR-4433-3p gene" or "hsa-miR-4433-3p" used herein includes the hsa-miR-4433-3p gene (miRBase Accession No. MIMAT0018949) described in SEQ ID NO: 57, a homolog or an ortholog of a different organism species, and the like. The hsa-miR-4433-3p gene can be obtained by a method described in Jima D D et al., 2010, Blood, Vol. 116, e118-e127. Also, "hsa-mir-4433" (miRBase Accession No. MI0016773, SEQ ID NO: 207) having a hairpin-like structure is known as a precursor of "hsa-miR-4433-3p".

The term "hsa-miR-1227-5p gene" or "hsa-miR-1227-5p" used herein includes the hsa-miR-1227-5p gene (miRBase Accession No. MIMAT0022941) described in SEQ ID NO: 58, a homolog or an ortholog of a different organism species, and the like. The hsa-miR-1227-5p gene can be obtained by a method described in Berezikov E et al., 2007, Mol Cell, Vol. 28, p. 328-336. Also, "hsa-mir-1227" (miRBase Accession No. MI0006316, SEQ ID NO: 208) having a hairpin-like structure is known as a precursor of "hsa-miR-1227-5p".

The term "hsa-miR-3188 gene" or "hsa-miR-3188" used herein includes the hsa-miR-3188 gene (miRBase Accession No. MIMAT0015070) described in SEQ ID NO: 59, a homolog or an ortholog of a different organism species, and the like. The hsa-miR-3188 gene can be obtained by a method described in Stark M S et al., 2010, PLoS One, Vol.

5, e9685. Also, "hsa-mir-3188" (miRBase Accession No. MI0014232, SEQ ID NO: 209) having a hairpin-like structure is known as a precursor of "hsa-miR-3188".

The term "hsa-miR-7704 gene" or "hsa-miR-7704" used herein includes the hsa-miR-7704 gene (miRBase Accession No. MIMAT0030019) described in SEQ ID NO: 60, a homolog or an ortholog of a different organism species, and the like. The hsa-miR-7704 gene can be obtained by a method described in Swaminathan S et al., 2013, Biochem Biophys Res Commun, Vol. 434, p. 228-234. Also, "hsa-mir-7704" (miRBase Accession No. MI0025240, SEQ ID NO: 210) having a hairpin-like structure is known as a precursor of "hsa-miR-7704".

The term "hsa-miR-3185 gene" or "hsa-miR-3185" used herein includes the hsa-miR-3185 gene (miRBase Accession No. MIMAT0015065) described in SEQ ID NO: 61, a homolog or an ortholog of a different organism species, and the like. The hsa-miR-3185 gene can be obtained by a method described in Stark M S et al., 2010, PLoS One. Vol. 5, e9685. Also, "hsa-mir-3185" (miRBase Accession No. MI0014227. SEQ ID NO: 211) having a hairpin-like structure is known as a precursor of "hsa-miR-3185".

The term "hsa-miR-1908-3p gene" or "hsa-miR-1908-3p" used herein includes the hsa-miR-1908-3p gene (miRBase Accession No. MIMAT0026916) described in SEQ ID NO: 62, a homolog or an ortholog of a different organism species, and the like. The hsa-miR-1908-3p gene can be obtained by a method described in Bar M et al., 2008, Stem Cells, Vol. 26, p. 2496-2505. Also, "hsa-mir-1908" (miRBase Accession No. MI0008329, SEQ ID NO: 212) having a hairpin-like structure is known as a precursor of "hsa-miR-1908-3p".

The term "hsa-miR-6781-5p gene" or "hsa-miR-6781-5p" used herein includes the hsa-miR-6781-5p gene (miRBase Accession No. MIMAT0027462) described in SEQ ID NO: 63, a homolog or an ortholog of a different organism species, and the like. The hsa-miR-6781-5p gene can be obtained by a method described in Ladewig E et al., 2012, Genome Res, Vol. 22, p. 1634-1645. Also, "hsa-mir-6781" (miRBase Accession No. MI0022626, SEQ ID NO: 213) having a hairpin-like structure is known as a precursor of "hsa-miR-6781-5p".

The term "hsa-miR-6805-5p gene" or "hsa-miR-6805-5p" used herein includes the hsa-miR-6805-5p gene (miRBase Accession No. MIMAT0027510) described in SEQ ID NO: 64, a homolog or an ortholog of a different organism species, and the like. The hsa-miR-6805-5p gene can be obtained by a method described in Ladewig E et al., 2012, Genome Res, Vol. 22, p. 1634-1645. Also, "hsa-mir-6805" (miRBase Accession No. MI0022650, SEQ ID NO: 214) having a hairpin-like structure is known as a precursor of "hsa-miR-6805-5p".

The term "hsa-miR-8089 gene" or "hsa-miR-8089" used herein includes the hsa-miR-8089 gene (miRBase Accession No. MIMAT0031016) described in SEQ ID NO: 65, a homolog or an ortholog of a different organism species, and the like. The hsa-miR-8089 gene can be obtained by a method described in Wang H J et al., 2013, Shock, Vol. 39, p. 480-487. Also, "hsa-mir-8089" (miRBase Accession No. MI0025925, SEQ ID NO: 215) having a hairpin-like structure is known as a precursor of "hsa-miR-8089".

The term "hsa-miR-665 gene" or "hsa-miR-665" used herein includes the hsa-miR-665 gene (miRBase Accession No. MIMAT0004952) described in SEQ ID NO: 66, a homolog or an ortholog of a different organism species, and the like. The hsa-miR-665 gene can be obtained by a method described in Berezikov E et al., 2006, Genome Res, Vol. 16, p. 1289-1298. Also, "hsa-mir-665" (miRBase Accession No. MI0005563, SEQ ID NO: 216) having a hairpin-like structure is known as a precursor of "hsa-miR-665".

The term "hsa-miR-4486 gene" or "hsa-miR-4486" used herein includes the hsa-miR-4486 gene (miRBase Accession No. MIMAT0019020) described in SEQ ID NO: 67, a homolog or an ortholog of a different organism species, and the like. The hsa-miR-4486 gene can be obtained by a method described in Jima D D et al., 2010, Blood, Vol. 116, e118-e127. Also, "hsa-mir-4486" (miRBase Accession No. MI0016847, SEQ ID NO: 217) having a hairpin-like structure is known as a precursor of "hsa-miR-4486".

The term "hsa-miR-6722-3p gene" or "hsa-miR-6722-3p" used herein includes the hsa-miR-6722-3p gene (miRBase Accession No. MIMAT0025854) described in SEQ ID NO: 68, a homolog or an ortholog of a different organism species, and the like. The hsa-miR-6722-3p gene can be obtained by a method described in Li Y et al., 2012, Gene, Vol. 497, p. 330-335. Also, "hsa-mir-6722" (miRBase Accession No. MI0022557, SEQ ID NO: 218) having a hairpin-like structure is known as a precursor of "hsa-miR-6722-3p".

The term "hsa-miR-1260a gene" or "hsa-miR-1260a" used herein includes the hsa-miR-1260a gene (miRBase Accession No. MIMAT0005911) described in SEQ ID NO: 69, a homolog or an ortholog of a different organism species, and the like. The hsa-miR-1260a gene can be obtained by a method described in Morin R D et al., 2008, Genome Res, Vol. 18, p. 610-621. Also, "hsa-mir-1260a" (miRBase Accession No. MI0006394, SEQ ID NO: 219) having a hairpin-like structure is known as a precursor of "hsa-miR-1260a".

The term "hsa-miR-4707-5p gene" or "hsa-miR-4707-5p" used herein includes the hsa-miR-4707-5p gene (miRBase Accession No. MIMAT0019807) described in SEQ ID NO: 70, a homolog or an ortholog of a different organism species, and the like. The hsa-miR-4707-5p gene can be obtained by a method described in Persson H et al., 2011, Cancer Res, Vol. 71, p. 78-86. Also, "hsa-mir-4707" (miRBase Accession No. MI0017340, SEQ ID NO: 220) having a hairpin-like structure is known as a precursor of "hsa-miR-4707-5p".

The term "hsa-miR-6741-5p gene" or "hsa-miR-6741-5p" used herein includes the hsa-miR-6741-5p gene (miRBase Accession No. MIMAT0027383) described in SEQ ID NO: 71, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. MI0022586, SEQ ID NO: 221) having a hairpin-like structure is known as a precursor of "hsa-miR-6741-5p".

The term "hsa-miR-1260b gene" or "hsa-miR-1260b" used herein includes the hsa-miR-1260b gene (miRBase Accession No. MIMAT0015041) described in SEQ ID NO: 72, a homolog or an ortholog of a different organism species, and the like. The hsa-miR-1260b gene can be obtained by a method described in Stark M S et al., 2010, PLoS One, Vol. 5, e9685. Also, "hsa-mir-1260b" (miRBase Accession No. MI0014197, SEQ ID NO: 222) having a hairpin-like structure is known as a precursor of "hsa-miR-1260b".

The term "hsa-miR-1246 gene" or "hsa-miR-1246" used herein includes the hsa-miR-1246 gene (miRBase Accession No. MIMAT0005898) described in SEQ ID NO: 73, a homolog or an ortholog of a different organism species, and the like. The hsa-miR-1246 gene can be obtained by a method described in Morin R D et al., 2008, Genome Res, Vol. 18, p. 610-621. Also, "hsa-mir-1246" (miRBase Accession No. MI0006381, SEQ ID NO: 223) having a hairpin-like structure is known as a precursor of "hsa-miR-1246".

The term "hsa-miR-6845-5p gene" or "hsa-miR-6845-5p" used herein includes the hsa-miR-6845-5p gene (miRBase Accession No. MIMAT0027590) described in SEQ ID NO: 74, a homolog or an ortholog of a different organism species, and the like. The hsa-miR-6845-5p gene can be obtained by a method described in Ladewig E et al., 2012, Genome Res, Vol. 22, p. 1634-1645. Also, "hsa-mir-6845" (miRBase Accession No. MI0022691, SEQ ID NO: 224) having a hairpin-like structure is known as a precursor of "hsa-miR-6845-5p".

The term "hsa-miR-4638-5p gene" or "hsa-miR-4638-5p" used herein includes the hsa-miR-4638-5p gene (miRBase Accession No. MIMAT0019695) described in SEQ ID NO: 75, a homolog or an ortholog of a different organism species, and the like. The hsa-miR-4638-5p gene can be obtained by a method described in Persson H et al., 2011, Cancer Res, Vol. 71, p. 78-86. Also, "hsa-mir-4638" (miRBase Accession No. MI0017265, SEQ ID NO: 225) having a hairpin-like structure is known as a precursor of "hsa-miR-4638-5p".

The term "hsa-miR-6085 gene" or "hsa-miR-6085" used herein includes the hsa-miR-6085 gene (miRBase Accession No. MIMAT0023710) described in SEQ ID NO: 76, a homolog or an ortholog of a different organism species, and the like. The hsa-miR-6085 gene can be obtained by a method described in Voellenkle C et al., 2012, RNA, Vol. 18, p. 472-484. Also, "hsa-mir-6085" (miRBase Accession No. MI0020362, SEQ ID NO: 226) having a hairpin-like structure is known as a precursor of "hsa-miR-6085".

The term "hsa-miR-1228-3p gene" or "hsa-miR-1228-3p" used herein includes the hsa-miR-1228-3p gene (miRBase Accession No. MIMAT0005583) described in SEQ ID NO: 77, a homolog or an ortholog of a different organism species, and the like. The hsa-miR-1228-3p gene can be obtained by a method described in Berezikov E et al., 2007, Mol Cell, Vol. 28, p. 328-336. Also, "hsa-mir-1228" (miRBase Accession No. MI0006318, SEQ ID NO: 227) having a hairpin-like structure is known as a precursor of "hsa-miR-1228-3p".

The term "hsa-miR-4534 gene" or "hsa-miR-4534" used herein includes the hsa-miR-4534 gene (miRBase Accession No. MIMAT0019073) described in SEQ ID NO: 78, a homolog or an ortholog of a different organism species, and the like. The hsa-miR-4534 gene can be obtained by a method described in Jima D D et al., 2010, Blood. Vol. 116, e118-e127. Also, "hsa-mir-4534" (miRBase Accession No. MI0016901, SEQ ID NO: 228) having a hairpin-like structure is known as a precursor of "hsa-miR-4534".

The term "hsa-miR-5585-3p gene" or "hsa-miR-5585-3p" used herein includes the hsa-miR-5585-3p gene (miRBase Accession No. MIMAT0022286) described in SEQ ID NO: 79, a homolog or an ortholog of a different organism species, and the like. The hsa-miR-5585-3p gene can be obtained by a method described in Friedlander M R et al., 2012, Nucleic Acids Res, Vol. 40, p. 37-52. Also, "hsa-mir-5585" (miRBase Accession No. MI0019142, SEQ ID NO: 229) having a hairpin-like structure is known as a precursor of "hsa-miR-5585-3p".

The term "hsa-miR-4741 gene" or "hsa-miR-4741" used herein includes the hsa-miR-4741 gene (miRBase Accession No. MIMAT0019871) described in SEQ ID NO: 80, a homolog or an ortholog of a different organism species, and the like. The hsa-miR-4741 gene can be obtained by a method described in Persson H et al., 2011, Cancer Res, Vol. 71, p. 78-86. Also, "hsa-mir-4741" (miRBase Accession No. MI0017379, SEQ ID NO: 230) having a hairpin-like structure is known as a precursor of "hsa-miR-4741".

The term "hsa-miR-4433b-3p gene" or "hsa-miR-4433b-3p" used herein includes the hsa-miR-4433b-3p gene (miRBase Accession No. MIMAT0030414) described in SEQ ID NO: 81, a homolog or an ortholog of a different organism species, and the like. The hsa-miR-4433b-3p gene can be obtained by a method described in Ple H et al., 2012, PLoS One, Vol. 7, e50746. Also, "hsa-mir-4433b" (miRBase Accession No. MI0025511, SEQ ID NO: 231) having a hairpin-like structure is known as a precursor of "hsa-miR-4433b-3p".

The term "hsa-miR-197-5p gene" or "hsa-miR-197-5p" used herein includes the hsa-miR-197-5p gene (miRBase Accession No. MIMAT0022691) described in SEQ ID NO: 82, a homolog or an ortholog of a different organism species, and the like. The hsa-miR-197-5p gene can be obtained by a method described in Lagos-Quintana M et al., 2003, RNA. Vol. 9, p. 175-179. Also, "hsa-mir-197" (miRBase Accession No. MI0000239, SEQ ID NO: 232) having a hairpin-like structure is known as a precursor of "hsa-miR-197-5p".

The term "hsa-miR-718 gene" or "hsa-miR-718" used herein includes the hsa-miR-718 gene (miRBase Accession No. MIMAT0012735) described in SEQ ID NO: 83, a homolog or an ortholog of a different organism species, and the like. The hsa-miR-718 gene can be obtained by a method described in Artzi S et al., 2008, BMC Bioinformatics, Vol. 9, p. 39. Also, "hsa-mir-718" (miRBase Accession No. MI0012489, SEQ ID NO: 233) having a hairpin-like structure is known as a precursor of "hsa-miR-718".

The term "hsa-miR-4513 gene" or "hsa-miR-4513" used herein includes the hsa-miR-4513 gene (miRBase Accession No. MIMAT0019050) described in SEQ ID NO: 84, a homolog or an ortholog of a different organism species, and the like. The hsa-miR-4513 gene can be obtained by a method described in Jima D D et al., 2010, Blood, Vol. 116, e118-e127. Also, "hsa-mir-4513" (miRBase Accession No. MI0016879, SEQ ID NO: 234) having a hairpin-like structure is known as a precursor of "hsa-miR-4513".

The term "hsa-miR-4446-3p gene" or "hsa-miR-4446-3p" used herein includes the hsa-miR-4446-3p gene (miRBase Accession No. MIMAT0018965) described in SEQ ID NO: 85, a homolog or an ortholog of a different organism species, and the like. The hsa-miR-4446-3p gene can be obtained by a method described in Jima D D et al., 2010, Blood, Vol. 116, e118-e127. Also, "hsa-mir-4446" (miRBase Accession No. MI0016789, SEQ ID NO: 235) having a hairpin-like structure is known as a precursor of "hsa-miR-4446-3p".

The term "hsa-miR-619-5p gene" or "hsa-miR-619-5p" used herein includes the hsa-miR-619-5p gene (miRBase Accession No. MIMAT0026622) described in SEQ ID NO: 86, a homolog or an ortholog of a different organism species, and the like. The hsa-miR-619-5p gene can be obtained by a method described in Cummins J M et al., 2006, Proc Natl Acad Sci USA, Vol. 103, p. 3687-3692. Also, "hsa-mir-619" (miRBase Accession No. MI0003633, SEQ ID NO: 236) having a hairpin-like structure is known as a precursor of "hsa-miR-619-5p".

The term "hsa-miR-6816-5p gene" or "hsa-miR-6816-5p" used herein includes the hsa-miR-6816-5p gene (miRBase Accession No. MIMAT0027532) described in SEQ ID NO: 87, a homolog or an ortholog of a different organism species, and the like. The hsa-miR-6816-5p gene can be obtained by a method described in Ladewig E et al., 2012, Genome Res, Vol. 22, p. 1634-1645. Also, "hsa-mir-6816" (miRBase Accession No. MI0022661, SEQ ID NO: 237) having a hairpin-like structure is known as a precursor of “hsa-miR-6816-5p”.

The term “hsa-miR-6778-5p gene” or “hsa-miR-6778-5p” used herein includes the hsa-miR-6778-5p gene (miRBase Accession No. MIMAT0027456) described in SEQ ID NO: 88, a homolog or an ortholog of a different organism species, and the like. The hsa-miR-6778-5p gene can be obtained by a method described in Ladewig E et al., 2012, Genome Res, Vol. 22, p. 1634-1645. Also, “hsa-mir-6778” (miRBase Accession No. MI0022623, SEQ ID NO: 238) having a hairpin-like structure is known as a precursor of “hsa-miR-6778-5p”.

The term “hsa-miR-24-3p gene” or “hsa-miR-24-3p” used herein includes the hsa-miR-24-3p gene (miRBase Accession No. MIMAT0000080) described in SEQ ID NO: 89, a homolog or an ortholog of a different organism species, and the like. The hsa-miR-24-3p gene can be obtained by a method described in Lagos-Quintana M et al., 2001, Science, Vol. 294, p. 853-858. Also, “hsa-mir-24-1” and “hsa-mir-24-2” (miRBase Accession Nos. M10000080 and MI0000081, SEQ ID NOs: 239 and 240) having a hairpin-like structure are known as precursors of “hsa-miR-24-3p”.

The term “hsa-miR-1915-3p gene” or “hsa-miR-1915-3p” used herein includes the hsa-miR-1915-3p gene (miRBase Accession No. MIMAT0007892) described in SEQ ID NO: 90, a homolog or an ortholog of a different organism species, and the like. The hsa-miR-1915-3p gene can be obtained by a method described in Bar M et al., 2008, Stem Cells, Vol. 26, p. 2496-2505. Also, “hsa-mir-1915” (miRBase Accession No. MI0008336, SEQ ID NO: 241) having a hairpin-like structure is known as a precursor of “hsa-miR-1915-3p”.

The term “hsa-miR-4665-3p gene” or “hsa-miR-4665-3p” used herein includes the hsa-miR-4665-3p gene (miRBase Accession No. MIMAT0019740) described in SEQ ID NO: 91, a homolog or an ortholog of a different organism species, and the like. The hsa-miR-4665-3p gene can be obtained by a method described in Persson H et al., 2011, Cancer Res, Vol. 71, p. 78-86. Also, “hsa-mir-4665” (miRBase Accession No. MI0017295, SEQ ID NO: 201) having a hairpin-like structure is known as a precursor of “hsa-miR-4665-3p”.

The term “hsa-miR-4449 gene” or “hsa-miR-4449” used herein includes the hsa-miR-4449 gene (miRBase Accession No. MIMAT0018968) described in SEQ ID NO: 92, a homolog or an ortholog of a different organism species, and the like. The hsa-miR-4449 gene can be obtained by a method described in Jima D D et al., 2010, Blood, Vol. 116, e118-e127. Also, “hsa-mir-4449” (miRBase Accession No. MI0016792, SEQ ID NO: 242) having a hairpin-like structure is known as a precursor of “hsa-miR-4449”.

The term “hsa-miR-6889-5p gene” or “hsa-miR-6889-5p” used herein includes the hsa-miR-6889-5p gene (miRBase Accession No. MIMAT0027678) described in SEQ ID NO: 93, a homolog or an ortholog of a different organism species, and the like. The hsa-miR-6889-5p gene can be obtained by a method described in Ladewig E et al., 2012, Genome Res, Vol. 22, p. 1634-1645. Also, “hsa-mir-6889” (miRBase Accession No. MI0022736, SEQ ID NO: 243) having a hairpin-like structure is known as a precursor of “hsa-miR-6889-5p”.

The term “hsa-miR-486-3p gene” or “hsa-miR-486-3p” used herein includes the hsa-miR-486-3p gene (miRBase Accession No. MIMAT0004762) described in SEQ ID NO: 94, a homolog or an ortholog of a different organism species, and the like. The hsa-miR-486-3p gene can be obtained by a method described in Fu H et al., 2005, FEBS Lett, Vol. 579, p. 3849-3854. Also, “hsa-mir-486, hsa-mir-486-2” (miRBase Accession No. MI0002470, MI0023622, SEQ ID NO: 244, 245) having a hairpin-like structure is known as a precursor of “hsa-miR-486-3p”.

The term “hsa-miR-7113-3p gene” or “hsa-miR-7113-3p” used herein includes the hsa-miR-7113-3p gene (miRBase Accession No. MIMAT0028124) described in SEQ ID NO: 95, a homolog or an ortholog of a different organism species, and the like. The hsa-miR-7113-3p gene can be obtained by a method described in Ladewig E et al., 2012, Genome Res, Vol. 22, p. 1634-1645. Also, “hsa-mir-7113” (miRBase Accession No. MI0022964, SEQ ID NO: 246) having a hairpin-like structure is known as a precursor of “hsa-miR-7113-3p”.

The term “hsa-miR-642a-3p gene” or “hsa-miR-642a-3p” used herein includes the hsa-miR-642a-3p gene (miRBase Accession No. MIMAT0020924) described in SEQ ID NO: 96, a homolog or an ortholog of a different organism species, and the like. The hsa-miR-642a-3p gene can be obtained by a method described in Cummins J M et al., 2006, Proc Natl Acad Sci USA, Vol. 103, p. 3687-3692. Also, “hsa-mir-642a” (miRBase Accession No. MI0003657, SEQ ID NO: 247) having a hairpin-like structure is known as a precursor of “hsa-miR-642a-3p”.

The term “hsa-miR-7847-3p gene” or “hsa-miR-7847-3p” used herein includes the hsa-miR-7847-3p gene (miRBase Accession No. MIMAT0030422) described in SEQ ID NO: 97, a homolog or an ortholog of a different organism species, and the like. The hsa-miR-7847-3p gene can be obtained by a method described in Ple H et al., 2012, PLoS One, Vol. 7, e50746. Also, “hsa-mir-7847” (miRBase Accession No. MI0025517, SEQ ID NO: 248) having a hairpin-like structure is known as a precursor of “hsa-miR-7847-3p”.

The term “hsa-miR-6768-5p gene” or “hsa-miR-6768-5p” used herein includes the hsa-miR-6768-5p gene (miRBase Accession No. MIMAT0027436) described in SEQ ID NO: 98, a homolog or an ortholog of a different organism species, and the like. The hsa-miR-6768-5p gene can be obtained by a method described in Ladewig E et al., 2012, Genome Res, Vol. 22, p. 1634-1645. Also, “hsa-mir-6768” (miRBase Accession No. MI0022613, SEQ ID NO: 249) having a hairpin-like structure is known as a precursor of “hsa-miR-6768-5p”.

The term “hsa-miR-1290 gene” or “hsa-miR-1290” used herein includes the hsa-miR-1290 gene (miRBase Accession No. MIMAT0005880) described in SEQ ID NO: 99, a homolog or an ortholog of a different organism species, and the like. The hsa-miR-1290 gene can be obtained by a method described in Morin R D et al., 2008, Genome Res, Vol. 18, p. 610-621. Also, “hsa-mir-1290” (miRBase Accession No. MI0006352, SEQ ID NO: 250) having a hairpin-like structure is known as a precursor of “hsa-miR-1290”.

The term “hsa-miR-7108-5p gene” or “hsa-miR-7108-5p” used herein includes the hsa-miR-7108-5p gene (miRBase Accession No. MIMAT0028113) described in SEQ ID NO: 100, a homolog or an ortholog of a different organism species, and the like. The hsa-miR-7108-5p gene can be obtained by a method described in Ladewig E et al., 2012, Genome Res. Vol. 22, p. 1634-1645. Also, “hsa-mir-7108” (miRBase Accession No. MI0022959, SEQ ID NO: 251) having a hairpin-like structure is known as a precursor of “hsa-miR-7108-5p”.

The term “hsa-miR-92b-5p gene” or “hsa-miR-92b-5p” used herein includes the hsa-miR-92b-5p gene (miRBase Accession No. MIMAT0004792) described in SEQ ID NO: 101, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, “hsa-mir-92b” (miRBase Accession No. MI0003560, SEQ ID NO: 252) having a hairpin-like structure is known as a precursor of “hsa-miR-92b-5p”.

The term “hsa-miR-663b gene” or “hsa-miR-663b” used herein includes the hsa-miR-663b gene (miRBase Accession No. MIMAT0005867) described in SEQ ID NO: 102, a homolog or an ortholog of a different organism species, and the like. The hsa-miR-663b gene can be obtained by a method described in Takada S et al., 2008, Leukemia, Vol. 22, p. 1274-1278. Also, “hsa-mir-663b” (miRBase Accession No. MI0006336, SEQ ID NO: 253) having a hairpin-like structure is known as a precursor of “hsa-miR-663b”.

The term “hsa-miR-3940-5p gene” or “hsa-miR-3940-5p” used herein includes the hsa-miR-3940-5p gene (miRBase Accession No. MIMAT0019229) described in SEQ ID NO: 103, a homolog or an ortholog of a different organism species, and the like. The hsa-miR-3940-5p gene can be obtained by a method described in Liao J Y et al., 2010, PLoS One, Vol. 5, e10563. Also, “hsa-mir-3940” (miRBase Accession No. MI0016597, SEQ ID NO: 254) having a hairpin-like structure is known as a precursor of “hsa-miR-3940-5p”.

The term “hsa-miR-4467 gene” or “hsa-miR-4467” used herein includes the hsa-miR-4467 gene (miRBase Accession No. MIMAT0018994) described in SEQ ID NO: 104, a homolog or an ortholog of a different organism species, and the like. The hsa-miR-4467 gene can be obtained by a method described in Jima D D et al., 2010, Blood, Vol. 116, e118-e127. Also, “hsa-mir-4467” (miRBase Accession No. MI0016818, SEQ ID NO: 255) having a hairpin-like structure is known as a precursor of “hsa-miR-4467”.

The term “hsa-miR-6858-5p gene” or “hsa-miR-6858-5p” used herein includes the hsa-miR-6858-5p gene (miRBase Accession No. MIMAT0027616) described in SEQ ID NO: 105, a homolog or an ortholog of a different organism species, and the like. The hsa-miR-6858-5p gene can be obtained by a method described in Ladewig E et al., 2012, Genome Res, Vol. 22, p. 1634-1645. Also, “hsa-mir-6858” (miRBase Accession No. MI0022704, SEQ ID NO: 256) having a hairpin-like structure is known as a precursor of “hsa-miR-6858-5p”.

The term “hsa-miR-4417 gene” or “hsa-miR-4417” used herein includes the hsa-miR-4417 gene (miRBase Accession No. MIMAT0018929) described in SEQ ID NO: 106, a homolog or an ortholog of a different organism species, and the like. The hsa-miR-4417 gene can be obtained by a method described in Jima D D et al., 2010, Blood. Vol. 116, e118-e127. Also, “hsa-mir-4417” (miRBase Accession No. MI0016753, SEQ ID NO: 257) having a hairpin-like structure is known as a precursor of “hsa-miR-4417”.

The term “hsa-miR-3665 gene” or “hsa-miR-3665” used herein includes the hsa-miR-3665 gene (miRBase Accession No. MIMAT0018087) described in SEQ ID NO: 107, a homolog or an ortholog of a different organism species, and the like. The hsa-miR-3665 gene can be obtained by a method described in Xie X et al., 2005, Nature, Vol. 434, p. 338-345. Also, “hsa-mir-3665” (miRBase Accession No. MI0016066, SEQ ID NO: 258) having a hairpin-like structure is known as a precursor of “hsa-miR-3665”.

The term “hsa-miR-4736 gene” or “hsa-miR-4736” used herein includes the hsa-miR-4736 gene (miRBase Accession No. MIMAT0019862) described in SEQ ID NO: 108, a homolog or an ortholog of a different organism species, and the like. The hsa-miR-4736 gene can be obtained by a method described in Persson H et al., 2011, Cancer Res, Vol. 71, p. 78-86. Also, “hsa-mir-4736” (miRBase Accession No. MI0017373, SEQ ID NO: 259) having a hairpin-like structure is known as a precursor of “hsa-miR-4736”.

The term “hsa-miR-4687-3p gene” or “hsa-miR-4687-3p” used herein includes the hsa-miR-4687-3p gene (miRBase Accession No. MIMAT0019775) described in SEQ ID NO: 109, a homolog or an ortholog of a different organism species, and the like. The hsa-miR-4687-3p gene can be obtained by a method described in Persson H et al., 2011, Cancer Res, Vol. 71, p. 78-86. Also, “hsa-mir-4687” (miRBase Accession No. MI0017319, SEQ ID NO: 260) having a hairpin-like structure is known as a precursor of “hsa-miR-4687-3p”.

The term “hsa-miR-1908-5p gene” or “hsa-miR-1908-5p” used herein includes the hsa-miR-1908-5p gene (miRBase Accession No. MIMAT0007881) described in SEQ ID NO: 110, a homolog or an ortholog of a different organism species, and the like. The hsa-miR-1908-5p gene can be obtained by a method described in Bar M et al., 2008, Stem Cells, Vol. 26, p. 2496-2505. Also, “hsa-mir-1908” (miRBase Accession No. MI0008329, SEQ ID NO: 212) having a hairpin-like structure is known as a precursor of “hsa-miR-1908-5p”.

The term “hsa-miR-5195-3p gene” or “hsa-miR-5195-3p” used herein includes the hsa-miR-5195-3p gene (miRBase Accession No. MIMAT0021127) described in SEQ ID NO: 111, a homolog or an ortholog of a different organism species, and the like. The hsa-miR-5195-3p gene can be obtained by a method described in Schotte D et al., 2011, Leukemia, Vol. 25, p. 1389-1399. Also, “hsa-mir-5195” (miRBase Accession No. MI0018174, SEQ ID NO: 261) having a hairpin-like structure is known as a precursor of “hsa-miR-5195-3p”.

The term “hsa-miR-4286 gene” or “hsa-miR-4286” used herein includes the hsa-miR-4286 gene (miRBase Accession No. MIMAT0016916) described in SEQ ID NO: 112, a homolog or an ortholog of a different organism species, and the like. The hsa-miR-4286 gene can be obtained by a method described in Goff L A et al., 2009, PLoS One, Vol. 4, e7192. Also, “hsa-mir-4286” (miRBase Accession No. MI0015894, SEQ ID NO: 262) having a hairpin-like structure is known as a precursor of “hsa-miR-4286”.

The term “hsa-miR-3679-3p gene” or “hsa-miR-3679-3p” used herein includes the hsa-miR-3679-3p gene (miRBase Accession No. MIMAT0018105) described in SEQ ID NO: 113, a homolog or an ortholog of a different organism species, and the like. The hsa-miR-3679-3p gene can be obtained by a method described in Creighton C J et al., 2010, PLoS One, Vol. 5, e9637. Also, “hsa-mir-3679” (miRBase Accession No. MI0016080, SEQ ID NO: 263) having a hairpin-like structure is known as a precursor of “hsa-miR-3679-3p”.

The term “hsa-miR-6791-5p gene” or “hsa-miR-6791-5p” used herein includes the hsa-miR-6791-5p gene (miRBase Accession No. MIMAT0027482) described in SEQ ID NO: 114, a homolog or an ortholog of a different organism species, and the like. The hsa-miR-6791-5p gene can be obtained by a method described in Ladewig E et al., 2012, Genome Res, Vol. 22, p. 1634-1645. Also, “hsa-mir-6791” (miRBase Accession No. MI0022636, SEQ ID NO: 264) having a hairpin-like structure is known as a precursor of “hsa-miR-6791-5p”.

The term “hsa-miR-1202 gene” or “hsa-miR-1202” used herein includes the hsa-miR-1202 gene (miRBase Accession No. MIMAT0005865) described in SEQ ID NO: 115, a homolog or an ortholog of a different organism species, and the like. The hsa-miR-1202 gene can be obtained by a method described in Marton S et al., 2008, Leukemia, Vol. 22, p. 330-338. Also, “hsa-mir-1202” (miRBase Accession No. MI0006334, SEQ ID NO: 265) having a hairpin-like structure is known as a precursor of “hsa-miR-1202”.

The term “hsa-miR-3656 gene” or “hsa-miR-3656” used herein includes the hsa-miR-3656 gene (miRBase Accession No. MIMAT0018076) described in SEQ ID NO: 116, a homolog or an ortholog of a different organism species, and the like. The hsa-miR-3656 gene can be obtained by a method described in Meiri E et al., 2010, Nucleic Acids Res, Vol. 38, p. 6234-6246. Also, “hsa-mir-3656” (miRBase Accession No. MI0016056, SEQ ID NO: 266) having a hairpin-like structure is known as a precursor of “hsa-miR-3656”.

The term “hsa-miR-4746-3p gene” or “hsa-miR-4746-3p” used herein includes the hsa-miR-4746-3p gene (miRBase Accession No. MIMAT0019881) described in SEQ ID NO: 117, a homolog or an ortholog of a different organism species, and the like. The hsa-miR-4746-3p gene can be obtained by a method described in Persson H et al., 2011, Cancer Res, Vol. 71, p. 78-86. Also, “hsa-mir-4746” (miRBase Accession No. MI0017385, SEQ ID NO: 267) having a hairpin-like structure is known as a precursor of “hsa-miR-4746-3p”.

The term “hsa-miR-3184-5p gene” or “hsa-miR-3184-5p” used herein includes the hsa-miR-3184-5p gene (miRBase Accession No. MIMAT0015064) described in SEQ ID NO: 118, a homolog or an ortholog of a different organism species, and the like. The hsa-miR-3184-5p gene can be obtained by a method described in Stark M S et al., 2010, PLoS One, Vol. 5, e9685. Also, “hsa-mir-3184” (miRBase Accession No. MI0014226, SEQ ID NO: 268) having a hairpin-like structure is known as a precursor of “hsa-miR-3184-5p”.

The term “hsa-miR-3937 gene” or “hsa-miR-3937” used herein includes the hsa-miR-3937 gene (miRBase Accession No. MIMAT0018352) described in SEQ ID NO: 119, a homolog or an ortholog of a different organism species, and the like. The hsa-miR-3937 gene can be obtained by a method described in Liao J Y et al., 2010, PLoS One, Vol. 5, e10563. Also, “hsa-mir-3937” (miRBase Accession No. MI0016593, SEQ ID NO: 269) having a hairpin-like structure is known as a precursor of “hsa-miR-3937”.

The term “hsa-miR-6515-3p gene” or “hsa-miR-6515-3p” used herein includes the hsa-miR-6515-3p gene (miRBase Accession No. MIMAT0025487) described in SEQ ID NO: 120, a homolog or an ortholog of a different organism species, and the like. The hsa-miR-6515-3p gene can be obtained by a method described in Joyce C E et al., 2011, Hum Mol Genet, Vol. 20, p. 4025-4040. Also, “hsa-mir-6515” (miRBase Accession No. MI0022227, SEQ ID NO: 270) having a hairpin-like structure is known as a precursor of “hsa-miR-6515-3p”.

The term “hsa-miR-6132 gene” or “hsa-miR-6132” used herein includes the hsa-miR-6132 gene (miRBase Accession No. MIMAT0024616) described in SEQ ID NO: 121, a homolog or an ortholog of a different organism species, and the like. The hsa-miR-6132 gene can be obtained by a method described in Dannemann M et al., 2012, Genome Biol Evol, Vol. 4, p. 552-564. Also, “hsa-mir-6132” (miRBase Accession No. MI0021277. SEQ ID NO: 271) having a hairpin-like structure is known as a precursor of “hsa-miR-6132”.

The term “hsa-miR-187-5p gene” or “hsa-miR-187-5p” used herein includes the hsa-miR-187-5p gene (miRBase Accession No. MIMAT0004561) described in SEQ ID NO: 122, a homolog or an ortholog of a different organism species, and the like. The hsa-miR-187-5p gene can be obtained by a method described in Lim L P et al., 2003, Science, Vol. 299, p. 1540. Also, “hsa-mir-187” (miRBase Accession No. MI0000274, SEQ ID NO: 272) having a hairpin-like structure is known as a precursor of “hsa-miR-187-5p”.

The term “hsa-miR-7111-5p gene” or “hsa-miR-7111-5p” used herein includes the hsa-miR-7111-5p gene (miRBase Accession No. MIMAT0028119) described in SEQ ID NO: 123, a homolog or an ortholog of a different organism species, and the like. The hsa-miR-7111-5p gene can be obtained by a method described in Ladewig E et al., 2012, Genome Res, Vol. 22, p. 1634-1645. Also, “hsa-mir-7111” (miRBase Accession No. MI0022962, SEQ ID NO: 273) having a hairpin-like structure is known as a precursor of “hsa-miR-711-5p”.

The term “hsa-miR-5787 gene” or “hsa-miR-5787” used herein includes the hsa-miR-5787 gene (miRBase Accession No. MIMAT0023252) described in SEQ ID NO: 124, a homolog or an ortholog of a different organism species, and the like. The hsa-miR-5787 gene can be obtained by a method described in Yoo H et al., 2011, Biochem Biophys Res Commun, Vol. 415, p. 567-572. Also, “hsa-mir-5787” (miRBase Accession No. MI0019797, SEQ ID NO: 274) having a hairpin-like structure is known as a precursor of “hsa-miR-5787”.

The term “hsa-miR-6779-5p gene” or “hsa-miR-6779-5p” used herein includes the hsa-miR-6779-5p gene (miRBase Accession No. MIMAT0027458) described in SEQ ID NO: 125, a homolog or an ortholog of a different organism species, and the like. The hsa-miR-6779-5p gene can be obtained by a method described in Ladewig E et al., 2012, Genome Res, Vol. 22, p. 1634-1645. Also, “hsa-mir-6779” (miRBase Accession No. MI0022624, SEQ ID NO: 275) having a hairpin-like structure is known as a precursor of “hsa-miR-6779-5p”.

The term “hsa-miR-6808-5p gene” or “hsa-miR-6808-5p” used herein includes the hsa-miR-6808-5p gene (miRBase Accession No. MIMAT0027516) described in SEQ ID NO: 126, a homolog or an ortholog of a different organism species, and the like. The hsa-miR-6808-5p gene can be obtained by a method described in Ladewig E et al., 2012, Genome Res, Vol. 22, p. 1634-1645. Also, “hsa-mir-6808” (miRBase Accession No. MI0022653, SEQ ID NO: 276) having a hairpin-like structure is known as a precursor of “hsa-miR-6808-5p”.

The term “hsa-miR-6774-5p gene” or “hsa-miR-6774-5p” used herein includes the hsa-miR-6774-5p gene (miRBase Accession No. MIMAT0027448) described in SEQ ID NO: 127, a homolog or an ortholog of a different organism species, and the like. The hsa-miR-6774-5p gene can be obtained by a method described in Ladewig E et al., 2012, Genome Res, Vol. 22, p. 1634-1645. Also, “hsa-mir-6774” (miRBase Accession No. MI0022619, SEQ ID NO: 277) having a hairpin-like structure is known as a precursor of “hsa-miR-6774-5p”.

The term “hsa-miR-4656 gene” or “hsa-miR-4656” used herein includes the hsa-miR-4656 gene (miRBase Accession No. MIMAT0019723) described in SEQ ID NO: 128, a homolog or an ortholog of a different organism species, and the like. The hsa-miR-4656 gene can be obtained by a method described in Persson H et al., 2011, Cancer Res, Vol. 71, p. 78-86. Also, “hsa-mir-4656” (miRBase Accession No. MI0017284, SEQ ID NO: 278) having a hairpin-like structure is known as a precursor of “hsa-miR-4656”.

The term “hsa-miR-6806-5p gene” or “hsa-miR-6806-5p” used herein includes the hsa-miR-6806-5p gene (miRBase Accession No. MIMAT0027512) described in SEQ ID NO: 129, a homolog or an ortholog of a different organism species, and the like. The hsa-miR-6806-5p gene can be obtained by a method described in Ladewig E et al., 2012, Genome Res, Vol. 22, p. 1634-1645. Also, "hsa-mir-6806" (miRBase Accession No. MI0022651, SEQ ID NO: 279) having a hairpin-like structure is known as a precursor of "hsa-miR-6806-5p".

The term "hsa-miR-1233-5p gene" or "hsa-miR-1233-5p" used herein includes the hsa-miR-1233-5p gene (miRBase Accession No. MIMAT0022943) described in SEQ ID NO: 130, a homolog or an ortholog of a different organism species, and the like. The hsa-miR-1233-5p gene can be obtained by a method described in Berezikov E et al., 2007. Mol Cell, Vol. 28, p. 328-336. Also, "hsa-mir-1233-1" and "hsa-mir-1233-2" (miRBase Accession Nos. MI0006323 and M10015973, SEQ ID NOs: 280 and 281) having a hairpin-like structure are known as precursors of "hsa-miR-1233-5p".

The term "hsa-miR-328-5p gene" or "hsa-miR-328-5p" used herein includes the hsa-miR-328-5p gene (miRBase Accession No. MIMAT0026486) described in SEQ ID NO: 131, a homolog or an ortholog of a different organism species, and the like. The hsa-miR-328-5p gene can be obtained by a method described in Kim J et al., 2004, Proc Natl Acad Sci USA, Vol. 101, p. 360-365. Also, "hsa-mir-328" (miRBase Accession No. MI0000804, SEQ ID NO: 282) having a hairpin-like structure is known as a precursor of "hsa-miR-328-5p".

The term "hsa-miR-4674 gene" or "hsa-miR-4674" used herein includes the hsa-miR-4674 gene (miRBase Accession No. MIMAT0019756) described in SEQ ID NO: 132, a homolog or an ortholog of a different organism species, and the like. The hsa-miR-4674 gene can be obtained by a method described in Persson H et al., 2011, Cancer Res, Vol. 71, p. 78-86. Also, "hsa-mir-4674" (miRBase Accession No. MI0017305, SEQ ID NO: 283) having a hairpin-like structure is known as a precursor of "hsa-miR-4674".

The term "hsa-miR-2110 gene" or "hsa-miR-2110" used herein includes the hsa-miR-2110 gene (miRBase Accession No. MIMAT0010133) described in SEQ ID NO: 133, a homolog or an ortholog of a different organism species, and the like. The hsa-miR-2110 gene can be obtained by a method described in Zhu J Y et al., 2009, J Virol, Vol. 83, p. 3333-3341. Also, "hsa-mir-2110" (miRBase Accession No. MI0010629, SEQ ID NO: 284) having a hairpin-like structure is known as a precursor of "hsa-miR-2110".

The term "hsa-miR-6076 gene" or "hsa-miR-6076" used herein includes the hsa-miR-6076 gene (miRBase Accession No. MIMAT0023701) described in SEQ ID NO: 134, a homolog or an ortholog of a different organism species, and the like. The hsa-miR-6076 gene can be obtained by a method described in Voellenkle C et al., 2012, RNA, Vol. 18, p. 472-484. Also, "hsa-mir-6076" (miRBase Accession No. MI0020353, SEQ ID NO: 285) having a hairpin-like structure is known as a precursor of "hsa-miR-6076".

The term "hsa-miR-3619-3p gene" or "hsa-miR-3619-3p" used herein includes the hsa-miR-3619-3p gene (miRBase Accession No. MIMAT0019219) described in SEQ ID NO: 135, a homolog or an ortholog of a different organism species, and the like. The hsa-miR-3619-3p gene can be obtained by a method described in Witten D et al., 2010, BMC Biol, Vol. 8, p. 58. Also, "hsa-mir-3619" (miRBase Accession No. MI0016009, SEQ ID NO: 286) having a hairpin-like structure is known as a precursor of "hsa-miR-3619-3p".

The term "hsa-miR-92a-2-5p gene" or "hsa-miR-92a-2-5p" used herein includes the hsa-miR-92a-2-5p gene (miRBase Accession No. MIMAT0004508) described in SEQ ID NO: 136, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094. SEQ ID NO: 287) having a hairpin-like structure is known as a precursor of "hsa-miR-92a-2-5p".

The term "hsa-miR-128-1-5p gene" or "hsa-miR-128-1-5p" used herein includes the hsa-miR-128-1-5p gene (miRBase Accession No. MIMAT0026477) described in SEQ ID NO: 137, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. MI0000447. SEQ ID NO: 288) having a hairpin-like structure is known as a precursor of "hsa-miR-128-1-5p".

The term "hsa-miR-638 gene" or "hsa-miR-638" used herein includes the hsa-miR-638 gene (miRBase Accession No. MIMAT0003308) described in SEQ ID NO: 138, a homolog or an ortholog of a different organism species, and the like. The hsa-miR-638 gene can be obtained by a method described in Cummins J M et al., 2006, Proc Natl Acad Sci USA, Vol. 103, p. 3687-3692. Also, "hsa-mir-638" (miRBase Accession No. MI0003653, SEQ ID NO: 289) having a hairpin-like structure is known as a precursor of "hsa-miR-638".

The term "hsa-miR-2861 gene" or "hsa-miR-2861" used herein includes the hsa-miR-2861 gene (miRBase Accession No. MIMAT0013802) described in SEQ ID NO: 139, a homolog or an ortholog of a different organism species, and the like. The hsa-miR-2861 gene can be obtained by a method described in Li H et al., 2009, J Clin Invest, Vol. 119, p. 3666-3677. Also, "hsa-mir-2861" (miRBase Accession No. MI0013006, SEQ ID NO: 290) having a hairpin-like structure is known as a precursor of "hsa-miR-2861".

The term "hsa-miR-371a-5p gene" or "hsa-miR-371a-5p" used herein includes the hsa-miR-371a-5p gene (miRBase Accession No. MIMAT0004687) described in SEQ ID NO: 140, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 291) having a hairpin-like structure is known as a precursor of "hsa-miR-371a-5p".

The term "hsa-miR-211-3p gene" or "hsa-miR-211-3p" used herein includes the hsa-miR-211-3p gene (miRBase Accession No. MIMAT0022694) described in SEQ ID NO: 141, a homolog or an ortholog of a different organism species, and the like. The hsa-miR-211-3p gene can be obtained by a method described in Lim L P et al., 2003, Science, Vol. 299, p. 1540. Also, "hsa-mir-211" (miRBase Accession No. MI0000287. SEQ ID NO: 292) having a hairpin-like structure is known as a precursor of "hsa-miR-211-3p".

The term "hsa-miR-1273g-3p gene" or "hsa-miR-1273g-3p" used herein includes the hsa-miR-1273g-3p gene (miRBase Accession No. MIMAT0022742) described in SEQ ID NO: 142, a homolog or an ortholog of a different organism species, and the like. The hsa-miR-1273g-3p gene can be obtained by a method described in Reshmi G et al., 2011, Genomics, Vol. 97, p. 333-340. Also, "hsa-mir-1273g"

(miRBase Accession No. MI0018003, SEQ ID NO: 293) having a hairpin-like structure is known as a precursor of "hsa-miR-1273g-3p".

The term "hsa-miR-1203 gene" or "hsa-miR-1203" used herein includes the hsa-miR-1203 gene (miRBase Accession No. MIMAT0005866) described in SEQ ID NO: 143, a homolog or an ortholog of a different organism species, and the like. The hsa-miR-1203 gene can be obtained by a method described in Marton S et al., 2008, Leukemia, Vol. 22, p. 330-338. Also, "hsa-mir-1203" (miRBase Accession No. MI0006335, SEQ ID NO: 294) having a hairpin-like structure is known as a precursor of "hsa-miR-1203".

The term "hsa-miR-122-5p gene" or "hsa-miR-122-5p" used herein includes the hsa-miR-122-5p gene (miRBase Accession No. MIMAT0000421) described in SEQ ID NO: 144, a homolog or an ortholog of a different organism species, and the like. The hsa-miR-122-5p gene can be obtained by a method described in Lagos-Quintana M et al., 2002, Curr Biol, Vol. 12, p. 735-739. Also, "hsa-mir-122" (miRBase Accession No. MI00000442, SEQ ID NO: 295) having a hairpin-like structure is known as a precursor of "hsa-miR-122-5p".

The term "hsa-miR-4258 gene" or "hsa-miR-4258" used herein includes the hsa-miR-4258 gene (miRBase Accession No. MIMAT0016879) described in SEQ ID NO: 145, a homolog or an ortholog of a different organism species, and the like. The hsa-miR-4258 gene can be obtained by a method described in Goff L A et al., 2009, PLoS One, Vol. 4, e7192. Also, "hsa-mir-4258" (miRBase Accession No. MI0015857, SEQ ID NO: 296) having a hairpin-like structure is known as a precursor of "hsa-miR-4258".

The term "hsa-miR-4484 gene" or "hsa-miR-4484" used herein includes the hsa-miR-4484 gene (miRBase Accession No. MIMAT0019018) described in SEQ ID NO: 146, a homolog or an ortholog of a different organism species, and the like. The hsa-miR-4484 gene can be obtained by a method described in Jima D D et al., 2010, Blood. Vol. 116, e118-e127. Also, "hsa-mir-4484" (miRBase Accession No. MI0016845, SEQ ID NO: 297) having a hairpin-like structure is known as a precursor of "hsa-miR-4484".

The term "hsa-miR-4648 gene" or "hsa-miR-4648" used herein includes the hsa-miR-4648 gene (miRBase Accession No. MIMAT0019710) described in SEQ ID NO: 147, a homolog or an ortholog of a different organism species, and the like. The hsa-miR-4648 gene can be obtained by a method described in Persson H et al., 2011, Cancer Res, Vol. 71, p. 78-86. Also, "hsa-mir-4648" (miRBase Accession No. MI0017275, SEQ ID NO: 298) having a hairpin-like structure is known as a precursor of "hsa-miR-4648".

The term "hsa-miR-6780b-5p gene" or "hsa-miR-6780b-5p" used herein includes the hsa-miR-6780b-5p gene (miRBase Accession No. MIMAT0027572) described in SEQ ID NO: 148, a homolog or an ortholog of a different organism species, and the like. The hsa-miR-6780b-5p gene can be obtained by a method described in Ladewig E et al., 2012. Genome Res, Vol. 22, p. 1634-1645. Also, "hsa-mir-6780b" (miRBase Accession No. MI0022681, SEQ ID NO: 299) having a hairpin-like structure is known as a precursor of "hsa-miR-6780b-5p".

The term "hsa-miR-4516 gene" or "hsa-miR-4516" used herein includes the hsa-miR-4516 gene (miRBase Accession No. MIMAT0019053) described in SEQ ID NO: 466, a homolog or an ortholog of a different organism species, and the like. The hsa-miR-4516 gene can be obtained by a method described in Jima D D et al., 2010, Blood., Vol. 116, p. e118-e127. Also, "hsa-mir-4516" (miRBase Accession No. MI0016882, SEQ ID NO: 479) having a hairpin-like structure is known as a precursor of "hsa-miR-4516".

The term "hsa-miR-4649-5p gene" or "hsa-miR-4649-5p" used herein includes the hsa-miR-4649-5p gene (miRBase Accession No. MIMAT0019711) described in SEQ ID NO: 467, a homolog or an ortholog of a different organism species, and the like. The hsa-miR-4649-5p gene can be obtained by a method described in Persson H et al., 2011, Cancer Res., Vol. 71, p. 78-86. Also, "hsa-mir-4649" (miRBase Accession No. MI0017276, SEQ ID NO: 480) having a hairpin-like structure is known as a precursor of "hsa-miR-4649-5p".

The term "hsa-miR-760 gene" or "hsa-miR-760" used herein includes the hsa-miR-760 gene (miRBase Accession No. MIMAT0004957) described in SEQ ID NO: 468, a homolog or an ortholog of a different organism species, and the like. The hsa-miR-760 gene can be obtained by a method described in Berezikov E et al., 2006, Genome Res., Vol. 16, p. 289-1298. Also, "hsa-mir-760" (miRBase Accession No. MI0005567, SEQ ID NO: 481) having a hairpin-like structure is known as a precursor of "hsa-miR-760".

The term "hsa-miR-3162-5p gene" or "hsa-miR-3162-5p" used herein includes the hsa-miR-3162-5p gene (miRBase Accession No. MIMAT0015036) described in SEQ ID NO: 469, a homolog or an ortholog of a different organism species, and the like. The hsa-miR-3162-5p gene can be obtained by a method described in Stark M S et al., 2010, PLoS One., Vol. 5, e9685. Also, "hsa-mir-3162" (miRBase Accession No. MI0014192, SEQ ID NO: 482) having a hairpin-like structure is known as a precursor of "hsa-miR-3162-5p".

The term "hsa-miR-3178 gene" or "hsa-miR-3178" used herein includes the hsa-miR-3178 gene (miRBase Accession No. MIMAT0015055) described in SEQ ID NO: 470, a homolog or an ortholog of a different organism species, and the like. The hsa-miR-3178 gene can be obtained by a method described in Stark M S et al., 2010, PLoS One., Vol. 5, e9685. Also, "hsa-mir-3178" (miRBase Accession No. MI0014212, SEQ ID NO: 483) having a hairpin-like structure is known as a precursor of "hsa-miR-3178".

The term "hsa-miR-940 gene" or "hsa-miR-940" used herein includes the hsa-miR-940 gene (miRBase Accession No. MIMAT0004983) described in SEQ ID NO: 471, a homolog or an ortholog of a different organism species, and the like. The hsa-miR-940 gene can be obtained by a method described in Lui W O et al., 2007, Cancer Res., Vol. 67, p. 6031-6043. Also, "hsa-mir-940" (miRBase Accession No. MI0005762, SEQ ID NO: 484) having a hairpin-like structure is known as a precursor of "hsa-miR-940".

The term "hsa-miR-4271 gene" or "hsa-miR-4271" used herein includes the hsa-miR-4271 gene (miRBase Accession No. MIMAT0016901) described in SEQ ID NO: 472, a homolog or an ortholog of a different organism species, and the like. The hsa-miR-4271 gene can be obtained by a method described in Goff L A et al., 2009, PLoS One., Vol. 4, e7192. Also, "hsa-mir-4271" (miRBase Accession No. MI0015879, SEQ ID NO: 485) having a hairpin-like structure is known as a precursor of "hsa-miR-4271".

The term "hsa-miR-6769b-5p gene" or "hsa-miR-6769b-5p" used herein includes the hsa-miR-6769b-5p gene (miRBase Accession No. MIMAT0027620) described in SEQ ID NO: 473, a homolog or an ortholog of a different organism species, and the like. The hsa-miR-6769b-5p gene can be obtained by a method described in Ladewig E et al., 2012, Genome Res., Vol. 22, p. 1634-1645. Also, "hsa-mir-6769b"

(miRBase Accession No. MI0022706, SEQ ID NO: 486) having a hairpin-like structure is known as a precursor of "hsa-miR-6769b-5p".

The term "hsa-miR-4508 gene" or "hsa-miR-4508" used herein includes the hsa-miR-4508 gene (miRBase Accession No. MIMAT0019045) described in SEQ ID NO: 474, a homolog or an ortholog of a different organism species, and the like. The hsa-miR-4508 gene can be obtained by a method described in Jima D D et al., 2010, Blood., Vol. 116, e118-e127. Also, "hsa-mir-4508" (miRBase Accession No. MI0016872, SEQ ID NO: 487) having a hairpin-like structure is known as a precursor of "hsa-miR-4508".

The term "hsa-miR-6826-5p gene" or "hsa-miR-6826-5p" used herein includes the hsa-miR-6826-5p gene (miRBase Accession No. MIMAT0027552) described in SEQ ID NO: 475, a homolog or an ortholog of a different organism species, and the like. The hsa-miR-6826-5p gene can be obtained by a method described in Ladewig E et al., 2012, Genome Res., Vol. 22, p. 1634-1645. Also, "hsa-mir-6826" (miRBase Accession No. MI0022671, SEQ ID NO: 488) having a hairpin-like structure is known as a precursor of "hsa-miR-6826-5p".

The term "hsa-miR-6757-5p gene" or "hsa-miR-6757-5p" used herein includes the hsa-miR-6757-5p gene (miRBase Accession No. MIMAT0027414) described in SEQ ID NO: 476, a homolog or an ortholog of a different organism species, and the like. The hsa-miR-6757-5p gene can be obtained by a method described in Ladewig E et al., 2012, Genome Res., Vol. 22, p. 1634-1645. Also, "hsa-mir-6757" (miRBase Accession No. MI0022602, SEQ ID NO: 489) having a hairpin-like structure is known as a precursor of "hsa-miR-6757-5p".

The term "hsa-miR-3131 gene" or "hsa-miR-3131" used herein includes the hsa-miR-3131 gene (miRBase Accession No. MIMAT0014996) described in SEQ ID NO: 477, a homolog or an ortholog of a different organism species, and the like. The hsa-miR-3131 gene can be obtained by a method described in Stark M S et al., 2010, PLoS One., Vol. 5, e9685. Also, "hsa-mir-3131" (miRBase Accession No. MI0014151, SEQ ID NO: 490) having a hairpin-like structure is known as a precursor of "hsa-miR-3131".

The term "hsa-miR-1343-3p gene" or "hsa-miR-1343-3p" used herein includes the hsa-miR-1343-3p gene (miRBase Accession No. MIMAT0019776) described in SEQ ID NO: 478, a homolog or an ortholog of a different organism species, and the like. The hsa-miR-1343-3p gene can be obtained by a method described in Persson H et al., 2011, Cancer Res., Vol. 71, p. 78-86. Also, "hsa-mir-1343" (miRBase Accession No. MI0017320, SEQ ID NO: 491) having a hairpin-like structure is known as a precursor of "hsa-miR-1343-3p".

A mature miRNA may become a variant due to the sequence cleaved shorter or longer by one to several flanking nucleotides, or nucleotide substitution, when cleaved as the mature miRNA from its RNA precursor which has a hairpin-like structure. This variant is called isomiR (Morin R D. et al., 2008, Genome Research, Vol. 18, p. 610-621). miRBase Release 20 shows the nucleotide sequences represented by SEQ ID NOs: 1 to 148 and 466 to 478 as well as a large number of the nucleotide sequence variants and fragments represented by SEQ ID NOs: 300 to 465 and 492 to 509, called isomiRs. These variants can also be obtained as miRNAs having a nucleotide sequence represented by any of SEQ ID NOs: 1 to 148 and 466 to 478.

Specifically, among the variants of polynucleotides that consist of a nucleotide sequence represented by any of SEQ ID NOs: 1, 3, 4, 6, 14, 16, 17, 18, 22, 23, 24, 25, 30, 31, 34, 35, 37, 42, 43, 44, 47, 48, 49, 50, 51, 52, 55, 57, 59, 61, 62, 66, 67, 69, 70, 72, 73, 75, 77, 79, 80, 82, 83, 84, 85, 86, 89, 90, 92, 94, 96, 99, 101, 102, 103, 104, 106, 107, 109, 110, 111, 112, 113, 115, 116, 120, 121, 122, 124, 130, 131, 132, 133, 136, 137, 138, 139, 140, 141, 142, 144, 146, 147, 466, 467, 468, 469, 470, 471, 474, 477, and 478, or a nucleotide sequence derived from the nucleotide sequence by the replacement of u with t according to the present invention, examples of the longest variants registered in miRBase Release 20 include polynucleotides represented by SEQ ID NOs: 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 492, 494, 496, 498, 500, 502, 504, 506, and 508, respectively.

Also, among the variants of polynucleotides consisting of a nucleotide sequence represented by any of SEQ ID NOs: 1, 3, 4, 6, 14, 16, 17, 18, 22, 23, 24, 25, 30, 31, 34, 35, 37, 42, 43, 44, 47, 48, 49, 50, 51, 52, 55, 57, 59, 61, 62, 66, 67, 69, 70, 72, 73, 75, 77, 79, 80, 82, 83, 84, 85, 86, 89, 90, 92, 94, 96, 99, 101, 102, 103, 104, 106, 107, 109, 110, 111, 112, 113, 115, 116, 120, 121, 122, 124, 130, 131, 132, 133, 136, 137, 138, 139, 140, 141, 142, 144, 146, 147, 466, 467, 468, 469, 470, 471, 474, 477, and 478, or a nucleotide sequence derived from the nucleotide sequence by the replacement of u with t according to the present invention, examples of the shortest variants registered in miRBase Release 20 include polynucleotides having sequences represented by SEQ ID NOs: 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 493, 495, 497, 499, 501, 503, 505, 507, and 509, respectively. In addition to these variants and fragments, examples thereof include a large number of isomiR polynucleotides of SEQ ID NOs: 1, 3, 4, 6, 14, 16, 17, 18, 22, 23, 24, 25, 30, 31, 34, 35, 37, 42, 43, 44, 47, 48, 49, 50, 51, 52, 55, 57, 59, 61, 62, 66, 67, 69, 70, 72, 73, 75, 77, 79, 80, 82, 83, 84, 85, 86, 89, 90, 92, 94, 96, 99, 101, 102, 103, 104, 106, 107, 109, 110, 111, 112, 113, 115, 116, 120, 121, 122, 124, 130, 131, 132, 133, 136, 137, 138, 139, 140, 141, 142, 144, 146 and 147 registered in miRBase, Examples of the polynucleotide comprising a nucleotide sequence represented by any of SEQ ID NOs: 1 to 148, 466 to 478 include a polynucleotide represented by any of SEQ ID NOs: 149 to 299, 479 to 491, which are their respective precursors.

The names and miRBase Accession Nos. (registration numbers) of the genes represented by SEQ ID NOs: 1 to 509 are shown in Table 1.

As used herein, the term "capable of specifically binding" means that the nucleic acid probe or the primer used in the present invention binds to a particular target nucleic acid and cannot substantially bind to other nucleic acids.

TABLE 1

| SEQ ID NO: | Gene name | miRBase registration No. |
|---|---|---|
| 1 | hsa-miR-125a-3p | MIMAT0004602 |
| 2 | hsa-miR-6893-5p | MIMAT0027686 |
| 3 | hsa-miR-204-3p | MIMAT0022693 |

TABLE 1-continued

| SEQ ID NO: | Gene name | miRBase registration No. |
|---|---|---|
| 4 | hsa-miR-4476 | MIMAT0019003 |
| 5 | hsa-miR-4294 | MIMAT0016849 |
| 6 | hsa-miR-150-3p | MIMAT0004610 |
| 7 | hsa-miR-6729-5p | MIMAT0027359 |
| 8 | hsa-miR-7641 | MIMAT0029782 |
| 9 | hsa-miR-6765-3p | MIMAT0027431 |
| 10 | hsa-miR-6820-5p | MIMAT0027540 |
| 11 | hsa-miR-575 | MIMAT0003240 |
| 12 | hsa-miR-6836-3p | MIMAT0027575 |
| 13 | hsa-miR-1469 | MIMAT0007347 |
| 14 | hsa-miR-663a | MIMAT0003326 |
| 15 | hsa-miR-6075 | MIMAT0023700 |
| 16 | hsa-miR-4634 | MIMAT0019691 |
| 17 | hsa-miR-423-5p | MIMAT0004748 |
| 18 | hsa-miR-4454 | MIMAT0018976 |
| 19 | hsa-miR-7109-5p | MIMAT0028115 |
| 20 | hsa-miR-6789-5p | MIMAT0027478 |
| 21 | hsa-miR-6877-5p | MIMAT0027654 |
| 22 | hsa-miR-4792 | MIMAT0019964 |
| 23 | hsa-miR-4530 | MIMAT0019069 |
| 24 | hsa-miR-7975 | MIMAT0031178 |
| 25 | hsa-miR-6724-5p | MIMAT0025856 |
| 26 | hsa-miR-8073 | MIMAT0031000 |
| 27 | hsa-miR-7977 | MIMAT0031180 |
| 28 | hsa-miR-1231 | MIMAT0005586 |
| 29 | hsa-miR-6799-5p | MIMAT0027498 |
| 30 | hsa-miR-615-5p | MIMAT0004804 |
| 31 | hsa-miR-4450 | MIMAT0018971 |
| 32 | hsa-miR-6726-5p | MIMAT0027353 |
| 33 | hsa-miR-6875-5p | MIMAT0027650 |
| 34 | hsa-miR-4734 | MIMAT0019859 |
| 35 | hsa-miR-16-5p | MIMAT0000069 |
| 36 | hsa-miR-602 | MIMAT0003270 |
| 37 | hsa-miR-4651 | MIMAT0019715 |
| 38 | hsa-miR-8069 | MIMAT0030996 |
| 39 | hsa-miR-1238-5p | MIMAT0022947 |
| 40 | hsa-miR-6880-5p | MIMAT0027660 |
| 41 | hsa-miR-8072 | MIMAT0030999 |
| 42 | hsa-miR-4723-5p | MIMAT0019838 |
| 43 | hsa-miR-4732-5p | MIMAT0019855 |
| 44 | hsa-miR-6125 | MIMAT0024598 |
| 45 | hsa-miR-6090 | MIMAT0023715 |
| 46 | hsa-miR-7114-5p | MIMAT0028125 |
| 47 | hsa-miR-564 | MIMAT0003228 |
| 48 | hsa-miR-451a | MIMAT0001631 |
| 49 | hsa-miR-3135b | MIMAT0018985 |
| 50 | hsa-miR-4497 | MIMAT0019032 |
| 51 | hsa-miR-4665-5p | MIMAT0019739 |
| 52 | hsa-miR-3622a-5p | MIMAT0018003 |
| 53 | hsa-miR-6850-5p | MIMAT0027600 |
| 54 | hsa-miR-6821-5p | MIMAT0027542 |
| 55 | hsa-miR-5100 | MIMAT0022259 |
| 56 | hsa-miR-6872-3p | MIMAT0027645 |
| 57 | hsa-miR-4433-3p | MIMAT0018949 |
| 58 | hsa-miR-1227-5p | MIMAT0022941 |
| 59 | hsa-miR-3188 | MIMAT0015070 |
| 60 | hsa-miR-7704 | MIMAT0030019 |
| 61 | hsa-miR-3185 | MIMAT0015065 |
| 62 | hsa-miR-1908-3p | MIMAT0026916 |
| 63 | hsa-miR-6781-5p | MIMAT0027462 |
| 64 | hsa-miR-6805-5p | MIMAT0027510 |
| 65 | hsa-miR-8089 | MIMAT0031016 |
| 66 | hsa-miR-665 | MIMAT0004952 |
| 67 | hsa-miR-4486 | MIMAT0019020 |
| 68 | hsa-miR-6722-3p | MIMAT0025854 |
| 69 | hsa-miR-1260a | MIMAT0005911 |
| 70 | hsa-miR-4707-5p | MIMAT0019807 |
| 71 | hsa-miR-6741-5p | MIMAT0027383 |
| 72 | hsa-miR-1260b | MIMAT0015041 |
| 73 | hsa-miR-1246 | MIMAT0005898 |
| 74 | hsa-miR-6845-5p | MIMAT0027590 |
| 75 | hsa-miR-4638-5p | MIMAT0019695 |
| 76 | hsa-miR-6085 | MIMAT0023710 |
| 77 | hsa-miR-1228-3p | MIMAT0005583 |
| 78 | hsa-miR-4534 | MIMAT0019073 |
| 79 | hsa-miR-5585-3p | MIMAT0022286 |
| 80 | hsa-miR-4741 | MIMAT0019871 |

TABLE 1-continued

| SEQ ID NO: | Gene name | miRBase registration No. |
|---|---|---|
| 81 | hsa-miR-4433b-3p | MIMAT0030414 |
| 82 | hsa-miR-197-5p | MIMAT0022691 |
| 83 | hsa-miR-718 | MIMAT0012735 |
| 84 | hsa-miR-4513 | MIMAT0019050 |
| 85 | hsa-miR-4446-3p | MIMAT0018965 |
| 86 | hsa-miR-619-5p | MIMAT0026622 |
| 87 | hsa-miR-6816-5p | MIMAT0027532 |
| 88 | hsa-miR-6778-5p | MIMAT0027456 |
| 89 | hsa-miR-24-3p | MIMAT0000080 |
| 90 | hsa-miR-1915-3p | MIMAT0007892 |
| 91 | hsa-miR-4665-3p | MIMAT0019740 |
| 92 | hsa-miR-4449 | MIMAT0018968 |
| 93 | hsa-miR-6889-5p | MIMAT0027678 |
| 94 | hsa-miR-486-3p | MIMAT0004762 |
| 95 | hsa-miR-7113-3p | MIMAT0028124 |
| 96 | hsa-miR-642a-3p | MIMAT0020924 |
| 97 | hsa-miR-7847-3p | MIMAT0030422 |
| 98 | hsa-miR-6768-5p | MIMAT0027436 |
| 99 | hsa-miR-1290 | MIMAT0005880 |
| 100 | hsa-miR-7108-5p | MIMAT0028113 |
| 101 | hsa-miR-92b-5p | MIMAT0004792 |
| 102 | hsa-miR-663b | MIMAT0005867 |
| 103 | hsa-miR-3940-5p | MIMAT0019229 |
| 104 | hsa-miR-4467 | MIMAT0018994 |
| 105 | hsa-miR-6858-5p | MIMAT0027616 |
| 106 | hsa-miR-4417 | MIMAT0018929 |
| 107 | hsa-miR-3665 | MIMAT0018087 |
| 108 | hsa-miR-4736 | MIMAT0019862 |
| 109 | hsa-miR-4687-3p | MIMAT0019775 |
| 110 | hsa-miR-1908-5p | MIMAT0007881 |
| 111 | hsa-miR-5195-3p | MIMAT0021127 |
| 112 | hsa-miR-4286 | MIMAT0016916 |
| 113 | hsa-miR-3679-3p | MIMAT0018105 |
| 114 | hsa-miR-6791-5p | MIMAT0027482 |
| 115 | hsa-miR-1202 | MIMAT0005865 |
| 116 | hsa-miR-3656 | MIMAT0018076 |
| 117 | hsa-miR-4746-3p | MIMAT0019881 |
| 118 | hsa-miR-3184-5p | MIMAT0015064 |
| 119 | hsa-miR-3937 | MIMAT0018352 |
| 120 | hsa-miR-6515-3p | MIMAT0025487 |
| 121 | hsa-miR-6132 | MIMAT0024616 |
| 122 | hsa-miR-187-5p | MIMAT0004561 |
| 123 | hsa-miR-7111-5p | MIMAT0028119 |
| 124 | hsa-miR-5787 | MIMAT0023252 |
| 125 | hsa-miR-6779-5p | MIMAT0027458 |
| 126 | hsa-miR-6808-5p | MIMAT0027516 |
| 127 | hsa-miR-6774-5p | MIMAT0027448 |
| 128 | hsa-miR-4656 | MIMAT0019723 |
| 129 | hsa-miR-6806-5p | MIMAT0027512 |
| 130 | hsa-miR-1233-5p | MIMAT0022943 |
| 131 | hsa-miR-328-5p | MIMAT0026486 |
| 132 | hsa-miR-4674 | MIMAT0019756 |
| 133 | hsa-miR-2110 | MIMAT0010133 |
| 134 | hsa-miR-6076 | MIMAT0023701 |
| 135 | hsa-miR-3619-3p | MIMAT0019219 |
| 136 | hsa-miR-92a-2-5p | MIMAT0004508 |
| 137 | hsa-miR-128-1-5p | MIMAT0026477 |
| 138 | hsa-miR-638 | MIMAT0003308 |
| 139 | hsa-miR-2861 | MIMAT0013802 |
| 140 | hsa-miR-371a-5p | MIMAT0004687 |
| 141 | hsa-miR-211-3p | MIMAT0022694 |
| 142 | hsa-miR-1273g-3p | MIMAT0022742 |
| 143 | hsa-miR-1203 | MIMAT0005866 |
| 144 | hsa-miR-122-5p | MIMAT0000421 |
| 145 | hsa-miR-4258 | MIMAT0016879 |
| 146 | hsa-miR-4484 | MIMAT0019018 |
| 147 | hsa-miR-4648 | MIMAT0019710 |
| 148 | hsa-miR-6780b-5p | MIMAT0027572 |
| 149 | hsa-mir-125a | MI0000469 |
| 150 | hsa-mir-6893 | MI0022740 |
| 151 | hsa-mir-204 | MI0000284 |
| 152 | hsa-mir-4476 | MI0016828 |
| 153 | hsa-mir-4294 | MI0015827 |
| 154 | hsa-mir-150 | MI0000479 |
| 155 | hsa-mir-6729 | MI0022574 |
| 156 | hsa-mir-7641-1 | MI0024975 |
| 157 | hsa-mir-7641-2 | MI0024976 |

TABLE 1-continued

| SEQ ID NO: | Gene name | miRBase registration No. |
|---|---|---|
| 158 | hsa-mir-6765 | MI0022610 |
| 159 | hsa-mir-6820 | MI0022665 |
| 160 | hsa-mir-575 | MI0003582 |
| 161 | hsa-mir-6836 | MI0022682 |
| 162 | hsa-mir-1469 | MI0007074 |
| 163 | hsa-mir-663a | MI0003672 |
| 164 | hsa-mir-6075 | MI0020352 |
| 165 | hsa-mir-4634 | MI0017261 |
| 166 | hsa-mir-423 | MI0001445 |
| 167 | hsa-mir-4454 | MI0016800 |
| 168 | hsa-mir-7109 | MI0022960 |
| 169 | hsa-mir-6789 | MI0022634 |
| 170 | hsa-mir-6877 | MI0022724 |
| 171 | hsa-mir-4792 | MI0017439 |
| 172 | hsa-mir-4530 | MI0016897 |
| 173 | hsa-mir-7975 | MI0025751 |
| 174 | hsa-mir-6724 | MI0022559 |
| 175 | hsa-mir-8073 | MI0025909 |
| 176 | hsa-mir-7977 | MI0025753 |
| 177 | hsa-mir-1231 | MI0006321 |
| 178 | hsa-mir-6799 | MI0022644 |
| 179 | hsa-mir-615 | MI0003628 |
| 180 | hsa-mir-4450 | MI0016795 |
| 181 | hsa-mir-6726 | MI0022571 |
| 182 | hsa-mir-6875 | MI0022722 |
| 183 | hsa-mir-4734 | MI0017371 |
| 184 | hsa-mir-16-1 | MI0000070 |
| 185 | hsa-mir-16-2 | MI0000115 |
| 186 | hsa-mir-602 | MI0003615 |
| 187 | hsa-mir-4651 | MI0017279 |
| 188 | hsa-mir-8069 | MI0025905 |
| 189 | hsa-mir-1238 | MI0006328 |
| 190 | hsa-mir-6880 | MI0022727 |
| 191 | hsa-mir-8072 | MI0025908 |
| 192 | hsa-mir-4723 | MI0017359 |
| 193 | hsa-mir-4732 | MI0017369 |
| 194 | hsa-mir-6125 | MI0021259 |
| 195 | hsa-mir-6090 | MI0020367 |
| 196 | hsa-mir-7114 | MI0022965 |
| 197 | hsa-mir-564 | MI0003570 |
| 198 | hsa-mir-451a | MI0001729 |
| 199 | hsa-mir-3135b | MI0016809 |
| 200 | hsa-mir-4497 | MI0016859 |
| 201 | hsa-mir-4665 | MI0017295 |
| 202 | hsa-mir-3622a | MI0016013 |
| 203 | hsa-mir-6850 | MI0022696 |
| 204 | hsa-mir-6821 | MI0022666 |
| 205 | hsa-mir-5100 | MI0019116 |
| 206 | hsa-mir-6872 | MI0022719 |
| 207 | hsa-mir-4433 | MI0016773 |
| 208 | hsa-mir-1227 | MI0006316 |
| 209 | hsa-mir-3188 | MI0014232 |
| 210 | hsa-mir-7704 | MI0025240 |
| 211 | hsa-mir-3185 | MI0014227 |
| 212 | hsa-mir-1908 | MI0008329 |
| 213 | hsa-mir-6781 | MI0022626 |
| 214 | hsa-mir-6805 | MI0022650 |
| 215 | hsa-mir-8089 | MI0025925 |
| 216 | hsa-mir-665 | MI0005563 |
| 217 | hsa-mir-4486 | MI0016847 |
| 218 | hsa-mir-6722 | MI0022557 |
| 219 | hsa-mir-1260a | MI0006394 |
| 220 | hsa-mir-4707 | MI0017340 |
| 221 | hsa-mir-6741 | MI0022586 |
| 222 | hsa-mir-1260b | MI0014197 |
| 223 | hsa-mir-1246 | MI0006381 |
| 224 | hsa-mir-6845 | MI0022691 |
| 225 | hsa-mir-4638 | MI0017265 |
| 226 | hsa-mir-6085 | MI0020362 |
| 227 | hsa-mir-1228 | MI0006318 |
| 228 | hsa-mir-4534 | MI0016901 |
| 229 | hsa-mir-5585 | MI0019142 |
| 230 | hsa-mir-4741 | MI0017379 |
| 231 | hsa-mir-4433b | MI0025511 |
| 232 | hsa-mir-197 | MI0000239 |
| 233 | hsa-mir-718 | MI0012489 |
| 234 | hsa-mir-4513 | MI0016879 |

TABLE 1-continued

| SEQ ID NO: | Gene name | miRBase registration No. |
|---|---|---|
| 235 | hsa-mir-4446 | MI0016789 |
| 236 | hsa-mir-619 | MI0003633 |
| 237 | hsa-mir-6816 | MI0022661 |
| 238 | hsa-mir-6778 | MI0022623 |
| 239 | hsa-mir-24-1 | MI0000080 |
| 240 | hsa-mir-24-2 | MI0000081 |
| 241 | hsa-mir-1915 | MI0008336 |
| 242 | hsa-mir-4449 | MI0016792 |
| 243 | hsa-mir-6889 | MI0022736 |
| 244 | hsa-mir-486 | MI0002470 |
| 245 | hsa-mir-486-2 | MI0023622 |
| 246 | hsa-mir-7113 | MI0022964 |
| 247 | hsa-mir-642a | MI0003657 |
| 248 | hsa-mir-7847 | MI0025517 |
| 249 | hsa-mir-6768 | MI0022613 |
| 250 | hsa-mir-1290 | MI0006352 |
| 251 | hsa-mir-7108 | MI0022959 |
| 252 | hsa-mir-92b | MI0003560 |
| 253 | hsa-mir-663b | MI0006336 |
| 254 | hsa-mir-3940 | MI0016597 |
| 255 | hsa-mir-4467 | MI0016818 |
| 256 | hsa-mir-6858 | MI0022704 |
| 257 | hsa-mir-4417 | MI0016753 |
| 258 | hsa-mir-3665 | MI0016066 |
| 259 | hsa-mir-4736 | MI0017373 |
| 260 | hsa-mir-4687 | MI0017319 |
| 261 | hsa-mir-5195 | MI0018174 |
| 262 | hsa-mir-4286 | MI0015894 |
| 263 | hsa-mir-3679 | MI0016080 |
| 264 | hsa-mir-6791 | MI0022636 |
| 265 | hsa-mir-1202 | MI0006334 |
| 266 | hsa-mir-3656 | MI0016056 |
| 267 | hsa-mir-4746 | MI0017385 |
| 268 | hsa-mir-3184 | MI0014226 |
| 269 | hsa-mir-3937 | MI0016593 |
| 270 | hsa-mir-6515 | MI0022227 |
| 271 | hsa-mir-6132 | MI0021277 |
| 272 | hsa-mir-187 | MI0000274 |
| 273 | hsa-mir-7111 | MI0022962 |
| 274 | hsa-mir-5787 | MI0019797 |
| 275 | hsa-mir-6779 | MI0022624 |
| 276 | hsa-mir-6808 | MI0022653 |
| 277 | hsa-mir-6774 | MI0022619 |
| 278 | hsa-mir-4656 | MI0017284 |
| 279 | hsa-mir-6806 | MI0022651 |
| 280 | hsa-mir-1233-1 | MI0006323 |
| 281 | hsa-mir-1233-2 | MI0015973 |
| 282 | hsa-mir-328 | MI0000804 |
| 283 | hsa-mir-4674 | MI0017305 |
| 284 | hsa-mir-2110 | MI0010629 |
| 285 | hsa-mir-6076 | MI0020353 |
| 286 | hsa-mir-3619 | MI0016009 |
| 287 | hsa-mir-92a-2 | MI0000094 |
| 288 | hsa-mir-128-1 | MI0000447 |
| 289 | hsa-mir-638 | MI0003653 |
| 290 | hsa-mir-2861 | MI0013006 |
| 291 | hsa-mir-371a | MI0000779 |
| 292 | hsa-mir-211 | MI0000287 |
| 293 | hsa-mir-1273g | MI0018003 |
| 294 | hsa-mir-1203 | MI0006335 |
| 295 | hsa-mir-122 | MI0000442 |
| 296 | hsa-mir-4258 | MI0015857 |
| 297 | hsa-mir-4484 | MI0016845 |
| 298 | hsa-mir-4648 | MI0017275 |
| 299 | hsa-mir-6780b | MI0022681 |
| 300 | isomiR example 1 of SEQ ID NO: 1 | — |
| 301 | isomiR example 2 of SEQ ID NO: 1 | — |
| 302 | isomiR example 1 of SEQ ID NO: 3 | — |
| 303 | isomiR example 2 of SEQ ID NO: 3 | — |
| 304 | isomiR example 1 of SEQ ID NO: 4 | — |
| 305 | isomiR example 2 of SEQ ID NO: 4 | — |

TABLE 1-continued

| SEQ ID NO: | Gene name | miRBase registration No. |
|---|---|---|
| 306 | isomiR example 1 of SEQ ID NO: 6 | — |
| 307 | isomiR example 2 of SEQ ID NO: 6 | — |
| 308 | isomiR example 1 of SEQ ID NO: 14 | — |
| 309 | isomiR example 2 of SEQ ID NO: 14 | — |
| 310 | isomiR example 1 of SEQ ID NO: 16 | — |
| 311 | isomiR example 2 of SEQ ID NO: 16 | — |
| 312 | isomiR example 1 of SEQ ID NO: 17 | — |
| 313 | isomiR example 2 of SEQ ID NO: 17 | — |
| 314 | isomiR example 1 of SEQ ID NO: 18 | — |
| 315 | isomiR example 2 of SEQ ID NO: 18 | — |
| 316 | isomiR example 1 of SEQ ID NO: 22 | — |
| 317 | isomiR example 2 of SEQ ID NO: 22 | — |
| 318 | isomiR example 1 of SEQ ID NO: 23 | — |
| 319 | isomiR example 2 of SEQ ID NO: 23 | — |
| 320 | isomiR example 1 of SEQ ID NO: 24 | — |
| 321 | isomiR example 2 of SEQ ID NO: 24 | — |
| 322 | isomiR example 1 of SEQ ID NO: 25 | — |
| 323 | isomiR example 2 of SEQ ID NO: 25 | — |
| 324 | isomiR example 1 of SEQ ID NO: 30 | — |
| 325 | isomiR example 2 of SEQ ID NO: 30 | — |
| 326 | isomiR example 1 of SEQ ID NO: 31 | — |
| 327 | isomiR example 2 of SEQ ID NO: 31 | — |
| 328 | isomiR example 1 of SEQ ID NO: 34 | — |
| 329 | isomiR example 2 of SEQ ID NO: 34 | — |
| 330 | isomiR example 1 of SEQ ID NO: 35 | — |
| 331 | isomiR example 2 of SEQ ID NO: 35 | — |
| 332 | isomiR example 1 of SEQ ID NO: 37 | — |
| 333 | isomiR example 2 of SEQ ID NO: 37 | — |
| 334 | isomiR example 1 of SEQ ID NO: 42 | — |
| 335 | isomiR example 2 of SEQ ID NO: 42 | — |
| 336 | isomiR example 1 of SEQ ID NO: 43 | — |
| 337 | isomiR example 2 of SEQ ID NO: 43 | — |
| 338 | isomiR example 1 of SEQ ID NO: 44 | — |
| 339 | isomiR example 2 of SEQ ID NO: 44 | — |
| 340 | isomiR example 1 of SEQ ID NO: 47 | — |
| 341 | isomiR example 2 of SEQ ID NO: 47 | — |
| 342 | isomiR example 1 of SEQ ID NO: 48 | — |
| 343 | isomiR example 2 of SEQ ID NO: 48 | — |

TABLE 1-continued

| SEQ ID NO: | Gene name | miRBase registration No. |
|---|---|---|
| 344 | isomiR example 1 of SEQ ID NO: 49 | — |
| 345 | isomiR example 2 of SEQ ID NO: 49 | — |
| 346 | isomiR example 1 of SEQ ID NO: 50 | — |
| 347 | isomiR example 2 of SEQ ID NO: 50 | — |
| 348 | isomiR example 1 of SEQ ID NO: 51 | — |
| 349 | isomiR example 2 of SEQ ID NO: 51 | — |
| 350 | isomiR example 1 of SEQ ID NO: 52 | — |
| 351 | isomiR example 2 of SEQ ID NO: 52 | — |
| 352 | isomiR example 1 of SEQ ID NO: 55 | — |
| 353 | isomiR example 2 of SEQ ID NO: 55 | — |
| 354 | isomiR example 1 of SEQ ID NO: 57 | — |
| 355 | isomiR example 2 of SEQ ID NO: 57 | — |
| 356 | isomiR example 1 of SEQ ID NO: 59 | — |
| 357 | isomiR example 2 of SEQ ID NO: 59 | — |
| 358 | isomiR example 1 of SEQ ID NO: 61 | — |
| 359 | isomiR example 2 of SEQ ID NO: 61 | — |
| 360 | isomiR example 1 of SEQ ID NO: 62 | — |
| 361 | isomiR example 2 of SEQ ID NO: 62 | — |
| 362 | isomiR example 1 of SEQ ID NO: 66 | — |
| 363 | isomiR example 2 of SEQ ID NO: 66 | — |
| 364 | isomiR example 1 of SEQ ID NO: 67 | — |
| 365 | isomiR example 2 of SEQ ID NO: 67 | — |
| 366 | isomiR example 1 of SEQ ID NO: 69 | — |
| 367 | isomiR example 2 of SEQ ID NO: 69 | — |
| 368 | isomiR example 1 of SEQ ID NO: 70 | — |
| 369 | isomiR example 2 of SEQ ID NO: 70 | — |
| 370 | isomiR example 1 of SEQ ID NO: 72 | — |
| 371 | isomiR example 2 of SEQ ID NO: 72 | — |
| 372 | isomiR example 1 of SEQ ID NO: 73 | — |
| 373 | isomiR example 2 of SEQ ID NO: 73 | — |
| 374 | isomiR example 1 of SEQ ID NO: 75 | — |
| 375 | isomiR example 2 of SEQ ID NO: 75 | — |
| 376 | isomiR example 1 of SEQ ID NO: 77 | — |
| 377 | isomiR example 2 of SEQ ID NO: 77 | — |
| 378 | isomiR example 1 of SEQ ID NO: 79 | — |
| 379 | isomiR example 2 of SEQ ID NO: 79 | — |
| 380 | isomiR example 1 of SEQ ID NO: 80 | — |
| 381 | isomiR example 2 of SEQ ID NO: 80 | — |

TABLE 1-continued

| SEQ ID NO: | Gene name | miRBase registration No. |
|---|---|---|
| 382 | isomiR example 1 of SEQ ID NO: 82 | — |
| 383 | isomiR example 2 of SEQ ID NO: 82 | — |
| 384 | isomiR example 1 of SEQ ID NO: 83 | — |
| 385 | isomiR example 2 of SEQ ID NO: 83 | — |
| 386 | isomiR example 1 of SEQ ID NO: 84 | — |
| 387 | isomiR example 2 of SEQ ID NO: 84 | — |
| 388 | isomiR example 1 of SEQ ID NO: 85 | — |
| 389 | isomiR example 2 of SEQ ID NO: 85 | — |
| 390 | isomiR example 1 of SEQ ID NO: 86 | — |
| 391 | isomiR example 2 of SEQ ID NO: 86 | — |
| 392 | isomiR example 1 of SEQ ID NO: 89 | — |
| 393 | isomiR example 2 of SEQ ID NO: 89 | — |
| 394 | isomiR example 1 of SEQ ID NO: 90 | — |
| 395 | isomiR example 2 of SEQ ID NO: 90 | — |
| 396 | isomiR example 1 of SEQ ID NO: 92 | — |
| 397 | isomiR example 2 of SEQ ID NO: 92 | — |
| 398 | isomiR example 1 of SEQ ID NO: 94 | — |
| 399 | isomiR example 2 of SEQ ID NO: 94 | — |
| 400 | isomiR example 1 of SEQ ID NO: 96 | — |
| 401 | isomiR example 2 of SEQ ID NO: 96 | — |
| 402 | isomiR example 1 of SEQ ID NO: 99 | — |
| 403 | isomiR example 2 of SEQ ID NO: 99 | — |
| 404 | isomiR example 1 of SEQ ID NO: 101 | — |
| 405 | isomiR example 2 of SEQ ID NO: 101 | — |
| 406 | isomiR example 1 of SEQ ID NO: 102 | — |
| 407 | isomiR example 2 of SEQ ID NO: 102 | — |
| 408 | isomiR example 1 of SEQ ID NO: 103 | — |
| 409 | isomiR example 2 of SEQ ID NO: 103 | — |
| 410 | isomiR example 1 of SEQ ID NO: 104 | — |
| 411 | isomiR example 2 of SEQ ID NO: 104 | — |
| 412 | isomiR example 1 of SEQ ID NO: 106 | — |
| 413 | isomiR example 2 of SEQ ID NO: 106 | — |
| 414 | isomiR example 1 of SEQ ID NO: 107 | — |
| 415 | isomiR example 2 of SEQ ID NO: 107 | — |
| 416 | isomiR example 1 of SEQ ID NO: 109 | — |
| 417 | isomiR example 2 of SEQ ID NO: 109 | — |
| 418 | isomiR example 1 of SEQ ID NO: 110 | — |
| 419 | isomiR example 2 of SEQ ID NO: 110 | — |

TABLE 1-continued

| SEQ ID NO: | Gene name | miRBase registration No. |
|---|---|---|
| 420 | isomiR example 1 of SEQ ID NO: 111 | — |
| 421 | isomiR example 2 of SEQ ID NO: 111 | — |
| 422 | isomiR example 1 of SEQ ID NO: 112 | — |
| 423 | isomiR example 2 of SEQ ID NO: 112 | — |
| 424 | isomiR example 1 of SEQ ID NO: 113 | — |
| 425 | isomiR example 2 of SEQ ID NO: 113 | — |
| 426 | isomiR example 1 of SEQ ID NO: 115 | — |
| 427 | isomiR example 2 of SEQ ID NO: 115 | — |
| 428 | isomiR example 1 of SEQ ID NO: 116 | — |
| 429 | isomiR example 2 of SEQ ID NO: 116 | — |
| 430 | isomiR example 1 of SEQ ID NO: 120 | — |
| 431 | isomiR example 2 of SEQ ID NO: 120 | — |
| 432 | isomiR example 1 of SEQ ID NO: 121 | — |
| 433 | isomiR example 2 of SEQ ID NO: 121 | — |
| 434 | isomiR example 1 of SEQ ID NO: 122 | — |
| 435 | isomiR example 2 of SEQ ID NO: 122 | — |
| 436 | isomiR example 1 of SEQ ID NO: 124 | — |
| 437 | isomiR example 2 of SEQ ID NO: 124 | — |
| 438 | isomiR example 1 of SEQ ID NO: 130 | — |
| 439 | isomiR example 2 of SEQ ID NO: 130 | — |
| 440 | isomiR example 1 of SEQ ID NO: 131 | — |
| 441 | isomiR example 2 of SEQ ID NO: 131 | — |
| 442 | isomiR example 1 of SEQ ID NO: 132 | — |
| 443 | isomiR example 2 of SEQ ID NO: 132 | — |
| 444 | isomiR example 1 of SEQ ID NO: 133 | — |
| 445 | isomiR example 2 of SEQ ID NO: 133 | — |
| 446 | isomiR example 1 of SEQ ID NO: 136 | — |
| 447 | isomiR example 2 of SEQ ID NO: 136 | — |
| 448 | isomiR example 1 of SEQ ID NO: 137 | — |
| 449 | isomiR example 2 of SEQ ID NO: 137 | — |
| 450 | isomiR example 1 of SEQ ID NO: 138 | — |
| 451 | isomiR example 2 of SEQ ID NO: 138 | — |
| 452 | isomiR example 1 of SEQ ID NO: 139 | — |
| 453 | isomiR example 2 of SEQ ID NO: 139 | — |
| 454 | isomiR example 1 of SEQ ID NO: 140 | — |
| 455 | isomiR example 2 of SEQ ID NO: 140 | — |
| 456 | isomiR example 1 of SEQ ID NO: 141 | — |
| 457 | isomiR example 2 of SEQ ID NO: 141 | — |

TABLE 1-continued

| SEQ ID NO: | Gene name | miRBase registration No. |
|---|---|---|
| 458 | isomiR example 1 of SEQ ID NO: 142 | — |
| 459 | isomiR example 2 of SEQ ID NO: 142 | — |
| 460 | isomiR example 1 of SEQ ID NO: 144 | — |
| 461 | isomiR example 2 of SEQ ID NO: 144 | — |
| 462 | isomiR example 1 of SEQ ID NO: 146 | — |
| 463 | isomiR example 2 of SEQ ID NO: 146 | — |
| 464 | isomiR example 1 of SEQ ID NO: 147 | — |
| 465 | isomiR example 2 of SEQ ID NO: 147 | — |
| 466 | hsa-miR-4516 | MIMAT0019053 |
| 467 | hsa-miR-4649-5p | MIMAT0019711 |
| 468 | hsa-miR-760 | MIMAT0004957 |
| 469 | hsa-miR-3162-5p | MIMAT0015036 |
| 470 | hsa-miR-3178 | MIMAT0015055 |
| 471 | hsa-miR-940 | MIMAT0004983 |
| 472 | hsa-miR-4271 | MIMAT0016901 |
| 473 | hsa-miR-6769b-5p | MIMAT0027620 |
| 474 | hsa-miR-4508 | MIMAT0019045 |
| 475 | hsa-miR-6826-5p | MIMAT0027552 |
| 476 | hsa-miR-6757-5p | MIMAT0027414 |
| 477 | hsa-miR-3131 | MIMAT0014996 |
| 478 | hsa-miR-1343-3p | MIMAT0019776 |
| 479 | hsa-mir-4516 | MI0016882 |
| 480 | hsa-mir-4649 | MI0017276 |
| 481 | hsa-mir-760 | MI0005567 |
| 482 | hsa-mir-3162 | MI0014192 |
| 483 | hsa-mir-3178 | MI0014212 |
| 484 | hsa-mir-940 | MI0005762 |
| 485 | hsa-mir-4271 | MI0015879 |
| 486 | hsa-mir-6769b | MI0022706 |
| 487 | hsa-mir-4508 | MI0016872 |
| 488 | hsa-mir-6826 | MI0022671 |
| 489 | hsa-mir-6757 | MI0022602 |
| 490 | hsa-mir-3131 | MI0014151 |
| 491 | hsa-mir-1343 | MI0017320 |
| 492 | isomiR example 1 of SEQ ID NO: 479 | — |
| 493 | isomiR example 2 of SEQ ID NO: 479 | — |
| 494 | isomiR example 1 of SEQ ID NO: 480 | — |
| 495 | isomiR example 2 of SEQ ID NO: 480 | — |
| 496 | isomiR example 1 of SEQ ID NO: 481 | — |
| 497 | isomiR example 2 of SEQ ID NO: 481 | — |
| 498 | isomiR example 1 of SEQ ID NO: 482 | — |
| 499 | isomiR example 2 of SEQ ID NO: 482 | — |
| 500 | isomiR example 1 of SEQ ID NO: 483 | — |
| 501 | isomiR example 2 of SEQ ID NO: 483 | — |
| 502 | isomiR example 1 of SEQ ID NO: 484 | — |
| 503 | isomiR example 2 of SEQ ID NO: 484 | — |
| 504 | isomiR example 1 of SEQ ID NO: 487 | — |
| 505 | isomiR example 2 of SEQ ID NO: 487 | — |
| 506 | isomiR example 1 of SEQ ID NO: 490 | — |
| 507 | isomiR example 2 of SEQ ID NO: 490 | — |
| 508 | isomiR example 1 of SEQ ID NO: 491 | — |
| 509 | isomiR example 2 of SEQ ID NO: 491 | — |

The present specification encompasses the contents described in the specifications and drawings of Japanese Patent Application Nos. 2014-120884 and 2014-185733 on which the priority of the present application is based.

Advantageous Effects of Invention

According to the present invention, biliary tract cancer can be detected easily and highly accurately. For example, the presence or absence of biliary tract cancer in a patient can be easily detected by using, as an indicator, the measurement values of several miRNAs in blood, serum, and/or plasma of the patient, which can be collected with limited invasiveness.

DESCRIPTION OF EMBODIMENTS

Figure 1:
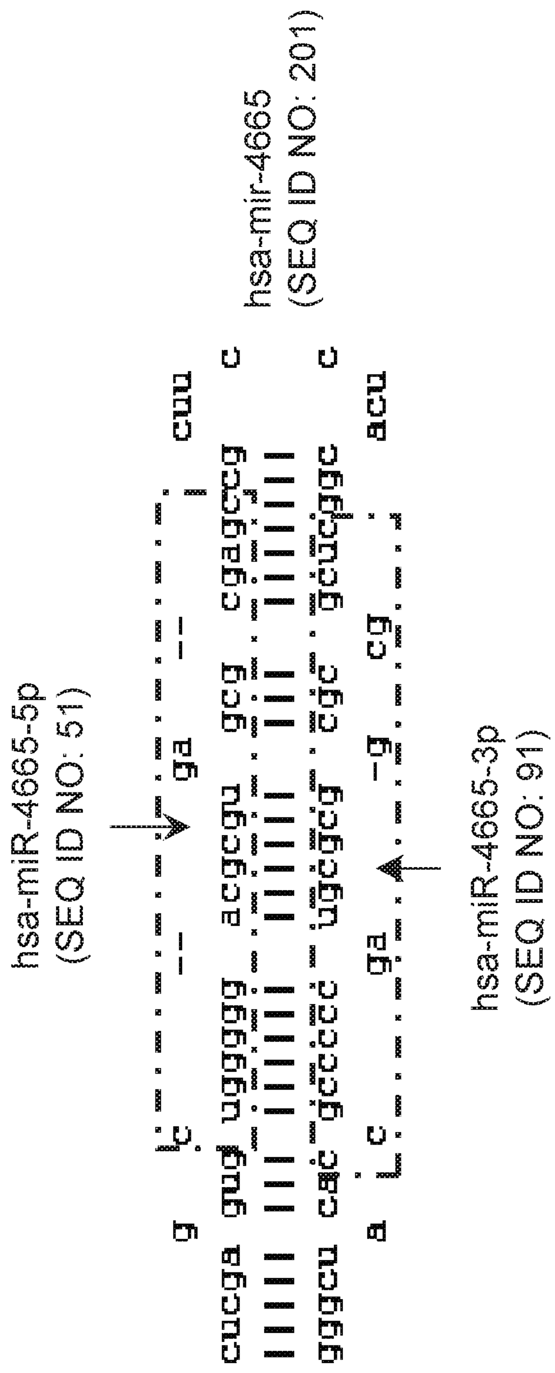
FIG. 1 This figure shows the relationship between the nucleotide sequences of hsa-miR-4665-5p represented by SEQ ID NO: 51 and hsa-miR-4665-3p represented by SEQ ID NO: 91, which are produced from a precursor hsa-mir-4665 represented by SEQ ID NO: 201.

Hereinafter, the present invention will be further described specifically.

1. Target Nucleic Acid for Biliary Tract Cancer

A primary target nucleic acid as a biliary tract cancer marker for detecting the presence and/or absence of biliary tract cancer or biliary tract cancer cells using the nucleic acid probe or the primer for the detection of biliary tract cancer defined above according to the present invention can be at least one or more miRNA(s) selected from the group consisting of hsa-miR-125a-3p, hsa-miR-6893-5p, hsa-miR-204-3p, hsa-miR-4476, hsa-miR-4294, hsa-miR-150-3p, hsa-miR-6729-5p, hsa-miR-7641, hsa-miR-6765-3p, hsa-miR-6820-5p, hsa-miR-575, hsa-miR-6836-3p, hsa-miR-1469, hsa-miR-663a, hsa-miR-6075, hsa-miR-4634, hsa-miR-423-5p, hsa-miR-4454, hsa-miR-7109-5p, hsa-miR-6789-5p, hsa-miR-6877-5p, hsa-miR-4792, hsa-miR-4530, hsa-miR-7975, hsa-miR-6724-5p, hsa-miR-8073, hsa-miR-7977, hsa-miR-1231, hsa-miR-6799-5p, hsa-miR-615-5p, hsa-miR-4450, hsa-miR-6726-5p, hsa-miR-6875-5p, hsa-miR-4734, hsa-miR-16-5p, hsa-miR-602, hsa-miR-4651, hsa-miR-8069, hsa-miR-1238-5p, hsa-miR-6880-5p, hsa-miR-8072, hsa-miR-4723-5p, hsa-miR-4732-5p, hsa-miR-6125, hsa-miR-6090, hsa-miR-7114-5p, hsa-miR-564, hsa-miR-451a, hsa-miR-3135b, hsa-miR-4497, hsa-miR-4665-5p, hsa-miR-3622a-5p, hsa-miR-6850-5p, hsa-miR-6821-5p, hsa-miR-5100, hsa-miR-6872-3p, hsa-miR-4433-3p, hsa-miR-1227-5p, hsa-miR-3188, hsa-miR-7704, hsa-miR-3185, hsa-miR-1908-3p, hsa-miR-6781-5p, hsa-miR-6805-5p, hsa-miR-8089, hsa-miR-665, hsa-miR-4486, hsa-miR-6722-3p, hsa-miR-1260a, hsa-miR-4707-5p, hsa-miR-6741-5p, hsa-miR-1260b, hsa-miR-1246, hsa-miR-6845-5p, hsa-miR-4638-5p, hsa-miR-6085, hsa-miR-1228-3p, hsa-miR-4534, hsa-miR-5585-3p, hsa-miR-4741, hsa-miR-4433b-3p, hsa-miR-197-5p, hsa-miR-718, hsa-miR-4513, hsa-miR-4446-3p, hsa-miR-619-5p, hsa-miR-6816-5p, hsa-miR-6778-5p, hsa-miR-24-3p, hsa-miR-1915-3p, hsa-miR-4665-3p, hsa-miR-4449, hsa-miR-6889-5p, hsa-miR-486-3p, hsa-miR-7113-3p, hsa-miR-642a-3p, hsa-miR-7847-3p, hsa-miR-6768-5p, hsa-miR-1290, hsa-miR-7108-5p, hsa-miR-92b-5p, hsa-miR-663b, hsa-miR-3940-5p, hsa-miR-4467, hsa-miR-6858-5p, hsa-miR-4417, hsa-miR-3665, hsa-miR-4736, hsa-miR-4687-3p, hsa-miR-1908-5p, hsa-miR-5195-3p, hsa-miR-4286, hsa-miR-3679-3p, hsa-miR-6791-5p, hsa-miR-1202, hsa-miR-3656, hsa-miR-4746-3p, hsa-miR-3184-5p, hsa-miR-3937, hsa-miR-6515-3p, hsa-miR-6132, hsa-miR-187-5p, hsa-miR-7111-5p, hsa-miR-5787, hsa-miR-6779-5p, hsa-miR-4516, hsa-miR-4649-5p, hsa-miR-760, hsa-miR-3162-5p, hsa-miR-3178, hsa-miR-940, hsa-miR-4271, hsa-miR-6769b-5p, hsa-miR-4508, hsa-miR-6826-5p, hsa-miR-6757-5p, hsa-miR-3131, and hsa-miR-1343-3p. Furthermore, at least one or more miRNA(s) selected from the group consisting of other biliary tract cancer markers that can be combined with these miRNAs, i.e., hsa-miR-6808-5p, hsa-miR-6774-5p, hsa-miR-4656, hsa-miR-6806-5p, hsa-miR-1233-5p, hsa-miR-328-5p, hsa-miR-4674, hsa-miR-2110, hsa-miR-6076, hsa-miR-3619-3p, hsa-miR-92a-2-5p, hsa-miR-128-1-5p, hsa-miR-638, hsa-miR-2861, hsa-miR-371a-5p, hsa-miR-211-3p, hsa-miR-1273g-3p, hsa-miR-1203, hsa-miR-122-5p, hsa-miR-4258, hsa-miR-4484, hsa-miR-4648 and hsa-miR-6780b-5p can also be preferably used as a target nucleic acid.

These miRNAs include, for example, a human gene comprising a nucleotide sequence represented by any of SEQ ID NOs: 1 to 148, 466 to 478 (i.e., hsa-miR-125a-3p, hsa-miR-6893-5p, hsa-miR-204-3p, hsa-miR-4476, hsa-miR-4294, hsa-miR-150-3p, hsa-miR-6729-5p, hsa-miR-7641, hsa-miR-6765-3p, hsa-miR-6820-5p, hsa-miR-575, hsa-miR-6836-3p, hsa-miR-1469, hsa-miR-663a, hsa-miR-6075, hsa-miR-4634, hsa-miR-423-5p, hsa-miR-4454, hsa-miR-7109-5p, hsa-miR-6789-5p, hsa-miR-6877-5p, hsa-miR-4792, hsa-miR-4530, hsa-miR-7975, hsa-miR-6724-5p, hsa-miR-8073, hsa-miR-7977, hsa-miR-1231, hsa-miR-6799-5p, hsa-miR-615-5p, hsa-miR-4450, hsa-miR-6726-5p, hsa-miR-6875-5p, hsa-miR-4734, hsa-miR-16-5p, hsa-miR-602, hsa-miR-4651, hsa-miR-8069, hsa-miR-1238-5p, hsa-miR-6880-5p, hsa-miR-8072, hsa-miR-4723-5p, hsa-miR-4732-5p, hsa-miR-6125, hsa-miR-6090, hsa-miR-7114-5p, hsa-miR-564, hsa-miR-451a, hsa-miR-3135b, hsa-miR-4497, hsa-miR-4665-5p, hsa-miR-3622a-5p, hsa-miR-6850-5p, hsa-miR-6821-5p, hsa-miR-5100, hsa-miR-6872-3p, hsa-miR-4433-3p, hsa-miR-1227-5p, hsa-miR-3188, hsa-miR-7704, hsa-miR-3185, hsa-miR-1908-3p, hsa-miR-6781-5p, hsa-miR-6805-5p, hsa-miR-8089, hsa-miR-665, hsa-miR-4486, hsa-miR-6722-3p, hsa-miR-1260a, hsa-miR-4707-5p, hsa-miR-6741-5p, hsa-miR-1260b, hsa-miR-1246, hsa-miR-6845-5p, hsa-miR-4638-5p, hsa-miR-6085, hsa-miR-1228-3p, hsa-miR-4534, hsa-miR-5585-3p, hsa-miR-4741, hsa-miR-4433b-3p, hsa-miR-197-5p, hsa-miR-718, hsa-miR-4513, hsa-miR-4446-3p, hsa-miR-619-5p, hsa-miR-6816-5p, hsa-miR-6778-5p, hsa-miR-24-3p, hsa-miR-1915-3p, hsa-miR-4665-3p, hsa-miR-4449, hsa-miR-6889-5p, hsa-miR-486-3p, hsa-miR-7113-3p, hsa-miR-642a-3p, hsa-miR-7847-3p, hsa-miR-6768-5p, hsa-miR-1290, hsa-miR-7108-5p, hsa-miR-92b-5p, hsa-miR-663b, hsa-miR-3940-5p, hsa-miR-4467, hsa-miR-6858-5p, hsa-miR-4417, hsa-miR-3665, hsa-miR-4736, hsa-miR-4687-3p, hsa-miR-1908-5p, hsa-miR-5195-3p, hsa-miR-4286, hsa-miR-3679-3p, hsa-miR-6791-5p, hsa-miR-1202, hsa-miR-3656, hsa-miR-4746-3p, hsa-miR-3184-5p, hsa-miR-3937, hsa-miR-6515-3p, hsa-miR-6132, hsa-miR-187-5p, hsa-miR-7111-5p, hsa-miR-5787, hsa-miR-6779-5p, hsa-miR-6808-5p, hsa-miR-6774-5p, hsa-miR-4656, hsa-miR-6806-5p, hsa-miR-1233-5p, hsa-miR-328-5p, hsa-miR-4674, hsa-miR-2110, hsa-miR-6076, hsa-miR-3619-3p, hsa-miR-92a-2-5p, hsa-miR-128-1-5p, hsa-miR-638, hsa-miR-2861, hsa-miR-371a-5p, hsa-miR-211-3p, hsa-miR-1273g-3p, hsa-miR-1203, hsa-miR-122-5p, hsa-miR-4258, hsa-miR-4484, hsa-miR-4648, hsa-miR-6780b-5p, hsa-miR-4516, hsa-miR-4649-5p, hsa-miR-760, hsa-miR-3162-5p, hsa-miR-3178, hsa-miR-940, hsa-miR-4271, hsa-miR-6769b-5p, hsa-miR-4508, hsa-miR-6826-5p, hsa-miR-6757-5p, hsa-miR-3131, and hsa-miR-1343-3p, respectively), a congener thereof, a transcript thereof, and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 509 or a transcript thereof, more preferably the transcript, i.e., a miRNA or its precursor RNA (pri-miRNA or pre-miRNA).

The first target gene is the hsa-miR-125a-3p gene, a congener thereof, a transcript thereof, or a variant or a derivative thereof. None of the previously known reports show that change in the expression of the gene or the transcript thereof can serve as a marker for biliary tract cancer.

The second target gene is the hsa-miR-6893-5p gene, a congener thereof, a transcript thereof, or a variant or a derivative thereof. None of the previously known reports show that change in the expression of the gene or the transcript thereof can serve as a marker for biliary tract cancer.

The third target gene is the hsa-miR-204-3p gene, a congener thereof, a transcript thereof, or a variant or a derivative thereof. None of the previously known reports show that change in the expression of the gene or the transcript thereof can serve as a marker for biliary tract cancer.

The fourth target gene is the hsa-miR-4476 gene, a congener thereof, a transcript thereof, or a variant or a derivative thereof. None of the previously known reports show that change in the expression of the gene or the transcript thereof can serve as a marker for biliary tract cancer.

The fifth target gene is the hsa-miR-4294 gene, a congener thereof, a transcript thereof, or a variant or a derivative thereof. None of the previously known reports show that change in the expression of the gene or the transcript thereof can serve as a marker for biliary tract cancer.

The sixth target gene is the hsa-miR-150-3p gene, a congener thereof, a transcript thereof, or a variant or a derivative thereof. None of the previously known reports show that change in the expression of the gene or the transcript thereof can serve as a marker for biliary tract cancer.

The seventh target gene is the hsa-miR-6729-5p gene, a congener thereof, a transcript thereof, or a variant or a derivative thereof. None of the previously known reports show that change in the expression of the gene or the transcript thereof can serve as a marker for biliary tract cancer.

The eighth target gene is the hsa-miR-7641 gene, a congener thereof, a transcript thereof, or a variant or a derivative thereof. None of the previously known reports show that change in the expression of the gene or the transcript thereof can serve as a marker for biliary tract cancer.

The ninth target gene is the hsa-miR-6765-3p gene, a congener thereof, a transcript thereof, or a variant or a derivative thereof. None of the previously known reports show that change in the expression of the gene or the transcript thereof can serve as a marker for biliary tract cancer.

The 10th target gene is the hsa-miR-6820-5p gene, a congener thereof, a transcript thereof, or a variant or a derivative thereof. None of the previously known reports show that change in the expression of the gene or the transcript thereof can serve as a marker for biliary tract cancer.

The 11th target gene is the hsa-miR-575 gene, a congener thereof, a transcript thereof, or a variant or a derivative thereof. None of the previously known reports show that change in the expression of the gene or the transcript thereof can serve as a marker for biliary tract cancer.

The 12th target gene is the hsa-miR-6836-3p gene, a congener thereof, a transcript thereof, or a variant or a derivative thereof. None of the previously known reports show that change in the expression of the gene or the transcript thereof can serve as a marker for biliary tract cancer.

The 13th target gene is the hsa-miR-1469 gene, a congener thereof, a transcript thereof, or a variant or a derivative thereof. None of the previously known reports show that change in the expression of the gene or the transcript thereof can serve as a marker for biliary tract cancer.

The 14th target gene is the hsa-miR-663a gene, a congener thereof, a transcript thereof, or a variant or a derivative thereof. None of the previously known reports show that change in the expression of the gene or the transcript thereof can serve as a marker for biliary tract cancer.

The 15th target gene is the hsa-miR-6075 gene, a congener thereof, a transcript thereof, or a variant or a derivative thereof. None of the previously known reports show that change in the expression of the gene or the transcript thereof can serve as a marker for biliary tract cancer.

The 16th target gene is the hsa-miR-4634 gene, a congener thereof, a transcript thereof, or a variant or a derivative thereof. None of the previously known reports show that change in the expression of the gene or the transcript thereof can serve as a marker for biliary tract cancer.

The 17th target gene is the hsa-miR-423-5p gene, a congener thereof, a transcript thereof, or a variant or a derivative thereof. None of the previously known reports show that change in the expression of the gene or the transcript thereof can serve as a marker for biliary tract cancer.

The 18th target gene is the hsa-miR-4454 gene, a congener thereof, a transcript thereof, or a variant or a derivative thereof. None of the previously known reports show that change in the expression of the gene or the transcript thereof can serve as a marker for biliary tract cancer.

The 19th target gene is the hsa-miR-7109-5p gene, a congener thereof, a transcript thereof, or a variant or a derivative thereof. None of the previously known reports show that change in the expression of the gene or the transcript thereof can serve as a marker for biliary tract cancer.

The 20th target gene is the hsa-miR-6789-5p gene, a congener thereof, a transcript thereof, or a variant or a derivative thereof. None of the previously known reports show that change in the expression of the gene or the transcript thereof can serve as a marker for biliary tract cancer.

The 21 st target gene is the hsa-miR-6877-5p gene, a congener thereof, a transcript thereof, or a variant or a derivative thereof. None of the previously known reports show that change in the expression of the gene or the transcript thereof can serve as a marker for biliary tract cancer.

The 22nd target gene is the hsa-miR-4792 gene, a congener thereof, a transcript thereof, or a variant or a derivative thereof. None of the previously known reports show that change in the expression of the gene or the transcript thereof can serve as a marker for biliary tract cancer.

The 23rd target gene is the hsa-miR-4530 gene, a congener thereof, a transcript thereof, or a variant or a derivative thereof. None of the previously known reports show that change in the expression of the gene or the transcript thereof can serve as a marker for biliary tract cancer.

The 24th target gene is the hsa-miR-7975 gene, a congener thereof, a transcript thereof, or a variant or a derivative thereof. None of the previously known reports show that change in the expression of the gene or the transcript thereof can serve as a marker for biliary tract cancer.

The 25th target gene is the hsa-miR-6724-5p gene, a congener thereof, a transcript thereof, or a variant or a derivative thereof. None of the previously known reports show that change in the expression of the gene or the transcript thereof can serve as a marker for biliary tract cancer.

The 26th target gene is the hsa-miR-8073 gene, a congener thereof, a transcript thereof, or a variant or a derivative thereof. None of the previously known reports show that change in the expression of the gene or the transcript thereof can serve as a marker for biliary tract cancer.

The 27th target gene is the hsa-miR-7977 gene, a congener thereof, a transcript thereof, or a variant or a derivative thereof. None of the previously known reports show that change in the expression of the gene or the transcript thereof can serve as a marker for biliary tract cancer.

The 28th target gene is the hsa-miR-1231 gene, a congener thereof, a transcript thereof, or a variant or a derivative thereof. None of the previously known reports show that change in the expression of the gene or the transcript thereof can serve as a marker for biliary tract cancer.

The 29th target gene is the hsa-miR-6799-5p gene, a congener thereof, a transcript thereof, or a variant or a derivative thereof. None of the previously known reports show that change in the expression of the gene or the transcript thereof can serve as a marker for biliary tract cancer.

The 30th target gene is the hsa-miR-615-5p gene, a congener thereof, a transcript thereof, or a variant or a derivative thereof. None of the previously known reports show that change in the expression of the gene or the transcript thereof can serve as a marker for biliary tract cancer.

The 31st target gene is the hsa-miR-4450 gene, a congener thereof, a transcript thereof, or a variant or a derivative thereof. None of the previously known reports show that change in the expression of the gene or the transcript thereof can serve as a marker for biliary tract cancer.

The 32nd target gene is the hsa-miR-6726-5p gene, a congener thereof, a transcript thereof, or a variant or a derivative thereof. None of the previously known reports show that change in the expression of the gene or the transcript thereof can serve as a marker for biliary tract cancer.

The 33rd target gene is the hsa-miR-6875-5p gene, a congener thereof, a transcript thereof, or a variant or a derivative thereof. None of the previously known reports show that change in the expression of the gene or the transcript thereof can serve as a marker for biliary tract cancer.

The 34th target gene is the hsa-miR-4734 gene, a congener thereof, a transcript thereof, or a variant or a derivative thereof. None of the previously known reports show that change in the expression of the gene or the transcript thereof can serve as a marker for biliary tract cancer.

The 35th target gene is the hsa-miR-16-5p gene, a congener thereof, a transcript thereof, or a variant or a derivative thereof. None of the previously known reports show that change in the expression of the gene or the transcript thereof can serve as a marker for biliary tract cancer.

The 36th target gene is the hsa-miR-602 gene, a congener thereof, a transcript thereof, or a variant or a derivative thereof. None of the previously known reports show that change in the expression of the gene or the transcript thereof can serve as a marker for biliary tract cancer.

The 37th target gene is the hsa-miR-4651 gene, a congener thereof, a transcript thereof, or a variant or a derivative thereof. None of the previously known reports show that change in the expression of the gene or the transcript thereof can serve as a marker for biliary tract cancer.

The 38th target gene is the hsa-miR-8069 gene, a congener thereof, a transcript thereof, or a variant or a derivative thereof. None of the previously known reports show that change in the expression of the gene or the transcript thereof can serve as a marker for biliary tract cancer.

The 39th target gene is the hsa-miR-1238-5p gene, a congener thereof, a transcript thereof, or a variant or a derivative thereof. None of the previously known reports show that change in the expression of the gene or the transcript thereof can serve as a marker for biliary tract cancer.

The 40th target gene is the hsa-miR-6880-5p gene, a congener thereof, a transcript thereof, or a variant or a derivative thereof. None of the previously known reports show that change in the expression of the gene or the transcript thereof can serve as a marker for biliary tract cancer.

The 41st target gene is the hsa-miR-8072 gene, a congener thereof, a transcript thereof, or a variant or a derivative thereof. None of the previously known reports show that change in the expression of the gene or the transcript thereof can serve as a marker for biliary tract cancer.

The 42nd target gene is the hsa-miR-4723-5p gene, a congener thereof, a transcript thereof, or a variant or a derivative thereof. None of the previously known reports show that change in the expression of the gene or the transcript thereof can serve as a marker for biliary tract cancer.

The 43rd target gene is the hsa-miR-4732-5p gene, a congener thereof, a transcript thereof, or a variant or a derivative thereof. None of the previously known reports show that change in the expression of the gene or the transcript thereof can serve as a marker for biliary tract cancer.

The 44th target gene is the hsa-miR-6125 gene, a congener thereof, a transcript thereof, or a variant or a derivative thereof. None of the previously known reports show that change in the expression of the gene or the transcript thereof can serve as a marker for biliary tract cancer.

The 45th target gene is the hsa-miR-6090 gene, a congener thereof, a transcript thereof, or a variant or a derivative thereof. None of the previously known reports show that change in the expression of the gene or the transcript thereof can serve as a marker for biliary tract cancer.

The 46th target gene is the hsa-miR-7114-5p gene, a congener thereof, a transcript thereof, or a variant or a derivative thereof. None of the previously known reports show that change in the expression of the gene or the transcript thereof can serve as a marker for biliary tract cancer.

The 47th target gene is the hsa-miR-564 gene, a congener thereof, a transcript thereof, or a variant or a derivative thereof. None of the previously known reports show that change in the expression of the gene or the transcript thereof can serve as a marker for biliary tract cancer.

The 48th target gene is the hsa-miR-451a gene, a congener thereof, a transcript thereof, or a variant or a derivative thereof. None of the previously known reports show that change in the expression of the gene or the transcript thereof can serve as a marker for biliary tract cancer.

The 49th target gene is the hsa-miR-3135b gene, a congener thereof, a transcript thereof, or a variant or a derivative thereof. None of the previously known reports show that change in the expression of the gene or the transcript thereof can serve as a marker for biliary tract cancer.

The 50th target gene is the hsa-miR-4497 gene, a congener thereof, a transcript thereof, or a variant or a derivative thereof. None of the previously known reports show that change in the expression of the gene or the transcript thereof can serve as a marker for biliary tract cancer.

The 51st target gene is the hsa-miR-4665-5p gene, a congener thereof, a transcript thereof, or a variant or a derivative thereof. None of the previously known reports show that change in the expression of the gene or the transcript thereof can serve as a marker for biliary tract cancer.

The 52nd target gene is the hsa-miR-3622a-5p gene, a congener thereof, a transcript thereof, or a variant or a derivative thereof. None of the previously known reports show that change in the expression of the gene or the transcript thereof can serve as a marker for biliary tract cancer.

The 53rd target gene is the hsa-miR-6850-5p gene, a congener thereof, a transcript thereof, or a variant or a derivative thereof. None of the previously known reports show that change in the expression of the gene or the transcript thereof can serve as a marker for biliary tract cancer.

The 54th target gene is the hsa-miR-6821-5p gene, a congener thereof, a transcript thereof, or a variant or a derivative thereof. None of the previously known reports show that change in the expression of the gene or the transcript thereof can serve as a marker for biliary tract cancer.

The 55th target gene is the hsa-miR-5100 gene, a congener thereof, a transcript thereof, or a variant or a derivative thereof. None of the previously known reports show that change in the expression of the gene or the transcript thereof can serve as a marker for biliary tract cancer.

The 56th target gene is the hsa-miR-6872-3p gene, a congener thereof, a transcript thereof, or a variant or a derivative thereof. None of the previously known reports show that change in the expression of the gene or the transcript thereof can serve as a marker for biliary tract cancer.

The 57th target gene is the hsa-miR-4433-3p gene, a congener thereof, a transcript thereof, or a variant or a derivative thereof. None of the previously known reports show that change in the expression of the gene or the transcript thereof can serve as a marker for biliary tract cancer.

The 58th target gene is the hsa-miR-1227-5p gene, a congener thereof, a transcript thereof, or a variant or a derivative thereof. None of the previously known reports show that change in the expression of the gene or the transcript thereof can serve as a marker for biliary tract cancer.

The 59th target gene is the hsa-miR-3188 gene, a congener thereof, a transcript thereof, or a variant or a derivative thereof. None of the previously known reports show that change in the expression of the gene or the transcript thereof can serve as a marker for biliary tract cancer.

The 60th target gene is the hsa-miR-7704 gene, a congener thereof, a transcript thereof, or a variant or a derivative thereof. None of the previously known reports show that change in the expression of the gene or the transcript thereof can serve as a marker for biliary tract cancer.

The 61st target gene is the hsa-miR-3185 gene, a congener thereof, a transcript thereof, or a variant or a derivative thereof. None of the previously known reports show that change in the expression of the gene or the transcript thereof can serve as a marker for biliary tract cancer.

The 62nd target gene is the hsa-miR-1908-3p gene, a congener thereof, a transcript thereof, or a variant or a derivative thereof. None of the previously known reports show that change in the expression of the gene or the transcript thereof can serve as a marker for biliary tract cancer.

The 63rd target gene is the hsa-miR-6781-5p gene, a congener thereof, a transcript thereof, or a variant or a derivative thereof. None of the previously known reports show that change in the expression of the gene or the transcript thereof can serve as a marker for biliary tract cancer.

The 64th target gene is the hsa-miR-6805-5p gene, a congener thereof, a transcript thereof, or a variant or a derivative thereof. None of the previously known reports show that change in the expression of the gene or the transcript thereof can serve as a marker for biliary tract cancer.

The 65th target gene is the hsa-miR-8089 gene, a congener thereof, a transcript thereof, or a variant or a derivative thereof. None of the previously known reports show that change in the expression of the gene or the transcript thereof can serve as a marker for biliary tract cancer.

The 66th target gene is the hsa-miR-665 gene, a congener thereof, a transcript thereof, or a variant or a derivative thereof. None of the previously known reports show that change in the expression of the gene or the transcript thereof can serve as a marker for biliary tract cancer.

The 67th target gene is the hsa-miR-4486 gene, a congener thereof, a transcript thereof, or a variant or a derivative thereof. None of the previously known reports show that change in the expression of the gene or the transcript thereof can serve as a marker for biliary tract cancer.

The 68th target gene is the hsa-miR-6722-3p gene, a congener thereof, a transcript thereof, or a variant or a derivative thereof. None of the previously known reports show that change in the expression of the gene or the transcript thereof can serve as a marker for biliary tract cancer.

The 69th target gene is the hsa-miR-1260a gene, a congener thereof, a transcript thereof, or a variant or a derivative thereof. None of the previously known reports show that change in the expression of the gene or the transcript thereof can serve as a marker for biliary tract cancer.

The 70th target gene is the hsa-miR-4707-5p gene, a congener thereof, a transcript thereof, or a variant or a derivative thereof. None of the previously known reports show that change in the expression of the gene or the transcript thereof can serve as a marker for biliary tract cancer.

The 71st target gene is the hsa-miR-6741-5p gene, a congener thereof, a transcript thereof, or a variant or a derivative thereof. None of the previously known reports show that change in the expression of the gene or the transcript thereof can serve as a marker for biliary tract cancer.

The 72nd target gene is the hsa-miR-1260b gene, a congener thereof, a transcript thereof, or a variant or a derivative thereof. None of the previously known reports show that change in the expression of the gene or the transcript thereof can serve as a marker for biliary tract cancer.

The 73rd target gene is the hsa-miR-1246 gene, a congener thereof, a transcript thereof, or a variant or a derivative thereof. None of the previously known reports show that change in the expression of the gene or the transcript thereof can serve as a marker for biliary tract cancer.

The 74th target gene is the hsa-miR-6845-5p gene, a congener thereof, a transcript thereof, or a variant or a derivative thereof. None of the previously known reports show that change in the expression of the gene or the transcript thereof can serve as a marker for biliary tract cancer.

The 75th target gene is the hsa-miR-4638-5p gene, a congener thereof, a transcript thereof, or a variant or a derivative thereof. None of the previously known reports show that change in the expression of the gene or the transcript thereof can serve as a marker for biliary tract cancer.

The 76th target gene is the hsa-miR-6085 gene, a congener thereof, a transcript thereof, or a variant or a derivative thereof. None of the previously known reports show that change in the expression of the gene or the transcript thereof can serve as a marker for biliary tract cancer.

The 77th target gene is the hsa-miR-1228-3p gene, a congener thereof, a transcript thereof, or a variant or a derivative thereof. None of the previously known reports show that change in the expression of the gene or the transcript thereof can serve as a marker for biliary tract cancer.

The 78th target gene is the hsa-miR-4534 gene, a congener thereof, a transcript thereof, or a variant or a derivative thereof. None of the previously known reports show that change in the expression of the gene or the transcript thereof can serve as a marker for biliary tract cancer.

The 79th target gene is the hsa-miR-5585-3p gene, a congener thereof, a transcript thereof, or a variant or a derivative thereof. None of the previously known reports show that change in the expression of the gene or the transcript thereof can serve as a marker for biliary tract cancer.

The 80th target gene is the hsa-miR-4741 gene, a congener thereof, a transcript thereof, or a variant or a derivative thereof. None of the previously known reports show that change in the expression of the gene or the transcript thereof can serve as a marker for biliary tract cancer.

The 81st target gene is the hsa-miR-4433b-3p gene, a congener thereof, a transcript thereof, or a variant or a derivative thereof. None of the previously known reports show that change in the expression of the gene or the transcript thereof can serve as a marker for biliary tract cancer.

The 82nd target gene is the hsa-miR-197-5p gene, a congener thereof, a transcript thereof, or a variant or a derivative thereof. None of the previously known reports show that change in the expression of the gene or the transcript thereof can serve as a marker for biliary tract cancer.

The 83rd target gene is the hsa-miR-718 gene, a congener thereof, a transcript thereof, or a variant or a derivative thereof. None of the previously known reports show that change in the expression of the gene or the transcript thereof can serve as a marker for biliary tract cancer.

The 84th target gene is the hsa-miR-4513 gene, a congener thereof, a transcript thereof, or a variant or a derivative thereof. None of the previously known reports show that change in the expression of the gene or the transcript thereof can serve as a marker for biliary tract cancer.

The 85th target gene is the hsa-miR-4446-3p gene, a congener thereof, a transcript thereof, or a variant or a derivative thereof. None of the previously known reports show that change in the expression of the gene or the transcript thereof can serve as a marker for biliary tract cancer.

The 86th target gene is the hsa-miR-619-5p gene, a congener thereof, a transcript thereof, or a variant or a derivative thereof. None of the previously known reports show that change in the expression of the gene or the transcript thereof can serve as a marker for biliary tract cancer.

The 87th target gene is the hsa-miR-6816-5p gene, a congener thereof, a transcript thereof, or a variant or a derivative thereof. None of the previously known reports show that change in the expression of the gene or the transcript thereof can serve as a marker for biliary tract cancer.

The 88th target gene is the hsa-miR-6778-5p gene, a congener thereof, a transcript thereof, or a variant or a derivative thereof. None of the previously known reports show that change in the expression of the gene or the transcript thereof can serve as a marker for biliary tract cancer.

The 89th target gene is the hsa-miR-24-3p gene, a congener thereof, a transcript thereof, or a variant or a derivative thereof. None of the previously known reports show that change in the expression of the gene or the transcript thereof can serve as a marker for biliary tract cancer.

The 90th target gene is the hsa-miR-1915-3p gene, a congener thereof, a transcript thereof, or a variant or a derivative thereof. None of the previously known reports show that change in the expression of the gene or the transcript thereof can serve as a marker for biliary tract cancer.

The 91st target gene is the hsa-miR-4665-3p gene, a congener thereof, a transcript thereof, or a variant or a derivative thereof. None of the previously known reports show that change in the expression of the gene or the transcript thereof can serve as a marker for biliary tract cancer.

The 92nd target gene is the hsa-miR-4449 gene, a congener thereof, a transcript thereof, or a variant or a derivative thereof. None of the previously known reports show that change in the expression of the gene or the transcript thereof can serve as a marker for biliary tract cancer.

The 93rd target gene is the hsa-miR-6889-5p gene, a congener thereof, a transcript thereof, or a variant or a derivative thereof. None of the previously known reports show that change in the expression of the gene or the transcript thereof can serve as a marker for biliary tract cancer.

The 94th target gene is the hsa-miR-486-3p gene, a congener thereof, a transcript thereof, or a variant or a derivative thereof. None of the previously known reports show that change in the expression of the gene or the transcript thereof can serve as a marker for biliary tract cancer.

The 95th target gene is the hsa-miR-7113-3p gene, a congener thereof, a transcript thereof, or a variant or a derivative thereof. None of the previously known reports show that change in the expression of the gene or the transcript thereof can serve as a marker for biliary tract cancer.

The 96th target gene is the hsa-miR-642a-3p gene, a congener thereof, a transcript thereof, or a variant or a derivative thereof. None of the previously known reports show that change in the expression of the gene or the transcript thereof can serve as a marker for biliary tract cancer.

The 97th target gene is the hsa-miR-7847-3p gene, a congener thereof, a transcript thereof, or a variant or a derivative thereof. None of the previously known reports show that change in the expression of the gene or the transcript thereof can serve as a marker for biliary tract cancer.

The 98th target gene is the hsa-miR-6768-5p gene, a congener thereof, a transcript thereof, or a variant or a derivative thereof. None of the previously known reports show that change in the expression of the gene or the transcript thereof can serve as a marker for biliary tract cancer.

The 99th target gene is the hsa-miR-1290 gene, a congener thereof, a transcript thereof, or a variant or a derivative thereof. None of the previously known reports show that change in the expression of the gene or the transcript thereof can serve as a marker for biliary tract cancer.

The 100th target gene is the hsa-miR-7108-5p gene, a congener thereof, a transcript thereof, or a variant or a derivative thereof. None of the previously known reports show that change in the expression of the gene or the transcript thereof can serve as a marker for biliary tract cancer.

The 101st target gene is the hsa-miR-92b-5p gene, a congener thereof, a transcript thereof, or a variant or a derivative thereof. None of the previously known reports show that change in the expression of the gene or the transcript thereof can serve as a marker for biliary tract cancer.

The 102nd target gene is the hsa-miR-663b gene, a congener thereof, a transcript thereof, or a variant or a derivative thereof. None of the previously known reports show that change in the expression of the gene or the transcript thereof can serve as a marker for biliary tract cancer.

The 103rd target gene is the hsa-miR-3940-5p gene, a congener thereof, a transcript thereof, or a variant or a derivative thereof. None of the previously known reports show that change in the expression of the gene or the transcript thereof can serve as a marker for biliary tract cancer.

The 104th target gene is the hsa-miR-4467 gene, a congener thereof, a transcript thereof, or a variant or a derivative thereof. None of the previously known reports show that change in the expression of the gene or the transcript thereof can serve as a marker for biliary tract cancer.

The 105th target gene is the hsa-miR-6858-5p gene, a congener thereof, a transcript thereof, or a variant or a derivative thereof. None of the previously known reports show that change in the expression of the gene or the transcript thereof can serve as a marker for biliary tract cancer.

The 106th target gene is the hsa-miR-4417 gene, a congener thereof, a transcript thereof, or a variant or a derivative thereof. None of the previously known reports show that change in the expression of the gene or the transcript thereof can serve as a marker for biliary tract cancer.

The 107th target gene is the hsa-miR-3665 gene, a congener thereof, a transcript thereof, or a variant or a derivative thereof. None of the previously known reports show that change in the expression of the gene or the transcript thereof can serve as a marker for biliary tract cancer.

The 108th target gene is the hsa-miR-4736 gene, a congener thereof, a transcript thereof, or a variant or a derivative thereof. None of the previously known reports show that change in the expression of the gene or the transcript thereof can serve as a marker for biliary tract cancer.

The 109th target gene is the hsa-miR-4687-3p gene, a congener thereof, a transcript thereof, or a variant or a derivative thereof. None of the previously known reports show that change in the expression of the gene or the transcript thereof can serve as a marker for biliary tract cancer.

The 110th target gene is the hsa-miR-1908-5p gene, a congener thereof, a transcript thereof, or a variant or a derivative thereof. None of the previously known reports show that change in the expression of the gene or the transcript thereof can serve as a marker for biliary tract cancer.

The 111th target gene is the hsa-miR-5195-3p gene, a congener thereof, a transcript thereof, or a variant or a derivative thereof. None of the previously known reports show that change in the expression of the gene or the transcript thereof can serve as a marker for biliary tract cancer.

The 112th target gene is the hsa-miR-4286 gene, a congener thereof, a transcript thereof, or a variant or a derivative thereof. None of the previously known reports show that change in the expression of the gene or the transcript thereof can serve as a marker for biliary tract cancer.

The 113th target gene is the hsa-miR-3679-3p gene, a congener thereof, a transcript thereof, or a variant or a derivative thereof. None of the previously known reports show that change in the expression of the gene or the transcript thereof can serve as a marker for biliary tract cancer.

The 114th target gene is the hsa-miR-6791-5p gene, a congener thereof, a transcript thereof, or a variant or a derivative thereof. None of the previously known reports show that change in the expression of the gene or the transcript thereof can serve as a marker for biliary tract cancer.

The 115th target gene is the hsa-miR-1202 gene, a congener thereof, a transcript thereof, or a variant or a derivative thereof. None of the previously known reports show that change in the expression of the gene or the transcript thereof can serve as a marker for biliary tract cancer.

The 116th target gene is the hsa-miR-3656 gene, a congener thereof, a transcript thereof, or a variant or a derivative thereof. None of the previously known reports show that change in the expression of the gene or the transcript thereof can serve as a marker for biliary tract cancer.

The 117th target gene is the hsa-miR-4746-3p gene, a congener thereof, a transcript thereof, or a variant or a derivative thereof. None of the previously known reports show that change in the expression of the gene or the transcript thereof can serve as a marker for biliary tract cancer.

The 118th target gene is the hsa-miR-3184-5p gene, a congener thereof, a transcript thereof, or a variant or a derivative thereof. None of the previously known reports show that change in the expression of the gene or the transcript thereof can serve as a marker for biliary tract cancer.

The 119th target gene is the hsa-miR-3937 gene, a congener thereof, a transcript thereof, or a variant or a derivative thereof. None of the previously known reports show that change in the expression of the gene or the transcript thereof can serve as a marker for biliary tract cancer.

The 120th target gene is the hsa-miR-6515-3p gene, a congener thereof, a transcript thereof, or a variant or a derivative thereof. None of the previously known reports show that change in the expression of the gene or the transcript thereof can serve as a marker for biliary tract cancer.

The 121st target gene is the hsa-miR-6132 gene, a congener thereof, a transcript thereof, or a variant or a derivative thereof. None of the previously known reports show that change in the expression of the gene or the transcript thereof can serve as a marker for biliary tract cancer.

The 122nd target gene is the hsa-miR-187-5p gene, a congener thereof, a transcript thereof, or a variant or a derivative thereof. None of the previously known reports show that change in the expression of the gene or the transcript thereof can serve as a marker for biliary tract cancer.

The 123rd target gene is the hsa-miR-7111-5p gene, a congener thereof, a transcript thereof, or a variant or a derivative thereof. None of the previously known reports show that change in the expression of the gene or the transcript thereof can serve as a marker for biliary tract cancer.

The 124th target gene is the hsa-miR-5787 gene, a congener thereof, a transcript thereof, or a variant or a derivative thereof. None of the previously known reports show that change in the expression of the gene or the transcript thereof can serve as a marker for biliary tract cancer.

The 125th target gene is the hsa-miR-6779-5p gene, a congener thereof, a transcript thereof, or a variant or a derivative thereof. None of the previously known reports show that change in the expression of the gene or the transcript thereof can serve as a marker for biliary tract cancer.

The 126th target gene is the hsa-miR-6808-5p gene, a congener thereof, a transcript thereof, or a variant or a derivative thereof. None of the previously known reports show that change in the expression of the gene or the transcript thereof can serve as a marker for biliary tract cancer.

The 127th target gene is the hsa-miR-6774-5p gene, a congener thereof, a transcript thereof, or a variant or a derivative thereof. None of the previously known reports show that change in the expression of the gene or the transcript thereof can serve as a marker for biliary tract cancer.

The 128th target gene is the hsa-miR-4656 gene, a congener thereof, a transcript thereof, or a variant or a derivative thereof. None of the previously known reports show that change in the expression of the gene or the transcript thereof can serve as a marker for biliary tract cancer.

The 129th target gene is the hsa-miR-6806-5p gene, a congener thereof, a transcript thereof, or a variant or a derivative thereof. None of the previously known reports show that change in the expression of the gene or the transcript thereof can serve as a marker for biliary tract cancer.

The 130th target gene is the hsa-miR-1233-5p gene, a congener thereof, a transcript thereof, or a variant or a derivative thereof. None of the previously known reports show that change in the expression of the gene or the transcript thereof can serve as a marker for biliary tract cancer.

The 131st target gene is the hsa-miR-328-5p gene, a congener thereof, a transcript thereof, or a variant or a derivative thereof. None of the previously known reports show that change in the expression of the gene or the transcript thereof can serve as a marker for biliary tract cancer.

The 132nd target gene is the hsa-miR-4674 gene, a congener thereof, a transcript thereof, or a variant or a derivative thereof. None of the previously known reports show that change in the expression of the gene or the transcript thereof can serve as a marker for biliary tract cancer.

The 133rd target gene is the hsa-miR-2110 gene, a congener thereof, a transcript thereof, or a variant or a derivative thereof. None of the previously known reports show that change in the expression of the gene or the transcript thereof can serve as a marker for biliary tract cancer.

The 134th target gene is the hsa-miR-6076 gene, a congener thereof, a transcript thereof, or a variant or a derivative thereof. None of the previously known reports show that change in the expression of the gene or the transcript thereof can serve as a marker for biliary tract cancer.

The 135th target gene is the hsa-miR-3619-3p gene, a congener thereof, a transcript thereof, or a variant or a derivative thereof. None of the previously known reports show that change in the expression of the gene or the transcript thereof can serve as a marker for biliary tract cancer.

The 136th target gene is the hsa-miR-92a-2-5p gene, a congener thereof, a transcript thereof, or a variant or a derivative thereof. None of the previously known reports show that change in the expression of the gene or the transcript thereof can serve as a marker for biliary tract cancer.

The 137th target gene is the hsa-miR-128-1-5p gene, a congener thereof, a transcript thereof, or a variant or a derivative thereof. None of the previously known reports show that change in the expression of the gene or the transcript thereof can serve as a marker for biliary tract cancer.

The 138th target gene is the hsa-miR-638 gene, a congener thereof, a transcript thereof, or a variant or a derivative thereof. None of the previously known reports show that change in the expression of the gene or the transcript thereof can serve as a marker for biliary tract cancer.

The 139th target gene is the hsa-miR-2861 gene, a congener thereof, a transcript thereof, or a variant or a derivative thereof. None of the previously known reports show that change in the expression of the gene or the transcript thereof can serve as a marker for biliary tract cancer.

The 140th target gene is the hsa-miR-371a-5p gene, a congener thereof, a transcript thereof, or a variant or a derivative thereof. None of the previously known reports show that change in the expression of the gene or the transcript thereof can serve as a marker for biliary tract cancer.

The 141st target gene is the hsa-miR-211-3p gene, a congener thereof, a transcript thereof, or a variant or a derivative thereof. None of the previously known reports show that change in the expression of the gene or the transcript thereof can serve as a marker for biliary tract cancer.

The 142nd target gene is the hsa-miR-1273g-3p gene, a congener thereof, a transcript thereof, or a variant or a derivative thereof. None of the previously known reports show that change in the expression of the gene or the transcript thereof can serve as a marker for biliary tract cancer.

The 143rd target gene is the hsa-miR-1203 gene, a congener thereof, a transcript thereof, or a variant or a derivative thereof. None of the previously known reports show that change in the expression of the gene or the transcript thereof can serve as a marker for biliary tract cancer.

The 144th target gene is the hsa-miR-122-5p gene, a congener thereof, a transcript thereof, or a variant or a derivative thereof. None of the previously known reports show that change in the expression of the gene or the transcript thereof can serve as a marker for biliary tract cancer.

The 145th target gene is the hsa-miR-4258 gene, a congener thereof, a transcript thereof, or a variant or a derivative thereof. None of the previously known reports show that change in the expression of the gene or the transcript thereof can serve as a marker for biliary tract cancer.

The 146th target gene is the hsa-miR-4484 gene, a congener thereof, a transcript thereof, or a variant or a derivative thereof. None of the previously known reports show that change in the expression of the gene or the transcript thereof can serve as a marker for biliary tract cancer.

The 147th target gene is the hsa-miR-4648 gene, a congener thereof, a transcript thereof, or a variant or a derivative thereof. None of the previously known reports show that change in the expression of the gene or the transcript thereof can serve as a marker for biliary tract cancer.

The 148th target gene is the hsa-miR-6780b-5p gene, a congener thereof, a transcript thereof, or a variant or a derivative thereof. None of the previously known reports show that change in the expression of the gene or the transcript thereof can serve as a marker for biliary tract cancer.

The 149th target gene is the hsa-miR-4516 gene, a congener thereof, a transcript thereof, or a variant or a derivative thereof. None of the previously known reports show that change in the expression of the gene or the transcript thereof can serve as a marker for biliary tract cancer.

The 150th target gene is the hsa-miR-4649-5p gene, a congener thereof, a transcript thereof, or a variant or a derivative thereof. None of the previously known reports show that change in the expression of the gene or the transcript thereof can serve as a marker for biliary tract cancer.

The 151st target gene is the hsa-miR-760 gene, a congener thereof, a transcript thereof, or a variant or a derivative thereof. None of the previously known reports show that change in the expression of the gene or the transcript thereof can serve as a marker for biliary tract cancer.

The 152nd target gene is the hsa-miR-3162-5p gene, a congener thereof, a transcript thereof, or a variant or a derivative thereof. None of the previously known reports show that change in the expression of the gene or the transcript thereof can serve as a marker for biliary tract cancer.

The 153rd target gene is the hsa-miR-3178 gene, a congener thereof, a transcript thereof, or a variant or a derivative thereof. None of the previously known reports show that change in the expression of the gene or the transcript thereof can serve as a marker for biliary tract cancer.

The 154th target gene is the hsa-miR-940 gene, a congener thereof, a transcript thereof, or a variant or a derivative thereof. None of the previously known reports show that change in the expression of the gene or the transcript thereof can serve as a marker for biliary tract cancer.

The 155th target gene is the hsa-miR-4271 gene, a congener thereof, a transcript thereof, or a variant or a derivative thereof. None of the previously known reports show that change in the expression of the gene or the transcript thereof can serve as a marker for biliary tract cancer.

The 156th target gene is the hsa-miR-6769b-5p gene, a congener thereof, a transcript thereof, or a variant or a derivative thereof. None of the previously known reports show that change in the expression of the gene or the transcript thereof can serve as a marker for biliary tract cancer.

The 157th target gene is the hsa-miR-4508 gene, a congener thereof, a transcript thereof, or a variant or a derivative thereof. None of the previously known reports show that change in the expression of the gene or the transcript thereof can serve as a marker for biliary tract cancer.

The 158th target gene is the hsa-miR-6826-5p gene, a congener thereof, a transcript thereof, or a variant or a derivative thereof. None of the previously known reports show that change in the expression of the gene or the transcript thereof can serve as a marker for biliary tract cancer.

The 159th target gene is the hsa-miR-6757-5p gene, a congener thereof, a transcript thereof, or a variant or a derivative thereof. None of the previously known reports show that change in the expression of the gene or the transcript thereof can serve as a marker for biliary tract cancer.

The 160th target gene is the hsa-miR-3131 gene, a congener thereof, a transcript thereof, or a variant or a derivative thereof. None of the previously known reports show that change in the expression of the gene or the transcript thereof can serve as a marker for biliary tract cancer.

The 161st target gene is the hsa-miR-1343-3p gene, a congener thereof, a transcript thereof, or a variant or a derivative thereof. None of the previously known reports show that change in the expression of the gene or the transcript thereof can serve as a marker for biliary tract cancer.

2. Nucleic Acid Probe or Primer for Detection of Biliary Tract Cancer

In the present invention, a nucleic acid capable of specifically binding to any of the target nucleic acids as the biliary tract cancer markers described above can be used as a nucleic acid, for example, a nucleic acid probe or a primer, for the detection or diagnosis of biliary tract cancer.

In the present invention, the nucleic acid probe or the primer that can be used for detecting biliary tract cancer or for diagnosing biliary tract cancer enables qualitative and/or quantitative measurement of the presence, expression level, or abundance of a target nucleic acid as the biliary tract cancer marker described above, for example, human-derived hsa-miR-125a-3p, hsa-miR-6893-5p, hsa-miR-204-3p, hsa-miR-4476, hsa-miR-4294, hsa-miR-150-3p, hsa-miR-6729-5p, hsa-miR-7641, hsa-miR-6765-3p, hsa-miR-6820-5p, hsa-miR-575, hsa-miR-6836-3p, hsa-miR-1469, hsa-miR-663a, hsa-miR-6075, hsa-miR-4634, hsa-miR-423-5p, hsa-miR-4454, hsa-miR-7109-5p, hsa-miR-6789-5p, hsa-miR-6877-5p, hsa-miR-4792, hsa-miR-4530, hsa-miR-7975, hsa-miR-6724-5p, hsa-miR-8073, hsa-miR-7977, hsa-miR-1231, hsa-miR-6799-5p, hsa-miR-615-5p, hsa-miR-4450, hsa-miR-6726-5p, hsa-miR-6875-5p, hsa-miR-4734, hsamiR-16-5p, hsa-miR-602, hsa-miR-4651, hsa-miR-8069, hsa-miR-1238-5p, hsa-miR-6880-5p, hsa-miR-8072, hsa-miR-4723-5p, hsa-miR-4732-5p, hsa-miR-6125, hsa-miR-6090, hsa-miR-7114-5p, hsa-miR-564, hsa-miR-451a, hsa-miR-3135b, hsa-miR-4497, hsa-miR-4665-5p, hsa-miR-3622a-5p, hsa-miR-6850-5p, hsa-miR-6821-5p, hsa-miR-5100, hsa-miR-6872-3p, hsa-miR-4433-3p, hsa-miR-1227-5p, hsa-miR-3188, hsa-miR-7704, hsa-miR-3185, hsa-miR-1908-3p, hsa-miR-6781-5p, hsa-miR-6805-5p, hsa-miR-8089, hsa-miR-665, hsa-miR-4486, hsa-miR-6722-3p, hsa-miR-1260a, hsa-miR-4707-5p, hsa-miR-6741-5p, hsa-miR-1260b, hsa-miR-1246, hsa-miR-6845-5p, hsa-miR-4638-5p, hsa-miR-6085, hsa-miR-1228-3p, hsa-miR-4534, hsa-miR-5585-3p, hsa-miR-4741, hsa-miR-4433b-3p, hsa-miR-197-5p, hsa-miR-718, hsa-miR-4513, hsa-miR-4446-3p, hsa-miR-619-5p, hsa-miR-6816-5p, hsa-miR-6778-5p, hsa-miR-24-3p, hsa-miR-1915-3p, hsa-miR-4665-3p, hsa-miR-4449, hsa-miR-6889-5p, hsa-miR-486-3p, hsa-miR-7113-3p, hsa-miR-642a-3p, hsa-miR-7847-3p, hsa-miR-6768-5p, hsa-miR-1290, hsa-miR-7108-5p, hsa-miR-92b-5p, hsa-miR-663b, hsa-miR-3940-5p, hsa-miR-4467, hsa-miR-6858-5p, hsa-miR-4417, hsa-miR-3665, hsa-miR-4736, hsa-miR-4687-3p, hsa-miR-1908-5p, hsa-miR-5195-3p, hsa-miR-4286, hsa-miR-3679-3p, hsa-miR-6791-5p, hsa-miR-1202, hsa-miR-3656, hsa-miR-4746-3p, hsa-miR-3184-5p, hsa-miR-3937, hsa-miR-6515-3p, hsa-miR-6132, hsa-miR-187-5p, hsa-miR-7111-5p, hsa-miR-5787, hsa-miR-6779-5p, hsa-miR-4516, hsa-miR-4649-5p, hsa-miR-760, hsa-miR-3162-5p, hsa-miR-3178, hsa-miR-940, hsa-miR-4271, hsa-miR-6769b-5p, hsa-miR-4508, hsa-miR-6826-5p, hsa-miR-6757-5p, hsa-miR-3131, or hsa-miR-1343-3p, or a combination thereof, or a congener thereof, a transcript thereof, or a variant or a derivative thereof, and, optionally in combination therewith, hsa-miR-6808-5p, hsa-miR-6774-5p, hsa-miR-4656, hsa-miR-6806-5p, hsa-miR-1233-5p, hsa-miR-328-5p, hsa-miR-4674, hsa-miR-2110, hsa-miR-6076, hsa-miR-3619-3p, hsa-miR-92a-2-5p, hsa-miR-128-1-5p, hsa-miR-638, hsa-miR-2861, hsa-miR-371a-5p, hsa-miR-211-3p, hsa-miR-1273g-3p, hsa-miR-1203, hsa-miR-122-5p, hsa-miR-4258, hsa-miR-4484, hsa-miR-4648 or hsa-miR-6780b-5p or a combination thereof, a congener thereof, a transcript thereof, or a variant or a derivative thereof.

The expression level of each target nucleic acid described above is increased or decreased (hereinafter, referred to as "increased/decreased) depending on the type of the target nucleic acid in a subject who has biliary tract cancer as compared with a healthy subject. Hence, the nucleic acid of the present invention can be effectively used for measuring the expression level of the target nucleic acid in a body fluid derived from a subject (e.g., a human) suspected of having biliary tract cancer and a body fluid derived from a healthy subject and comparing them to detect biliary tract cancer. The nucleic acid of the present invention can also be effectively used for measuring the expression level of the target nucleic acid in a body fluid derived from a subject (e.g., a human) suspected of having biliary tract cancer and body fluids derived from a colorectal cancer patient, a stomach cancer patient, an esophageal cancer patient, a liver cancer patient, and a benign pancreaticobiliary disease patient and comparing them to specifically detect biliary tract cancer from other cancers, benign diseases, and the like.

The nucleic acid probe or the primer that can be used in the present invention is a nucleic acid probe capable of specifically binding to a polynucleotide consisting of a nucleotide sequence represented by at least one of SEQ ID NOs: 1 to 125 (preferably SEQ ID NOs: 1, 2, and 4 to 125) and 466 to 478, or a primer for amplifying a polynucleotide consisting of a nucleotide sequence represented by at least one of SEQ ID NOs: 1 to 125 and 466 to 478.

The nucleic acid probe or the primer that can be further used in the present invention may comprise a nucleic acid probe capable of specifically binding to a polynucleotide consisting of a nucleotide sequence represented by at least one of SEQ ID NOs: 126 to 148, or a primer for amplifying a polynucleotide consisting of a nucleotide sequence represented by at least one of SEQ ID NOs: 126 to 148.

Specifically, these nucleic acid probes or primers comprise a combination of one or more polynucleotides selected from a group of polynucleotides comprising nucleotide sequences represented by any of SEQ ID NOs: 1 to 509 or nucleotide sequences derived from the nucleotide sequences by the replacement of u with t, and a group of complementary polynucleotides thereof, a group of polynucleotides respectively hybridizing under stringent conditions (mentioned later) to DNAs consisting of nucleotide sequences complementary to these nucleotide sequences, and a group of complementary polynucleotides thereof, and a group of polynucleotides comprising 15 or more, preferably 17 or more consecutive nucleotides in the nucleotide sequences of these polynucleotide groups. These polynucleotides can be used as nucleic acid probes and primers for detecting the biliary tract cancer markers as target nucleic acids.

More specifically, examples of the nucleic acid probe or the primer that can be used in the present invention include one or more polynucleotide(s) selected from the group consisting of the following polynucleotides (a) to (e):

(a) a polynucleotide consisting of a nucleotide sequence represented by any of SEQ ID NOs: 1 to 125 and 466 to 478 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 125 and 466 to 478, (c) a polynucleotide consisting of a nucleotide sequence complementary to a nucleotide sequence represented by any of SEQ ID NOs: 1 to 125 and 466 to 478 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 125 and 466 to 478 or a nucleotide sequence derived from the nucleotide sequence by the replacement of u with t, and (e) a polynucleotide hybridizing under stringent conditions to any of the polynucleotides (a) to (d).

In addition to at least one or more polynucleotide(s) selected from the group consisting of the polynucleotides (a) to (e), the nucleic acid probe or the primer that can be further used in the present invention may comprise polynucleotide(s) selected from the group consisting of the following polynucleotides (f) to (j):

(f) a polynucleotide consisting of a nucleotide sequence represented by any of SEQ ID NOs: 126 to 148 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 126 to 148.

(h) a polynucleotide consisting of a nucleotide sequence complementary to a nucleotide sequence represented by any of SEQ ID NOs: 126 to 148 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 126 to 148 or a nucleotide sequence derived from the nucleotide sequence by the replacement of u with t, and (j) a polynucleotide hybridizing under stringent conditions to any of the polynucleotides (f) to (i).

For these polynucleotides, the "fragment thereof comprising 15 or more consecutive nucleotides" can comprise the number of nucleotides in the range of, for example, 15 consecutive nucleotides to less than the total number of nucleotides of the sequence, 17 consecutive nucleotides to less than the total number of nucleotides of the sequence, or 19 consecutive nucleotides to less than the total number of nucleotides of the sequence, in the nucleotide sequence of each polynucleotide, though the fragment is not limited thereto.

These polynucleotides or fragments thereof used in the present invention may each be DNA or may each be RNA.

The polynucleotides that can be used in the present invention can each be prepared by use of a general technique such as a DNA recombination technique, PCR, or a method using an automatic DNA/RNA synthesizer.

The DNA recombination technique and the PCR can employ a technique described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-125a-3p, hsa-miR-6893-5p, hsa-miR-204-3p, hsa-miR-4476, hsa-miR-4294, hsa-miR-150-3p, hsa-miR-6729-5p, hsa-miR-7641, hsa-miR-6765-3p, hsa-miR-6820-5p, hsa-miR-575, hsa-miR-6836-3p, hsa-miR-1469, hsa-miR-663a, hsa-miR-6075, hsa-miR-4634, hsa-miR-423-5p, hsa-miR-4454, hsa-miR-7109-5p, hsa-miR-6789-5p, hsa-miR-6877-5p, hsa-miR-4792, hsa-miR-4530, hsa-miR-7975, hsa-miR-6724-5p, hsa-miR-8073, hsa-miR-7977, hsa-miR-1231, hsa-miR-6799-5p, hsa-miR-615-5p, hsa-miR-4450, hsa-miR-6726-5p, hsa-miR-6875-5p, hsa-miR-4734, hsa-miR-16-5p, hsa-miR-602, hsa-miR-4651, hsa-miR-8069, hsa-miR-1238-5p, hsa-miR-6880-5p, hsa-miR-8072, hsa-miR-4723-5p, hsa-miR-4732-5p, hsa-miR-6125, hsa-miR-6090, hsa-miR-7114-5p, hsa-miR-564, hsa-miR-451a, hsa-miR-3135b, hsa-miR-4497, hsa-miR-4665-5p, hsa-miR-3622a-5p, hsa-miR-6850-5p, hsa-miR-6821-5p, hsa-miR-5100, hsa-miR-6872-3p, hsa-miR-4433-3p, hsa-miR-1227-5p, hsa-miR-3188, hsa-miR-7704, hsa-miR-3185, hsa-miR-1908-3p, hsa-miR-6781-5p, hsa-miR-6805-5p, hsa-miR-8089, hsa-miR-665, hsa-miR-4486, hsa-miR-6722-3p, hsa-miR-1260a, hsa-miR-4707-5p, hsa-miR-6741-5p, hsa-miR-1260b, hsa-miR-1246, hsa-miR-6845-5p, hsa-miR-4638-5p, hsa-miR-6085, hsa-miR-1228-3p, hsa-miR-4534, hsa-miR-5585-3p, hsa-miR-4741, hsa-miR-4433b-3p, hsa-miR-197-5p, hsa-miR-718, hsa-miR-4513, hsa-miR-4446-3p, hsa-miR-619-5p, hsa-miR-6816-5p, hsa-miR-6778-5p, hsa-miR-24-3p, hsa-miR-1915-3p, hsa-miR-4665-3p, hsa-miR-4449, hsa-miR-6889-5p, hsa-miR-486-3p, hsa-miR-7113-3p, hsa-miR-642a-3p, hsa-miR-7847-3p, hsa-miR-6768-5p, hsa-miR-1290, hsa-miR-7108-5p, hsa-miR-92b-5p, hsa-miR-663b, hsa-miR-3940-5p, hsa-miR-4467, hsa-miR-6858-5p, hsa-miR-4417, hsa-miR-3665, hsa-miR-4736, hsa-miR-4687-3p, hsa-miR-1908-5p, hsa-miR-5195-3p, hsa-miR-4286, hsa-miR-3679-3p, hsa-miR-6791-5p, hsa-miR-1202, hsa-miR-3656, hsa-miR-4746-3p, hsa-miR-3184-5p, hsa-miR-3937, hsa-miR-6515-3p, hsa-miR-6132, hsa-miR-187-5p, hsa-miR-7111-5p, hsa-miR-5787, hsa-miR-6779-5p, hsa-miR-6808-5p, hsa-miR-6774-5p, hsa-miR-4656, hsa-miR-6806-5p, hsa-miR-1233-5p, hsa-miR-328-5p, hsa-miR-4674, hsa-miR-2110, hsa-miR-6076, hsa-miR-3619-3p, hsa-miR-92a-2-5p, hsa-miR-128-1-5p, hsa-miR-638, hsa-miR-2861, hsa-miR-371a-5p, hsa-miR-211-3p, hsa-miR-1273g-3p, hsa-miR-1203, hsa-miR-122-5p, hsa-miR-4258, hsa-miR-4484, hsa-miR-4648 and hsa-miR-6780b-5p represented by SEQ ID NOs: 1 to 148, 466 to 478 are known in the art, and their acquisition methods are also known as mentioned above. Therefore, each polynucleotide that can be used as a nucleic acid probe or a primer in the present invention can be prepared by cloning the gene.

Such a nucleic acid probe or a primer can be chemically synthesized using an automated DNA synthesizer. In general, a phosphoramidite method is used in this synthesis, and single-stranded DNA up to approximately 100 nucleotides can be automatically synthesized by this method. The automated DNA synthesizer is commercially available from, for example, Polygen GmbH, ABI, or Applied Biosystems, Inc.

Alternatively, the polynucleotide of the present invention can also be prepared by a cDNA cloning method. The cDNA cloning technique can employ, for example, microRNA Cloning Kit Wako.

In this context, the sequences of the nucleic acid probe and the primer for detecting the polynucleotide that consists of a nucleotide sequence represented by any of SEQ ID NOs: 1 to 148, 466 to 478 do not exist as miRNAs or precursors thereof in vivo. For example, the nucleotide sequences represented by SEQ ID NO: 51 and SEQ ID NO: 91 are produced from the precursor represented by SEQ ID NO: 201. This precursor has a hairpin-like structure as shown in FIG. 1, and the nucleotide sequences represented by SEQ ID NO: 51 and SEQ ID NO: 91 have mismatch sequences with each other. Therefore, a nucleotide sequence completely complementary to the nucleotide sequence represented by SEQ ID NO: 51 or SEQ ID NO: 91 is not naturally produced in vivo. Likewise, the nucleic acid probe and the primer for detecting the nucleotide sequence represented by any of SEQ ID NOs: 1 to 148 and 466 to 478 each has an artificial nucleotide sequence that does not exist in vivo.

3. Kit or Device for Detection of Biliary Tract Cancer

The present invention also provides a kit or a device for the detection of biliary tract cancer, comprising one or more polynucleotide(s) (which may include a variant, a fragment, or a derivative thereof; hereinafter, also referred to as a polynucleotide for detection) that can be used as a nucleic acid probe or a primer in the present invention for measuring a target nucleic acid as a biliary tract cancer marker.

The target nucleic acid as a biliary tract marker according to the present invention is preferably selected from the following group 1: miR-125a-3p, miR-6893-5p, miR-204-3p, miR-4476, miR-4294, miR-150-3p, miR-6729-5p, miR-7641, miR-6765-3p, miR-6820-5p, miR-575, miR-6836-3p, miR-1469, miR-663a, miR-6075, miR-4634, miR-423-5p, miR-4454, miR-7109-5p, miR-6789-5p, miR-6877-5p, miR-4792, miR-4530, miR-7975, miR-6724-5p, miR-8073, miR-7977, miR-1231, miR-6799-5p, miR-615-5p, miR-4450, miR-6726-5p, miR-6875-5p, miR-4734, miR-16-5p, miR-602, miR-4651, miR-8069, miR-1238-5p, miR-6880-5p, miR-8072, miR-4723-5p, miR-4732-5p, miR-6125, miR-6090, miR-7114-5p, miR-564, miR-451a, miR-3135b, miR-4497, miR-4665-5p, miR-3622a-5p, miR-6850-5p, miR-6821-5p, miR-5100, miR-6872-3p, miR-4433-3p, miR-1227-5p, miR-3188, miR-7704, miR-3185, miR-1908-3p, miR-6781-5p, miR-6805-5p, miR-8089, miR-665, miR-4486, miR-6722-3p, miR-1260a, miR-4707-5p, miR-6741-5p, miR-1260b, miR-1246, miR-6845-5p, miR-4638-5p, miR-6085, miR-1228-3p, miR-4534, miR-5585-3p, miR-4741, miR-4433b-3p, miR-197-5p, miR-718, miR-4513, miR-4446-3p, miR-619-5p, miR-6816-5p, miR-6778-5p, miR-24-3p, miR-1915-3p, miR-4665-3p, miR-4449, miR-6889-5p, miR-486-3p, miR-7113-3p, miR-642a-3p, miR-7847-3p, miR-6768-5p, miR-1290, miR-7108-5p, miR-92b-5p, miR-663b, miR-3940-5p, miR-4467, miR-6858-5p, miR-4417, miR-3665, miR-4736, miR-4687-3p, miR-1908-5p, miR-5195-3p, miR-4286, miR-3679-3p, miR-6791-5p, miR-1202, miR-3656, miR-4746-3p, miR-3184-5p, miR-3937, miR-6515-3p, miR-6132, miR-187-5p, miR-7111-5p, miR-5787, miR-6779-5p, miR-4516, miR-4649-5p, miR-760, miR-3162-5p, miR-3178, miR-940, miR-4271, miR-6769b-5p, miR-4508, miR-6826-5p, miR-6757-5p, miR-3131, and miR-1343-3p.

An additional target nucleic acid that may be optionally used in the measurement is preferably selected from the following group 2: miR-6808-5p, miR-6774-5p, miR-4656, miR-6806-5p, miR-1233-5p, miR-328-5p, miR-4674, miR-2110, miR-6076, miR-3619-3p, miR-92a-2-5p, miR-128-1-5p, miR-638, miR-2861, miR-371a-5p, miR-211-3p, miR-1273g-3p, miR-1203, miR-122-5p, miR-4258, miR-4484, miR-4648 and miR-6780b-5p.

The kit or the device of the present invention comprises nucleic acid(s) capable of specifically binding to any of the target nucleic acids as the biliary tract cancer markers described above, preferably one or more polynucleotide(s) selected from the nucleic acid probes or the primers described in Section 2 above, specifically, the polynucleotides described in Section 2 above, or variant(s) thereof.

Specifically, the kit or the device of the present invention may comprise at least one or more polynucleotide(s) comprising (or consisting of) a nucleotide sequence represented by any of SEQ ID NOs: 1 to 125, and 466 to 478 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, or variant(s) or fragment(s) comprising 15 or more consecutive nucleotides of any of these polynucleotide sequences.

The kit or the device of the present invention may further comprise one or more polynucleotide(s) comprising (or consisting of) a nucleotide sequence represented by any of SEQ ID NOs: 126 to 148 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The fragment that may be contained in the kit or the device of the present invention is, for example, one or more, preferably two or more polynucleotides selected from the group consisting of the following polynucleotides (1) to (2):

(1) a polynucleotide comprising 15 or more consecutive nucleotides in a nucleotide sequence derived from a nucleotide sequence represented by any of SEQ ID NOs: 1 to 125, 466 to 478 by the replacement of u with t, or a complementary sequence thereof:

(2) a polynucleotide comprising 15 or more consecutive nucleotides in a nucleotide sequence derived from a nucleotide sequence represented by any of SEQ ID NOs: 126 to 148 by the replacement of u with t, or a complementary sequence thereof; and In a preferred embodiment, the polynucleotide is a polynucleotide consisting of a nucleotide sequence represented by any of SEQ ID NOs: 1 to 125, 466 to 478 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 126 to 148 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment may be a polynucleotide comprising 15 or more, preferably 17 or more, more preferably 19 or more consecutive nucleotides.

In the present invention, the size of the polynucleotide fragment is the number of nucleotides in the range of, for example, 15 consecutive nucleotides to less than the total number of nucleotides of the sequence, 17 consecutive nucleotides to less than the total number of nucleotides of the sequence, or 19 consecutive nucleotides to less than the total number of nucleotides of the sequence, in the nucleotide sequence of each polynucleotide.

Specific examples of the aforementioned polynucleotide combination constituting the kit or the device of the present invention can include any combination of the polynucleotides consisting of nucleotide sequences represented by SEQ ID NOs shown in Table 1 mentioned later (SEQ ID NOs: 1 to 148 and 466 to 478 corresponding to the miRNA markers in Table 1) or complementary sequences thereof. However, these are given merely for illustrative purposes, and all of various other possible combinations are included in the present invention.

The aforementioned combination constituting the kit or the device for discriminating a biliary tract cancer patient from a healthy subject according to the present invention is desirably, for example, a combination of two or more of the aforementioned polynucleotides consisting of nucleotide sequences represented by SEQ ID NOs shown in Table 1. Usually, a combination of two of these polynucleotides can produce adequate performance.

Specifically, the combination of two polynucleotides consisting of the nucleotide sequences or the complementary sequences thereof for discriminating a biliary tract cancer patient from a healthy subject is preferably a combination comprising at least one or more of newly found polynucleotides consisting of the nucleotide sequences represented by SEQ ID NOs: 1 to 125 and 466 to 478, among the aforementioned combinations of two polynucleotides selected from the polynucleotides consisting of the nucleotide sequences represented by SEQ ID NOs: 1 to 148 and 466 to 478.

The combination of polynucleotides with cancer type specificity capable of discriminating a biliary tract cancer patient not only from a healthy subject but also from other cancer patients is preferably, for example, a combination of multiple polynucleotides comprising at least one polynucleotide selected from the group consisting of polynucleotides consisting of the nucleotide sequence represented by SEQ ID NOs: 1, 4, 5, 11, 12, 15, 23, 29, 39, 40, 54, 76, 79, 91, 103, 115, 121, 134, 143, 466, 469, 472, 473, and 474, or complementary sequences thereof (hereinafter, this group is referred to as "cancer type-specific polynucleotide group 1"), with any of the polynucleotides of the other SEQ ID NOs.

The combination of polynucleotides with cancer type specificity capable of discriminating a biliary tract cancer patient not only from a healthy subject but also from other cancer patients is more preferably a combination of multiple polynucleotides selected from the cancer type-specific polynucleotide group 1.

The combination of polynucleotides with cancer type specificity capable of discriminating a biliary tract cancer patient not only from a healthy subject but also from other cancer patients is more preferably a combination comprising at least one polynucleotide selected from the group consisting of polynucleotides consisting of the nucleotide sequences represented by SEQ ID NOs: 4, 5, 12, 15, and 40 or complementary sequences thereof (hereinafter, this group is referred to as "cancer type-specific polynucleotide group 2") included in the cancer type-specific polynucleotide group 1, among the combinations of multiple polynucleotides selected from the cancer type-specific polynucleotide group 1.

The number of the aforementioned polynucleotides with cancer type specificity in the combination can be 1, 2, 3, 4, 5, 6, 7, 8, 9, 10 or more in the combination and is more preferably 4 or more in the combination. Usually, the combination of 4 of the polynucleotides can produce adequate performance.

Non-limiting examples of the combination of the polynucleotide consisting of the nucleotide sequence represented by SEQ ID NO: 4 or a complementary sequence thereof with polynucleotides consisting of nucleotide sequences represented by SEQ ID NOs of three polynucleotides selected from the cancer type-specific polynucleotide group 1 or complementary sequences thereof are listed below.

(1) a combination of SEQ ID NOs: 4, 15, 54, and 115 (markers: miR-4476, miR-6075, miR-6821-5p, and miR-1202):

(2) a combination of SEQ ID NOs: 4, 5, 12, and 76 (markers: miR-4476, miR-4294, miR-6836-3p, and miR-6085):

(3) a combination of SEQ ID NOs: 4, 5, 12, and 115 (markers: miR-4476, miR-4294, miR-6836-3p, and miR-1202):

(4) a combination of SEQ ID NOs: 4, 12, 15, and 474 (markers: miR-4476, miR-6836-3p, miR-6075, and miR-4508);

(5) a combination of SEQ ID NOs: 4, 15, 29, and 115 (markers: miR-4476, miR-6075, miR-6799-5p, and miR-1202).

Non-limiting examples of the combination of the polynucleotide consisting of the nucleotide sequence represented by SEQ ID NO: 5 or a complementary sequence thereof with polynucleotides consisting of nucleotide sequences represented by SEQ ID NOs of three polynucleotides selected from the cancer type-specific polynucleotide group 1 or complementary sequences thereof are listed below.

(1) a combination of SEQ ID NOs: 5, 76, 12, and 115 (markers: hsa-miR-4294, hsa-miR-6085, hsa-miR-6836-3p, and hsa-miR-1202);

(2) a combination of SEQ ID NOs: 5, 76, 54, and 115 (markers: hsa-miR-4294, hsa-miR-6085, hsa-miR-6821-5p, and hsa-miR-1202):

(3) a combination of SEQ ID NOs: 5, 23, 12, and 115 (markers: hsa-miR-4294, hsa-miR-4530, hsa-miR-6836-3p, and hsa-miR-1202):

(4) a combination of SEQ ID NOs: 5, 12, 115, and 91 (markers: hsa-miR-4294, hsa-miR-6836-3p, hsa-miR-1202, and hsa-miR-4665-3p);

(5) a combination of SEQ ID NOs: 5, 1, 23, and 4 (markers: hsa-miR-4294, hsa-miR-125a-3p, hsa-miR-4530, and hsa-miR-4476).

Non-limiting examples of the combination of the polynucleotide consisting of the nucleotide sequence represented by SEQ ID NO: 12 or a complementary sequence thereof with polynucleotides consisting of nucleotide sequences represented by SEQ ID NOs of three polynucleotides selected from the cancer type-specific polynucleotide group 1 or complementary sequences thereof are listed below.

(1) a combination of SEQ ID NOs: 5, 12, 29, and 115 (markers: miR-4294, miR-6836-3p, miR-6799-5p, and miR-1202);

(2) a combination of SEQ ID NOs: 12, 15, 23, and 115 (markers: miR-6836-3p, miR-6075, miR-4530, and miR-1202);

(3) a combination of SEQ ID NOs: 5, 12, 115, and 469 (markers: miR-4294, miR-6836-3p, miR-3162-5p, and miR-1202);

(4) a combination of SEQ ID NOs: 5, 12, 115, and 472 (markers: miR-4294, miR-6836-3p, miR-1202, and miR-4271);

(5) a combination of SEQ ID NOs: 5, 12, 76, and 115 (markers: miR-4294, miR-6085, miR-1202, and miR-6836-3p).

Non-limiting examples of the combination of the polynucleotide consisting of the nucleotide sequence represented by SEQ ID NO: 15 or a complementary sequence thereof with polynucleotides consisting of nucleotide sequences represented by SEQ ID NOs of three polynucleotides selected from the cancer type-specific polynucleotide group 1 or complementary sequences thereof are listed below.

(1) a combination of SEQ ID NOs: 15, 29, 1, and 12 (markers: hsa-miR-6075, hsa-miR-6799-5p, hsa-miR-125a-3p, and hsa-miR-6836-3p);

(2) a combination of SEQ ID NOs: 15, 12, 11, and 143 (markers: hsa-miR-6075, hsa-miR-6836-3p, hsa-miR-575, and hsa-miR-1203);

(3) a combination of SEQ ID NOs: 15, 76, 121, and 39 (markers: hsa-miR-6075, hsa-miR-6085, hsa-miR-6132, and hsa-miR-1238-5p);

(4) a combination of SEQ ID NOs: 15, 76, 54, and 121 (markers: hsa-miR-6075, hsa-miR-6085, hsa-miR-6821-5p, and hsa-miR-6132):

(5) a combination of SEQ ID NOs: 15, 40, 1, and 23 (markers: hsa-miR-6075, hsa-miR-6880-5p, hsa-miR-125a-3p, and hsa-miR-4530).

Non-limiting examples of the combination of the polynucleotide consisting of the nucleotide sequence represented by SEQ ID NO: 40 or a complementary sequence thereof with polynucleotides consisting of nucleotide sequences represented by SEQ ID NOs of three polynucleotides selected from the cancer type-specific polynucleotide group 1 or complementary sequences thereof are listed below.

(1) a combination of SEQ ID NOs: 12, 40, 472, and 473 (markers: miR-6836-3p, miR-6880-5p, miR-4271, and miR-6769b-5p);

(2) a combination of SEQ ID NOs: 12, 23, 40, and 466 (markers: miR-6836-3p, miR-4530, miR-6880-5p, and miR-4516):

(3) a combination of SEQ ID NOs: 12, 23, 40, and 134 (markers: miR-6836-3p, miR-4530, miR-6880-5p, and miR-6076):

(4) a combination of SEQ ID NOs: 15, 40, 121, and 134 (markers: miR-6075, miR-6880-5p, miR-6132, and miR-6076);

(5) a combination of SEQ ID NOs: 15, 40, 54, and 76 (markers: miR-6075, miR-6880-5p, miR-6821-5p, and miR-6085).

The kit or the device of the present invention may also comprise a polynucleotide that is already known or that will be found in the future, to enable detection of biliary tract cancer, in addition to the polynucleotide(s) (which can include variant(s), fragment(s), and derivative(s)) according to the present invention as described above.

The kit of the present invention may also comprise an antibody for measuring a marker for biliary tract cancer examination known in the art, such as CEA, CA19-9, SPan-1, DUPAN-2, CA50, CA195, IL-6, CA242, TAG-72, urinary fucose, POA, or TPS, in addition to the polynucleotide(s) according to the present invention as described above.

These polynucleotides contained in the kit of the present invention may be packaged in different containers either individually or in any combination.

The kit of the present invention may comprise a kit for extracting a nucleic acid (e.g., total RNA) from body fluids, cells, or tissues; a fluorescent material for labeling, an enzyme and a medium for nucleic acid amplification, an instruction manual, etc.

The device of the present invention is a device for cancer marker measurement in which nucleic acids such as the polynucleotides according to the present invention described above are bound or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves binding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring target nucleic acids through the use of hybridization using this array.

The kit or the device of the present invention comprises nucleic acids capable of specifically binding to the polynucleotides of at least one or more, preferably at least two or more, more preferably at least three or more, most preferably at least five or more to all of the biliary tract cancer marker miRNAs, respectively, of the group 1 described above. The kit or the device of the present invention may optionally further comprise nucleic acids capable of specifically binding to the polynucleotides of at least one or more, preferably at least two or more, more preferably at least three or more, most preferably all of five of the biliary tract cancer marker miRNAs, respectively, of the group 2 described above.

The kit or the device of the present invention can be used for detecting biliary tract cancer as described in Section 4 below.

4. Method for Detecting Biliary Tract Cancer

The present invention further provides a method for detecting biliary tract cancer, comprising using the kit or the device of the present invention (comprising the above-mentioned nucleic acid(s) that can be used in the present invention) described in Section 3 above to measure expression level(s) of one or more liver cancer-derived gene(s) being an expression level of biliary tract cancer-derived gene(s) selected from the following group: miR-125a-3p, miR-6893-5p, miR-204-3p, miR-4476, miR-4294, miR-150-3p, miR-6729-5p, miR-7641, miR-6765-3p, miR-6820-5p, miR-575, miR-6836-3p, miR-1469, miR-663a, miR-6075, miR-4634, miR-423-5p, miR-4454, miR-7109-5p, miR-6789-5p, miR-6877-5p, miR-4792, miR-4530, miR-7975, miR-6724-5p, miR-8073, miR-7977, miR-1231, miR-6799-5p, miR-615-5p, miR-4450, miR-6726-5p, miR-6875-5p, miR-4734, miR-16-5p, miR-602, miR-4651, miR-8069, miR-1238-5p, miR-6880-5p, miR-8072, miR-4723-5p, miR-4732-5p, miR-6125, miR-6090, miR-7114-5p, miR-564, miR-451a, miR-3135b, miR-4497, miR-4665-5p, miR-3622a-5p, miR-6850-5p, miR-6821-5p, miR-5100, miR-6872-3p, miR-4433-3p, miR-1227-5p, miR-3188, miR-7704, miR-3185, miR-1908-3p, miR-6781-5p, miR-6805-5p, miR-8089, miR-665, miR-4486, miR-6722-3p, miR-1260a, miR-4707-5p, miR-6741-5p, miR-1260b, miR-1246, miR-6845-5p, miR-4638-5p, miR-6085, miR-1228-3p, miR-4534, miR-5585-3p, miR-4741, miR-4433b-3p, miR-197-5p, miR-718, miR-4513, miR-4446-3p, miR-619-5p, miR-6816-5p, miR-6778-5p, miR-24-3p, miR-1915-3p, miR-4665-3p, miR-4449, miR-6889-5p, miR-486-3p, miR-7113-3p, miR-642a-3p, miR-7847-3p, miR-6768-5p, miR-1290, miR-7108-5p, miR-92b-5p, miR-663b, miR-3940-5p, miR-4467, miR-6858-5p, miR-4417, miR-3665, miR-4736, miR-4687-3p, miR-1908-5p, miR-5195-3p, miR-4286, miR-3679-3p, miR-6791-5p, miR-1202, miR-3656, miR-4746-3p, miR-3184-5p, miR-3937, miR-6515-3p, miR-6132, miR-187-5p, miR-7111-5p, miR-5787 and miR-6779-5p, and optionally an expression level of biliary tract cancer-derived gene(s) selected from the following group: miR-6808-5p, miR-6774-5p, miR-4656, miR-6806-5p, miR-1233-5p, miR-328-5p, miR-4674, miR-2110, miR-6076, miR-3619-3p, miR-92a-2-5p, miR-128-1-5p, miR-638, miR-2861, miR-371a-5p, miR-211-3p, miR-1273g-3p, miR-1203, miR-122-5p, miR-4258, miR-4484, miR-4648, miR-6780b-5p, miR-4516, miR-4649-5p, miR-760, miR-3162-5p, miR-3178, miR-940, miR-4271, miR-6769b-5p, miR-4508, miR-6826-5p, miR-6757-5p, miR-3131, and miR-1343-3p in a sample in vitro, further comparing, for example, the expression level(s) of the gene(s) in the sample (e.g., blood, serum, or plasma) collected from a subject suspected of having biliary tract cancer with a control expression level in the sample collected from a healthy subject (including a non-biliary tract cancer patient), and evaluating the subject as having biliary tract cancer when the expression level(s) of the target nucleic acid(s) is statistically significantly different between the samples.

This method of the present invention enables a limitedly invasive, early diagnosis of the cancer with high sensitivity and high specificity and thereby brings about early treatment and improved prognosis. In addition, exacerbation of the disease or the effectiveness of surgical, radiotherapeutic, and chemotherapeutic treatments can be monitored.

The method for extracting the biliary tract cancer-derived gene from the sample such as blood, serum, or plasma according to the present invention is particularly preferably prepared by the addition of a reagent for RNA extraction in 3D-Gene® RNA extraction reagent from liquid sample kit (Toray Industries, Inc.). A general acidic phenol method (acid guanidinium-phenol-chloroform (AGPC)) may be used, or Trizol® (Life Technologies Corp.) may be used. The biliary tract cancer-derived gene may be prepared by the addition of a reagent for RNA extraction containing acidic phenol, such as Trizol (Life Technologies Corp.) or Isogen (Nippon Gene Co., Ltd.). Alternatively, a kit such as miRNeasy® Mini Kit (Qiagen N.V.) can be used, though the method is not limited thereto.

The present invention also provides use of the kit or the device of the present invention for detecting in vitro an expression product of a biliary tract cancer-derived miRNA gene in a sample derived from a subject.

In the method of the present invention, the kit or the device described above comprising a single polynucleotide or any possible combination of the polynucleotides that can be used in the present invention as described above is used.

In the detection or (genetic) diagnosis of biliary tract cancer according to the present invention, each polynucleotide contained in the kit or the device of the present invention can be used as a probe or a primer. In the case of using the polynucleotide as a primer, TaqMan® MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine of the subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of biliary tract cancer or the detection of the presence or absence of biliary tract cancer. Specifically, the detection of biliary tract cancer using the kit or the device can be performed by detecting in vitro an expression level of a gene using the nucleic acid probe or the primer contained in the kit or the device in a sample such as blood, serum, plasma, or urine from a subject suspected of having biliary tract cancer. The subject suspected of having biliary tract cancer can be evaluated as having biliary tract cancer when the expression level of a target miRNA marker measured using polynucleotide(s) (including variant(s), fragment(s), and derivative(s) thereof) consisting of a nucleotide sequence represented by at least one or more of SEQ ID NOs: 1 to 125, 466 to 478 or a complementary sequence thereof, and optionally a nucleotide sequence represented by one or more of SEQ ID NOs: 126 to 148 or a complementary sequence thereof in the sample such as blood, serum, plasma, or urine of the subject is statistically significantly different compared with the expression level thereof in the sample such as blood, serum, or plasma, or urine of a healthy subject.

The method of the present invention can be combined with a diagnostic imaging method such as abdominal ultrasonography, CT scanning, endoscopic retrograde cholangiopancreatography, or endoscopic ultrasonography. The method of the present invention is capable of specifically detecting biliary tract cancer and can substantially discriminate biliary tract cancer from the other cancers. Particularly, for pancreatic cancer, some miRNA markers for biliary tract cancer can be commonly used. However, biliary tract cancer can be discriminated from pancreatic cancer on the basis of a discriminant boundary adopted according to a discriminant. Alternatively, biliary tract cancer can be discriminated therefrom by combination with an additional diagnostic method such as the diagnostic imaging method as described above.

The method for detecting the absence of an expression product of a biliary tract cancer-derived gene or the presence of the expression product of a biliary tract cancer-derived gene in a sample using the kit or the device of the present invention comprises; collecting a body fluid such as blood, serum, plasma, or urine of a subject; measuring the expression level of the target gene contained therein using one or more polynucleotide(s) (including variant(s), fragment(s), or derivative(s)) selected from the polynucleotide group of the present invention; and evaluating the presence or absence of biliary tract cancer or to detect biliary tract cancer. Using the method for detecting biliary tract cancer according to the present invention, for example, the presence or absence of amelioration of the disease or the degree of amelioration thereof in a biliary tract cancer patient when a therapeutic drug is administered to the patient for amelioration of the disease can be evaluated or diagnosed.

The method of the present invention may comprise, for example, the following steps (a), (b), and (c):

(a) contacting in vitro a sample derived from a subject with a polynucleotide in the kit or the device of the present invention:

(b) measuring an expression level of the target nucleic acid in the sample using the polynucleotide as a nucleic acid probe or a primer; and (c) evaluating the presence or absence of biliary tract cancer (cells) in the subject on the basis of a measurement result obtained in the step (b).

Specifically, the present invention provides a method for detecting biliary tract cancer, comprising measuring an expression level of a target nucleic acid in a sample of a subject using nucleic acid(s) capable of specifically binding to at least one or more (preferably at least two or more) polynucleotide(s) selected from the group consisting of miR-125a-3p, miR-6893-5p, miR-204-3p, miR-4476, miR-4294, miR-150-3p, miR-6729-5p, miR-7641, miR-6765-3p, miR-6820-5p, miR-575, miR-6836-3p, miR-1469, miR-663a, miR-6075, miR-4634, miR-423-5p, miR-4454, miR-7109-5p, miR-6789-5p, miR-6877-5p, miR-4792, miR-4530, miR-7975, miR-6724-5p, miR-8073, miR-7977, miR-1231, miR-6799-5p, miR-615-5p, miR-4450, miR-6726-5p, miR-6875-5p, miR-4734, miR-16-5p, miR-602, miR-4651, miR-8069, miR-1238-5p, miR-6880-5p, miR-8072, miR-4723-5p, miR-4732-5p, miR-6125, miR-6090, miR-7114-5p, miR-564, miR-451a, miR-3135b, miR-4497, miR-4665-5p, miR-3622a-5p, miR-6850-5p, miR-6821-5p, miR-5100, miR-6872-3p, miR-4433-3p, miR-1227-5p, miR-3188, miR-7704, miR-3185, miR-1908-3p, miR-6781-5p, miR-6805-5p, miR-8089, miR-665, miR-4486, miR-6722-3p, miR-1260a, miR-4707-5p, miR-6741-5p, miR-1260b, miR-1246, miR-6845-5p, miR-4638-5p, miR-6085, miR-1228-3p, miR-4534, miR-5585-3p, miR-4741, miR-4433b-3p, miR-197-5p, miR-718, miR-4513, miR-4446-3p, miR-619-5p, miR-6816-5p, miR-6778-5p, miR-24-3p, miR-1915-3p, miR-4665-3p, miR-4449, miR-6889-5p, miR-486-3p, miR-7113-3p, miR-642a-3p, miR-7847-3p, miR-6768-5p, miR-1290, miR-7108-5p, miR-92b-5p, miR-663b, miR-3940-5p, miR-4467, miR-6858-5p, miR-4417, miR-3665, miR-4736, miR-4687-3p, miR-1908-5p, miR-5195-3p, miR-4286, miR-3679-3p, miR-6791-5p, miR-1202, miR-3656, miR-4746-3p, miR-3184-5p, miR-3937, miR-6515-3p, miR-6132, miR-187-5p, miR-7111-5p, miR-5787, miR-6779-5p, miR-4516, miR-4649-5p, miR-760, miR-3162-5p, miR-3178, miR-940, miR-4271, miR-6769b-5p, miR-4508, miR-6826-5p, miR-6757-5p, miR-3131, and miR-1343-3p and evaluating in vitro whether or not the subject has biliary tract cancer using the measured expression level and a control expression level of a healthy subject measured in the same way as above.

The term "evaluation" used herein is evaluation support based on results of in vitro examination, not physician's judgment.

As described above, in a preferred embodiment of the method of the present invention, specifically, miR-125a-3p is hsa-miR-125a-3p, miR-6893-5p is hsa-miR-6893-5p, miR-204-3p is hsa-miR-204-3p, miR-4476 is hsa-miR-4476, miR-4294 is hsa-miR-4294, miR-150-3p is hsa-miR-150-3p, miR-6729-5p is hsa-miR-6729-5p, miR-7641 is hsa-miR-7641, miR-6765-3p is hsa-miR-6765-3p, miR-6820-5p is hsa-miR-6820-5p, miR-575 is hsa-miR-575, miR-6836-3p is hsa-miR-6836-3p, miR-1469 is hsa-miR-1469, miR-663a is hsa-miR-663a, miR-6075 is hsa-miR-6075, miR-4634 is hsa-miR-4634, miR-423-5p is hsa-miR-423-5p, miR-4454 is hsa-miR-4454, miR-7109-5p is hsa-miR-7109-5p, miR-6789-5p is hsa-miR-6789-5p, miR-6877-5p is hsa-miR-6877-5p, miR-4792 is hsa-miR-4792, miR-4530 is hsa-miR-4530, miR-7975 is hsa-miR-7975, miR-6724-5p is hsa-miR-6724-5p, miR-8073 is hsa-miR-8073, miR-7977 is hsa-miR-7977, miR-1231 is hsa-miR-1231, miR-6799-5p is hsa-miR-6799-5p, miR-615-5p is hsa-miR-615-5p, miR-4450 is hsa-miR-4450, miR-6726-5p is hsa-miR-6726-5p, miR-6875-5p is hsa-miR-6875-5p, miR-4734 is hsa-miR-4734, miR-16-5p is hsa-miR-16-5p, miR-602 is hsa-miR-602, miR-4651 is hsa-miR-4651, miR-8069 is hsa-miR-8069, miR-1238-5p is hsa-miR-1238-5p, miR-6880-5p is hsa-miR-6880-5p, miR-8072 is hsa-miR-8072, miR-4723-5p is hsa-miR-4723-5p, miR-4732-5p is hsa-miR-4732-5p, miR-6125 is hsa-miR-6125, miR-6090) is hsa-miR-6090, miR-7114-5p is hsa-miR-7114-5p, miR-564 is hsa-miR-564, miR-451a is hsa-miR-451a, miR-3135b is hsa-miR-3135b, miR-4497 is hsa-miR-4497, miR-4665-5p is hsa-miR-4665-5p, miR-3622a-5p is hsa-miR-3622a-5p, miR-6850-5p is hsa-miR-6850-5p, miR-6821-5p is hsa-miR-6821-5p, miR-5100 is hsa-miR-5100, miR-6872-3p is hsa-miR-6872-3p, miR-4433-3p is hsa-miR-4433-3p, miR-1227-5p is hsa-miR-1227-5p, miR-3188 is hsa-miR-3188, miR-7704 is hsa-miR-7704, miR-3185 is hsa-miR-3185, miR-1908-3p is hsa-miR-1908-3p, miR-6781-5p is hsa-miR-6781-5p, miR-6805-5p is hsa-miR-6805-5p, miR-8089 is hsa-miR-8089, miR-665 is hsa-miR-665, miR-4486 is hsa-miR-4486, miR-6722-3p is hsa-miR-6722-3p, miR-1260a is hsa-miR-1260a, miR-4707-5p is hsa-miR-4707-5p, miR-6741-5p is hsa-miR-6741-5p, miR-1260b is hsa-miR-1260b, miR-1246 is hsa-miR-1246, miR-6845-5p is hsa-miR-6845-5p, miR-4638-5p is hsa-miR-4638-5p, miR-6085 is hsa-miR-6085, miR-1228-3p is hsa-miR-1228-3p, miR-4534 is hsa-miR-4534, miR-5585-3p is hsa-miR-5585-3p, miR-4741 is hsa-miR-4741, miR-4433b-3p is hsa-miR-4433b-3p, miR-197-5p is hsa-miR-197-5p, miR-718 is hsa-miR-718, miR-4513 is hsa-miR-4513, miR-4446-3p is hsa-miR-4446-3p, miR-619-5p is hsa-miR-619-5p, miR-6816-5p is hsa-miR-6816-5p, miR-6778-5p is hsa-miR-6778-5p, miR-24-3p is hsa-miR-24-3p, miR-1915-3p is hsa-miR-1915-3p, miR-4665-3p is hsa-miR-4665-3p, miR-4449 is hsa-miR-4449, miR-6889-5p is hsa-miR-6889-5p, miR-486-3p is hsa-miR-486-3p, miR-7113-3p is hsa-miR-7113-3p, miR-642a-3p is hsa-miR-642a-3p, miR-7847-3p is hsa-miR-7847-3p, miR-6768-5p is hsa-miR-6768-5p, miR-1290 is hsa-miR-1290, miR-7108-5p is hsa-miR-7108-5p, miR-92b-5p is hsa-miR-92b-5p, miR-663b is hsa-miR-663b, miR-3940-5p is hsa-miR-3940-5p, miR-4467 is hsa-miR-4467, miR-6858-5p is hsa-miR-6858-5p, miR-4417 is hsa-miR-4417, miR-3665 is hsa-miR-3665, miR-4736 is hsa-miR-4736, miR-4687-3p is hsa-miR-4687-3p, miR-1908-5p is hsa-miR-1908-5p, miR-5195-3p is hsa-miR-5195-3p, miR-4286 is hsa-miR-4286, miR-3679-3p is hsa-miR-3679-3p, miR-6791-5p is hsa-miR-6791-5p, miR-1202 is hsa-miR-1202, miR-3656 is hsa-miR-3656, miR-4746-3p is hsa-miR-4746-3p, miR-3184-5p is hsa-miR-3184-5p, miR-3937 is hsa-miR-3937, miR-6515-3p is hsa-miR-6515-3p, miR-6132 is hsa-miR-6132, miR-187-5p is hsa-miR-187-5p, miR-7111-5p is hsa-miR-7111-5p, miR-5787 is hsa-miR-5787, miR-6779-5p is hsa-miR-6779-5p, miR-4516 is hsa-miR-4516, miR-4649-5p is hsa-miR-4649-5p, miR-760 is hsa-miR-760, miR-3162-5p is hsa-miR-3162-5p, miR-3178 is hsa-miR-3178, miR-940 is hsa-miR-940, miR-4271 is hsa-miR-4271, miR-6769b-5p is hsa-miR-6769b-5p, miR-4508 is hsa-miR-4508, miR-6826-5p is hsa-miR-6826-5p, miR-6757-5p is hsa-miR-6757-5p, miR-3131 is hsa-miR-3131, and miR-1343-3p is hsa-miR-1343-3p.

In a preferred embodiment of the method of the present invention, specifically, the nucleic acid (specifically, probe or primer) is selected from the group consisting of the following polynucleotides (a) to (e):

(a) a polynucleotide consisting of a nucleotide sequence represented by any of SEQ ID NOs: 1 to 125 and 466 to 478 or a nucleotide sequence derived from the nucleotide sequence by the replacement of u with t, a variant thereof, a derivative thereof, or a fragment thereof comprising 15 or more consecutive nucleotides.

(b) a polynucleotide comprising a nucleotide sequence represented by any of SEQ ID NOs: 1 to 125 and 466 to 478, (c) a polynucleotide consisting of a nucleotide sequence complementary to a nucleotide sequence represented by any of SEQ ID NOs: 1 to 125 and 466 to 478, or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 125 and 466 to 478 or a nucleotide sequence derived from the nucleotide sequence by the replacement of u with t, and (e) a polynucleotide hybridizing under stringent conditions to any of the polynucleotides (a) to (d).

In the method of the present invention, nucleic acid(s) capable of specifically binding to at least one or more polynucleotide(s) selected from the followings: miR-6808-5p, miR-6774-5p, miR-4656, miR-6806-5p, miR-1233-5p, miR-328-5p, miR-4674, miR-2110, miR-6076, miR-3619-3p, miR-92a-2-5p, miR-128-1-5p, miR-638, miR-2861, miR-371a-5p, miR-211-3p, miR-1273g-3p, miR-1203, miR- 122-5p, miR-4258, miR-4484, miR-4648, miR-6780b-5p, miR-4516, miR-4649-5p, miR-760, miR-3162-5p, miR-3178, miR-940, miR-4271, miR-6769b-5p, miR-4508, miR-6826-5p, miR-6757-5p, miR-3131, and miR-1343-3p may be further used.

In a preferred embodiment, such a nucleic acid is specifically as follows: miR-6808-5p is hsa-miR-6808-5p, miR-6774-5p is hsa-miR-6774-5p, miR-4656 is hsa-miR-4656, miR-6806-5p is hsa-miR-6806-5p, miR-1233-5p is hsa-miR-1233-5p, miR-328-5p is hsa-miR-328-5p, miR-4674 is hsa-miR-4674, miR-2110 is hsa-miR-2110, miR-6076 is hsa-miR-6076, miR-3619-3p is hsa-miR-3619-3p, miR-92a-2-5p is hsa-miR-92a-2-5p, miR-128-1-5p is hsa-miR-128-1-5p, miR-638 is hsa-miR-638, miR-2861 is hsa-miR-2861, miR-371a-5p is hsa-miR-371a-5p, miR-211-3p is hsa-miR-211-3p, miR-1273g-3p is hsa-miR-1273g-3p, miR-1203 is hsa-miR-1203, miR-122-5p is hsa-miR-122-5p, miR-4258 is hsa-miR-4258, miR-4484 is hsa-miR-4484, miR-4648 is hsa-miR-4648, miR-6780b-5p is hsa-miR-6780b-5p, miR-4516 is hsa-miR-4516, miR-4649-5p is hsa-miR-4649-5p, miR-760 is hsa-miR-760, miR-3162-5p is hsa-miR-3162-5p, miR-3178 is hsa-miR-3178, miR-940 is hsa-miR-940, miR-4271 is hsa-miR-4271, miR-6769b-5p is hsa-miR-6769b-5p, miR-4508 is hsa-miR-4508, miR-6826-5p is hsa-miR-6826-5p, miR-6757-5p is hsa-miR-6757-5p, miR-3131 is hsa-miR-3131, and miR-1343-3p is hsa-miR-1343-3p.

In a preferred embodiment, specifically, such a nucleic acid is further selected from the group consisting of the following polynucleotides (f) to (j):

(f) a polynucleotide consisting of a nucleotide sequence represented by any of SEQ ID NOs: 126 to 148 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 126 to 148, (h) a polynucleotide consisting of a nucleotide sequence complementary to a nucleotide sequence represented by any of SEQ ID NOs: 126 to 148 or a nucleotide sequence derived from the nucleotide sequence by the replacement of u with t, a variant thereof, a derivative thereof, or a fragment thereof that comprises 15 or more consecutive nucleotides, (i) a polynucleotide comprising a nucleotide sequence complementary to a nucleotide sequence represented by any of SEQ ID NOs: 126 to 148 or a nucleotide sequence derived from the nucleotide sequence by the replacement of u with t, and (j) a polynucleotide hybridizing under stringent conditions to any of the polynucleotides (f) to (i).

Examples of the sample used in the method of the present invention can include samples prepared from a living tissue (preferably a biliary tract tissue) or a body fluid such as blood, serum, plasma, or urine of the subject. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

The subject used herein refers to a mammal, for example, a human, a monkey, a mouse and a rat, without any limitation, and is preferably a human.

The steps of the method of the present invention can be changed according to the type of the sample to be assayed.

In the case of using RNA as an analyte, the detection of biliary tract cancer (cells) may comprise, for example, the following steps (a), (b), and (c):

(a) binding RNA prepared from the sample of a subject or a complementary polynucleotide (cDNA) transcribed therefrom to a polynucleotide in the kit or the device of the present invention;

(b) measuring the sample-derived RNA or the cDNA synthesized from the RNA, bound with the polynucleotide by hybridization using the polynucleotide as a nucleic acid probe or by quantitative RT-PCR using the polynucleotide as a primer; and (c) evaluating the presence or absence of biliary tract cancer (or biliary tract cancer-derived gene expression) on the basis of the measurement results of the step (b).

For example, various hybridization methods can be used for detecting, examining, evaluating, or diagnosing biliary tract cancer (or biliary tract cancer-derived gene expression) in vitro according to the present invention. For example, Northern blot, Southern blot, RT-PCR, DNA chip analysis, in situ hybridization. Northern hybridization, or Southern hybridization can be used as such a hybridization method.

In the case of using the Northern blot, the presence or absence of expression of each gene or the expression level thereof in the RNA can be detected or measured by use of the nucleic acid probe that can be used in the present invention. Specific examples thereof can include a method which comprises labeling the nucleic acid probe (or a complementary strand) with a radioisotope ($^{32}$p, $^{33}$P, $^{35}$S, etc.), a fluorescent material, or the like, hybridizing the labeled product with the living tissue-derived RNA from the subject, which is transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which comprises preparing cDNA from the living tissue-derived RNA of the subject according to a routine method, hybridizing a pair of primers (that consist of a plus strand and a reverse strand binding to the cDNA) of the present invention with the cDNA such that the region of each target gene can be amplified with the cDNA as a template, and performing PCR according to a routine method to detect the obtained double-stranded DNA. The method for detecting the double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the nucleic acid probes (single-stranded or double-stranded) of the present invention are attached to a substrate (solid phase) is used. Regions having the attached nucleic acid probes are referred to as probe spots, and regions having no attached nucleic acid probe are referred to as blank spots. A group of genes immobilized on a solid-phase substrate is generally called a nucleic acid chip, a nucleic acid array, a microarray, or the like. The DNA or RNA array includes a DNA or RNA macroarray and a DNA or RNA microarray. The term "chip" used herein includes all of these arrays. 3D-Gene® Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal derived from the label on the nucleic acid probe using an image detector (examples thereof can include Typhoon 9410 (GE Healthcare Japan Corp.) and 3D-Gene® scanner (Toray Industries, Inc.)).

The "stringent conditions" used herein are, as mentioned above, conditions under which a nucleic acid probe hybridizes to its target sequence to a larger extent (e.g., a measurement value equal to or larger than a mean of background measurement values+a standard deviation of the background measurement values×2) than that for other sequences.

The stringent conditions are defined by conditions for hybridization and subsequent washing. Examples of the hybridization conditions include, but not limited to, 30° C. to 60° C. for 1 to 24 hours in a solution containing SSC, a surfactant, formamide, dextran sulfate, a blocking agent, etc. In this context, 1×SSC is an aqueous solution (pH 7.0) that contains 150 mM sodium chloride and 15 mM sodium citrate. The surfactant includes, for example, SDS (sodium dodecyl sulfate), Triton, or Tween. The hybridization conditions more preferably comprise 3 to 10×SSC and 0.1 to 1% SDS. Examples of the conditions for the washing, following the hybridization, which is another condition to define the stringent conditions, can include conditions comprising continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by the washing under such conditions. Specifically, examples of such a complementary strand can include a strand consisting of a nucleotide sequence in a completely complementary relationship with the nucleotide sequence of the target plus (+) strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using a polynucleotide fragment in the kit of the present invention as a primer include treatment for approximately 15 seconds to 1 minute at 5 to 10° C. plus a Tm value calculated from the sequence of the primer, using a PCR buffer having composition such as 10 mM Tris-HCL (pH 8.3), 50 mM KCL, and 1 to 2 mM $MgCl_2$. Examples of the method for calculating such a Tm value include Tm value=2×(the number of adenine residues+the number of thy mine residues)+4×(the number of guanine residues+the number of cytosine residues).

In the case of using the quantitative RT-PCR, a commercially available kit for measurement specially designed for quantitatively measuring miRNA, such as TaqMan® MicroRNA Assays (Life Technologies Corp.). LNA®-based MicroRNA PCR (Exiqon), or Ncode® miRNA qRT-PCT kit (Invitrogen Corp.) may be used.

For the calculation of gene expression levels, statistical analysis described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of $2^6$, preferably $2^8$, more preferably $2^{10}$, or larger, in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method comprising measuring a target gene or gene expression level in a sample derived from a subject using the polynucleotide, the kit, or the device (e.g., chip) for detection of the present invention, or a combination thereof, preparing a discriminant (discriminant function) with gene expression levels in a sample derived from a biliary tract cancer patient and a sample derived from a healthy subject as supervising samples, and determining or evaluating the presence and/or absence of the biliary tract cancer-derived gene in the sample.

Specifically, the present invention further provides the method comprising: a first step of measuring in vitro an expression level of a target gene (target nucleic acid) in multiple samples known to determine or evaluate the presence or absence of the biliary tract cancer-derived gene in the samples, using the polynucleotide, the kit, or the device (e.g., chip) for detection of the present invention, or a combination thereof; a second step of preparing a discriminant with the measurement values of the expression level of the target gene obtained in the first step as supervising samples; a third step of measuring in vitro an expression level of the target gene in a sample derived from a subject in the same way as in the first step; and a fourth step of substituting the measurement value of the expression level of the target gene obtained in the third step into the discriminant obtained in the second step, and determining or evaluating the presence and/or absence of the biliary tract cancer-derived gene in the sample on the basis of the results obtained from the discriminant, wherein the target gene can be detected using the polynucleotide or using a polynucleotide for detection contained in the kit or the device (e.g., chip). In this context, the discriminant can be prepared by use of Fisher's linear discriminant analysis, nonlinear discriminant analysis based on Mahalanobis' distance, neural network, Support Vector Machine (SVM), or the like, though the method is not limited thereto.

When a clustering boundary is a straight line or a hyperplane, the linear discriminant analysis is a method for determining the association of a cluster using Formula 1 as a discriminant. In Formula 1, x represents an explanatory variable, w represents a coefficient of the explanatory variable, and $w_0$ represents a constant term.

$$f(x) = w_0 + \sum_{i=1}^{n} w_i x_i \qquad \text{Formula 1}$$

Values obtained from the discriminant are referred to as discriminant scores. The measurement values of a newly offered data set can be substituted as explanatory variables into the discriminant to determine clusters on the basis of the signs of the discriminant scores.

The Fisher's linear discriminant analysis, one type of linear discriminant analysis, is a dimensionality reduction method for selecting a dimension suitable for discriminating classes, and constructs a highly discriminating synthetic variable by focusing on the variance of the synthetic variables and minimizing the variance of data that has the same label (Venables, W. N. et al., Modern Applied Statistics with S. Fourth edition. Springer., 2002). In the Fisher's linear discriminant analysis, direction w of projection is determined so as to maximize Formula 2. In Formula 2, μrepresents an average input, ng represents the number of data associated to class g, and μg represents an average input of the data associated to class g. The numerator and the denominator are interclass variance and intraclass variance, respectively, when each data is projected in the direction of the vector w. Discriminant coefficient w is determined by maximizing this ratio (Takafumi Kanamori et al., "Pattern Recognition", Kyoritsu Shuppan Co., Ltd. (2009); and Richard O. et al., Pattern Classification Second Edition., Wiley-Interscience, 2000).

$$J(w) = \frac{\sum_{g=1}^{G} n_g (w^T\mu_g - w^T\mu)(w^T\mu_g - w^T\mu)^T}{\sum_{g=1}^{G} \sum_{i:y_i=g} (w^T x_i - w^T\mu_g)(w^T x_i - w^T\mu_g)} \qquad \text{Formula 2}$$

$$\text{subject to } \mu = \sum_{i=1}^{n} \frac{x_i}{n},\ \mu_g = \sum_{i:u_i=g}^{n} \frac{x_i}{n_g}$$

The Mahalanobis' distance is calculated according to Formula 3 in consideration of data correlation and can be used as nonlinear discriminant analysis for determining a cluster to which a data point is associated, based on a short Mahalanobis' distance from the data point to that cluster. In Formula 3, p represents a central vector of each cluster, and $S^{-1}$ represents an inverse matrix of the variance-covariance matrix of the cluster. The central vector is calculated from explanatory variable x, and an average vector, a median value vector, or the like can be used.

$$D(x, \mu) = \{(x-\mu)^t S^{-1} (x-\mu)\}^{\frac{1}{2}} \qquad \text{Formula 3}$$

SVM is a discriminant analysis method devised by V. Vapnik (The Nature of Statistical Leaning Theory, Springer, 1995). Particular data points of a data set that has known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be substituted as explanatory variables into the discriminant to determine classes. In this respect, the result of the discriminant analysis may be classes, may be a probability of being classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, a RBF (radial basis function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (2004); Nello Cristianini et al., Introduction to SVM, Kyoritsu Shuppan Co., Ltd. (2008)).

C-support vector classification (C-SVC), one type of SVM, comprises preparing a hyperplane by supervising with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention is given below. First, all subjects are divided into two groups, i.e., a biliary tract cancer patient group and a healthy subject group. For example, biliary tract tissue examination can be used for confirming each subject either as a biliary tract patient or as a healthy subject.

Next, a data set consisting of comprehensive gene expression levels of serum-derived samples of the two divided groups (hereinafter, this data set is referred to as a training cohort) is prepared, and a C-SVC discriminant is determined by using genes found to differ clearly in their gene expression levels between the two groups as explanatory variables and objective variables (e.g., −1 and +1) that is this grouping. An optimizing objective function is represented by Formula 4 wherein e represents all input vectors. y represents an objective variable, a represents a Lagrange's undetermined multiplier vector, Q represents a positive definite matrix, and C represents a parameter for adjusting constrained conditions.

$$\min_a \frac{1}{2} a^T Q a - e^T a \qquad \text{Formula 4}$$

$$\text{subject to } y^T a = 0,\ 0 \le a_i \le C,\ i = 1, \ldots, l,$$

Formula 5 is a finally obtained discriminant, and a group to which the data point is associated can be determined on the basis of the sign of a value obtained according to the discriminant. In this formula, x represents a support vector, y represents a label indicating the associated group, a represents the corresponding coefficient, b represents a constant term, and K represents a kernel function.

$$f(x) = \mathrm{sgn}\left(\sum_{i=1}^{l} y_i a_i K(x_i, x) + b\right) \quad \text{Formula 5}$$

For example, a RBF kernel defined by Formula 6 can be used as the kernel function. In this formula, x represents a support vector, and y represents a kernel parameter for adjusting the complexity of the hyperplane.

$$K(x_i,x_j)=\exp(-r\|x_i-x_j\|^2),\ r<0 \quad \text{Formula 6}$$

In addition, an approach such as neural network, k-nearest neighbor algorithms, decision trees, or logistic regression analysis can be selected as a method for determining or evaluating the presence and/or absence of expression of a biliary tract cancer-derived target gene in a sample derived from a subject, or for evaluating the expression level thereof by comparison with a control derived from a healthy subject.

The method of the present invention can comprise, for example, the following steps (a), (b), and (c):

(a) measuring an expression level of a target gene in tissues containing biliary tract cancer-derived genes derived from biliary tract cancer patients and/or samples that are already known to contain no biliary tract cancer-derived gene derived from healthy subjects, using the polynucleotide, the kit, or the device (e.g., DNA chip) for detection according to the present invention;

(b) preparing the discriminants of Formulas 1 to 3, 5, and 6 described above from the measurement values of the expression level measured in the step (a); and (c) measuring an expression level of the target gene in a sample derived from a subject using the polynucleotide, the kit, or the device (e.g., DNA chip) for detection according to the present invention, substituting the measurement value into the discriminants prepared in the step (b), and determining or evaluating the presence and/or absence of the biliary tract cancer-derived target gene in the sample, or evaluating the expression level thereof by comparison with a healthy subject-derived control, on the basis of the obtained results. In this context, in the discriminants of Formulas 1 to 3, 5, and 6, x represents an explanatory variable and includes a value obtained by measuring a polynucleotide selected from the polynucleotides described above in Section 2, or a fragment thereof, etc. Specifically, the explanatory variable for discriminating a biliary tract cancer patient from a healthy subject according to the present invention is a gene expression level selected from, for example, the following expression levels (1) to (2):

(1) a gene expression level in the serum of a biliary tract cancer patient or a healthy subject measured by any DNA comprising 15 or more consecutive nucleotides in a nucleotide sequence represented by any of SEQ ID NOs: 1 to 125 and 466 to 478 or a complementary sequence thereof, and (2) a gene expression level in the serum of a biliary tract cancer patient or a healthy subject measured by any DNA comprising 15 or more consecutive nucleotides in a nucleotide sequence represented by any of SEQ ID NOs: 126 to 148 or a complementary sequence thereof.

As described above, for the method for determining or evaluating the presence and/or absence of a biliary tract cancer-derived gene in a sample derived from a subject, the preparation of a discriminant requires a discriminant prepared in a training cohort. For enhancing the discrimination accuracy of the discriminant, it is necessary for the discriminant to use genes that show clear difference between two groups in the training cohort when preparing the discriminant.

Each gene that is used for an explanatory variable in a discriminant is preferably determined as follows. First, comprehensive gene expression levels of a biliary tract cancer patient group and comprehensive gene expression levels of a healthy subject group, both of which are in a training cohort, are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) of the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the test, the absolute value (fold change) of an expression ratio of a median value of each gene expression level between gene expression levels of a biliary tract cancer patient group and gene expression levels of a healthy subject group may be calculated to select a gene that is used for an explanatory variable in a discriminant. Alternatively, ROC curves may be prepared using gene expression levels of a biliary tract cancer patient group and a healthy subject group, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discrimination accuracy include a method of constructing a discriminant in every combination of genes that satisfy the significance level being a P value, and a method of repetitively evaluating the genes for use in the construction of a discriminant while increasing the number of genes one by one in a descending order of difference in gene expression level (Furey T S. et al., 2000, Bioinformatics., Vol. 16, p. 906-14). A gene expression level of another independent biliary tract cancer patient or healthy subject is substituted as an explanatory variable into this discriminant to calculate discrimination results of the group to which this independent biliary tract cancer patient or healthy subject is associated. Specifically, the found gene set for diagnosis and the discriminant constructed using the gene set for diagnosis can be evaluated in an independent sample cohort to find a more universal gene set for diagnosis capable of detecting biliary tract cancer and a more universal method for discriminating biliary tract cancer.

Split-sample method is preferably used for evaluating the discriminant performance (generality) of the discriminant. Specifically, a data set is divided into a training cohort and a validation cohort, and gene selection by a statistical test and discriminant preparation are performed using the training cohort. To evaluate the performance of the discriminant, accuracy, sensitivity, and specificity are calculated using a result of discriminant analysis in a validation cohort according to the discriminant and a true group to which the validation cohort is associated. On the other hand, instead of dividing a data set, the gene selection by a statistical test and discriminant preparation may be performed using all of samples, and accuracy, sensitivity, and specificity can be calculated by the discriminant analysis using a newly prepared sample cohort for evaluation of the performance of the discriminant.

The present invention provides a polynucleotide for detection or for disease diagnosis useful in the diagnosis and treatment of biliary tract cancer, a method for detecting biliary tract cancer using the polynucleotide, and a kit and a device for the detection of biliary tract cancer, comprising the polynucleotide. Particularly, in order to select a gene for diagnosis and prepare a discriminant so as to exhibit accuracy beyond a biliary tract cancer diagnostic method using existing tumor markers CEA and CA19-9, a gene set for diagnosis and a discriminant for the method of the present invention can be constructed, which exhibit accuracy beyond CEA and CA19-9, for example, by comparing expressed genes in serum derived from a patient confirmed to be negative using CEA and CA19-9 but finally found to have biliary tract cancer by detailed examination such as computed tomography using a contrast medium, with genes expressed in serum derived from a patient having no biliary tract cancer.

For example, the gene set for diagnosis is set to any combination selected from one or two or more of the polynucleotides based on a nucleotide sequence represented by any of SEQ ID NOs: 1 to 125 and 466 to 478 or a complementary sequence thereof as described above; and optionally one or two or more of the polynucleotides based on a nucleotide sequence represented by any of SEQ ID NOs: 126 to 148 or a complementary sequence thereof. Further, a discriminant is constructed using expression levels of the gene set for diagnosis in samples derived from class I biliary tract cancer patients as a result of tissue diagnosis and samples derived from class II healthy subjects as a result of tissue diagnosis. As a result, the presence or absence of biliary tract cancer-derived genes in an unknown sample can be determined with 100% accuracy at the maximum by measuring expression levels of the gene set for diagnosis in an unknown sample.

EXAMPLES

Hereinafter, the present invention is described further specifically with reference to Examples below. However, the scope of the present invention is not intended to be limited by these Examples.

Reference Example 1

<Collection of Samples from Biliary Tract Cancer Patients and Healthy Subjects>

Sera were collected using VENOJECT II vacuum blood collecting tube VP-AS109K60 (Terumo Corp.) from 100 healthy subjects and 67 biliary tract cancer patients (1 case with stage IA, 8 cases with stage IB, 8 cases with stage II, 3 cases with stage IIA, 5 cases with stage IIB, 14 cases with stage III, 2 cases with stage IIIB, 1 case with stage IVa, and 25 cases with stage IVb) confirmed to have no primary cancer in organs other than the biliary tract after acquisition of informed consent, and used as a training cohort. Likewise, sera were collected using VENOJECT II vacuum blood collecting tube VP-AS109K60 (Terumo Corp.) from 50 healthy subjects and 33 biliary tract cancer patients (1 case with stage 0, 2 cases with stage I, 1 case with stage IA, 2 cases with stage IB, 2 cases with stage 11, 5 cases with stage IIA, 4 cases with stage IIB, 5 cases with stage III, 1 case with stage IV, 1 case with stage IVa, and 9 cases with stage IVb) confirmed to have no primary cancer in organs other than biliary tract after acquisition of informed consent, and used as a validation cohort.

<Extraction of Total RNA>

Total RNA was obtained from 300 μL of the serum sample obtained from each of 250 persons in total of 150 healthy subjects and 100 biliary tract cancer patients included in the training cohort and the validation cohort, using a reagent for RNA extraction in 3D-Gene® RNA extraction reagent from liquid sample kit (Toray Industries, Inc.) according to the protocol provided by the manufacturer.

<Measurement of Gene Expression Level> miRNAs in the total RNA obtained from the serum samples of each of 250 persons in total of 150 healthy subjects and 100 biliary tract cancer patients included in the training cohort and the validation cohort were fluorescently labeled using 3D-Gene® miRNA Labeling kit (Toray Industries, Inc.) according to the protocol (ver. 2.20) provided by the manufacturer. The oligo DNA chip used was 3D-Gene® Human miRNA Oligo chip (Toray Industries, Inc.) with attached probes having sequences complementary to 2,555 miRNAs among the miRNAs registered in miRBase Release 20. Hybridization between the miRNAs in the total RNA and the probes on the DNA chip under stringent conditions and washing following the hybridization were performed according to the protocol provided by the manufacturer. The DNA chip was scanned using 3D-Gene® scanner (Toray Industries, Inc.) to obtain images. Fluorescence intensity was digitized using 3D-Gene® Extraction (Toray Industries, Inc.). The digitized fluorescence intensity was converted to a logarithmic value having a base of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the sera were obtained for the 100 biliary tract cancer patients and the 150 healthy subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/.) and MASS package 7.3-30 (Venables, W. N. & Ripley, B. D. (2002) Modern Applied Statistics with S. Fourth Edition. Springer, New York. ISBN 0-387-95457-0).

Reference Example 2

<Collection of Samples from Patients with Other Cancers and Benign Diseases>

Sera were collected using VENOJECT II vacuum blood collecting tube VP-AS109K60 (Terumo Corp.) from each of 35 colorectal cancer patients, 37 stomach cancer patients, 32 esophageal cancer patients, 38 liver cancer patients, and 13 benign pancreaticobiliary disease patients confirmed to have no cancer in other organs after acquisition of informed consent, and used as a training cohort together with the samples of 67 biliary tract cancer patients (1 case with stage 0, 2 cases with stage I, 1 case with stage IA, 4 cases with stage IB, 8 cases with stage II, 4 cases with stage IIA, 6 cases with stage IIB, 14 cases with stage III, 1 case with stage IIIB, 25 cases with stage IV, and 1 case with stage IVa) and 93 healthy subjects of Reference Example 1. Likewise, sera were collected using VENOJECT II vacuum blood collecting tube VP-AS109K60 (Terumo Corp.) from each of 15 colorectal cancer patients, 13 stomach cancer patients, 18 esophageal cancer patients, 12 liver cancer patients, and 8 benign pancreaticobiliary disease patients confirmed to have no cancer in other organs after acquisition of informed consent, and used as a validation cohort together with the samples of 33 biliary tract cancer patients (1 case with stage IA, 6 cases with stage IB, 2 cases with stage II, 4 cases with stage IIA, 3 cases with stage IIB, 5 cases with stage III, 1 case with stage IIIB, and 11 cases with stage IV) and 57 healthy subjects of Reference Example 1. Subsequent extraction of total RNA and measurement and analysis of gene expression levels were conducted in the same way as in Reference Example 1.

Example 11

<Selection of Gene Marker Using Samples in the Training Cohort, and Method for Evaluating Cancer Discriminant Performance of Single Gene Marker Using Samples in the Validation Cohort>

In this Example, a gene marker for discriminating a biliary tract cancer patient from a healthy subject was selected from the training cohort, and a method for evaluating biliary tract cancer discriminant performance of each selected gene marker alone was studied in samples of the validation cohort independent from the training cohort.

Specifically, first, the miRNA expression levels of the training cohort and the validation cohort obtained in Reference Example 1 above were combined and normalized by quantile normalization.

Next, genes for diagnosis were selected using the training cohort. Here, in order to acquire diagnostic markers with higher reliability, only genes having the gene expression level of $2^6$ or higher in 50% or more of the samples in either of the biliary tract cancer patient group in the training cohort or the healthy subject group in the training cohort were selected. In order to further acquire statistically significant genes for discriminating a biliary tract cancer patient group from a healthy subject group, the P value obtained by two-tailed t-test assuming equal variance as to each gene expression level was corrected by the Bonferroni method, and genes that satisfied $p<0.01$ were acquired as gene markers for use in explanatory variables of a discriminant. The obtained genes are described in Table 2.

In this way, hsa-miR-125a-3p, hsa-miR-6893-5p, hsa-miR-204-3p, hsa-miR-4476, hsa-miR-4294, hsa-miR-150-3p, hsa-miR-6729-5p, hsa-miR-7641, hsa-miR-6765-3p, hsa-miR-6820-5p, hsa-miR-575, hsa-miR-6836-3p, hsa-miR-1469, hsa-miR-663a, hsa-miR-6075, hsa-miR-4634, hsa-miR-423-5p, hsa-miR-4454, hsa-miR-7109-5p, hsa-miR-6789-5p, hsa-miR-6877-5p, hsa-miR-4792, hsa-miR-4530, hsa-miR-7975, hsa-miR-6724-5p, hsa-miR-8073, hsa-miR-7977, hsa-miR-1231, hsa-miR-6799-5p, hsa-miR-615-5p, hsa-miR-4450, hsa-miR-6726-5p, hsa-miR-6875-5p, hsa-miR-4734, hsa-miR-16-5p, hsa-miR-602, hsa-miR-4651, hsa-miR-8069, hsa-miR-1238-5p, hsa-miR-6880-5p, hsa-miR-8072, hsa-miR-4723-5p, hsa-miR-4732-5p, hsa-miR-6125, hsa-miR-6090, hsa-miR-7114-5p, hsa-miR-564, hsa-miR-451a, hsa-miR-3135b, hsa-miR-4497, hsa-miR-4665-5p, hsa-miR-3622a-5p, hsa-miR-6850-5p, hsa-miR-6821-5p, hsa-miR-5100, hsa-miR-6872-3p, hsa-miR-4433-3p, hsa-miR-1227-5p, hsa-miR-3188, hsa-miR-7704, hsa-miR-3185, hsa-miR-1908-3p, hsa-miR-6781-5p, hsa-miR-6805-5p, hsa-miR-8089, hsa-miR-665, hsa-miR-4486, hsa-miR-6722-3p, hsa-miR-1260a, hsa-miR-4707-5p, hsa-miR-6741l-5p, hsa-miR-1260b, hsa-miR-1246, hsa-miR-6845-5p, hsa-miR-4638-5p, hsa-miR-6085, hsa-miR-1228-3p, hsa-miR-4534, hsa-miR-5585-3p, hsa-miR-4741, hsa-miR-4433b-3p, hsa-miR-1197-5p, hsa-miR-718, hsa-miR-4513, hsa-miR-4446-3p, hsa-miR-6119-5p, hsa-miR-6816-5p, hsa-miR-6778-5p, hsa-miR-24-3p, hsa-miR-1915-3p, hsa-miR-4665-3p, hsa-miR-4449, hsa-miR-6889-5p, hsa-miR-486-3p, hsa-miR-7113-3p, hsa-miR-642a-3p, hsa-miR-7847-3p, hsa-miR-6768-5p, hsa-miR-1290, hsa-miR-7108-5p, hsa-miR-92b-5p, hsa-miR-663b, hsa-miR-3940-5p, hsa-miR-4467, hsa-miR-6858-5p, hsa-miR-4417, hsa-miR-3665, hsa-miR-4736, hsa-miR-4687-3p, hsa-miR-1908-5p, hsa-miR-5195-3p, hsa-miR-4286, hsa-miR-3679-3p, hsa-miR-6791-5p, hsa-miR-1202, hsa-miR-3656, hsa-miR-4746-3p, hsa-miR-3184-5p, hsa-miR-3937, hsa-miR-6515-3p, hsa-miR-6132, hsa-miR-187-5p, hsa-miR-7111-5p, hsa-miR-5787 and hsa-miR-6779-5p genes represented by SEQ ID NOs: 1 to 125 related thereto were found as biliary tract cancer markers relative to the healthy subjects.

A discriminant for determining the presence or absence of biliary tract cancer was further prepared by Fisher's linear discriminant analysis with the expression levels of these genes as an indicator. Specifically, any newly found polynucleotide consisting of a nucleotide sequence represented by any of SEQ ID NOs: 1 to 125 among the 125 genes selected in the training cohort was applied to Formula 2 to construct a discriminant. Calculated accuracy, sensitivity, and specificity are shown in Table 3. In this respect, a discriminant coefficient and a constant term are shown in Table 4.

Figure 2:
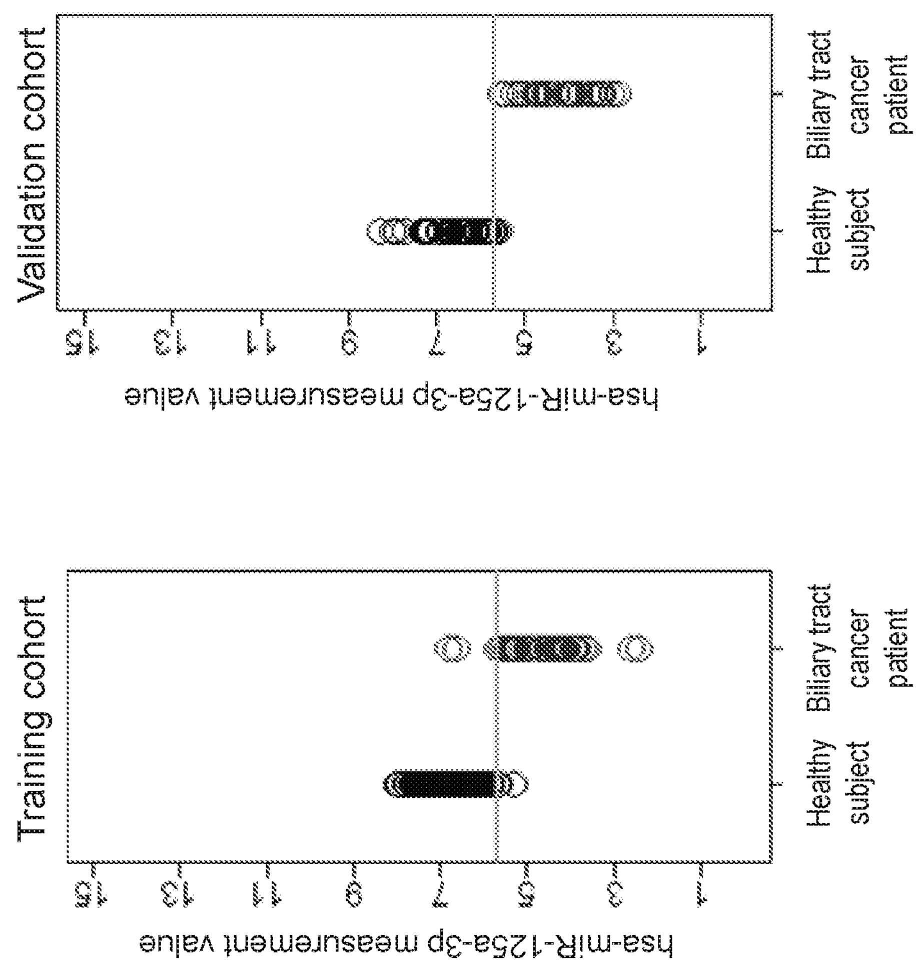
FIG. 2 Left diagram: the measurement values of hsa-miR-125a-3p (SEQ ID NO: 1) in healthy subjects (100 persons) and biliary tract cancer patients (67 persons) selected as a training cohort were each plotted on the ordinate. The horizontal line in the diagram depicts a threshold (5.69) that was optimized by Fisher's linear discriminant analysis and discriminated between the two groups. Right diagram: the measurement values of hsa-miR-125a-3p (SEQ ID NO: 1) in healthy subjects (50 persons) and biliary tract cancer patients (33 persons) selected as a validation cohort were each plotted on the ordinate. The horizontal line in the diagram depicts the threshold (5.69) that was set in the training cohort and discriminated between the two groups.

Accuracy, sensitivity, and specificity in the validation cohort were calculated using the discriminant thus prepared, and the discriminant performance of the selected polynucleotides was validated using the independent samples (Table 3). For example, the expression level measurement value of the nucleotide sequence represented by SEQ ID NO: 1 was compared between the healthy subjects (100 persons) and the biliary tract cancer patients (67 persons) in the training cohort. As a result, the gene expression level measurement values were found to be significantly lower in the biliary cancer patient group than in the healthy subject group (see the left diagram of FIG. 2). These results were also reproducible in the healthy subjects (50 persons) and the biliary tract cancer patients (33 persons) in the validation cohort (see the right diagram of FIG. 2). Likewise, the results obtained about the other polynucleotides shown in SEQ ID NOs: 2 to 125 showed that the gene expression level measurement values were significantly lower (−) or higher (+) in the biliary tract cancer patient group than in the healthy subject group (Table 2). These results were able to be validated in the validation cohort. For example, as for this nucleotide sequence represented by SEQ ID NO: 1, the number of correctly identified samples in the detection of biliary tract cancer was calculated using the threshold (5.69) that was set in the training cohort and discriminated between the two groups. As a result, 33 true positives, 49 true negatives, 1 false positive, and 0 false negatives were obtained. From these values, 99%6 accuracy, 100% sensitivity, and 98% specificity were obtained as the detection performance. In this way, the detection performance was calculated as to all of the polynucleotides shown in SEQ ID NOs: 1 to 125, and described in Table 3.

Among the polynucleotides consisting of the nucleotide sequences represented by SEQ ID NOs: 1 to 125 shown in Table 2, for example, 62 polynucleotides consisting of the nucleotide sequences represented by SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 34, 35, 36, 39, 40, 41, 42, 44, 45, 46, 47, 49, 50, 51, 52, 53, 54, 60, 62, 64, 65, 67, 68, 70, 74, 75, 76, 83, 84, 105, 107 exhibited sensitivity of 100%, 97%, 97%, 100%, 84.8%, 90.9%, 87.9%, 90.9%, 66.7%, 87.9%, 93.9%, 75.8%, 72.7%, 72.7%, 75.8%, 63.6%, 78.8%, 75.8%, 69.7%, 72.7%, 72.7%, 69.7%, 93.9%, 66.7%, 63.6%, 69.7%, 69.7%, 78.8%, 75.8%, 72.7%, 78.8%, 81.8%, 66.7%, 60.6%, 60.6%, 72.7%, 66.7%, 60.6%, 63.6%, 81.8%, 60.6%, 69.7%, 60.6%, 78.8%, 69.7%, 63.6%, 63.6%, 60.6%, 72.7%, 63.6%, 72.7%, 72.7%, 63.6%, 66.7%, 60.6%, 60.6%, 63.6%, 63.6%, 69.7%, 63.6%, 69.7%, 60.6%, respectively, in the validation cohort (Table 3). As seen from Comparative Example mentioned later, the existing markers CEA and CA19-9 had sensitivity of 33.3% and 59.4%, respectively, in the validation cohort (Table 5), demonstrating that, for example, the 62 polynucleotides consisting of the nucleotide sequences represented by SEQ ID Nos: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 34, 35, 36, 39, 40, 41, 42, 44, 45, 46, 47, 49, 50, 51, 52, 53, 54, 60, 62, 64, 65, 67, 68, 70, 74, 75, 76, 83, 84, 105, 107 can discriminate, each alone, biliary tract cancer in the validation cohort with sensitivity beyond the existing tumor marker CA19-9 in blood.

For example, the 9 polynucleotides consisting of the nucleotide sequences represented by SEQ ID NOs: 1, 2, 3, 4, 10, 11, 12, 23, and 64 were able to correctly discriminate biliary tract cancer for all of the 6 biliary tract cancer samples of stages 0 and 1 (including IA and IB) contained in the validation cohort. Thus, these polynucleotides can detect even early biliary tract cancer and contribute to the early diagnosis of biliary tract cancer.

Furthermore, these polynucleotides were able to correctly discriminate biliary tract cancer for all of the tumors occupying the extrahepatic bile duct, the intrahepatic bile duct, the gallbladder, or the papilla of the biliary tract in the validation cohort. Particularly, the polynucleotides were able to detect cancer of the lower bile duct or the papilla which reportedly has poor prognosis, and cancer in the intrahepatic bile duct which tends to progress asymptomatically.

Example 2

<Method for Evaluating Biliary Tract Cancer Discriminant Performance by Combination of Multiple Gene Markers Using Samples in the Validation Cohort>

Figure 3:
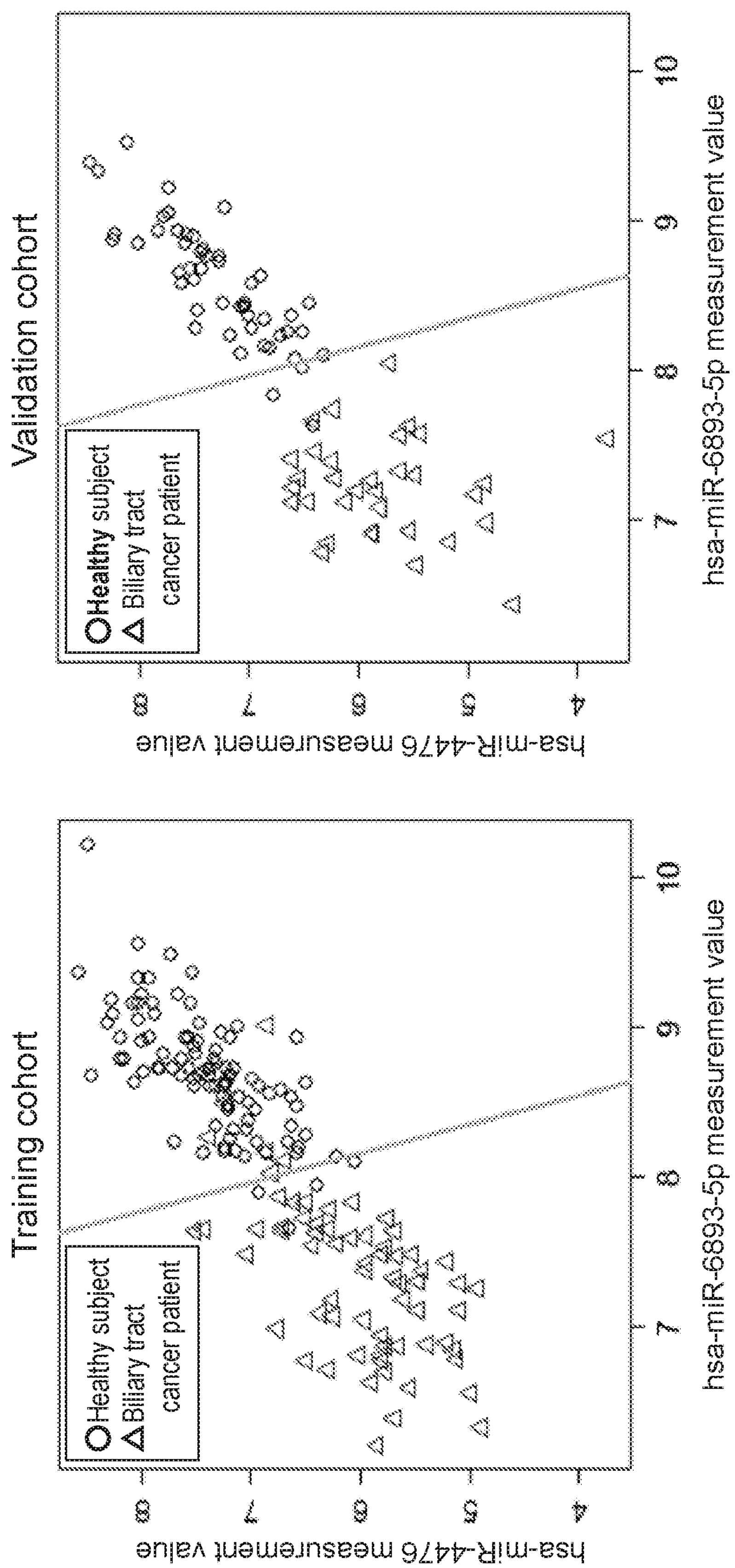
FIG. 3 Left diagram: the measurement values of hsa-miR-6893-5p (SEQ ID NO: 2) in healthy subjects (100 persons, circles) and biliary tract cancer patients (67 persons, triangles) selected as a training cohort were each plotted on the abscissa against their measurement values of hsa-miR-4476 (SEQ ID NO: 4) on the ordinate. The line in the diagram depicts a discriminant function (0=5.16x+y+48.11) that was optimized by Fisher's linear discriminant analysis and discriminated between the two groups. Right diagram: the measurement values of hsa-miR-6893-5p (SEQ ID NO: 2) in healthy subjects (50 persons, circles) and biliary tract cancer patients (33 persons, triangles) selected as a validation cohort were each plotted on the abscissa against their measurement values of hsa-miR-4476 (SEQ ID NO: 4) on the ordinate. The line in the diagram depicts the threshold (0=5.16x+y+48.11) that was set in the training cohort and discriminated between the two groups.

In this Example, a method for evaluating biliary tract cancer discriminant performance by a combination of the gene markers selected in Example 1 was studied. Specifically, Fisher's linear discriminant analysis was conducted as to 7,750 combinations of any two of the expression level measurement values of the polynucleotides consisting of the nucleotide sequences represented by SEQ ID NOs: 1 to 125 selected in Example 1, to construct a discriminant for determining the presence or absence of biliary tract cancer. Next, accuracy, sensitivity, and specificity in the validation cohort were calculated using the discriminant thus prepared, and the discriminant performance of the selected polynucleotides was validated using the independent samples. The biliary tract cancer discrimination in the validation cohort was carried out using the 7,750 combinations of the expression level measurement values of the polynucleotides. For example, the expression level measurement values of the polynucleotides consisting of the nucleotide sequences represented by SEQ ID NO: 2 and SEQ ID NO: 4 were compared between the healthy subjects (50 persons) and the biliary tract cancer patients (33 persons) in the validation cohort. As a result, a scatter diagram that significantly separated the expression level measurement values of the biliary tract cancer patient group from those of the healthy subject group was obtained in the training cohort (see the left diagram of FIG. 3). These results were also reproducible in the validation cohort (see the right diagram of FIG. 3). Likewise, a scatter diagram that significantly separated the expression level measurement values of the biliary tract cancer patient group from those of the healthy subject group was also obtained as to the other combinations of any two of the expression level measurement values of the newly found polynucleotides consisting of the nucleotide sequences represented by SEQ ID NOs: 1 to 125. These results were able to be validated in the validation cohort. For example, as for these nucleotide sequences represented by SEQ ID NO: 2 and SEQ ID NO: 4, the number of samples that were correctly or incorrectly identified as biliary tract cancer was calculated using the function ($0=5.16x+y+48.11$) that was set in the training cohort and discriminated between the two groups. As a result, 33 true positives, 48 true negatives, 2 false positives, and 0 false negatives were obtained. From these values, 98% accuracy, 100% sensitivity, and 96% specificity were obtained as the detection performance. In this way, the detection performance was calculated for all combinations of any two of the expression level measurement values of the newly found polynucleotides consisting of the nucleotide sequences represented by SEQ ID NOs: 1 to 125. Among them, 124 combinations of the polynucleotide consisting of the nucleotide sequence represented by SEQ ID NO: 1 with polynucleotides consisting of nucleotide sequences represented by the other SEQ ID NOs and their detection performance are described in Table 6 as an example. For example, all of the combinations of the expression level measurement values of the polynucleotides consisting of the nucleotide sequences represented by SEQ ID NOs: 1 and 7, SEQ ID NOs: 1 and 9, SEQ ID NOs: 1 and 25, and SEQ ID NOs: 1 and 66 also exhibited sensitivity of 100% in the validation cohort. In this way, 6,316 combinations of the expression level measurement values of the polynucleotides having sensitivity beyond the existing marker CA19-9 (75.8% in Table 5) were obtained in the validation cohort. All of the nucleotide sequences 1 to 125 described in Table 2 obtained in Example 1 were employed at least once in these combinations. These results demonstrated that the combinations of any two of the expression level measurement values of the polynucleotides consisting of the nucleotide sequences represented by SEQ ID NOs: 1 to 125 can discriminate biliary tract cancer with sensitivity beyond CA19-9 in the validation cohort.

Among the 7,750 combinations of any two of the expression level measurement values of the polynucleotides consisting of the nucleotide sequences represented by SEQ ID NOs: 1 to 125, 1,290 combinations of two of the expression level measurement values were able to correctly discriminate biliary tract cancer for all of the 6 biliary tract cancer samples of stages 0 and 1 (including IA and IB) contained in the validation cohort. The polynucleotides consisting of the nucleotide sequences represented by SEQ ID NOs: 1 to 125 were employed at least once in these 1,290 combinations of two thereof. Thus, these polynucleotides can detect even early biliary tract cancer and contribute to the early diagnosis of biliary tract cancer.

Thus, markers capable of detecting biliary tract cancer with excellent sensitivity are obtained even if 3, 4, 5, 6, 7, 8, 9, 10 or more of the expression level measurement values of the polynucleotides consisting of the nucleotide sequences represented by SEQ ID NOs: 1 to 125 are combined. For example, the polynucleotides consisting of the nucleotide sequences represented by SEQ ID NOs: 1 to 125 selected in Example 1 were ranked in the descending order of their P values which indicate statistical significance, and detection performance was calculated using combinations of one or more miRNAs to which the miRNAs were added one by one from the top to the bottom according to the rank. As a result, the sensitivity in the validation cohort was 100% for 1 miRNA, 100% for 2 miRNAs, 100% for 3 miRNAs, 100% for 5 miRNAs, 100% for 10 miRNAs, 100% for 20 miRNAs, 100% for 50 miRNAs, and 100% for 100 miRNAs. These values of the sensitivity were higher than the sensitivity of the existing tumor marker in blood, demonstrating that even combinations of the multiple miRNAs can serve as excellent markers for the detection of biliary tract cancer. In this context, the combinations of the multiple miRNAs are not limited to the combinations of the miRNAs added in the order of statistically significant difference as described above, and any combination of the multiple miRNAs can be used in the detection of biliary tract cancer.

From these results, it can be concluded that all of the polynucleotides consisting of the nucleotide sequences represented by SEQ ID NOs: 1 to 125 serve as excellent diagnostic markers for biliary tract cancer.

TABLE 2

| SEQ ID NO: | Gene name | P value after Bonferroni correction | Expression level in biliary tract cancer patient relative to healthy subject |
|---|---|---|---|
| 1 | has-miR-125a-3p | 7.84E−45 | − |
| 2 | has-miR-6893-5p | 7.26E−41 | − |
| 3 | hsa-miR-204-3p | 3.07E−40 | − |
| 4 | has-miR-4476 | 1.71E−29 | − |
| 5 | has-miR-4294 | 4.27E−29 | − |
| 6 | has-miR-150-3p | 7.62E−29 | − |
| 7 | has-miR-6729-5p | 3.45E−27 | + |
| 8 | has-miR-7641 | 3.59E−27 | − |
| 9 | has-miR-6765-3p | 1.23E−26 | − |
| 10 | has-miR-6820-5p | 1.94E−26 | − |
| 11 | hsa-miR-575 | 3.20E−22 | − |
| 12 | hsa-miR-6836-3p | 6.22E−22 | + |
| 13 | hsa-miR-1469 | 3.82E−21 | + |
| 14 | hsa-miR-663a | 3.20E−20 | + |
| 15 | hsa-miR-6075 | 3.39E−19 | + |
| 16 | hsa-miR-4634 | 3.45E−19 | + |
| 17 | hsa-miR-423-5p | 6.05E−19 | − |
| 18 | hsa-miR-4454 | 1.09E−18 | − |
| 19 | hsa-miR-7109-5p | 4.48E−17 | − |
| 20 | hsa-miR-6789-5p | 5.28E−17 | + |
| 21 | hsa-miR-6877-5p | 1.97E−16 | − |
| 22 | hsa-miR-4792 | 5.75E−16 | + |
| 23 | hsa-miR-4530 | 1.17E−15 | − |
| 24 | hsa-miR-7975 | 1.25E−15 | − |
| 25 | hsa-miR-6724-5p | 2.90E−15 | + |
| 26 | hsa-miR-8073 | 6.32E−15 | + |
| 27 | hsa-miR-7977 | 7.95E−15 | − |
| 28 | hsa-miR-1231 | 1.10E−14 | + |
| 29 | hsa-miR-6799-5p | 7.45E−14 | − |
| 30 | hsa-miR-615-5p | 1.20E−13 | − |
| 31 | hsa-miR-4450 | 1.31E−13 | − |
| 32 | hsa-miR-6726-5p | 6.23E−13 | − |
| 33 | hsa-miR-6875-5p | 9.36E−13 | + |
| 34 | hsa-miR-4734 | 1.18E−12 | + |
| 35 | hsa-miR-16-5p | 1.44E−12 | − |
| 36 | hsa-miR-602 | 2.13E−12 | + |
| 37 | hsa-miR-4651 | 3.44E−12 | − |
| 38 | hsa-miR-8069 | 3.87E−12 | + |
| 39 | hsa-miR-1238-5p | 4.47E−12 | + |

TABLE 2-continued

| SEQ ID NO: | Gene name | P value after Bonferroni correction | Expression level in biliary tract cancer patient relative to healthy subject |
|---|---|---|---|
| 40 | hsa-miR-6880-5p | 6.68E−12 | − |
| 41 | hsa-miR-8072 | 8.97E−12 | + |
| 42 | hsa-miR-4723-5p | 1.09E−11 | − |
| 43 | hsa-miR-4732-5p | 1.18E−11 | + |
| 44 | hsa-miR-6125 | 2.42E−11 | + |
| 45 | hsa-miR-6090 | 5.45E−11 | + |
| 46 | hsa-miR-7114-5p | 6.03E−11 | − |
| 47 | hsa-miR-564 | 7.38E−11 | − |
| 48 | hsa-miR-451a | 1.34E−10 | − |
| 49 | hsa-miR-3135b | 1.77E−10 | − |
| 50 | hsa-miR-4497 | 2.01E−10 | − |
| 51 | hsa-miR-4665-5p | 2.05E−10 | − |
| 52 | hsa-miR-3622a-5p | 2.06E−10 | − |
| 53 | hsa-miR-6850-5p | 4.73E−10 | + |
| 54 | hsa-miR-6821-5p | 1.08E−09 | − |
| 55 | hsa-miR-5100 | 1.24E−09 | − |
| 56 | hsa-miR-6872-3p | 1.30E−09 | − |
| 57 | hsa-miR-4433-3p | 1.82E−09 | + |
| 58 | hsa-miR-1227-5p | 2.00E−09 | + |
| 59 | hsa-miR-3188 | 2.76E−09 | + |
| 60 | hsa-miR-7704 | 2.85E−09 | − |
| 61 | hsa-miR-3185 | 5.63E−09 | + |
| 62 | hsa-miR-1908-3p | 1.55E−08 | + |
| 63 | hsa-miR-6781-5p | 4.49E−08 | + |
| 64 | hsa-miR-6805-5p | 5.45E−08 | + |
| 65 | hsa-miR-8089 | 5.74E−08 | − |
| 66 | hsa-miR-665 | 6.09E−08 | + |
| 67 | hsa-miR-4486 | 8.43E−08 | + |
| 68 | hsa-miR-6722-3p | 2.27E−07 | + |
| 69 | hsa-miR-1260a | 2.91E−07 | − |
| 70 | hsa-miR-4707-5p | 4.82E−07 | + |
| 71 | hsa-miR-6741-5p | 5.45E−07 | − |
| 72 | hsa-miR-1260b | 6.63E−07 | − |
| 73 | hsa-miR-1246 | 8.89E−07 | + |
| 74 | hsa-miR-6845-5p | 1.00E−06 | + |
| 75 | hsa-miR-4638-5p | 1.20E−06 | − |
| 76 | hsa-miR-6085 | 1.41E−06 | − |
| 77 | hsa-miR-1228-3p | 1.80E−06 | + |
| 78 | hsa-miR-4534 | 3.19E−06 | − |
| 79 | hsa-miR-5585-3p | 3.47E−06 | + |
| 80 | hsa-miR-4741 | 6.41E−06 | + |
| 81 | hsa-miR-4433b-3p | 1.18E−05 | + |
| 82 | hsa-miR-197-5p | 1.68E−05 | + |
| 83 | hsa-miR-718 | 1.86E−05 | + |
| 84 | hsa-miR-4513 | 2.50E−05 | − |
| 85 | hsa-miR-4446-3p | 2.73E−05 | + |
| 86 | hsa-miR-619-5p | 4.93E−05 | + |
| 87 | hsa-miR-6816-5p | 5.01E−05 | + |
| 88 | hsa-miR-6778-5p | 5.27E−05 | + |
| 89 | hsa-miR-24-3p | 7.57E−05 | − |
| 90 | hsa-miR-1915-3p | 8.30E−05 | + |
| 91 | hsa-miR-4665-3p | 8.98E−05 | + |
| 92 | hsa-miR-4449 | 1.08E−04 | + |
| 93 | hsa-miR-6889-5p | 1.20E−04 | − |
| 94 | hsa-miR-486-3p | 1.44E−04 | + |
| 95 | hsa-miR-7113-3p | 1.47E−04 | + |
| 96 | hsa-miR-642a-3p | 1.54E−04 | − |
| 97 | hsa-miR-7847-3p | 1.63E−04 | − |
| 98 | hsa-miR-6768-5p | 1.79E−04 | − |
| 99 | hsa-miR-1290 | 2.46E−04 | + |
| 100 | hsa-miR-7108-5p | 3.53E−04 | + |
| 101 | hsa-miR-92b-5p | 4.71E−04 | + |
| 102 | hsa-miR-663b | 5.05E−04 | + |
| 103 | hsa-miR-3940-5p | 5.20E−04 | + |
| 104 | hsa-miR-4467 | 7.73E−04 | + |
| 105 | hsa-miR-6858-5p | 8.31E−04 | + |
| 106 | hsa-miR-4417 | 8.55E−04 | + |
| 107 | hsa-miR-3665 | 1.00E−03 | + |
| 108 | hsa-miR-4736 | 1.42E−03 | + |
| 109 | hsa-miR-4687-3p | 1.53E−03 | − |
| 110 | hsa-miR-1908-5p | 1.64E−03 | + |
| 111 | hsa-miR-5195-3p | 1.91E−03 | − |
| 112 | hsa-miR-4286 | 2.65E−03 | − |
| 113 | hsa-miR-3679-3p | 2.91E−03 | + |
| 114 | hsa-miR-6791-5p | 2.94E−03 | + |

TABLE 2-continued

| SEQ ID NO: | Gene name | P value after Bonferroni correction | Expression level in biliary tract cancer patient relative to healthy subject |
|---|---|---|---|
| 115 | hsa-miR-1202 | 3.05E−03 | − |
| 116 | hsa-miR-3656 | 3.57E−03 | + |
| 117 | hsa-miR-4746-3p | 4.03E−03 | + |
| 118 | hsa-miR-3184-5p | 4.73E−03 | + |
| 119 | hsa-miR-3937 | 5.41E−03 | + |
| 120 | hsa-miR-6515-3p | 6.16E−03 | + |
| 121 | hsa-miR-6132 | 6.37E−03 | − |
| 122 | hsa-miR-187-5p | 7.26E−03 | − |
| 123 | hsa-miR-7111-5p | 7.97E−03 | − |
| 124 | hsa-miR-5787 | 8.07E−03 | − |
| 125 | hsa-miR-6779-5p | 8.44E−03 | − |

TABLE 3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1 | 97 | 94 | 99 | 98.8 | 100 | 98 |
| 2 | 95.2 | 91 | 98 | 96.4 | 97 | 96 |
| 3 | 92.2 | 83.6 | 98 | 92.8 | 97 | 90 |
| 4 | 86.2 | 79.1 | 91 | 91.6 | 100 | 86 |
| 5 | 88.6 | 79.1 | 95 | 88 | 84.8 | 90 |
| 6 | 86.8 | 80.6 | 91 | 81.9 | 90.9 | 76 |
| 7 | 86.2 | 80.6 | 90 | 86.7 | 87.9 | 86 |
| 8 | 85 | 82.1 | 87 | 89.2 | 90.9 | 88 |
| 9 | 88.6 | 80.6 | 94 | 84.3 | 66.7 | 96 |
| 10 | 88 | 79.1 | 94 | 86.7 | 87.9 | 86 |
| 11 | 88.6 | 77.6 | 96 | 91.6 | 93.9 | 90 |
| 12 | 85.6 | 74.6 | 93 | 84.3 | 75.8 | 90 |
| 13 | 85.6 | 71.6 | 95 | 83.1 | 72.7 | 90 |
| 14 | 82 | 61.2 | 96 | 88 | 72.7 | 98 |
| 15 | 83.2 | 61.2 | 98 | 90.4 | 75.8 | 100 |
| 16 | 82.6 | 77.6 | 86 | 74.7 | 63.6 | 82 |
| 17 | 81.4 | 67.2 | 91 | 79.5 | 78.8 | 80 |
| 18 | 81.4 | 68.7 | 90 | 84.3 | 75.8 | 90 |
| 19 | 78.4 | 70.1 | 84 | 75.9 | 69.7 | 80 |
| 20 | 82 | 73.1 | 88 | 80.7 | 72.7 | 86 |
| 21 | 81.4 | 70.1 | 89 | 80.7 | 72.7 | 86 |
| 22 | 82 | 71.6 | 89 | 81.9 | 69.7 | 90 |
| 23 | 80.2 | 70.1 | 87 | 86.7 | 93.9 | 82 |
| 24 | 74.3 | 56.7 | 86 | 81.9 | 66.7 | 92 |
| 25 | 78.4 | 68.7 | 85 | 74.7 | 63.6 | 82 |
| 26 | 80.2 | 65.7 | 90 | 81.9 | 69.7 | 90 |
| 27 | 78.4 | 61.2 | 90 | 81.9 | 69.7 | 90 |
| 28 | 82.6 | 68.7 | 92 | 81.9 | 78.8 | 84 |
| 29 | 76.6 | 67.2 | 83 | 80.7 | 75.8 | 84 |
| 30 | 77.2 | 71.6 | 81 | 77.1 | 72.7 | 80 |
| 31 | 79.6 | 61.2 | 92 | 80.7 | 78.8 | 82 |
| 32 | 77.2 | 55.2 | 92 | 75.9 | 54.5 | 90 |
| 33 | 74.3 | 61.2 | 83 | 72.3 | 57.6 | 82 |
| 34 | 75.4 | 68.7 | 80 | 81.9 | 81.8 | 82 |
| 35 | 80.8 | 64.2 | 92 | 81.9 | 66.7 | 92 |
| 36 | 74.9 | 64.2 | 82 | 74.7 | 60.6 | 84 |
| 37 | 77.2 | 55.2 | 92 | 78.3 | 54.5 | 94 |
| 38 | 78.4 | 61.2 | 90 | 79.5 | 57.6 | 94 |
| 39 | 79 | 55.2 | 95 | 81.9 | 60.6 | 96 |
| 40 | 79.6 | 65.7 | 89 | 83.1 | 72.7 | 90 |
| 41 | 79.6 | 65.7 | 89 | 73.5 | 66.7 | 78 |
| 42 | 77.8 | 58.2 | 91 | 77.1 | 60.6 | 88 |
| 43 | 79 | 58.2 | 93 | 74.7 | 51.5 | 90 |
| 44 | 76 | 64.2 | 84 | 77.1 | 63.6 | 86 |
| 45 | 73.7 | 70.1 | 76 | 74.7 | 81.8 | 70 |
| 46 | 73.1 | 56.7 | 84 | 79.5 | 60.6 | 92 |
| 47 | 80.8 | 59.7 | 95 | 81.9 | 69.7 | 90 |
| 48 | 80.2 | 59.7 | 94 | 78.3 | 57.6 | 92 |
| 49 | 80.8 | 70.1 | 88 | 78.3 | 60.6 | 90 |
| 50 | 75.4 | 59.7 | 86 | 77.1 | 78.8 | 76 |
| 51 | 76.6 | 61.2 | 87 | 77.1 | 69.7 | 82 |
| 52 | 76 | 46.3 | 96 | 77.1 | 63.6 | 86 |
| 53 | 76 | 62.7 | 85 | 73.5 | 63.6 | 80 |
| 54 | 73.7 | 59.7 | 83 | 67.5 | 60.6 | 72 |
| 55 | 77.2 | 56.7 | 91 | 77.1 | 57.6 | 90 |
| 56 | 73.7 | 58.2 | 84 | 73.5 | 57.6 | 84 |
| 57 | 74.9 | 65.7 | 81 | 68.7 | 51.5 | 80 |
| 58 | 74.3 | 53.7 | 88 | 77.1 | 57.6 | 90 |
| 59 | 79.6 | 65.7 | 89 | 77.1 | 51.5 | 94 |

TABLE 3-continued

| SEQ ID NO: | Training cohort Accuracy (%) | Training cohort Sensitivity (%) | Training cohort Specificity (%) | Validation cohort Accuracy (%) | Validation cohort Sensitivity (%) | Validation cohort Specificity (%) |
|---|---|---|---|---|---|---|
| 60 | 78.4 | 71.6 | 83 | 71.1 | 72.7 | 70 |
| 61 | 74.3 | 56.7 | 86 | 73.5 | 51.5 | 88 |
| 62 | 75.4 | 52.2 | 91 | 78.3 | 63.6 | 88 |
| 63 | 73.7 | 64.2 | 80 | 71.1 | 57.6 | 80 |
| 64 | 74.9 | 59.7 | 85 | 79.5 | 72.7 | 84 |
| 65 | 76 | 64.2 | 84 | 78.3 | 72.7 | 82 |
| 66 | 75.4 | 53.7 | 90 | 79.5 | 57.6 | 94 |
| 67 | 70.1 | 50.7 | 83 | 78.3 | 63.6 | 88 |
| 68 | 71.9 | 52.2 | 85 | 75.9 | 66.7 | 82 |
| 69 | 71.3 | 52.2 | 84 | 74.7 | 54.5 | 88 |
| 70 | 73.1 | 53.7 | 86 | 77.1 | 60.6 | 88 |
| 71 | 76.6 | 58.2 | 89 | 75.9 | 57.6 | 88 |
| 72 | 71.9 | 46.3 | 89 | 77.1 | 57.6 | 90 |
| 73 | 75.4 | 53.7 | 90 | 73.5 | 48.5 | 90 |
| 74 | 72.5 | 47.8 | 89 | 75.9 | 60.6 | 86 |
| 75 | 75.4 | 52.2 | 91 | 78.3 | 63.6 | 88 |
| 76 | 73.1 | 55.2 | 85 | 71.1 | 63.6 | 76 |
| 77 | 71.9 | 53.7 | 84 | 69.9 | 54.5 | 80 |
| 78 | 75.4 | 55.2 | 89 | 71.1 | 48.5 | 86 |
| 79 | 73.7 | 50.7 | 89 | 78.3 | 51.5 | 96 |
| 80 | 68.9 | 50.7 | 81 | 69.9 | 51.5 | 82 |
| 81 | 72.5 | 58.2 | 82 | 62.7 | 42.4 | 76 |
| 82 | 70.1 | 43.3 | 88 | 72.3 | 51.5 | 86 |
| 83 | 70.7 | 52.2 | 83 | 75.9 | 69.7 | 80 |
| 84 | 71.3 | 46.3 | 88 | 74.7 | 63.6 | 82 |
| 85 | 70.7 | 44.8 | 88 | 69.9 | 42.4 | 88 |
| 86 | 70.1 | 40.3 | 90 | 72.3 | 36.4 | 96 |
| 87 | 68.3 | 49.3 | 81 | 65.1 | 39.4 | 82 |
| 88 | 70.7 | 43.3 | 89 | 73.5 | 45.5 | 92 |
| 89 | 71.9 | 44.8 | 90 | 75.9 | 39.4 | 100 |
| 90 | 71.9 | 53.7 | 84 | 71.1 | 39.4 | 92 |
| 91 | 72.5 | 49.3 | 88 | 68.7 | 51.5 | 80 |
| 92 | 73.1 | 44.8 | 92 | 72.3 | 42.4 | 92 |
| 93 | 67.1 | 47.8 | 80 | 71.1 | 51.5 | 84 |
| 94 | 71.3 | 46.3 | 88 | 68.7 | 45.5 | 84 |
| 95 | 69.5 | 50.7 | 82 | 74.7 | 48.5 | 92 |
| 96 | 69.5 | 44.8 | 86 | 69.5 | 43.8 | 86 |
| 97 | 71.3 | 52.2 | 84 | 65.1 | 45.5 | 78 |
| 98 | 69.5 | 40.3 | 89 | 74.7 | 57.6 | 86 |
| 99 | 71.9 | 49.3 | 87 | 73.5 | 48.5 | 90 |
| 100 | 71.3 | 44.8 | 89 | 67.5 | 36.4 | 88 |
| 101 | 65.3 | 34.3 | 86 | 69.9 | 33.3 | 94 |
| 102 | 68.9 | 43.3 | 86 | 70.7 | 46.9 | 86 |
| 103 | 70.7 | 44.8 | 88 | 63.9 | 33.3 | 84 |
| 104 | 65.9 | 40.3 | 83 | 69.9 | 45.5 | 86 |
| 105 | 70.7 | 47.8 | 86 | 79.5 | 69.7 | 86 |
| 106 | 72.5 | 46.3 | 90 | 62.7 | 27.3 | 86 |
| 107 | 71.9 | 49.3 | 87 | 72.3 | 60.6 | 80 |
| 108 | 74.3 | 46.3 | 93 | 73.5 | 45.5 | 92 |
| 109 | 66.5 | 40.3 | 84 | 67.5 | 36.4 | 88 |
| 110 | 65.3 | 41.8 | 81 | 68.7 | 36.4 | 90 |
| 111 | 69.5 | 49.3 | 83 | 74.7 | 54.5 | 88 |
| 112 | 70.1 | 43.3 | 88 | 68.7 | 42.4 | 86 |
| 113 | 68.7 | 43.9 | 85 | 66.3 | 48.5 | 78 |
| 114 | 74.3 | 52.2 | 89 | 72.3 | 45.5 | 90 |
| 115 | 67.7 | 44.8 | 83 | 68.7 | 42.4 | 86 |
| 116 | 68.3 | 37.3 | 89 | 67.5 | 33.3 | 90 |
| 117 | 70.1 | 46.3 | 86 | 68.7 | 36.4 | 90 |
| 118 | 64.7 | 38.8 | 82 | 66.3 | 39.4 | 84 |
| 119 | 69.5 | 40.3 | 89 | 63.9 | 24.2 | 90 |
| 120 | 68.3 | 46.3 | 83 | 61.4 | 39.4 | 76 |
| 121 | 72.5 | 43.3 | 92 | 78.3 | 54.5 | 94 |
| 122 | 61.7 | 37.3 | 78 | 67.5 | 36.4 | 88 |
| 123 | 69.5 | 38.8 | 90 | 74.7 | 51.5 | 90 |
| 124 | 63.5 | 29.9 | 86 | 67.5 | 33.3 | 90 |
| 125 | 65.3 | 38.8 | 83 | 68.7 | 39.4 | 88 |

TABLE 4

| SEQ ID NO: | Discriminant coefficient | Constant Term |
|---|---|---|
| 1 | 1.490 | 8.485 |
| 2 | 2.192 | 17.571 |
| 3 | 1.628 | 20.108 |
| 4 | 1.724 | 11.587 |
| 5 | 2.263 | 22.296 |
| 6 | 2.463 | 15.985 |
| 7 | 8.833 | 111.338 |
| 8 | 1.386 | 9.644 |
| 9 | 1.528 | 12.721 |
| 10 | 3.092 | 21.901 |
| 11 | 1.550 | 8.821 |
| 12 | 3.319 | 29.422 |
| 13 | 3.849 | 39.694 |
| 14 | 3.265 | 33.699 |
| 15 | 2.090 | 18.362 |
| 16 | 5.589 | 55.229 |
| 17 | 2.126 | 15.004 |
| 18 | 1.892 | 21.549 |
| 19 | 5.212 | 38.369 |
| 20 | 4.357 | 43.428 |
| 21 | 3.893 | 27.592 |
| 22 | 1.938 | 13.174 |
| 23 | 2.212 | 20.328 |
| 24 | 1.832 | 17.827 |
| 25 | 4.296 | 42.971 |
| 26 | 2.836 | 18.443 |
| 27 | 1.791 | 17.167 |
| 28 | 3.102 | 20.737 |
| 29 | 4.166 | 33.600 |
| 30 | 2.570 | 16.779 |
| 31 | 1.408 | 7.919 |
| 32 | 2.548 | 24.931 |
| 33 | 3.348 | 30.220 |
| 34 | 5.146 | 61.548 |
| 35 | 1.007 | 5.891 |
| 36 | 3.423 | 22.158 |
| 37 | 4.459 | 48.437 |
| 38 | 5.239 | 67.494 |
| 39 | 2.724 | 18.139 |
| 40 | 2.096 | 14.981 |
| 41 | 5.185 | 64.019 |
| 42 | 2.496 | 21.820 |
| 43 | 1.601 | 10.850 |
| 44 | 5.154 | 61.778 |
| 45 | 7.100 | 92.650 |
| 46 | 4.122 | 28.093 |
| 47 | 1.389 | 8.063 |
| 48 | 0.844 | 7.028 |
| 49 | 2.714 | 21.126 |
| 50 | 2.184 | 27.536 |
| 51 | 2.782 | 26.220 |
| 52 | 2.507 | 14.755 |
| 53 | 5.248 | 59.794 |
| 54 | 4.258 | 36.410 |
| 55 | 2.093 | 21.342 |
| 56 | 2.375 | 14.357 |
| 57 | 3.716 | 27.368 |
| 58 | 6.005 | 57.298 |
| 59 | 3.141 | 19.304 |
| 60 | 6.949 | 95.964 |
| 61 | 2.207 | 15.598 |
| 62 | 2.528 | 17.814 |
| 63 | 5.205 | 54.268 |
| 64 | 5.578 | 63.641 |
| 65 | 3.305 | 21.681 |
| 66 | 2.302 | 16.671 |
| 67 | 2.960 | 21.294 |
| 68 | 5.934 | 50.718 |
| 69 | 2.315 | 15.993 |
| 70 | 3.992 | 29.367 |
| 71 | 3.564 | 24.617 |
| 72 | 2.022 | 17.112 |
| 73 | 1.347 | 11.081 |
| 74 | 3.284 | 31.457 |
| 75 | 1.545 | 9.348 |
| 76 | 4.433 | 46.093 |
| 77 | 4.257 | 27.033 |

TABLE 4-continued

| SEQ ID NO: | Discriminant coefficient | Constant Term |
|---|---|---|
| 78 | 2.935 | 19.713 |
| 79 | 1.452 | 8.384 |
| 80 | 3.495 | 34.503 |
| 81 | 3.632 | 29.142 |
| 82 | 3.294 | 23.460 |
| 83 | 3.861 | 26.420 |
| 84 | 3.328 | 20.006 |
| 85 | 2.105 | 16.080 |
| 86 | 1.341 | 10.397 |
| 87 | 4.228 | 42.421 |
| 88 | 2.047 | 16.460 |
| 89 | 1.719 | 10.767 |
| 90 | 4.014 | 44.217 |
| 91 | 4.300 | 25.371 |
| 92 | 2.984 | 19.534 |
| 93 | 2.882 | 20.272 |
| 94 | 2.143 | 17.783 |
| 95 | 2.782 | 16.404 |
| 96 | 2.452 | 18.600 |
| 97 | 3.952 | 25.528 |
| 98 | 3.062 | 28.862 |
| 99 | 1.303 | 7.532 |
| 100 | 4.019 | 36.628 |
| 101 | 2.486 | 19.866 |
| 102 | 2.977 | 26.894 |
| 103 | 4.826 | 59.068 |
| 104 | 2.101 | 20.436 |
| 105 | 4.536 | 33.697 |
| 106 | 4.937 | 40.293 |
| 107 | 6.731 | 92.497 |
| 108 | 2.367 | 14.257 |
| 109 | 3.432 | 32.608 |
| 110 | 4.107 | 47.065 |
| 111 | 3.209 | 22.271 |
| 112 | 2.121 | 15.790 |
| 113 | 3.358 | 20.358 |
| 114 | 3.889 | 35.598 |
| 115 | 3.145 | 20.800 |
| 116 | 4.368 | 50.242 |
| 117 | 2.562 | 16.673 |
| 118 | 2.261 | 17.941 |
| 119 | 3.886 | 33.439 |
| 120 | 4.225 | 28.465 |
| 121 | 3.315 | 25.324 |
| 122 | 2.292 | 23.043 |
| 123 | 4.989 | 37.060 |
| 124 | 4.447 | 57.475 |
| 125 | 5.665 | 40.490 |

TABLE 5-1

| Training cohort | | | |
|---|---|---|---|
| Sample name | Cancer stage | CEA(ng/mL) | CA19-9(U/mL) |
| B01 | IB | 2 | 18.2 |
| B05 | IB | 2.6 | 24.7 |
| B06 | II | 2.6 | 88.7(+) |
| B07 | IIA | 1.5 | 41.8(+) |
| B09 | IVb | 20.3(+) | 271.6(+) |
| B10 | IVb | 3.4 | 3170(+) |
| B11 | IVb | 51.7(+) | 32.1 |
| B12 | IVb | 2.1 | 5420(+) |
| B13 | III | 5 | 92.5(+) |
| B14 | III | 48.9(+) | 1900(+) |
| B17 | IB | 0.9 | 16.4 |
| B18 | IIB | 4916(+) | 1.5 |
| B19 | IIIB | 1.8 | 80.1(+) |
| B21 | II | 0.7 | 8.3 |
| B25 | III | 30.3(+) | 1364(+) |
| B26 | IVb | 10.4(+) | 2226(+) |
| B27 | IVb | 39.8(+) | 3490(+) |
| B29 | III | 1.7 | 8.2 |

TABLE 5-1-continued

| Training cohort | | | |
|---|---|---|---|
| Sample name | Cancer stage | CEA(ng/mL) | CA19-9(U/mL) |
| B33 | IVb | 5 | 200.6(+) |
| B35 | IVb | 14.6(+) | 0.1 |
| B39 | IIB | 0.8 | 51.7(+) |
| B40 | III | 2.7 | 36.4 |
| B43 | IVa | 4.4 | 85.3(+) |
| B44 | IIB | 6.3(+) | 67.6(+) |
| B45 | II | 2.2 | 59.2(+) |
| B48 | IB | 3.2 | 33.4 |
| B49 | IA | 4.3 | 289(+) |
| B50 | IVb | 0.8 | |
| B51 | II | 6.3(+) | 16 |
| B52 | IIB | 3.6 | 214.9(+) |
| B54 | II | 1 | 98.3(+) |
| B55 | II | 1.7 | 36.8 |
| B56 | II | 1.6 | 6.8 |
| B57 | II | 6.8(+) | 4538(+) |
| B58 | IB | 1.8 | 63.9(+) |
| B59 | IB | 10.6(+) | 46.4(+) |
| B61 | IIA | 0.9 | 9.5 |
| B62 | IB | 2.3 | 11.2 |
| B63 | IIB | 7.2(+) | 385.2(+) |
| B64 | IIA | 1.9 | 48.3(+) |
| B67 | IB | 1.6 | 66.2(+) |
| B69 | III | 26.2(+) | 76.5(+) |
| B73 | III | 3.7 | 156.6(+) |
| B74 | IVb | 4.1 | 14820(+) |
| B75 | IVb | 306.7(+) | 2098(+) |
| B77 | IVb | 1.2 | 74.2(+) |
| B78 | IVb | 2.3 | 5.3 |
| B81 | III | 4.9 | 240.8(+) |
| B82 | III | 7.9(+) | 1275(+) |
| B83 | IVb | 1.6 | 1641(+) |
| B85 | IVb | 29.7(+) | 11130(+) |
| B86 | III | 3.5 | 23.8 |
| B89 | IVb | 5.2(+) | 1920(+) |
| B90 | III | 1.6 | 125.7(+) |
| B91 | IVb | 3.2 | 1175(+) |
| B92 | IIIB | 4.9 | 19750(+) |
| B93 | IVb | None | |
| B94 | III | 2.6 | 2670(+) |
| B95 | IVb | 2030(+) | 23.8 |
| B96 | IVb | 15.2(+) | 68120(+) |
| B97 | IVb | 19.5(+) | 2.6 |
| B98 | IVb | 2.3 | 4308(+) |
| B99 | IVb | 1.3 | 35.2 |
| B100 | IVb | 2.4 | 47(+) |
| B101 | III | 3.5 | 40.3(+) |
| B102 | IVb | 0.2 | 3304(+) |

TABLE 5-1-continued

| Training cohort | | | |
|---|---|---|---|
| Sample name | Cancer stage | CEA(ng/mL) | CA19-9(U/mL) |
| B103 | III | 2.2 | 2434(+) |
| | Sensitivity (%) | 31.3 | 68.2 |

TABLE 5-2

| Validation cohort | | | |
|---|---|---|---|
| Sample name | Cancer stage | CEA(ng/mL) | CA19-9(U/mL) |
| B02 | IB | 3.1 | 17.1 |
| B03 | IIB | 3.9 | 12.9 |
| B04 | IIA | 2.3 | 15.8 |
| B08 | 0 | 2.7 | 19.8 |
| B15 | IVb | 13 | 328.4 |
| B16 | II | 1.1 | 9.6 |
| B20 | IIB | 2.3 | 189.8 |
| B22 | I | 7.8 | 49.2 |
| B23 | III | 0.8 | 8.2 |
| B24 | IV | 11.6 | |
| B28 | III | 2.4 | 64.9 |
| B30 | IVb | 194.7 | 4597 |
| B31 | IVb | 3.4 | 483.3 |
| B32 | IIB | 2.7 | 35.2 |
| B34 | III | 1.6 | 123.5 |
| B36 | IVb | 2.7 | 3374 |
| B37 | III | 5.5 | 145.1 |
| B41 | IB | 2 | 27.8 |
| B42 | IIA | 7 | 37.8 |
| B46 | IA | 2.1 | 38.8 |
| B53 | I | 2.5 | 6.4 |
| B60 | IIA | 2.5 | 105.5 |
| B65 | IIA | 1.7 | 11.9 |
| B66 | IIA | 4.6 | 11.1 |
| B68 | IIB | 1.1 | 7.2 |
| B70 | II | 1.6 | 123.5 |
| B71 | IVa | 6.5 | 925 |
| B76 | IVb | 1482 | 15.6 |
| B79 | IVb | 65 | 6510 |
| B80 | IVb | 5 | 229.9 |
| B84 | III | 3.1 | 52.5 |
| B88 | IVb | 76.9 | 777 |
| P91 | IVb | 2.3 | 4308 |
| | Sensitivity (%) | 33.3 | 59.4 |

In Table 5, 5 ng/ml or lower of CEA was indicated as "−", and 37 U/ml or lower of CA19-9 was indicated as "−", while values exceeding these were "+"

TABLE 6

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_2 | 97 | 94 | 99 | 100 | 100 | 100 |
| 1_3 | 95.8 | 91 | 99 | 100 | 100 | 100 |
| 1_4 | 95.8 | 92.5 | 98 | 97.6 | 100 | 96 |
| 1_5 | 97.6 | 95.5 | 99 | 98.8 | 100 | 98 |
| 1_6 | 96.4 | 92.5 | 99 | 96.4 | 100 | 94 |
| 1_7 | 98.8 | 98.5 | 99 | 100 | 100 | 100 |
| 1_8 | 98.2 | 95.5 | 100 | 98.8 | 100 | 98 |
| 1_9 | 98.8 | 97 | 100 | 100 | 100 | 100 |
| 1_10 | 95.8 | 94 | 97 | 97.6 | 100 | 96 |
| 1_11 | 97 | 94 | 99 | 98.8 | 100 | 98 |
| 1_12 | 96.4 | 92.5 | 99 | 98.8 | 97 | 100 |
| 1_13 | 97 | 94 | 99 | 100 | 100 | 100 |
| 1_14 | 97 | 95.5 | 98 | 100 | 100 | 100 |
| 1_15 | 96.4 | 92.5 | 99 | 98.8 | 97 | 100 |
| 1_16 | 97.6 | 95.5 | 99 | 96.4 | 97 | 96 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_17 | 97.6 | 95.5 | 99 | 98.8 | 100 | 98 |
| 1_18 | 96.4 | 92.5 | 99 | 98.8 | 97 | 100 |
| 1_19 | 98.2 | 95.5 | 100 | 98.8 | 100 | 98 |
| 1_20 | 97.6 | 95.5 | 99 | 98.8 | 100 | 98 |
| 1_21 | 97.6 | 95.5 | 99 | 98.8 | 100 | 98 |
| 1_22 | 98.8 | 97 | 100 | 98.8 | 97 | 100 |
| 1_23 | 95.8 | 91 | 99 | 98.8 | 100 | 98 |
| 1_24 | 96.4 | 92.5 | 99 | 98.8 | 97 | 100 |
| 1_25 | 98.8 | 97 | 100 | 100 | 100 | 100 |
| 1_26 | 96.4 | 92.5 | 99 | 96.4 | 97 | 96 |
| 1_27 | 95.8 | 92.5 | 98 | 98.8 | 97 | 100 |
| 1_28 | 97.6 | 97 | 98 | 100 | 100 | 100 |
| 1_29 | 95.8 | 92.5 | 98 | 97.6 | 97 | 98 |
| 1_30 | 97 | 92.5 | 100 | 100 | 100 | 100 |
| 1_31 | 96.4 | 92.5 | 99 | 97.6 | 97 | 98 |
| 1_32 | 97.6 | 95.5 | 99 | 98.8 | 100 | 98 |
| 1_33 | 96.4 | 94 | 98 | 100 | 100 | 100 |
| 1_34 | 96.4 | 92.5 | 99 | 100 | 100 | 100 |
| 1_35 | 96.4 | 91 | 100 | 98.8 | 100 | 98 |
| 1_36 | 97 | 95.5 | 98 | 100 | 100 | 100 |
| 1_37 | 97 | 94 | 99 | 100 | 100 | 100 |
| 1_38 | 97 | 94 | 99 | 98.8 | 100 | 98 |
| 1_39 | 96.4 | 92.5 | 99 | 97.6 | 97 | 98 |
| 1_40 | 97 | 95.5 | 98 | 100 | 100 | 100 |
| 1_41 | 96.4 | 94 | 98 | 98.8 | 97 | 100 |
| 1_42 | 97.6 | 94 | 100 | 100 | 100 | 100 |
| 1_43 | 95.8 | 92.5 | 98 | 97.6 | 100 | 96 |
| 1_44 | 97 | 94 | 99 | 98.8 | 100 | 98 |
| 1_45 | 97.6 | 95.5 | 99 | 96.4 | 100 | 94 |
| 1_46 | 97 | 94 | 99 | 100 | 100 | 100 |
| 1_47 | 97 | 94 | 99 | 97.6 | 100 | 96 |
| 1_48 | 95.8 | 91 | 99 | 100 | 100 | 100 |
| 1_49 | 98.2 | 95.5 | 100 | 100 | 100 | 100 |
| 1_50 | 97 | 94 | 99 | 98.8 | 100 | 98 |
| 1_51 | 97 | 94 | 99 | 98.8 | 100 | 98 |
| 1_52 | 97 | 94 | 99 | 98.8 | 100 | 98 |
| 1_53 | 96.4 | 94 | 98 | 98.8 | 97 | 100 |
| 1_54 | 97 | 94 | 99 | 98.8 | 100 | 98 |
| 1_55 | 96.4 | 94 | 98 | 97.6 | 97 | 98 |
| 1_56 | 95.8 | 94 | 97 | 98.8 | 97 | 100 |
| 1_57 | 95.8 | 92.5 | 98 | 100 | 100 | 100 |
| 1_58 | 96.4 | 92.5 | 99 | 100 | 100 | 100 |
| 1_59 | 95.2 | 91 | 98 | 98.8 | 100 | 98 |
| 1_60 | 96.4 | 94 | 98 | 97.6 | 100 | 96 |
| 1_61 | 98.2 | 97 | 99 | 100 | 100 | 100 |
| 1_62 | 97.6 | 95.5 | 99 | 98.8 | 100 | 98 |
| 1_63 | 95.2 | 89.6 | 99 | 97.6 | 97 | 98 |
| 1_64 | 94.6 | 89.6 | 98 | 98.8 | 100 | 98 |
| 1_65 | 97 | 94 | 99 | 96.4 | 97 | 96 |
| 1_66 | 95.8 | 92.5 | 98 | 98.8 | 97 | 100 |
| 1_67 | 97 | 94 | 99 | 100 | 100 | 100 |
| 1_68 | 97.6 | 95.5 | 99 | 97.6 | 100 | 96 |
| 1_69 | 95.8 | 92.5 | 98 | 97.6 | 97 | 98 |
| 1_70 | 95.8 | 94 | 97 | 98.8 | 100 | 98 |
| 1_71 | 98.2 | 97 | 99 | 98.8 | 100 | 98 |
| 1_72 | 95.8 | 92.5 | 98 | 98.8 | 97 | 100 |
| 1_73 | 97 | 94 | 99 | 100 | 100 | 100 |
| 1_74 | 96.4 | 94 | 98 | 98.8 | 100 | 98 |
| 1_75 | 96.4 | 94 | 98 | 97.6 | 100 | 96 |
| 1_76 | 96.4 | 92.5 | 99 | 97.6 | 97 | 98 |
| 1_77 | 97 | 95.5 | 98 | 97.6 | 97 | 98 |
| 1_78 | 96.4 | 92.5 | 99 | 98.8 | 97 | 100 |
| 1_79 | 95.8 | 91 | 99 | 98.8 | 97 | 100 |
| 1_80 | 95.8 | 91 | 99 | 100 | 100 | 100 |
| 1_81 | 95.8 | 92.5 | 98 | 98.8 | 100 | 98 |
| 1_82 | 97 | 95.5 | 98 | 100 | 100 | 100 |
| 1_83 | 97.6 | 95.5 | 99 | 96.4 | 97 | 96 |
| 1_84 | 97 | 94 | 99 | 98.8 | 100 | 98 |
| 1_85 | 97 | 94 | 99 | 98.8 | 100 | 98 |
| 1_86 | 95.2 | 91 | 98 | 98.8 | 97 | 100 |
| 1_87 | 95.8 | 92.5 | 98 | 100 | 100 | 100 |
| 1_88 | 95.8 | 92.5 | 98 | 98.8 | 97 | 100 |
| 1_89 | 96.4 | 94 | 98 | 98.8 | 100 | 98 |
| 1_90 | 96.4 | 92.5 | 99 | 98.8 | 100 | 98 |
| 1_91 | 95.8 | 94 | 97 | 97.6 | 97 | 98 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_92 | 97.6 | 95.5 | 99 | 98.8 | 100 | 98 |
| 1_93 | 96.4 | 94 | 98 | 98.8 | 100 | 98 |
| 1_94 | 97 | 94 | 99 | 98.8 | 100 | 98 |
| 1_95 | 95.8 | 92.5 | 98 | 98.8 | 97 | 100 |
| 1_96 | 97.6 | 94 | 100 | 100 | 100 | 100 |
| 1_97 | 95.8 | 91 | 99 | 97.6 | 93.9 | 100 |
| 1_98 | 97 | 94 | 99 | 98.8 | 100 | 98 |
| 1_99 | 95.8 | 92.5 | 98 | 100 | 100 | 100 |
| 1_100 | 97 | 94 | 99 | 98.8 | 100 | 98 |
| 1_101 | 97.6 | 95.5 | 99 | 100 | 100 | 100 |
| 1_102 | 97 | 94 | 99 | 100 | 100 | 100 |
| 1_103 | 96.4 | 94 | 98 | 100 | 100 | 100 |
| 1_104 | 97.6 | 97 | 98 | 98.8 | 100 | 98 |
| 1_105 | 97 | 94 | 99 | 98.8 | 100 | 98 |
| 1_106 | 97 | 94 | 99 | 100 | 100 | 100 |
| 1_107 | 97 | 94 | 99 | 98.8 | 100 | 98 |
| 1_108 | 97 | 94 | 99 | 98.8 | 100 | 98 |
| 1_109 | 97.6 | 95.5 | 99 | 100 | 100 | 100 |
| 1_110 | 96.4 | 91 | 100 | 98.8 | 97 | 100 |
| 1_111 | 95.2 | 89.6 | 99 | 98.8 | 97 | 100 |
| 1_112 | 96.4 | 94 | 98 | 97.6 | 97 | 98 |
| 1_113 | 97 | 93.9 | 99 | 100 | 100 | 100 |
| 1_114 | 97 | 94 | 99 | 100 | 100 | 100 |
| 1_115 | 97 | 94 | 99 | 98.8 | 100 | 98 |
| 1_116 | 97.6 | 95.5 | 99 | 100 | 100 | 100 |
| 1_117 | 97.6 | 94 | 100 | 98.8 | 100 | 98 |
| 1_118 | 95.8 | 92.5 | 98 | 98.8 | 100 | 98 |
| 1_119 | 97 | 95.5 | 98 | 100 | 100 | 100 |
| 1_120 | 97 | 94 | 99 | 100 | 100 | 100 |
| 1_121 | 97 | 94 | 99 | 98.8 | 100 | 98 |
| 1_122 | 97 | 92.5 | 100 | 100 | 100 | 100 |
| 1_123 | 97 | 95.5 | 98 | 97.6 | 100 | 96 |
| 1_124 | 98.2 | 97 | 99 | 100 | 100 | 100 |
| 1_125 | 95.8 | 91 | 99 | 97.6 | 97 | 98 |

Example 3

<Selection of Gene Marker Using all Samples and Method for Evaluating Biliary Tract Cancer Discriminant Performance of Acquired Gene Marker>

In this Example, the samples of the training cohort and the validation cohort used in Examples 1 and Example 2 were integrated, and selection of a gene marker and evaluation of its biliary tract cancer discriminant performance were conducted using all of the samples.

Specifically, the miRNA expression levels in the serum of the 100 biliary tract cancer patients and the 150 healthy subjects obtained in Reference Example 1 above were normalized by quantile normalization. In order to acquire diagnostic markers with higher reliability, only genes having a gene expression level of $2^6$ or higher in 50% or more of the samples in either of the biliary tract cancer patient group or the healthy subject group were selected in the gene marker selection. In order to further acquire statistical significance for discriminating a biliary tract cancer patient group from a healthy subject group, the P value obtained by two-tailed t-test assuming equal variance as to each gene expression level was corrected by the Bonferroni method, and genes that satisfied $p<0.01$ were selected as gene markers for use in explanatory variables of a discriminant. The obtained genes are described in Table 7. In this way, hsa-miR-6808-5p, hsa-miR-6774-5p, hsa-miR-4656, hsa-miR-6806-5p, hsa-miR-1233-5p, hsa-miR-328-5p, hsa-miR-4674, hsa-miR-2110, hsa-miR-6076, hsa-miR-3619-3p, hsa-miR-92a-2-5p, hsa-miR-128-1-5p, hsa-miR-638, hsa-miR-2861, hsa-miR-371a-5p, hsa-miR-211-3p, hsa-miR-1273g-3p, hsa-miR-1203, hsa-miR-122-5p, hsa-miR-4258, hsa-miR-4484, hsa-miR-4648 and hsa-miR-6780b-5p genes represented by SEQ ID NOs: 126 to 148 were found as biliary tract cancer markers relative to the healthy subjects, in addition to the genes described in Table 2. As with the polynucleotides shown in SEQ ID NOs: 1 to 125, the results obtained about the polynucleotides shown in SEQ ID NOs: 126 to 148 also showed that the expression level measurement values were significantly lower (−) or higher (+) in the biliary tract cancer patient group than in the healthy subject group (Table 7). These results were able to be validated in the validation cohort. The presence or absence of biliary tract cancer in the newly obtained samples can be determined by the methods described in Examples 1 and 2 by using the gene expression level measurement values described in Table 7 either alone or in combination with the gene expression level measurement values described in Table 2.

TABLE 7

| SEQ ID NO: | Gene name | P value after Bonferroni correction | Expression level in biliary tract cancer patient relative to healthy subject |
|---|---|---|---|
| 1 | hsa-miR-125a-3p | 4.28E−69 | − |
| 2 | hsa-miR-6893-5p | 1.09E−65 | − |
| 3 | hsa-miR-204-3p | 6.70E−61 | − |
| 4 | hsa-miR-4476 | 7.27E−46 | − |
| 5 | hsa-miR-4294 | 1.68E−46 | − |
| 6 | hsa-miR-150-3p | 1.80E−39 | − |
| 7 | hsa-miR-6729-5p | 5.38E−43 | + |
| 8 | hsa-miR-7641 | 3.05E−42 | − |

TABLE 7-continued

| SEQ ID NO: | Gene name | P value after Bonferroni correction | Expression level in biliary tract cancer patient relative to healthy subject |
|---|---|---|---|
| 9 | hsa-miR-6765-3p | 2.49E−39 | − |
| 10 | hsa-miR-6820-5p | 5.67E−39 | − |
| 11 | hsa-miR-575 | 8.34E−40 | − |
| 12 | hsa-miR-6836-3p | 5.59E−31 | + |
| 13 | hsa-miR-1469 | 9.68E−31 | + |
| 14 | hsa-miR-663a | 5.12E−34 | + |
| 15 | hsa-miR-6075 | 1.26E−32 | + |
| 16 | hsa-miR-4634 | 1.02E−21 | + |
| 17 | hsa-miR-423-5p | 1.35E−29 | − |
| 18 | hsa-miR-4454 | 1.49E−28 | − |
| 19 | hsa-miR-7109-5p | 4.86E−24 | − |
| 20 | hsa-miR-6789-5p | 1.58E−25 | + |
| 21 | hsa-miR-6877-5p | 2.13E−27 | − |
| 22 | hsa-miR-4792 | 2.19E−22 | + |
| 23 | hsa-miR-4530 | 5.55E−28 | − |
| 24 | hsa-miR-7975 | 1.41E−23 | − |
| 25 | hsa-miR-6724-5p | 6.21E−22 | + |
| 26 | hsa-miR-8073 | 6.99E−22 | + |
| 27 | hsa-miR-7977 | 1.59E−24 | − |
| 28 | hsa-miR-1231 | 9.43E−24 | + |
| 29 | hsa-miR-6799-5p | 1.15E−19 | − |
| 30 | hsa-miR-615-5p | 4.36E−22 | − |
| 31 | hsa-miR-4450 | 3.74E−25 | − |
| 32 | hsa-miR-6726-5p | 8.86E−19 | − |
| 33 | hsa-miR-6875-5p | 8.34E−18 | + |
| 34 | hsa-miR-4734 | 1.61E−21 | + |
| 35 | hsa-miR-16-5p | 5.06E−19 | − |
| 36 | hsa-miR-602 | 6.21E−19 | + |
| 37 | hsa-miR-4651 | 8.62E−19 | − |
| 38 | hsa-miR-8069 | 3.51E−17 | + |
| 39 | hsa-miR-1238-5p | 1.46E−20 | + |
| 40 | hsa-miR-6880-5p | 3.97E−20 | − |
| 41 | hsa-miR-8072 | 4.77E−19 | + |
| 42 | hsa-miR-4723-5p | 8.13E−18 | − |
| 43 | hsa-miR-4732-5p | 3.25E−17 | + |
| 44 | hsa-miR-6125 | 1.01E−16 | + |
| 45 | hsa-miR-6090 | 1.38E−17 | + |
| 46 | hsa-miR-7114-5p | 1.97E−15 | − |
| 47 | hsa-miR-564 | 3.73E−21 | − |
| 48 | hsa-miR-451a | 4.72E−16 | − |
| 49 | hsa-miR-3135b | 1.59E−11 | − |
| 50 | hsa-miR-4497 | 2.02E−19 | − |
| 51 | hsa-miR-4665-5p | 4.12E−17 | − |
| 52 | hsa-miR-3622a-5p | 1.48E−18 | − |
| 53 | hsa-miR-6850-5p | 3.84E−15 | + |
| 54 | hsa-miR-6821-5p | 2.55E−13 | − |
| 55 | hsa-miR-5100 | 1.10E−14 | − |
| 56 | hsa-miR-6872-3p | 5.30E−16 | − |
| 57 | hsa-miR-4433-3p | 2.69E−12 | + |
| 58 | hsa-miR-1227-5p | 3.37E−17 | + |
| 59 | hsa-miR-3188 | 2.17E−14 | + |
| 60 | hsa-miR-7704 | 1.24E−13 | − |
| 61 | hsa-miR-3185 | 1.95E−12 | + |
| 62 | hsa-miR-1908-3p | 2.94E−15 | + |
| 63 | hsa-miR-6781-5p | 4.29E−12 | + |
| 64 | hsa-miR-6805-5p | 1.17E−15 | + |
| 65 | hsa-miR-8089 | 1.47E−13 | − |
| 66 | hsa-miR-665 | 8.11E−15 | + |
| 67 | hsa-miR-4486 | 3.16E−13 | + |
| 68 | hsa-miR-6722-3p | 1.65E−13 | + |
| 69 | hsa-miR-1260a | 2.60E−11 | − |
| 70 | hsa-miR-4707-5p | 2.00E−10 | + |
| 71 | hsa-miR-6741-5p | 6.59E−09 | − |
| 72 | hsa-miR-1260b | 5.25E−12 | − |
| 73 | hsa-miR-1246 | 1.34E−11 | + |
| 74 | hsa-miR-6845-5p | 1.26E−11 | + |
| 75 | hsa-miR-4638-5p | 3.28E−13 | − |
| 76 | hsa-miR-6085 | 5.78E−10 | − |
| 77 | hsa-miR-1228-3p | 3.27E−06 | + |
| 78 | hsa-miR-4534 | 3.91E−08 | − |
| 79 | hsa-miR-5585-3p | 6.28E−11 | + |
| 80 | hsa-miR-4741 | 3.46E−08 | + |
| 81 | hsa-miR-4433b-3p | 1.39E−05 | + |
| 82 | hsa-miR-197-5p | 8.04E−09 | + |
| 83 | hsa-miR-718 | 3.74E−08 | + |
| 84 | hsa-miR-4513 | 1.21E−10 | − |
| 85 | hsa-miR-4446-3p | 1.77E−08 | + |
| 86 | hsa-miR-619-5p | 1.39E−08 | + |
| 87 | hsa-miR-6816-5p | 1.57E−06 | + |
| 88 | hsa-miR-6778-5p | 4.15E−09 | + |
| 89 | hsa-miR-24-3p | 7.20E−08 | − |
| 90 | hsa-miR-1915-3p | 7.39E−09 | + |
| 91 | hsa-miR-4665-3p | 2.19E−07 | + |
| 92 | hsa-miR-4449 | 1.44E−08 | + |
| 93 | hsa-miR-6889-5p | 4.03E−09 | − |
| 94 | hsa-miR-486-3p | 3.07E−07 | + |
| 95 | hsa-miR-7113-3p | 7.17E−05 | + |
| 96 | hsa-miR-642a-3p | 2.16E−05 | − |
| 97 | hsa-miR-7847-3p | 1.01E−03 | − |
| 98 | hsa-miR-6768-5p | 5.36E−06 | − |
| 99 | hsa-miR-1290 | 1.38E−07 | + |
| 100 | hsa-miR-7108-5p | 1.70E−05 | + |
| 101 | hsa-miR-92b-5p | 5.47E−05 | + |
| 102 | hsa-miR-663b | 1.10E−05 | + |
| 103 | hsa-miR-3940-5p | 9.32E−06 | + |
| 104 | hsa-miR-4467 | 9.80E−07 | + |
| 105 | hsa-miR-6858-5p | 6.11E−08 | + |
| 106 | hsa-miR-4417 | 2.44E−04 | + |
| 107 | hsa-miR-3665 | 4.03E−06 | + |
| 108 | hsa-miR-4736 | 1.16E−05 | + |
| 109 | hsa-miR-4687-3p | 2.65E−07 | − |
| 110 | hsa-miR-1908-5p | 1.15E−04 | + |
| 111 | hsa-miR-5195-3p | 7.52E−06 | − |
| 112 | hsa-miR-4286 | 8.49E−06 | − |
| 113 | hsa-miR-3679-3p | 6.22E−04 | + |
| 114 | hsa-miR-6791-5p | 2.88E−05 | + |
| 115 | hsa-miR-1202 | 7.99E−06 | − |
| 116 | hsa-miR-3656 | 1.87E−06 | + |
| 117 | hsa-miR-4746-3p | 3.71E−05 | + |
| 118 | hsa-miR-3184-5p | 2.22E−05 | + |
| 119 | hsa-miR-3937 | 5.36E−03 | + |
| 120 | hsa-miR-6515-3p | 7.18E−02 | + |
| 121 | hsa-miR-6132 | 3.43E−04 | − |
| 122 | hsa-miR-187-5p | 1.16E−06 | − |
| 123 | hsa-miR-7111-5p | 5.89E−05 | − |
| 124 | hsa-miR-5787 | 1.91E−04 | − |
| 125 | hsa-miR-6779-5p | 1.86E−03 | − |
| 126 | hsa-miR-6808-5p | 2.64E−06 | + |
| 127 | hsa-miR-6774-5p | 2.50E−05 | + |
| 128 | hsa-miR-4656 | 7.70E−05 | + |
| 129 | hsa-miR-6806-5p | 1.02E−04 | + |
| 130 | hsa-miR-1233-5p | 1.23E−04 | + |
| 131 | hsa-miR-328-5p | 1.31E−04 | − |
| 132 | hsa-miR-4674 | 2.45E−04 | + |
| 133 | hsa-miR-2110 | 5.98E−04 | − |
| 134 | hsa-miR-6076 | 6.44E−04 | − |
| 135 | hsa-miR-3619-3p | 9.16E−04 | + |
| 136 | hsa-miR-92a-2-5p | 9.76E−04 | − |
| 137 | hsa-miR-128-1-5p | 1.22E−03 | + |
| 138 | hsa-miR-638 | 1.54E−03 | + |
| 139 | hsa-miR-2861 | 1.95E−03 | − |
| 140 | hsa-miR-371a-5p | 3.24E−03 | − |
| 141 | hsa-miR-211-3p | 3.44E−03 | + |
| 142 | hsa-miR-1273g-3p | 4.10E−03 | + |
| 143 | hsa-miR-1203 | 5.55E−03 | − |
| 144 | hsa-miR-122-5p | 5.81E−03 | + |
| 145 | hsa-miR-4258 | 5.82E−03 | + |
| 146 | hsa-miR-4484 | 7.10E−03 | + |
| 147 | hsa-miR-4648 | 8.55E−03 | + |
| 148 | hsa-miR-6780b-5p | 9.46E−03 | + |

Example 4

<Method for Evaluating Biliary Tract Cancer-Specific Discriminant Performance by Combination of Multiple Gene Markers Using Samples in the Validation Cohort>

In this Example, additional gene markers for diagnosis were selected by comparing gene expression levels of miR- NAs in sera of biliary tract cancer patients with those of a control group consisting of healthy subjects, colorectal cancer patients, stomach cancer patients, esophageal cancer patients, liver cancer patients, and benign pancreaticobiliary disease patients, in the same way as the method described in Example 1, and targeting the training cohort as the sample group described in Reference Example 2. One or two or more markers selected from the group consisting of the additional gene markers for diagnosis (SEQ ID NOs: 466 to 478; see Table 1) thus selected and the gene markers selected in Example 1 in combination were used to evaluate biliary tract cancer-specific discriminant performance.

Specifically, first, the miRNA expression levels in the training cohort and the validation cohort obtained in Reference Example 2 mentioned above were combined and normalized by quantile normalization. Next, Fisher's discriminant analysis was conducted to construct a discriminant for determining the presence or absence of biliary tract cancer, by using combinations of 1 to 4 expression level measurement values comprising at least one or more of the expression level measurement values of the polynucleotides consisting of the nucleotide sequences represented by SEQ ID NOs: 1 to 148, 466 to 478. Next, accuracy, sensitivity, and specificity in the validation cohort were calculated using the discriminant thus prepared, with a positive sample group that consists of the biliary tract cancer patient group, and a negative sample group that consists of the healthy subject group, the colorectal cancer patient group, the stomach cancer patient group, the esophageal cancer patient group, the liver cancer patient group, and the benign pancreaticobiliary disease patient group. The discriminant performance of the selected polynucleotides was validated using the independent samples.

Most of polynucleotides consisting of the nucleotide sequences represented by these SEQ ID NOs (SEQ ID NOs: 1 to 148, and 466 to 478 corresponding to the miRNA markers of Table 1) or complementary sequences thereof mentioned above were able to provide relatively high accuracy, sensitivity, and specificity in the determination of the presence or absence of biliary tract cancer, and furthermore, were able to specifically discriminate biliary tract cancer from the other cancers. For example, among the combinations of multiple polynucleotides selected from the group consisting of polynucleotides consisting of the nucleotide sequences represented by SEQ ID NOs: 1, 4, 5, 11, 12, 15, 23, 29, 39, 40, 54, 76, 79, 91, 103, 115, 121, 134, 143, 466, 469, 472, 473, and 474 or complementary sequences thereof (the cancer type-specific polynucleotide group 1) listed as polynucleotides capable of specifically binding to target markers, combinations comprising at least one polynucleotide selected from the group consisting of polynucleotides consisting of the nucleotide sequences represented by SEQ ID NOs: 4, 5, 12, 15, and 40 or complementary sequences thereof (the cancer type-specific polynucleotide group 2) were able to specifically discriminate biliary tract cancer from the other cancers with high accuracy.

The number of the polynucleotides with cancer type specificity in the combination mentioned above can be 1, 2, 3, 4, 5, 6, 7, 8, 9, 10 or more for the combination. The combinations of 4 or more polynucleotides were able to exhibit discrimination accuracy of 80% or higher.

Specifically, the discrimination accuracy of the measurement using the polynucleotide consisting of the nucleotide sequence represented by SEQ ID NO: 4 or a complementary sequence thereof is given below. The measurement using alone (one) the polynucleotide consisting of the nucleotide sequence represented by SEQ ID NO: 4 or a complementary sequence thereof exhibited accuracy of 81.9% in the training cohort and accuracy of 76.9% in the validation cohort (Table 8). Also, for example, the measurement using the combinations of two polynucleotides comprising at least one polynucleotide consisting of the nucleotide sequence represented by SEQ ID NO: 4 or a complementary sequence thereof exhibited the highest accuracy of 86.0% in the training cohort and accuracy of 85.3% in the validation cohort (Table 9; "SEQ ID NO" in the table represents the combinations of SEQ ID NOs of the two polynucleotides used). Furthermore, for example, the measurement using the combinations of three polynucleotides comprising at least one polynucleotide consisting of the nucleotide sequence represented by SEQ ID NO: 4 or a complementary sequence thereof exhibited the highest accuracy of 89.5% in the training cohort and accuracy of 90.4% in the validation cohort (Table 10; "SEQ ID NO" in the table represents the combinations of SEQ ID NOs of the three polynucleotides used). Furthermore, for example, the measurement using the combinations of four polynucleotides comprising at least one polynucleotide consisting of the nucleotide sequence represented by SEQ ID NO: 4 or a complementary sequence thereof exhibited the highest accuracy of 91.1% in the training cohort and accuracy of 92.3% in the validation cohort (Table 11; "SEQ ID NO" in the table represents the combinations of SEQ ID NOs of the four polynucleotides used).

Specifically, the discrimination accuracy of the measurement using the polynucleotide consisting of the nucleotide sequence represented by SEQ ID NO: 5 or a complementary sequence thereof is given below. The measurement using alone (one) the polynucleotide consisting of the nucleotide sequence represented by SEQ ID NO: 5 or a complementary sequence thereof exhibited accuracy of 79.0% in the training cohort and accuracy of 80.8% in the validation cohort (Table 8). Also, for example, the measurement using the combinations of two polynucleotides comprising at least one polynucleotide consisting of the nucleotide sequence represented by SEQ ID NO: 5 or a complementary sequence thereof exhibited the highest accuracy of 81.9% in the training cohort and accuracy of 86.5% in the validation cohort (Table 9). Furthermore, for example, the measurement using the combinations of three polynucleotides comprising at least one polynucleotide consisting of the nucleotide sequence represented by SEQ ID NO: 5 or a complementary sequence thereof exhibited the highest accuracy of 87.6% in the training cohort and accuracy of 89.7% in the validation cohort (Table 10). Furthermore, for example, the measurement using the combinations of four polynucleotides comprising at least one polynucleotide consisting of the nucleotide sequence represented by SEQ ID NO: 5 or a complementary sequence thereof exhibited the highest accuracy of 93.0% in the training cohort and accuracy of 91.0% in the validation cohort (Table 11).

Specifically, the discrimination accuracy of the measurement using the polynucleotide consisting of the nucleotide sequence represented by SEQ ID NO: 12 or a complementary sequence thereof is given below. The measurement using alone (one) the polynucleotide consisting of the nucleotide sequence represented by SEQ ID NO: 12 or a complementary sequence thereof exhibited accuracy of 80.6% in the training cohort and accuracy of 76.9% in the validation cohort (Table 8). Also, for example, the measurement using the combinations of two polynucleotides comprising at least one polynucleotide consisting of the nucleotide sequence represented by SEQ ID NO: 12 or a complementary sequence thereof exhibited the highest accuracy of 86.3% in the training cohort and accuracy of 85.9% in the validation cohort (Table 9). Furthermore, for example, the measurement using the combinations of three polynucleotides comprising at least one polynucleotide consisting of the nucleotide sequence represented by SEQ ID NO: 12 or a complementary sequence thereof exhibited the highest accuracy of 90.2% in the training cohort and accuracy of 91.7% in the validation cohort (Table 10). Furthermore, for example, the measurement using the combinations of four polynucleotides comprising at least one polynucleotide consisting of the nucleotide sequence represented by SEQ ID NO: 12 or a complementary sequence thereof exhibited the highest accuracy of 93.0% in the training cohort and accuracy of 94.2% in the validation cohort (Table 11).

Specifically, the discrimination accuracy of the measurement using the polynucleotide consisting of the nucleotide sequence represented by SEQ ID NO: 15 or a complementary sequence thereof is given below. The measurement using alone (one) the polynucleotide consisting of the nucleotide sequence represented by SEQ ID NO: 15 or a complementary sequence thereof exhibited accuracy of 83.8% in the training cohort and accuracy of 84.0% in the validation cohort (Table 8). Also, for example, the measurement using the combinations of two polynucleotides comprising at least one polynucleotide consisting of the nucleotide sequence represented by SEQ ID NO: 15 or a complementary sequence thereof exhibited the highest accuracy of 89.5% in the training cohort and accuracy of 89.1% in the validation cohort (Table 9). Furthermore, for example, the measurement using the combinations of three polynucleotides comprising at least one polynucleotide consisting of the nucleotide sequence represented by SEQ ID NO: 15 or a complementary sequence thereof exhibited the highest accuracy of 90.5% in the training cohort and accuracy of 92.3% in the validation cohort (Table 10). Furthermore, for example, the measurement using the combinations of four polynucleotides comprising at least one polynucleotide consisting of the nucleotide sequence represented by SEQ ID NO: 15 or a complementary sequence thereof exhibited the highest accuracy of 93.0% in the training cohort and accuracy of 94.2% in the validation cohort (Table 11).

Specifically, the discrimination accuracy of the measurement using the polynucleotide consisting of the nucleotide sequence represented by SEQ ID NO: 40 or a complementary sequence thereof is given below. The measurement using alone (one) the polynucleotide consisting of the nucleotide sequence represented by SEQ ID NO: 40 or a complementary sequence thereof exhibited accuracy of 80.0% in the training cohort and accuracy of 76.9% in the validation cohort (Table 8). Also, for example, the measurement using the combinations of two polynucleotides comprising at least one polynucleotide consisting of the nucleotide sequence represented by SEQ ID NO: 40 or a complementary sequence thereof exhibited the highest accuracy of 81.9% in the training cohort and accuracy of 86.5% in the validation cohort (Table 9). Furthermore, for example, the measurement using the combinations of three polynucleotides comprising at least one polynucleotide consisting of the nucleotide sequence represented by SEQ ID NO: 40 or a complementary sequence thereof exhibited the highest accuracy of 86.7% in the training cohort and accuracy of 89.7% in the validation cohort (Table 10). Furthermore, for example, the measurement using the combinations of four polynucleotides comprising at least one polynucleotide consisting of the nucleotide sequence represented by SEQ ID NO: 40 or a complementary sequence thereof exhibited the highest accuracy of 91.4% in the training cohort and accuracy of 91.7% in the validation cohort (Table 11).

Figure 4:
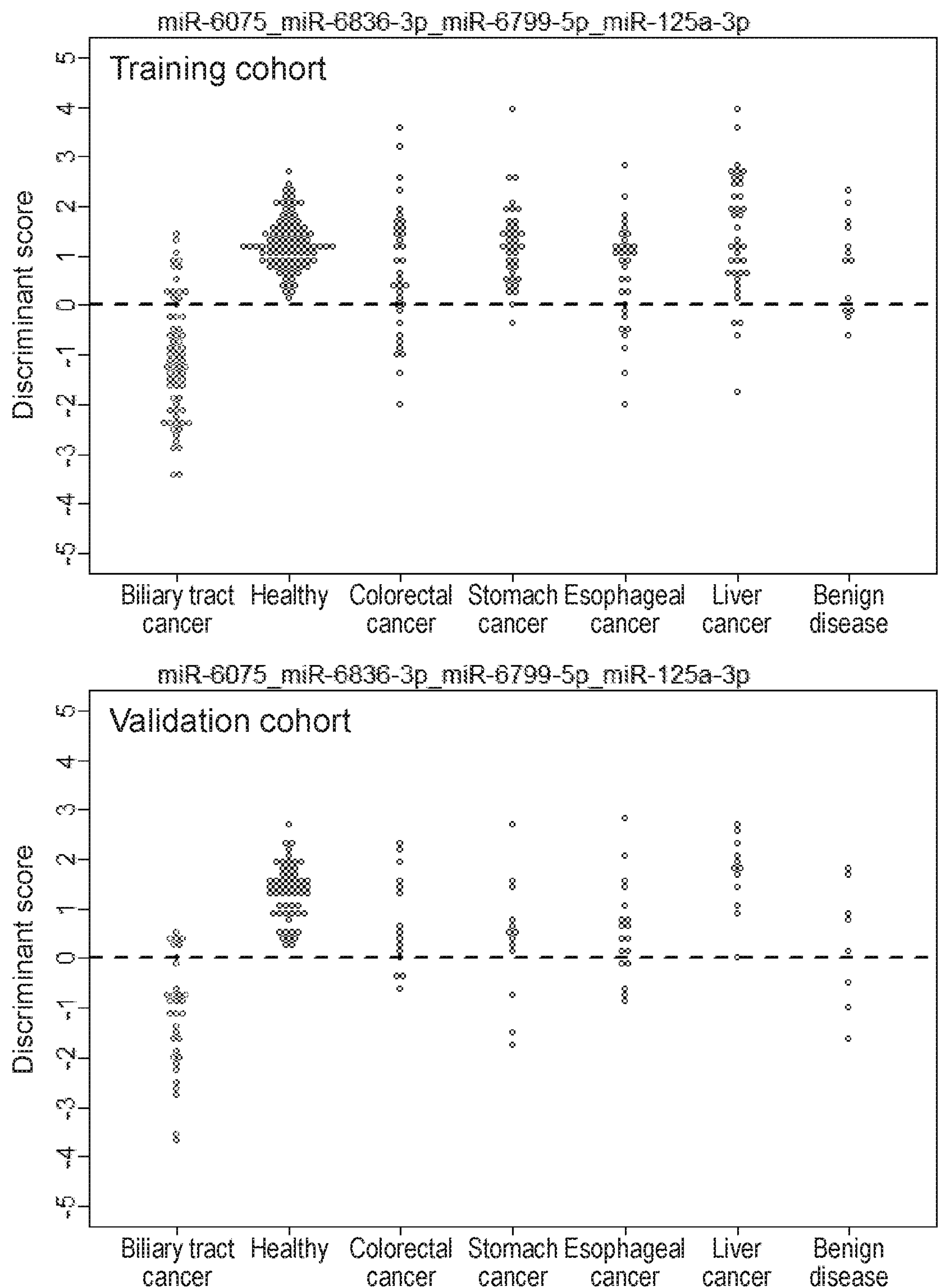
FIG. 4 Upper diagram: a discriminant (−1.25×hsa-miR-6075-1.06×hsa-miR-6836-3p+0.53×hsa-miR-6799-5p+0.18×hsa-miR-125a-3p+15.41) was prepared by use of Fisher's linear discriminant analysis from the measurement values of hsa-miR-6075 (SEQ ID NO: 15), hsa-miR-6836-3p (SEQ ID NO: 12), hsa-miR-6799-5p (SEQ ID NO: 29), and hsa-miR-125a-3p (SEQ ID NO: 1) in 67 biliary tract cancer patients, 93 healthy subjects, 35 colorectal cancer patients, 37 stomach cancer patients, 32 esophageal cancer patients, 38 liver cancer patients, and 13 benign pancreaticobiliary disease patients selected in a training cohort, and discriminant scores obtained from the discriminant were plotted on the ordinate against the sample groups on the abscissa. The dotted line in the diagram depicts a discriminant boundary that offered a discriminant score of 0 and discriminated between the groups. Lower diagram: discriminant scores obtained from the discriminant prepared from the training cohort as to the measurement values of hsa-miR-6075 (SEQ ID NO: 15), hsa-miR-6836-3p (SEQ ID NO: 12), hsa-miR-6799-5p (SEQ ID NO: 29), hsa-miR-125a-3p (SEQ ID NO: 1) in 33 biliary tract cancer patients, 57 healthy subjects, 15 colorectal cancer patients, 13 stomach cancer patients, 18 esophageal cancer patients, 12 liver cancer patients, and 8 benign pancreaticobiliary disease patients selected as a validation cohort were plotted on the ordinate against the sample groups on the abscissa. The dotted line in the diagram depicts the discriminant boundary that offered a discriminant score of 0 and discriminated between the two groups.

The expression level measurement values of the nucleotide sequences represented by SEQ ID NOs: 15, 5, 4, 12, 40 were compared among 67 biliary tract cancer patients, 93 healthy subjects, 35 colorectal cancer patients, 37 stomach cancer patients, 32 esophageal cancer patients, 38 liver cancer patients, and 13 benign pancreaticobiliary disease patients in the training cohort. As a result, a scatter diagram that significantly separated the discriminant score of the biliary tract cancer patient group from the other discriminant scores was obtained in the training cohort (see the upper diagram of FIG. 4). These results were also reproducible in the validation cohort (see the lower diagram of FIG. 4).

TABLE 8

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 4 | 81.9 | 82.3 | 80.6 | 76.9 | 78.9 | 69.7 |
| 5 | 79 | 79 | 79.1 | 80.8 | 80.5 | 81.8 |
| 11 | 77.1 | 76.6 | 79.1 | 74.4 | 73.2 | 78.8 |
| 12 | 80.6 | 80.2 | 82.1 | 76.9 | 77.2 | 75.8 |
| 15 | 83.8 | 88.7 | 65.7 | 84 | 88.6 | 66.7 |
| 23 | 76.8 | 75.8 | 80.6 | 70.5 | 66.7 | 84.8 |
| 29 | 76.2 | 74.6 | 82.1 | 73.7 | 70.7 | 84.8 |
| 39 | 79.7 | 83.5 | 65.7 | 74.4 | 78.9 | 57.6 |
| 40 | 80 | 81 | 76.1 | 76.9 | 76.4 | 78.8 |
| 54 | 61.9 | 60.1 | 68.7 | 65.4 | 61.8 | 78.8 |
| 76 | 76.2 | 77.4 | 71.6 | 69.9 | 75.6 | 48.5 |
| 91 | 59.7 | 60.5 | 56.7 | 55.1 | 53.7 | 60.6 |
| 115 | 56.2 | 56.5 | 55.2 | 58.3 | 61 | 48.5 |
| 121 | 70.2 | 70.2 | 70.1 | 73.1 | 74.8 | 66.7 |
| 143 | 70.8 | 73.8 | 59.7 | 67.9 | 71.5 | 54.5 |

TABLE 9

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 15_121 | 89.5 | 93.5 | 74.6 | 89.1 | 91.1 | 81.8 |
| 15_88 | 85.1 | 89.9 | 67.2 | 86.5 | 91.1 | 69.7 |
| 15_471 | 86.7 | 91.5 | 68.7 | 86.5 | 91.1 | 69.7 |
| 5_40 | 81.9 | 83.9 | 74.6 | 86.5 | 86.2 | 87.9 |
| 15_12 | 86.3 | 89.1 | 76.1 | 85.9 | 88.6 | 75.8 |
| 15_39 | 87.3 | 90.3 | 76.1 | 85.9 | 88.6 | 75.8 |
| 15_29 | 86.3 | 89.1 | 76.1 | 85.9 | 88.6 | 75.8 |
| 4_15 | 86 | 87.9 | 79.1 | 85.3 | 87 | 78.8 |

TABLE 10

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 15_121_115 | 90.5 | 94 | 77.6 | 92.3 | 92.7 | 90.9 |
| 15_121_91 | 90.2 | 93.5 | 77.6 | 91.7 | 93.5 | 84.8 |
| 15_12_121 | 90.2 | 93.5 | 77.6 | 91.7 | 92.7 | 87.9 |
| 15_121_109 | 89.8 | 93.1 | 77.6 | 91 | 92.7 | 84.8 |
| 15_102_121 | 90.1 | 93.1 | 78.8 | 91 | 91.9 | 87.9 |
| 15_62_121 | 90.8 | 94 | 79.1 | 91 | 91.1 | 90.9 |
| 15_39_121 | 90.8 | 94.4 | 77.6 | 90.4 | 91.9 | 84.8 |
| 15_23_121 | 89.8 | 93.1 | 77.6 | 90.4 | 90.2 | 90.9 |
| 15_4_121 | 89.5 | 91.9 | 80.6 | 90.4 | 90.2 | 90.9 |
| 15_76_121 | 89.5 | 93.5 | 74.6 | 89.7 | 91.9 | 81.8 |
| 15_121_31 | 90.5 | 94 | 77.6 | 89.7 | 91.9 | 81.8 |
| 15_121_64 | 89.8 | 93.5 | 76.1 | 89.7 | 91.9 | 81.8 |
| 15_121_468 | 90.5 | 93.1 | 80.6 | 89.7 | 91.9 | 81.8 |
| 15_94_121 | 90.2 | 93.5 | 77.6 | 89.7 | 91.1 | 84.8 |
| 15_121_143 | 89.8 | 94 | 74.6 | 89.7 | 91.1 | 84.8 |
| 15_121_108 | 89.5 | 93.1 | 76.1 | 89.7 | 91.1 | 84.8 |
| 5_39_115 | 87.6 | 89.1 | 82.1 | 89.7 | 91.1 | 84.8 |
| 40_12_64 | 86.7 | 87.9 | 82.1 | 89.7 | 91.1 | 84.8 |
| 15_20_121 | 91.4 | 92.3 | 88.1 | 89.1 | 91.1 | 81.8 |
| 15_11_121 | 89.2 | 93.1 | 74.6 | 89.1 | 91.1 | 81.8 |
| 15_121_54 | 89.5 | 93.5 | 74.6 | 89.1 | 91.1 | 81.8 |
| 15_121_79 | 90.2 | 94.8 | 73.1 | 89.1 | 91.1 | 81.8 |
| 15_121_134 | 89.2 | 93.1 | 74.6 | 89.1 | 91.1 | 81.8 |
| 15_121_471 | 89.2 | 94 | 71.6 | 89.1 | 91.1 | 81.8 |
| 15_121_474 | 89.5 | 93.5 | 74.6 | 89.1 | 91.1 | 81.8 |
| 40_39_121 | 90.8 | 94 | 79.1 | 89.1 | 91.1 | 81.8 |
| 15_40_121 | 91.7 | 94.4 | 82.1 | 89.1 | 90.2 | 84.8 |
| 15_29_121 | 90.8 | 94 | 79.1 | 89.1 | 89.4 | 87.9 |
| 5_40_121 | 85.7 | 86.3 | 83.6 | 89.1 | 88.6 | 90.9 |
| 15_88_471 | 86 | 91.1 | 67.2 | 88.5 | 93.5 | 69.7 |
| 15_39_115 | 86 | 89.9 | 71.6 | 88.5 | 91.9 | 75.8 |
| 40_39_89 | 88.9 | 92.7 | 74.6 | 88.5 | 91.9 | 75.8 |
| 40_4_88 | 86 | 86.7 | 83.6 | 88.5 | 91.1 | 78.8 |
| 15_5_115 | 87.3 | 89.9 | 77.6 | 88.5 | 90.2 | 81.8 |
| 15_12_115 | 90.5 | 93.5 | 79.1 | 88.5 | 90.2 | 81.8 |
| 15_121_466 | 89.2 | 93.5 | 73.1 | 88.5 | 90.2 | 81.8 |
| 15_121_145 | 88.6 | 93.1 | 71.6 | 88.5 | 90.2 | 81.8 |
| 15_121_135 | 89.5 | 92.7 | 77.6 | 88.5 | 90.2 | 81.8 |
| 15_121_89 | 89.5 | 93.5 | 74.6 | 88.5 | 89.4 | 84.8 |
| 5_12_115 | 90.2 | 90.7 | 88.1 | 88.5 | 89.4 | 84.8 |
| 5_12_91 | 86.7 | 87.5 | 83.6 | 88.5 | 88.6 | 87.9 |
| 5_471_115 | 87.3 | 88.7 | 82.1 | 88.5 | 88.6 | 87.9 |
| 12_121_468 | 84.1 | 85.9 | 77.6 | 88.5 | 88.6 | 87.9 |
| 40_39_79 | 88.3 | 91.9 | 74.6 | 87.8 | 93.5 | 66.7 |
| 15_79_471 | 87.6 | 92.7 | 68.7 | 87.8 | 92.7 | 69.7 |
| 15_39_102 | 89.2 | 92.3 | 77.3 | 87.8 | 91.9 | 72.7 |
| 15_102_115 | 86 | 89.9 | 71.2 | 87.8 | 91.1 | 75.8 |
| 15_54_64 | 85.1 | 89.5 | 68.7 | 87.8 | 91.1 | 75.8 |
| 15_12_473 | 86.3 | 89.5 | 74.6 | 87.8 | 90.2 | 78.8 |
| 15_4_471 | 88.3 | 90.7 | 79.1 | 87.8 | 90.2 | 78.8 |
| 15_121_467 | 89.5 | 93.5 | 74.6 | 87.8 | 90.2 | 78.8 |
| 15_121_472 | 91.7 | 94.4 | 82.1 | 87.8 | 90.2 | 78.8 |
| 40_64_88 | 82.5 | 83.9 | 77.6 | 87.8 | 90.2 | 78.8 |
| 15_121_88 | 89.8 | 93.5 | 76.1 | 87.8 | 89.4 | 81.8 |
| 15_121_470 | 91.1 | 93.1 | 83.6 | 87.8 | 89.4 | 81.8 |
| 15_121_473 | 89.2 | 93.5 | 73.1 | 87.8 | 89.4 | 81.8 |

TABLE 10-continued

| SEQ ID NO: | Training cohort Accuracy (%) | Training cohort Sensitivity (%) | Training cohort Specificity (%) | Validation cohort Accuracy (%) | Validation cohort Sensitivity (%) | Validation cohort Specificity (%) |
|---|---|---|---|---|---|---|
| 15_64_88 | 84.4 | 89.9 | 64.2 | 87.2 | 92.7 | 66.7 |
| 15_88_79 | 86 | 91.1 | 67.2 | 87.2 | 91.9 | 69.7 |
| 15_108_471 | 86.7 | 91.5 | 68.7 | 87.2 | 91.9 | 69.7 |
| 15_102_470 | 86.9 | 89.9 | 75.8 | 87.2 | 91.1 | 72.7 |
| 15_11_88 | 83.8 | 88.3 | 67.2 | 87.2 | 91.1 | 72.7 |
| 40_4_76 | 86.3 | 87.9 | 80.6 | 87.2 | 91.1 | 72.7 |
| 40_39_473 | 87.6 | 90.7 | 76.1 | 87.2 | 91.1 | 72.7 |
| 15_12_145 | 87.6 | 89.9 | 79.1 | 87.2 | 90.2 | 75.8 |
| 15_23_115 | 85.7 | 89.1 | 73.1 | 87.2 | 90.2 | 75.8 |
| 40_39_64 | 87.3 | 90.3 | 76.1 | 87.2 | 90.2 | 75.8 |
| 40_20_79 | 83.2 | 85.5 | 74.6 | 87.2 | 90.2 | 75.8 |
| 15_11_115 | 86 | 90.7 | 68.7 | 87.2 | 89.4 | 78.8 |
| 5_76_115 | 87.9 | 88.7 | 85.1 | 87.2 | 89.4 | 78.8 |
| 40_20_64 | 86.7 | 87.9 | 82.1 | 87.2 | 89.4 | 78.8 |
| 40_11_64 | 84.1 | 85.1 | 80.6 | 87.2 | 89.4 | 78.8 |
| 40_467_64 | 84.8 | 86.7 | 77.6 | 87.2 | 89.4 | 78.8 |
| 15_4_29 | 86.3 | 87.5 | 82.1 | 87.2 | 88.6 | 81.8 |
| 15_5_121 | 90.8 | 93.5 | 80.6 | 87.2 | 87.8 | 84.8 |
| 5_121_79 | 83.8 | 85.5 | 77.6 | 87.2 | 87 | 87.9 |
| 5_39_121 | 86.3 | 87.9 | 80.6 | 87.2 | 86.2 | 90.9 |
| 15_76_471 | 86 | 90.7 | 68.7 | 86.5 | 91.9 | 66.7 |
| 15_94_471 | 86.3 | 91.1 | 68.7 | 86.5 | 91.1 | 69.7 |
| 15_31_88 | 84.4 | 89.1 | 67.2 | 86.5 | 91.1 | 69.7 |
| 15_31_471 | 86.3 | 91.1 | 68.7 | 86.5 | 91.1 | 69.7 |
| 15_54_115 | 87.6 | 92.3 | 70.1 | 86.5 | 91.1 | 69.7 |
| 15_109_88 | 85.1 | 89.9 | 67.2 | 86.5 | 91.1 | 69.7 |
| 15_109_471 | 86.7 | 91.5 | 68.7 | 86.5 | 91.1 | 69.7 |
| 15_467_88 | 84.1 | 88.7 | 67.2 | 86.5 | 91.1 | 69.7 |
| 15_64_471 | 86 | 91.5 | 65.7 | 86.5 | 91.1 | 69.7 |
| 15_88_145 | 84.4 | 89.1 | 67.2 | 86.5 | 91.1 | 69.7 |
| 15_88_134 | 84.4 | 89.1 | 67.2 | 86.5 | 91.1 | 69.7 |
| 15_88_473 | 84.4 | 89.1 | 67.2 | 86.5 | 91.1 | 69.7 |
| 15_145_471 | 86.7 | 91.5 | 68.7 | 86.5 | 91.1 | 69.7 |
| 15_470_471 | 87.3 | 91.9 | 70.1 | 86.5 | 91.1 | 69.7 |
| 15_471_135 | 86.7 | 91.5 | 68.7 | 86.5 | 91.1 | 69.7 |
| 15_471_89 | 86.7 | 91.5 | 68.7 | 86.5 | 91.1 | 69.7 |
| 15_471_472 | 87 | 91.9 | 68.7 | 86.5 | 91.1 | 69.7 |
| 15_471_474 | 87 | 91.9 | 68.7 | 86.5 | 91.1 | 69.7 |
| 40_39_467 | 89.8 | 93.1 | 77.6 | 86.5 | 91.1 | 69.7 |
| 15_40_64 | 85.4 | 89.5 | 70.1 | 86.5 | 90.2 | 72.7 |
| 15_23_470 | 86.3 | 88.3 | 79.1 | 86.5 | 90.2 | 72.7 |
| 15_39_470 | 87 | 89.9 | 76.1 | 86.5 | 90.2 | 72.7 |
| 15_39_471 | 88.9 | 92.7 | 74.6 | 86.5 | 90.2 | 72.7 |
| 15_29_31 | 87 | 90.3 | 74.6 | 86.5 | 90.2 | 72.7 |
| 15_20_79 | 85.7 | 90.3 | 68.7 | 86.5 | 90.2 | 72.7 |
| 40_4_470 | 86 | 86.7 | 83.6 | 86.5 | 90.2 | 72.7 |
| 15_40_12 | 87.3 | 90.7 | 74.6 | 86.5 | 89.4 | 75.8 |
| 15_12_467 | 86.3 | 89.1 | 76.1 | 86.5 | 89.4 | 75.8 |
| 15_12_143 | 86.3 | 89.1 | 76.1 | 86.5 | 89.4 | 75.8 |
| 15_12_108 | 87.3 | 90.3 | 76.1 | 86.5 | 89.4 | 75.8 |
| 15_12_470 | 87.9 | 89.9 | 80.6 | 86.5 | 89.4 | 75.8 |
| 15_12_471 | 89.5 | 92.3 | 79.1 | 86.5 | 89.4 | 75.8 |
| 15_12_89 | 87 | 89.9 | 76.1 | 86.5 | 89.4 | 75.8 |
| 15_12_472 | 87 | 89.5 | 77.6 | 86.5 | 89.4 | 75.8 |
| 15_12_474 | 86.7 | 89.5 | 76.1 | 86.5 | 89.4 | 75.8 |
| 15_23_102 | 86.3 | 89.9 | 72.7 | 86.5 | 89.4 | 75.8 |
| 15_39_54 | 87.3 | 90.3 | 76.1 | 86.5 | 89.4 | 75.8 |
| 15_29_62 | 85.7 | 89.1 | 73.1 | 86.5 | 89.4 | 75.8 |
| 15_102_11 | 85.7 | 89.5 | 71.2 | 86.5 | 89.4 | 75.8 |
| 40_23_39 | 87.9 | 90.7 | 77.6 | 86.5 | 89.4 | 75.8 |
| 40_39_62 | 88.6 | 92.3 | 74.6 | 86.5 | 89.4 | 75.8 |
| 40_39_11 | 88.3 | 91.1 | 77.6 | 86.5 | 89.4 | 75.8 |
| 40_39_88 | 87.9 | 91.5 | 74.6 | 86.5 | 89.4 | 75.8 |
| 40_64_472 | 84.4 | 86.7 | 76.1 | 86.5 | 89.4 | 75.8 |
| 4_39_91 | 84.4 | 87.5 | 73.1 | 86.5 | 89.4 | 75.8 |
| 4_76_115 | 86.7 | 89.1 | 77.6 | 86.5 | 89.4 | 75.8 |
| 15_40_11 | 84.4 | 87.9 | 71.6 | 86.5 | 88.6 | 78.8 |
| 15_20_115 | 87.6 | 90.7 | 76.1 | 86.5 | 88.6 | 78.8 |
| 5_40_64 | 84.1 | 85.5 | 79.1 | 86.5 | 88.6 | 78.8 |
| 40_62_64 | 83.2 | 84.7 | 77.6 | 86.5 | 88.6 | 78.8 |
| 40_121_467 | 87.6 | 89.5 | 80.6 | 86.5 | 88.6 | 78.8 |
| 4_62_115 | 82.2 | 83.1 | 79.1 | 86.5 | 88.6 | 78.8 |
| 15_5_91 | 86.3 | 89.9 | 73.1 | 86.5 | 87.8 | 81.8 |
| 40_12_4 | 86.3 | 87.1 | 83.6 | 86.5 | 87.8 | 81.8 |
| 40_12_79 | 85.7 | 87.9 | 77.6 | 86.5 | 87.8 | 81.8 |

TABLE 10-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 40_4_121 | 86 | 87.9 | 79.1 | 86.5 | 87.8 | 81.8 |
| 12_4_468 | 86.3 | 87.5 | 82.1 | 86.5 | 87.8 | 81.8 |
| 12_4_115 | 85.1 | 85.9 | 82.1 | 86.5 | 87.8 | 81.8 |
| 4_88_115 | 83.8 | 83.9 | 83.6 | 86.5 | 87.8 | 81.8 |
| 5_40_88 | 83.5 | 84.7 | 79.1 | 86.5 | 87 | 84.8 |
| 5_40_20 | 84.4 | 85.1 | 82.1 | 86.5 | 86.2 | 87.9 |
| 5_40_54 | 82.2 | 83.9 | 76.1 | 86.5 | 86.2 | 87.9 |
| 5_40_109 | 82.2 | 83.9 | 76.1 | 86.5 | 86.2 | 87.9 |
| 5_40_471 | 82.9 | 85.1 | 74.6 | 86.5 | 86.2 | 87.9 |
| 5_40_473 | 82.2 | 83.5 | 77.6 | 86.5 | 86.2 | 87.9 |
| 40_12_88 | 85.1 | 85.5 | 83.6 | 86.5 | 86.2 | 87.9 |
| 40_12_121 | 87 | 87.9 | 83.6 | 86.5 | 85.4 | 90.9 |
| 15_88_89 | 84.8 | 89.5 | 67.2 | 85.9 | 91.1 | 66.7 |
| 15_40_88 | 84.8 | 89.5 | 67.2 | 85.9 | 90.2 | 69.7 |
| 15_39_88 | 87.3 | 91.5 | 71.6 | 85.9 | 90.2 | 69.7 |
| 15_39_79 | 87.9 | 91.9 | 73.1 | 85.9 | 90.2 | 69.7 |
| 15_62_64 | 84.8 | 89.1 | 68.7 | 85.9 | 90.2 | 69.7 |
| 15_62_79 | 85.7 | 90.3 | 68.7 | 85.9 | 90.2 | 69.7 |
| 15_466_88 | 84.1 | 88.7 | 67.2 | 85.9 | 90.2 | 69.7 |
| 15_88_472 | 85.1 | 89.9 | 67.2 | 85.9 | 90.2 | 69.7 |
| 15_88_474 | 85.1 | 89.9 | 67.2 | 85.9 | 90.2 | 69.7 |
| 15_143_471 | 86.3 | 91.5 | 67.2 | 85.9 | 90.2 | 69.7 |
| 15_468_471 | 86.7 | 91.5 | 68.7 | 85.9 | 90.2 | 69.7 |
| 15_469_471 | 86.3 | 91.1 | 68.7 | 85.9 | 90.2 | 69.7 |
| 15_134_471 | 87 | 91.9 | 68.7 | 85.9 | 90.2 | 69.7 |
| 15_471_115 | 87.3 | 92.7 | 67.2 | 85.9 | 90.2 | 69.7 |
| 15_29_88 | 85.1 | 88.7 | 71.6 | 85.9 | 89.4 | 72.7 |
| 15_29_469 | 86.3 | 89.1 | 76.1 | 85.9 | 89.4 | 72.7 |
| 15_102_467 | 86.9 | 90.7 | 72.7 | 85.9 | 89.4 | 72.7 |
| 15_102_64 | 85.4 | 89.5 | 69.7 | 85.9 | 89.4 | 72.7 |
| 15_102_79 | 86.3 | 90.7 | 69.7 | 85.9 | 89.4 | 72.7 |
| 15_102_471 | 86.9 | 91.1 | 71.2 | 85.9 | 89.4 | 72.7 |
| 15_470_115 | 85.1 | 88.3 | 73.1 | 85.9 | 89.4 | 72.7 |
| 40_39_94 | 88.6 | 91.9 | 76.1 | 85.9 | 89.4 | 72.7 |
| 40_39_466 | 89.5 | 93.1 | 76.1 | 85.9 | 89.4 | 72.7 |
| 40_39_31 | 88.6 | 92.3 | 74.6 | 85.9 | 89.4 | 72.7 |
| 40_39_468 | 89.2 | 92.7 | 76.1 | 85.9 | 89.4 | 72.7 |
| 40_39_471 | 88.6 | 92.3 | 74.6 | 85.9 | 89.4 | 72.7 |
| 40_39_472 | 89.2 | 92.7 | 76.1 | 85.9 | 89.4 | 72.7 |
| 15_5_23 | 84.8 | 87.1 | 76.1 | 85.9 | 88.6 | 75.8 |
| 15_40_470 | 85.4 | 87.5 | 77.6 | 85.9 | 88.6 | 75.8 |
| 15_12_31 | 86.7 | 89.5 | 76.1 | 85.9 | 88.6 | 75.8 |
| 15_12_54 | 87 | 89.9 | 76.1 | 85.9 | 88.6 | 75.8 |
| 15_12_468 | 86.3 | 89.1 | 76.1 | 85.9 | 88.6 | 75.8 |
| 15_12_134 | 86.3 | 89.1 | 76.1 | 85.9 | 88.6 | 75.8 |
| 15_12_135 | 86.3 | 89.1 | 76.1 | 85.9 | 88.6 | 75.8 |
| 15_23_39 | 87.9 | 90.3 | 79.1 | 85.9 | 88.6 | 75.8 |
| 15_39_31 | 87.3 | 90.3 | 76.1 | 85.9 | 88.6 | 75.8 |
| 15_39_109 | 87.3 | 90.3 | 76.1 | 85.9 | 88.6 | 75.8 |
| 15_39_108 | 87.3 | 90.3 | 76.1 | 85.9 | 88.6 | 75.8 |
| 15_39_135 | 87.3 | 90.3 | 76.1 | 85.9 | 88.6 | 75.8 |
| 15_39_89 | 87.3 | 90.3 | 76.1 | 85.9 | 88.6 | 75.8 |
| 15_39_472 | 87.3 | 90.3 | 76.1 | 85.9 | 88.6 | 75.8 |
| 15_29_76 | 86.3 | 89.1 | 76.1 | 85.9 | 88.6 | 75.8 |
| 15_29_102 | 87.3 | 90.7 | 74.2 | 85.9 | 88.6 | 75.8 |
| 15_29_466 | 86.3 | 89.1 | 76.1 | 85.9 | 88.6 | 75.8 |
| 15_29_54 | 86 | 88.7 | 76.1 | 85.9 | 88.6 | 75.8 |
| 15_29_143 | 86.3 | 89.5 | 74.6 | 85.9 | 88.6 | 75.8 |
| 15_29_134 | 86 | 88.7 | 76.1 | 85.9 | 88.6 | 75.8 |
| 15_29_108 | 86.3 | 89.1 | 76.1 | 85.9 | 88.6 | 75.8 |
| 15_29_471 | 87 | 90.3 | 74.6 | 85.9 | 88.6 | 75.8 |
| 15_29_89 | 86.7 | 89.5 | 76.1 | 85.9 | 88.6 | 75.8 |
| 15_29_472 | 86.3 | 89.1 | 76.1 | 85.9 | 88.6 | 75.8 |
| 15_121_469 | 90.5 | 94.4 | 76.1 | 85.9 | 88.6 | 75.8 |
| 40_4_31 | 86.3 | 87.5 | 82.1 | 85.9 | 88.6 | 75.8 |
| 40_39_143 | 87.6 | 90.7 | 76.1 | 85.9 | 88.6 | 75.8 |
| 40_39_108 | 87.3 | 90.7 | 74.6 | 85.9 | 88.6 | 75.8 |
| 40_20_468 | 84.1 | 85.9 | 77.6 | 85.9 | 88.6 | 75.8 |
| 40_31_79 | 82.9 | 85.5 | 73.1 | 85.9 | 88.6 | 75.8 |
| 4_76_91 | 86 | 87.5 | 80.6 | 85.9 | 88.6 | 75.8 |
| 15_5_4 | 84.4 | 85.9 | 79.1 | 85.9 | 87.8 | 78.8 |
| 15_40_23 | 85.1 | 88.3 | 73.1 | 85.9 | 87.8 | 78.8 |
| 15_40_115 | 86.3 | 89.1 | 76.1 | 85.9 | 87.8 | 78.8 |
| 15_12_23 | 87.9 | 91.1 | 76.1 | 85.9 | 87.8 | 78.8 |
| 15_4_54 | 85.7 | 87.5 | 79.1 | 85.9 | 87.8 | 78.8 |

TABLE 10-continued

| SEQ ID NO: | Training cohort Accuracy (%) | Training cohort Sensitivity (%) | Training cohort Specificity (%) | Validation cohort Accuracy (%) | Validation cohort Sensitivity (%) | Validation cohort Specificity (%) |
|---|---|---|---|---|---|---|
| 15_4_88 | 86.3 | 87.9 | 80.6 | 85.9 | 87.8 | 78.8 |
| 15_4_143 | 86.7 | 88.7 | 79.1 | 85.9 | 87.8 | 78.8 |
| 15_4_468 | 85.7 | 87.5 | 79.1 | 85.9 | 87.8 | 78.8 |
| 15_4_469 | 86 | 87.9 | 79.1 | 85.9 | 87.8 | 78.8 |
| 15_4_91 | 89.5 | 91.9 | 80.6 | 85.9 | 87.8 | 78.8 |
| 5_40_79 | 83.8 | 85.9 | 76.1 | 85.9 | 87.8 | 78.8 |
| 5_79_115 | 84.8 | 85.9 | 80.6 | 85.9 | 87.8 | 78.8 |
| 40_4_20 | 85.1 | 85.5 | 83.6 | 85.9 | 87.8 | 78.8 |
| 40_20_145 | 85.4 | 86.7 | 80.6 | 85.9 | 87.8 | 78.8 |
| 40_121_79 | 84.8 | 86.7 | 77.6 | 85.9 | 87.8 | 78.8 |
| 4_54_468 | 84.1 | 86.7 | 74.6 | 85.9 | 87.8 | 78.8 |
| 15_5_40 | 83.5 | 87.5 | 68.7 | 85.9 | 87 | 81.8 |
| 15_12_4 | 87.6 | 89.9 | 79.1 | 85.9 | 87 | 81.8 |
| 15_4_102 | 86.3 | 87.9 | 80.3 | 85.9 | 87 | 81.8 |
| 15_29_115 | 89.8 | 91.9 | 82.1 | 85.9 | 87 | 81.8 |
| 5_20_115 | 87.6 | 87.9 | 86.6 | 85.9 | 87 | 81.8 |
| 5_121_115 | 86.7 | 88.3 | 80.6 | 85.9 | 87 | 81.8 |
| 5_64_115 | 86 | 86.3 | 85.1 | 85.9 | 87 | 81.8 |
| 5_469_91 | 85.4 | 86.7 | 80.6 | 85.9 | 87 | 81.8 |
| 40_23_4 | 85.1 | 85.1 | 85.1 | 85.9 | 87 | 81.8 |
| 40_4_29 | 86 | 85.5 | 88.1 | 85.9 | 87 | 81.8 |
| 40_20_88 | 81.3 | 81.9 | 79.1 | 85.9 | 87 | 81.8 |
| 40_31_88 | 81.3 | 81.5 | 80.6 | 85.9 | 87 | 81.8 |
| 12_39_121 | 89.8 | 91.5 | 83.6 | 85.9 | 87 | 81.8 |
| 12_11_91 | 84.8 | 85.5 | 82.1 | 85.9 | 87 | 81.8 |
| 12_31_91 | 84.4 | 85.1 | 82.1 | 85.9 | 87 | 81.8 |
| 4_88_91 | 83.5 | 83.1 | 85.1 | 85.9 | 87 | 81.8 |
| 5_40_11 | 81.9 | 83.9 | 74.6 | 85.9 | 86.2 | 84.8 |
| 5_40_467 | 83.5 | 85.5 | 76.1 | 85.9 | 86.2 | 84.8 |
| 5_40_108 | 81.9 | 83.9 | 74.6 | 85.9 | 86.2 | 84.8 |
| 5_121_468 | 86.3 | 87.5 | 82.1 | 85.9 | 86.2 | 84.8 |
| 40_12_11 | 84.8 | 85.9 | 80.6 | 85.9 | 86.2 | 84.8 |
| 4_88_143 | 82.9 | 83.5 | 80.6 | 85.9 | 86.2 | 84.8 |
| 5_40_29 | 81.9 | 83.1 | 77.6 | 85.9 | 85.4 | 87.9 |
| 5_40_143 | 82.9 | 83.5 | 80.6 | 85.9 | 85.4 | 87.9 |
| 5_40_89 | 82.9 | 84.3 | 77.6 | 85.9 | 85.4 | 87.9 |
| 12_121_115 | 83.8 | 84.7 | 80.6 | 85.9 | 85.4 | 87.9 |
| 12_31_471 | 85.1 | 86.3 | 80.6 | 85.9 | 85.4 | 87.9 |

TABLE 11

| SEQ ID NO: | Training cohort Accuracy (%) | Training cohort Sensitivity (%) | Training cohort Specificity (%) | Validation cohort Accuracy (%) | Validation cohort Sensitivity (%) | Validation cohort Specificity (%) |
|---|---|---|---|---|---|---|
| 15_40_115_121 | 91.1 | 94 | 80.6 | 94.2 | 95.1 | 90.9 |
| 12_15_115_121 | 93 | 95.6 | 83.6 | 94.2 | 95.1 | 90.9 |
| 15_115_121_471 | 91.4 | 94.8 | 79.1 | 94.2 | 95.1 | 90.9 |
| 15_91_115_121 | 91.4 | 94 | 82.1 | 94.2 | 95.1 | 90.9 |
| 12_15_64_115 | 89.5 | 92.7 | 77.6 | 93.6 | 95.1 | 87.9 |
| 15_39_115_121 | 91.1 | 94.8 | 77.6 | 92.9 | 95.1 | 84.8 |
| 15_20_115_121 | 92.4 | 93.1 | 89.6 | 92.9 | 94.3 | 87.9 |
| 15_23_115_121 | 91.1 | 93.5 | 82.1 | 92.9 | 93.5 | 90.9 |
| 15_94_115_121 | 91.4 | 94 | 82.1 | 92.9 | 93.5 | 90.9 |
| 15_62_115_121 | 91.4 | 94.4 | 80.6 | 92.9 | 93.5 | 90.9 |
| 15_115_121_143 | 90.5 | 93.5 | 79.1 | 92.9 | 93.5 | 90.9 |
| 15_115_121_134 | 90.8 | 94.4 | 77.6 | 92.9 | 93.5 | 90.9 |
| 12_15_91_115 | 90.2 | 92.7 | 80.6 | 92.3 | 95.1 | 81.8 |
| 12_15_121_145 | 89.5 | 91.5 | 82.1 | 92.3 | 94.3 | 84.8 |
| 15_91_121_143 | 91.1 | 94.8 | 77.6 | 92.3 | 94.3 | 84.8 |
| 15_91_121_145 | 89.8 | 93.1 | 77.6 | 92.3 | 94.3 | 84.8 |
| 5_12_15_121 | 90.8 | 93.1 | 82.1 | 92.3 | 93.5 | 87.9 |
| 12_15_29_121 | 91.1 | 94 | 80.6 | 92.3 | 93.5 | 87.9 |
| 12_15_88_121 | 90.5 | 93.5 | 79.1 | 92.3 | 93.5 | 87.9 |
| 12_15_79_121 | 89.8 | 93.5 | 76.1 | 92.3 | 93.5 | 87.9 |
| 12_15_121_471 | 90.5 | 94 | 77.6 | 92.3 | 93.5 | 87.9 |
| 12_15_121_473 | 90.2 | 93.5 | 77.6 | 92.3 | 93.5 | 87.9 |
| 15_23_91_121 | 91.4 | 93.1 | 85.1 | 92.3 | 93.5 | 87.9 |
| 15_62_91_121 | 92.1 | 94.4 | 83.6 | 92.3 | 93.5 | 87.9 |
| 15_102_115_121 | 91.1 | 94 | 80.3 | 92.3 | 93.5 | 87.9 |
| 15_108_115_121 | 90.5 | 93.5 | 79.1 | 92.3 | 93.5 | 87.9 |

TABLE 11-continued

| SEQ ID NO: | Training cohort Accuracy (%) | Training cohort Sensitivity (%) | Training cohort Specificity (%) | Validation cohort Accuracy (%) | Validation cohort Sensitivity (%) | Validation cohort Specificity (%) |
|---|---|---|---|---|---|---|
| 12_15_40_121 | 90.8 | 94 | 79.1 | 92.3 | 92.7 | 90.9 |
| 4_12_15_121 | 89.2 | 91.5 | 80.6 | 92.3 | 92.7 | 90.9 |
| 12_15_20_121 | 90.8 | 92.7 | 83.6 | 92.3 | 92.7 | 90.9 |
| 4_15_115_121 | 91.1 | 94 | 80.6 | 92.3 | 92.7 | 90.9 |
| 15_115_121_474 | 90.5 | 94 | 77.6 | 92.3 | 92.7 | 90.9 |
| 5_39_102_115 | 88.5 | 89.5 | 84.8 | 92.3 | 92.7 | 90.9 |
| 5_39_115_471 | 89.5 | 91.1 | 83.6 | 92.3 | 92.7 | 90.9 |
| 12_40_64_473 | 87 | 87.9 | 83.6 | 92.3 | 92.7 | 90.9 |
| 15_39_115_471 | 89.2 | 93.1 | 74.6 | 91.7 | 95.9 | 75.8 |
| 15_31_91_121 | 89.5 | 93.1 | 76.1 | 91.7 | 94.3 | 81.8 |
| 39_40_121_135 | 91.4 | 94.4 | 80.6 | 91.7 | 94.3 | 81.8 |
| 15_40_91_121 | 90.5 | 93.5 | 79.1 | 91.7 | 93.5 | 84.8 |
| 11_12_15_121 | 90.2 | 93.5 | 77.6 | 91.7 | 93.5 | 84.8 |
| 12_15_31_121 | 90.8 | 94 | 79.1 | 91.7 | 93.5 | 84.8 |
| 12_15_115_471 | 91.1 | 94 | 80.6 | 91.7 | 93.5 | 84.8 |
| 15_91_94_121 | 90.2 | 93.5 | 77.6 | 91.7 | 93.5 | 84.8 |
| 15_76_115_121 | 90.2 | 93.5 | 77.6 | 91.7 | 93.5 | 84.8 |
| 15_91_102_121 | 91.1 | 93.5 | 81.8 | 91.7 | 93.5 | 84.8 |
| 11_15_91_121 | 90.5 | 93.5 | 79.1 | 91.7 | 93.5 | 84.8 |
| 15_31_115_121 | 91.1 | 94.4 | 79.1 | 91.7 | 93.5 | 84.8 |
| 15_54_91_121 | 90.2 | 93.5 | 77.6 | 91.7 | 93.5 | 84.8 |
| 15_91_121_134 | 90.8 | 94 | 79.1 | 91.7 | 93.5 | 84.8 |
| 15_91_108_121 | 90.2 | 93.5 | 77.6 | 91.7 | 93.5 | 84.8 |
| 15_91_121_471 | 90.8 | 93.5 | 80.6 | 91.7 | 93.5 | 84.8 |
| 15_89_91_121 | 89.5 | 93.1 | 76.1 | 91.7 | 93.5 | 84.8 |
| 15_91_121_473 | 90.2 | 93.5 | 77.6 | 91.7 | 93.5 | 84.8 |
| 15_91_121_474 | 90.2 | 93.5 | 77.6 | 91.7 | 93.5 | 84.8 |
| 5_12_39_115 | 92.1 | 93.1 | 88.1 | 91.7 | 93.5 | 84.8 |
| 5_39_115_135 | 87.9 | 89.5 | 82.1 | 91.7 | 93.5 | 84.8 |
| 5_12_15_115 | 89.8 | 92.3 | 80.6 | 91.7 | 92.7 | 87.9 |
| 5_15_115_121 | 90.8 | 93.5 | 80.6 | 91.7 | 92.7 | 87.9 |
| 12_15_23_121 | 90.2 | 93.1 | 79.1 | 91.7 | 92.7 | 87.9 |
| 4_12_15_115 | 89.5 | 92.3 | 79.1 | 91.7 | 92.7 | 87.9 |
| 12_15_76_121 | 90.2 | 93.5 | 77.6 | 91.7 | 92.7 | 87.9 |
| 12_15_54_121 | 91.4 | 94 | 82.1 | 91.7 | 92.7 | 87.9 |
| 12_15_109_121 | 90.5 | 93.5 | 79.1 | 91.7 | 92.7 | 87.9 |
| 12_15_121_468 | 91.4 | 94 | 82.1 | 91.7 | 92.7 | 87.9 |
| 12_15_121_134 | 90.2 | 93.5 | 77.6 | 91.7 | 92.7 | 87.9 |
| 12_15_108_121 | 90.8 | 94 | 79.1 | 91.7 | 92.7 | 87.9 |
| 12_15_89_121 | 89.8 | 93.1 | 77.6 | 91.7 | 92.7 | 87.9 |
| 12_15_91_121 | 92.1 | 94.4 | 83.6 | 91.7 | 92.7 | 87.9 |
| 12_15_121_474 | 90.5 | 94 | 77.6 | 91.7 | 92.7 | 87.9 |
| 4_11_15_121 | 89.8 | 92.7 | 79.1 | 91.7 | 92.7 | 87.9 |
| 11_15_102_121 | 90.1 | 93.1 | 78.8 | 91.7 | 92.7 | 87.9 |
| 15_54_102_121 | 90.1 | 93.1 | 78.8 | 91.7 | 92.7 | 87.9 |
| 15_102_108_121 | 89.8 | 92.7 | 78.8 | 91.7 | 92.7 | 87.9 |
| 15_115_121_466 | 90.5 | 94 | 77.6 | 91.7 | 92.7 | 87.9 |
| 15_54_115_121 | 91.4 | 94.4 | 80.6 | 91.7 | 92.7 | 87.9 |
| 15_109_115_121 | 91.7 | 94.4 | 82.1 | 91.7 | 92.7 | 87.9 |
| 15_64_115_121 | 91.7 | 95.2 | 79.1 | 91.7 | 92.7 | 87.9 |
| 15_88_115_121 | 90.2 | 93.5 | 77.6 | 91.7 | 92.7 | 87.9 |
| 15_79_115_121 | 91.7 | 95.6 | 77.6 | 91.7 | 92.7 | 87.9 |
| 15_115_121_145 | 90.5 | 94 | 77.6 | 91.7 | 92.7 | 87.9 |
| 15_115_121_468 | 90.8 | 93.5 | 80.6 | 91.7 | 92.7 | 87.9 |
| 15_23_121_471 | 90.8 | 93.5 | 80.6 | 91.7 | 91.9 | 90.9 |
| 4_15_109_121 | 90.8 | 93.1 | 82.1 | 91.7 | 91.9 | 90.9 |
| 15_62_121_471 | 91.4 | 94.8 | 79.1 | 91.7 | 91.9 | 90.9 |
| 11_15_115_121 | 90.5 | 93.5 | 79.1 | 91.7 | 91.9 | 90.9 |
| 15_39_40_115 | 88.6 | 91.5 | 77.6 | 91 | 95.1 | 75.8 |
| 15_31_40_121 | 89.2 | 93.1 | 74.6 | 91 | 94.3 | 78.8 |
| 15_23_39_115 | 87.3 | 91.1 | 73.1 | 91 | 94.3 | 78.8 |
| 15_31_39_121 | 91.1 | 95.2 | 76.1 | 91 | 94.3 | 78.8 |
| 15_79_121_468 | 91.7 | 95.6 | 77.6 | 91 | 94.3 | 78.8 |
| 20_39_40_115 | 90.5 | 92.7 | 82.1 | 91 | 94.3 | 78.8 |
| 12_15_115_134 | 90.2 | 93.5 | 77.6 | 91 | 93.5 | 81.8 |
| 15_39_121_468 | 91.4 | 94.4 | 80.6 | 91 | 93.5 | 81.8 |
| 15_39_91_121 | 91.4 | 94.8 | 79.1 | 91 | 93.5 | 81.8 |
| 15_31_109_121 | 90.8 | 94.4 | 77.6 | 91 | 93.5 | 81.8 |
| 15_31_64_121 | 90.2 | 94.4 | 74.6 | 91 | 93.5 | 81.8 |
| 15_64_121_134 | 89.8 | 94 | 74.6 | 91 | 93.5 | 81.8 |
| 15_88_91_121 | 90.5 | 94.4 | 76.1 | 91 | 93.5 | 81.8 |
| 15_79_91_121 | 91.4 | 95.2 | 77.6 | 91 | 93.5 | 81.8 |

TABLE 11-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 5_12_91_115 | 93 | 93.5 | 91 | 91 | 91.1 | 90.9 |
| 5_12_76_115 | 90.8 | 91.9 | 86.6 | 89.7 | 91.9 | 81.8 |
| 4_15_29_115 | 91.1 | 92.3 | 86.6 | 89.7 | 91.1 | 84.8 |
| 12_15_23_115 | 90.2 | 92.7 | 80.6 | 89.7 | 92.7 | 78.8 |
| 5_12_115_472 | 91.1 | 91.5 | 89.6 | 89.7 | 91.1 | 84.8 |
| 15_39_76_121 | 91.1 | 94.4 | 79.1 | 89.7 | 91.9 | 81.8 |
| 12_15_23_115 | 90.2 | 92.7 | 80.6 | 89.7 | 92.7 | 78.8 |
| 15_40_121_134 | 90.8 | 93.5 | 80.6 | 89.7 | 91.1 | 84.8 |
| 4_5_12_115 | 89.5 | 90.3 | 86.6 | 89.1 | 88.6 | 90.9 |
| 5_12_115_469 | 90.8 | 91.5 | 88.1 | 89.1 | 91.1 | 81.8 |
| 5_12_115_143 | 91.1 | 91.9 | 88.1 | 88.5 | 88.6 | 87.9 |
| 5_12_40_115 | 90.5 | 91.1 | 88.1 | 88.5 | 89.4 | 84.8 |
| 5_12_23_115 | 88.9 | 89.5 | 86.6 | 87.8 | 88.6 | 84.8 |
| 5_12_29_115 | 89.8 | 89.9 | 89.6 | 87.8 | 88.6 | 84.8 |
| 12_40_472_473 | 86.3 | 87.5 | 82.1 | 87.2 | 87.8 | 84.8 |
| 1_12_15_29 | 86.3 | 88.3 | 79.1 | 86.5 | 88.6 | 78.8 |
| 4_15_54_115 | 88.9 | 90.7 | 82.1 | 86.5 | 88.6 | 78.8 |
| 5_54_76_115 | 87.9 | 89.1 | 83.6 | 86.5 | 90.2 | 72.7 |
| 4_12_15_474 | 88.3 | 90.3 | 80.6 | 85.9 | 87 | 81.8 |
| 15_54_76_79 | 85.4 | 90.3 | 67.2 | 85.3 | 89.4 | 69.7 |
| 15_54_76_473 | 84.8 | 88.7 | 70.1 | 85.3 | 90.2 | 66.7 |
| 15_54_76_115 | 88.3 | 93.5 | 68.7 | 85.3 | 88.6 | 72.7 |
| 15_40_54_76 | 85.7 | 89.1 | 73.1 | 85.3 | 88.6 | 72.7 |
| 12_23_40_466 | 86.3 | 87.9 | 80.6 | 84 | 84.6 | 81.8 |
| 12_23_40_134 | 85.7 | 85.1 | 88.1 | 83.3 | 82.9 | 84.8 |
| 4_5_12_76 | 85.4 | 86.3 | 82.1 | 82.1 | 83.7 | 75.8 |

Comparative Example 1

<Biliary Tract Cancer Discriminant Performance of Existing Tumor Markers in Blood>

The concentrations of the existing tumor markers CEA and CA19-9 in blood were measured in the training cohort and the validation cohort obtained in Reference Example 1 above. When the concentrations of these tumor markers in blood are higher than the reference values described in Non-patent Literature 2 (CEA: 5 ng/mL. CA19-9: 37 U/mL), subjects are usually suspected of having cancer. Thus, whether or not the concentrations of CEA and CA19-9 in blood exceeded their reference values was confirmed for each sample, and the obtained results were assessed for the ability of these tumor markers to detect cancer in biliary tract cancer patients. The sensitivity of each existing marker in the training cohort and the validation cohort was calculated. The results are shown in Table 5. The sensitivity of CEA and CA19-9 was as low as 31.3% and 68.2%, respectively, in the training cohort, and was as low as 33.3% and 59.4%, respectively, in the validation cohort, demonstrating that neither of the markers is useful in the detection of biliary tract cancer (Table 5).

On the other hand, as shown above in Tables 3 and 4 of Examples 1 and 2, it can be concluded that all of the polynucleotides consisting of the nucleotide sequences represented by SEQ ID NOs: 1 to 125 have combinations of 1, 2 or more polynucleotides exhibiting sensitivity beyond the existing biliary tract cancer markers and thus serve as excellent diagnosis markers.

As shown in these Examples and Comparative Example, the kit, etc. and the method of the present invention can detect biliary tract cancer with higher sensitivity than the existing tumor markers and therefore permit early decision to carry out the surgical resection of a cancer site. As a result, improvement in 5-year survival rate and reduction in the rate of recurrence can be achieved.

INDUSTRIAL APPLICABILITY

According to the present invention, biliary tract cancer can be effectively detected by a simple and inexpensive method. This enables early detection, diagnosis and treatment of biliary tract cancer. The method of the present invention can detect biliary tract cancer with limited invasiveness using the blood of a patient and therefore allows biliary tract cancer to be detected conveniently and rapidly.

All publications, patents, and patent applications cited herein are incorporated herein by reference in their entirety.

The invention claimed is:

1. A method for detecting biliary tract cancer in a human subject, comprising:

measuring an expression level of hsa-miR-665 in a blood, serum or plasma sample from the subject;

comparing the measured expression level of hsa-miR-665 to a control expression level for a healthy subject;

detecting an increased level of hsa-miR-665 in the sample from the subject as compared to the control expression level from the sample from the healthy subject;

wherein the increased level of hsa-miR-665 indicates that the subject has biliary tract cancer; and wherein the method further comprises treating the subject for the biliary tract cancer or performing a diagnostic procedure on the subject with the biliary tract cancer;

wherein the treating comprises surgery, radiotherapy, chemotherapy or a combination thereof; and wherein the diagnostic procedure comprises a biochemical examination of hepatic dysfunction markers in the sample, detecting a concentration of biliary tract tumor biomarker protein in the sample, or imaging the biliary tract of the human subject.

2. The method according to claim 1, comprising performing the diagnostic procedure on the subject.

3. The method according to claim 1, wherein the expression level of hsa-miR-665 in the sample is measured by using a device comprising a nucleic acid(s) that specifically binds to hsa-miR-665.

4. The method according to claim 3, wherein the device further comprises nucleic acid(s) capable of specifically binding to one or more polynucleotide(s) selected from the group consisting of other biliary tract cancer markers: miR-125a-3p, miR-6893-5p, miR-4476, miR-4294, miR-150-3p, miR-6729-5p, miR-7641, miR-6765-3p, miR-6820-5p, miR-575, miR-1469, miR-663a, miR-6075, miR-4634, miR-423-5p, miR-4454, miR-7109-5p, miR-6789-5p, miR-6877-5p, miR-4792, miR-4530, miR-7975, miR-6724-5p, miR-8073, miR-7977, miR-1231, miR-6799-5p, miR-615-5p, miR-4450, miR-6726-5p, miR-6875-5p, miR-4734, miR-16-5p, miR-602, miR-4651, miR-8069, miR-1238-5p, miR-6880-5p, miR-8072, miR-4723-5p, miR-4732-5p, miR-6125, miR-6090, miR-7114-5p, miR-564, miR-451a, miR-3135b, miR-4497, miR-4665-5p, miR-3622a-5p, miR-6850-5p, miR-6821-5p, miR-5100, miR-6872-3p, miR-4433-3p, miR-1227-5p, miR-3188, miR-7704, miR-3185, miR-1908-3p, miR-6781-5p, miR-6805-5p, miR-8089, miR-4486, miR-6722-3p, miR-1260a, miR-4707-5p, miR-6741-5p, miR-1260b, miR-1246, miR-6845-5p, miR-4638-5p, miR-6085, miR-1228-3p, miR-4534, miR-5585-3p, miR-4741, miR-4433b-3p, miR-197-5p, miR-718, miR-4513, miR-4446-3p, miR-619-5p, miR-6816-5p, miR-6778-5p, miR-24-3p, miR-1915-3p, miR-4665-3p, miR-4449, miR-6889-5p, miR-486-3p, miR-7113-3p, miR-642a-3p, miR-7847-3p, miR-6768-5p, miR-1290, miR-7108-5p, miR-92b-5p, miR-663b, miR-3940-5p, miR-4467, miR-6858-5p, miR-4417, miR-3665, miR-4736, miR-4687-3p, miR-1908-5p, miR-5195-3p, miR-4286, miR-3679-3p, miR-6791-5p, miR-1202, miR-3656, miR-4746-3p, miR-3184-5p, miR-3937, miR-6515-3p, miR-6132, miR-187-5p, miR-7111-5p, miR-5787, miR-6779-5p, miR-4516, miR-4649-5p, miR-760, miR-3162-5p, miR-3178, miR-940, miR-4271, miR-6769b-5p, miR-4508, miR-6826-5p, miR-6757-5p, miR-3131, and miR-1343-3p; and/or miR-6808-5p, miR-6774-5p, miR-4656, miR-6806-5p, miR-1233-5p, miR-328-5p, miR-4674, miR-2110, miR-6076, miR-3619-3p, miR-92a-2-5p, miR-128-1-5p, miR-638, miR-2861, miR-371a-5p, miR-211-3p, miR-1273g-3p, miR-1203, miR-122-5p, miR-4258, miR-4484, miR-4648 and miR-6780b-5p.

5. The method according to claim 1, wherein the expression level of hsa-miR-665 in the sample is measured by using a kit comprising a nucleic acid(s) that specifically binds to hsa-miR-665.

6. The method according to claim 5, wherein the kit further comprises nucleic acid(s) capable of specifically binding to one or more polynucleotide(s) selected from the group consisting of other biliary tract cancer markers: miR-125a-3p, miR-6893-5p, miR-4476, miR-4294, miR-150-3p, miR-6729-5p, miR-7641, miR-6765-3p, miR-6820-5p, miR-575, miR-1469, miR-663a, miR-6075, miR-4634, miR-423-5p, miR-4454, miR-7109-5p, miR-6789-5p, miR-6877-5p, miR-4792, miR-4530, miR-7975, miR-6724-5p, miR-8073, miR-7977, miR-1231, miR-6799-5p, miR-615-5p, miR-4450, miR-6726-5p, miR-6875-5p, miR-4734, miR-16-5p, miR-602, miR-4651, miR-8069, miR-1238-5p, miR-6880-5p, miR-8072, miR-4723-5p, miR-4732-5p, miR-6125, miR-6090, miR-7114-5p, miR-564, miR-451a, miR-3135b, miR-4497, miR-4665-5p, miR-3622a-5p, miR-6850-5p, miR-6821-5p, miR-5100, miR-6872-3p, miR-4433-3p, miR-1227-5p, miR-3188, miR-7704, miR-3185, miR-1908-3p, miR-6781-5p, miR-6805-5p, miR-8089, miR-4486, miR-6722-3p, miR-1260a, miR-4707-5p, miR-6741-5p, miR-1260b, miR-1246, miR-6845-5p, miR-4638-5p, miR-6085, miR-1228-3p, miR-4534, miR-5585-3p, miR-4741, miR-4433b-3p, miR-197-5p, miR-718, miR-4513, miR-4446-3p, miR-619-5p, miR-6816-5p, miR-6778-5p, miR-24-3p, miR-1915-3p, miR-4665-3p, miR-4449, miR-6889-5p, miR-486-3p, miR-7113-3p, miR-642a-3p, miR-7847-3p, miR-6768-5p, miR-1290, miR-7108-5p, miR-92b-5p, miR-663b, miR-3940-5p, miR-4467, miR-6858-5p, miR-4417, miR-3665, miR-4736, miR-4687-3p, miR-1908-5p, miR-5195-3p, miR-4286, miR-3679-3p, miR-6791-5p, miR-1202, miR-3656, miR-4746-3p, miR-3184-5p, miR-3937, miR-6515-3p, miR-6132, miR-187-5p, miR-7111-5p, miR-5787, miR-6779-5p, miR-4516, miR-4649-5p, miR-760, miR-3162-5p, miR-3178, miR-940, miR-4271, miR-6769b-5p, miR-4508, miR-6826-5p, miR-6757-5p, miR-3131, and miR-1343-3p; and/or miR-6808-5p, miR-6774-5p, miR-4656, miR-6806-5p, miR-1233-5p, miR-328-5p, miR-4674, miR-2110, miR-6076, miR-3619-3p, miR-92a-2-5p, miR-128-1-5p, miR-638, miR-2861, miR-371a-5p, miR-211-3p, miR-1273g-3p, miR-1203, miR-122-5p, miR-4258, miR-4484, miR-4648 and miR-6780b-5p.

* * * * *

SEQUENCE LISTING

```
<160> NUMBER OF SEQ ID NOS: 509

<210> SEQ ID NO 1
<211> LENGTH: 22
<212> TYPE: RNA
<213> ORGANISM: Homo sapiens

<400> SEQUENCE: 1

acaggugagg uucuugggag cc                                           22
```

<210> SEQ ID NO 2
<211> LENGTH: 21
<212> TYPE: RNA
<213> ORGANISM: Homo sapiens

<400> SEQUENCE: 2
caggcaggug uagggguggag c 21

<210> SEQ ID NO 3
<211> LENGTH: 21
<212> TYPE: RNA
<213> ORGANISM: Homo sapiens

<400> SEQUENCE: 3
gcugggaagg caaagggacg u 21

<210> SEQ ID NO 4
<211> LENGTH: 22
<212> TYPE: RNA
<213> ORGANISM: Homo sapiens

<400> SEQUENCE: 4
caggaaggau uuagggacag gc 22

<210> SEQ ID NO 5
<211> LENGTH: 17
<212> TYPE: RNA
<213> ORGANISM: Homo sapiens

<400> SEQUENCE: 5
gggagucuac agcaggg 17

<210> SEQ ID NO 6
<211> LENGTH: 22
<212> TYPE: RNA
<213> ORGANISM: Homo sapiens

<400> SEQUENCE: 6
cugguacagg ccugggggac ag 22

<210> SEQ ID NO 7
<211> LENGTH: 22
<212> TYPE: RNA
<213> ORGANISM: Homo sapiens

<400> SEQUENCE: 7
ugggcgaggg cggcugagcg gc 22

<210> SEQ ID NO 8
<211> LENGTH: 19
<212> TYPE: RNA
<213> ORGANISM: Homo sapiens

<400> SEQUENCE: 8
uugaucucgg aagcuaagc 19

<210> SEQ ID NO 9
<211> LENGTH: 21
<212> TYPE: RNA
<213> ORGANISM: Homo sapiens

<400> SEQUENCE: 9
ucaccuggcu ggcccgccca g 21

<210> SEQ ID NO 10
<211> LENGTH: 19
<212> TYPE: RNA
<213> ORGANISM: Homo sapiens

<400> SEQUENCE: 10
ugcggcagag cuggggguca 19

<210> SEQ ID NO 11
<211> LENGTH: 19
<212> TYPE: RNA
<213> ORGANISM: Homo sapiens

<400> SEQUENCE: 11
gagccaguug gacaggagc 19

<210> SEQ ID NO 12
<211> LENGTH: 21
<212> TYPE: RNA
<213> ORGANISM: Homo sapiens

<400> SEQUENCE: 12
augccucccc cggccccgca g 21

<210> SEQ ID NO 13
<211> LENGTH: 22
<212> TYPE: RNA
<213> ORGANISM: Homo sapiens

<400> SEQUENCE: 13
cucggcgcgg ggcgcgggcu cc 22

<210> SEQ ID NO 14
<211> LENGTH: 22
<212> TYPE: RNA
<213> ORGANISM: Homo sapiens

<400> SEQUENCE: 14
aggcggggcg ccgcgggacc gc 22

<210> SEQ ID NO 15
<211> LENGTH: 21
<212> TYPE: RNA
<213> ORGANISM: Homo sapiens

<400> SEQUENCE: 15
acggcccagg cggcauuggu g 21

<210> SEQ ID NO 16
<211> LENGTH: 19
<212> TYPE: RNA
<213> ORGANISM: Homo sapiens

<400> SEQUENCE: 16
cggcgcgacc ggcccgggg 19

<210> SEQ ID NO 17
<211> LENGTH: 23
<212> TYPE: RNA
<213> ORGANISM: Homo sapiens

<400> SEQUENCE: 17
ugaggggcag agagcgagac uuu 23

<210> SEQ ID NO 18
<211> LENGTH: 20
<212> TYPE: RNA
<213> ORGANISM: Homo sapiens

<400> SEQUENCE: 18
ggauccgagu cacggcacca 20

<210> SEQ ID NO 19
<211> LENGTH: 21
<212> TYPE: RNA
<213> ORGANISM: Homo sapiens

<400> SEQUENCE: 19 cugggggag gagacccugc u 21

<210> SEQ ID NO 20
<211> LENGTH: 24
<212> TYPE: RNA
<213> ORGANISM: Homo sapiens

<400> SEQUENCE: 20
guaggggcgu cccgggcgcg cggg 24

<210> SEQ ID NO 21
<211> LENGTH: 22
<212> TYPE: RNA
<213> ORGANISM: Homo sapiens

<400> SEQUENCE: 21
agggccgaag gguggaagcu gc 22

<210> SEQ ID NO 22
<211> LENGTH: 18
<212> TYPE: RNA
<213> ORGANISM: Homo sapiens

<400> SEQUENCE: 22
cggugagcgc ucgcuggc 18

<210> SEQ ID NO 23
<211> LENGTH: 18
<212> TYPE: RNA
<213> ORGANISM: Homo sapiens

<400> SEQUENCE: 23
cccagcagga cgggagcg 18

<210> SEQ ID NO 24
<211> LENGTH: 18
<212> TYPE: RNA
<213> ORGANISM: Homo sapiens

<400> SEQUENCE: 24
auccuaguca cggcacca 18

<210> SEQ ID NO 25
<211> LENGTH: 23
<212> TYPE: RNA
<213> ORGANISM: Homo sapiens

<400> SEQUENCE: 25
cugggcccgc ggcgggcgug ggg 23

<210> SEQ ID NO 26
<211> LENGTH: 22
<212> TYPE: RNA
<213> ORGANISM: Homo sapiens

<400> SEQUENCE: 26
accuggcagc agggagcguc gu 22

<210> SEQ ID NO 27
<211> LENGTH: 18
<212> TYPE: RNA
<213> ORGANISM: Homo sapiens

<400> SEQUENCE: 27
uucccagcca acgcacca 18

<210> SEQ ID NO 28
<211> LENGTH: 20
<212> TYPE: RNA
<213> ORGANISM: Homo sapiens

<400> SEQUENCE: 28
gugucugggc ggacagcugc 20

<210> SEQ ID NO 29
<211> LENGTH: 20
<212> TYPE: RNA
<213> ORGANISM: Homo sapiens

<400> SEQUENCE: 29
ggggaggugu gcagggcugg 20

<210> SEQ ID NO 30
<211> LENGTH: 22
<212> TYPE: RNA
<213> ORGANISM: Homo sapiens

<400> SEQUENCE: 30
gggggucccc ggugcucgga uc 22

<210> SEQ ID NO 31
<211> LENGTH: 22
<212> TYPE: RNA
<213> ORGANISM: Homo sapiens

<400> SEQUENCE: 31
uggggauuug gagaagugggu ga 22

<210> SEQ ID NO 32
<211> LENGTH: 21
<212> TYPE: RNA
<213> ORGANISM: Homo sapiens

<400> SEQUENCE: 32
cgggagcugg ggucugcagg u 21

<210> SEQ ID NO 33
<211> LENGTH: 21
<212> TYPE: RNA
<213> ORGANISM: Homo sapiens

<400> SEQUENCE: 33
ugagggaccc aggacaggag a 21

<210> SEQ ID NO 34
<211> LENGTH: 22
<212> TYPE: RNA
<213> ORGANISM: Homo sapiens

<400> SEQUENCE: 34
gcugcgggcu gcggucaggg cg 22

<210> SEQ ID NO 35
<211> LENGTH: 22
<212> TYPE: RNA
<213> ORGANISM: Homo sapiens

<400> SEQUENCE: 35
uagcagcacg uaaauauugg cg 22

<210> SEQ ID NO 36
<211> LENGTH: 23
<212> TYPE: RNA
<213> ORGANISM: Homo sapiens

<400> SEQUENCE: 36
gacacgggcg acagcugcgg ccc 23

<210> SEQ ID NO 37
<211> LENGTH: 20
<212> TYPE: RNA
<213> ORGANISM: Homo sapiens

<400> SEQUENCE: 37
cggggugggu gaggucgggc 20

<210> SEQ ID NO 38
<211> LENGTH: 23
<212> TYPE: RNA
<213> ORGANISM: Homo sapiens

<400> SEQUENCE: 38
ggaugguugg gggcggucgg cgu 23

<210> SEQ ID NO 39
<211> LENGTH: 23
<212> TYPE: RNA
<213> ORGANISM: Homo sapiens

<400> SEQUENCE: 39
gugaguggga gccccagugu gug 23

<210> SEQ ID NO 40
<211> LENGTH: 22
<212> TYPE: RNA
<213> ORGANISM: Homo sapiens

<400> SEQUENCE: 40
ugguggagga agagggcagc uc 22

<210> SEQ ID NO 41
<211> LENGTH: 20
<212> TYPE: RNA
<213> ORGANISM: Homo sapiens

<400> SEQUENCE: 41
ggcggcgggg agguaggcag 20

<210> SEQ ID NO 42
<211> LENGTH: 24
<212> TYPE: RNA
<213> ORGANISM: Homo sapiens

<400> SEQUENCE: 42 uggggagcc augagauaag agca 24

<210> SEQ ID NO 43
<211> LENGTH: 23
<212> TYPE: RNA
<213> ORGANISM: Homo sapiens

<400> SEQUENCE: 43
uguagagcag ggagcaggaa gcu 23

<210> SEQ ID NO 44
<211> LENGTH: 20
<212> TYPE: RNA
<213> ORGANISM: Homo sapiens

<400> SEQUENCE: 44
gcggaaggcg gagcggcgga 20

<210> SEQ ID NO 45
<211> LENGTH: 19
<212> TYPE: RNA
<213> ORGANISM: Homo sapiens

<400> SEQUENCE: 45
ggggagcgag ggcggggc 19

<210> SEQ ID NO 46
<211> LENGTH: 21
<212> TYPE: RNA
<213> ORGANISM: Homo sapiens

<400> SEQUENCE: 46
ucuguggagu ggggugccug u 21

<210> SEQ ID NO 47
<211> LENGTH: 19
<212> TYPE: RNA
<213> ORGANISM: Homo sapiens

<400> SEQUENCE: 47
aggcacggug ucagcaggc 19

<210> SEQ ID NO 48
<211> LENGTH: 22
<212> TYPE: RNA
<213> ORGANISM: Homo sapiens

<400> SEQUENCE: 48
aaaccguuac cauuacugag uu 22

<210> SEQ ID NO 49
<211> LENGTH: 22
<212> TYPE: RNA
<213> ORGANISM: Homo sapiens

<400> SEQUENCE: 49
ggcuggagcg agugcagugg ug 22

<210> SEQ ID NO 50
<211> LENGTH: 17
<212> TYPE: RNA
<213> ORGANISM: Homo sapiens

<400> SEQUENCE: 50
cuccgggacg gcugggc 17

<210> SEQ ID NO 51
<211> LENGTH: 23
<212> TYPE: RNA
<213> ORGANISM: Homo sapiens

<400> SEQUENCE: 51
cugggggacg cgugagcgcg agc 23

<210> SEQ ID NO 52
<211> LENGTH: 22
<212> TYPE: RNA
<213> ORGANISM: Homo sapiens

<400> SEQUENCE: 52
caggcacggg agcucaggug ag 22

<210> SEQ ID NO 53
<211> LENGTH: 22
<212> TYPE: RNA
<213> ORGANISM: Homo sapiens

<400> SEQUENCE: 53
gugcggaacg cuggccgggg cg 22

<210> SEQ ID NO 54
<211> LENGTH: 23
<212> TYPE: RNA
<213> ORGANISM: Homo sapiens

<400> SEQUENCE: 54
gugcguggug gcucgaggcg ggg 23

<210> SEQ ID NO 55
<211> LENGTH: 22
<212> TYPE: RNA
<213> ORGANISM: Homo sapiens

<400> SEQUENCE: 55
uucagauccc agcggugccu cu 22

<210> SEQ ID NO 56
<211> LENGTH: 21
<212> TYPE: RNA
<213> ORGANISM: Homo sapiens

<400> SEQUENCE: 56
cccaugccuc cugccgcggu c 21

<210> SEQ ID NO 57
<211> LENGTH: 21
<212> TYPE: RNA
<213> ORGANISM: Homo sapiens

<400> SEQUENCE: 57
acaggagugg gggugggaca u 21

<210> SEQ ID NO 58
<211> LENGTH: 17
<212> TYPE: RNA
<213> ORGANISM: Homo sapiens

<400> SEQUENCE: 58
guggggccag gcggugg 17

<210> SEQ ID NO 59
<211> LENGTH: 23
<212> TYPE: RNA
<213> ORGANISM: Homo sapiens

<400> SEQUENCE: 59
agaggcuuug ugcggauacg ggg 23

<210> SEQ ID NO 60
<211> LENGTH: 19
<212> TYPE: RNA
<213> ORGANISM: Homo sapiens

<400> SEQUENCE: 60
cggggucggc ggcgacgug 19

<210> SEQ ID NO 61
<211> LENGTH: 23
<212> TYPE: RNA
<213> ORGANISM: Homo sapiens

<400> SEQUENCE: 61
agaagaaggc ggucggucug cgg 23

<210> SEQ ID NO 62
<211> LENGTH: 21
<212> TYPE: RNA
<213> ORGANISM: Homo sapiens

<400> SEQUENCE: 62
ccggccgccg gcuccgcccc g 21

<210> SEQ ID NO 63
<211> LENGTH: 21
<212> TYPE: RNA
<213> ORGANISM: Homo sapiens

<400> SEQUENCE: 63
cgggccggag gucaagggcg u 21

<210> SEQ ID NO 64
<211> LENGTH: 22
<212> TYPE: RNA
<213> ORGANISM: Homo sapiens

<400> SEQUENCE: 64
uagggggcgg cuuguggagu gu 22

<210> SEQ ID NO 65
<211> LENGTH: 24
<212> TYPE: RNA
<213> ORGANISM: Homo sapiens

<400> SEQUENCE: 65
ccuggggaca ggggauuggg gcag 24

<210> SEQ ID NO 66
<211> LENGTH: 20
<212> TYPE: RNA
<213> ORGANISM: Homo sapiens

<400> SEQUENCE: 66
accaggaggc ugaggccccu 20

<210> SEQ ID NO 67
<211> LENGTH: 17
<212> TYPE: RNA
<213> ORGANISM: Homo sapiens

<400> SEQUENCE: 67
gcugggcgag gcuggca 17

<210> SEQ ID NO 68
<211> LENGTH: 22
<212> TYPE: RNA
<213> ORGANISM: Homo sapiens

<400> SEQUENCE: 68
ugcaggggug gggugggcca gg 22

<210> SEQ ID NO 69
<211> LENGTH: 18
<212> TYPE: RNA
<213> ORGANISM: Homo sapiens

<400> SEQUENCE: 69
aucccaccuc ugccacca 18

<210> SEQ ID NO 70
<211> LENGTH: 23
<212> TYPE: RNA
<213> ORGANISM: Homo sapiens

<400> SEQUENCE: 70
gccccggcgc gggcggguuc ugg 23

<210> SEQ ID NO 71
<211> LENGTH: 22
<212> TYPE: RNA
<213> ORGANISM: Homo sapiens

<400> SEQUENCE: 71
gugggugcug gugggagccg ug 22

<210> SEQ ID NO 72
<211> LENGTH: 19
<212> TYPE: RNA
<213> ORGANISM: Homo sapiens

<400> SEQUENCE: 72
aucccaccac ugccaccau 19

<210> SEQ ID NO 73
<211> LENGTH: 19
<212> TYPE: RNA
<213> ORGANISM: Homo sapiens

<400> SEQUENCE: 73
aauggauuuu uggagcagg 19

<210> SEQ ID NO 74
<211> LENGTH: 19
<212> TYPE: RNA
<213> ORGANISM: Homo sapiens

<400> SEQUENCE: 74
cggggccaga gcagagagc 19

<210> SEQ ID NO 75
<211> LENGTH: 21
<212> TYPE: RNA
<213> ORGANISM: Homo sapiens

<400> SEQUENCE: 75
acucggcugc gguggacaag u 21

<210> SEQ ID NO 76
<211> LENGTH: 19
<212> TYPE: RNA
<213> ORGANISM: Homo sapiens

<400> SEQUENCE: 76
aaggggcugg gggagcaca 19

<210> SEQ ID NO 77
<211> LENGTH: 20
<212> TYPE: RNA
<213> ORGANISM: Homo sapiens

<400> SEQUENCE: 77
ucacaccugc cucgcccccc 20

<210> SEQ ID NO 78
<211> LENGTH: 17
<212> TYPE: RNA
<213> ORGANISM: Homo sapiens

<400> SEQUENCE: 78
ggauggagga ggggucu 17

<210> SEQ ID NO 79
<211> LENGTH: 22
<212> TYPE: RNA
<213> ORGANISM: Homo sapiens

<400> SEQUENCE: 79
cugaauagcu gggacuacag gu 22

<210> SEQ ID NO 80
<211> LENGTH: 23
<212> TYPE: RNA
<213> ORGANISM: Homo sapiens

<400> SEQUENCE: 80
cgggcugucc ggaggggucg gcu 23

<210> SEQ ID NO 81
<211> LENGTH: 21
<212> TYPE: RNA
<213> ORGANISM: Homo sapiens

<400> SEQUENCE: 81
caggaguggg gggugggacg u 21

<210> SEQ ID NO 82
<211> LENGTH: 23
<212> TYPE: RNA
<213> ORGANISM: Homo sapiens

<400> SEQUENCE: 82
cggguagaga gggcaguggg agg 23

<210> SEQ ID NO 83
<211> LENGTH: 21
<212> TYPE: RNA
<213> ORGANISM: Homo sapiens

<400> SEQUENCE: 83
cuuccgcccc gccgggcguc g 21

<210> SEQ ID NO 84
<211> LENGTH: 22
<212> TYPE: RNA
<213> ORGANISM: Homo sapiens

<400> SEQUENCE: 84
agacugacgg cuggaggccc au 22

<210> SEQ ID NO 85
<211> LENGTH: 22
<212> TYPE: RNA
<213> ORGANISM: Homo sapiens

<400> SEQUENCE: 85
cagggcuggc agugacaugg gu 22

<210> SEQ ID NO 86
<211> LENGTH: 22
<212> TYPE: RNA
<213> ORGANISM: Homo sapiens

<400> SEQUENCE: 86
gcugggauua caggcaugag cc 22

<210> SEQ ID NO 87
<211> LENGTH: 21
<212> TYPE: RNA
<213> ORGANISM: Homo sapiens

<400> SEQUENCE: 87
uggggcgggg caggucccug c 21

<210> SEQ ID NO 88
<211> LENGTH: 22
<212> TYPE: RNA
<213> ORGANISM: Homo sapiens

<400> SEQUENCE: 88
agugggagga caggaggcag gu 22

<210> SEQ ID NO 89
<211> LENGTH: 22
<212> TYPE: RNA
<213> ORGANISM: Homo sapiens

<400> SEQUENCE: 89
uggcucaguu cagcaggaac ag 22

<210> SEQ ID NO 90
<211> LENGTH: 20
<212> TYPE: RNA
<213> ORGANISM: Homo sapiens

<400> SEQUENCE: 90
ccccagggcg acgcggcggg 20

<210> SEQ ID NO 91
<211> LENGTH: 26
<212> TYPE: RNA
<213> ORGANISM: Homo sapiens

<400> SEQUENCE: 91
cucggccgcg gcgcguagcc cccgcc 26

<210> SEQ ID NO 92
<211> LENGTH: 22
<212> TYPE: RNA
<213> ORGANISM: Homo sapiens

<400> SEQUENCE: 92
cgucccgggg cugcgcgagg ca 22

<210> SEQ ID NO 93
<211> LENGTH: 23
<212> TYPE: RNA
<213> ORGANISM: Homo sapiens

<400> SEQUENCE: 93
ucggggaguc uggggucegg aau 23

<210> SEQ ID NO 94
<211> LENGTH: 21
<212> TYPE: RNA
<213> ORGANISM: Homo sapiens

<400> SEQUENCE: 94
cggggcagcu caguacagga u 21

<210> SEQ ID NO 95
<211> LENGTH: 23
<212> TYPE: RNA
<213> ORGANISM: Homo sapiens

<400> SEQUENCE: 95
ccucccugcc cgccucucug cag 23

<210> SEQ ID NO 96
<211> LENGTH: 22
<212> TYPE: RNA
<213> ORGANISM: Homo sapiens

<400> SEQUENCE: 96
agacacauuu ggagagggaa cc 22

<210> SEQ ID NO 97
<211> LENGTH: 21
<212> TYPE: RNA
<213> ORGANISM: Homo sapiens

<400> SEQUENCE: 97
cguggaggac gaggaggagg c 21

<210> SEQ ID NO 98
<211> LENGTH: 23
<212> TYPE: RNA
<213> ORGANISM: Homo sapiens

<400> SEQUENCE: 98
cacacaggaa aagcggggcc cug 23

<210> SEQ ID NO 99
<211> LENGTH: 19
<212> TYPE: RNA
<213> ORGANISM: Homo sapiens

<400> SEQUENCE: 99
uggauuuuug gaucaggga 19

<210> SEQ ID NO 100
<211> LENGTH: 21
<212> TYPE: RNA
<213> ORGANISM: Homo sapiens

<400> SEQUENCE: 100
guguggccgg caggcgggug g 21

<210> SEQ ID NO 101
<211> LENGTH: 22
<212> TYPE: RNA
<213> ORGANISM: Homo sapiens

<400> SEQUENCE: 101
agggacggga cgcggugcag ug 22

<210> SEQ ID NO 102
<211> LENGTH: 22
<212> TYPE: RNA
<213> ORGANISM: Homo sapiens

<400> SEQUENCE: 102
gguggcccgg ccgugccuga gg 22

<210> SEQ ID NO 103
<211> LENGTH: 20
<212> TYPE: RNA
<213> ORGANISM: Homo sapiens

<400> SEQUENCE: 103
guggguuggg gcgggcucug 20

<210> SEQ ID NO 104
<211> LENGTH: 22
<212> TYPE: RNA
<213> ORGANISM: Homo sapiens

<400> SEQUENCE: 104
uggcggcggu aguuaugggc uu 22

<210> SEQ ID NO 105
<211> LENGTH: 22
<212> TYPE: RNA
<213> ORGANISM: Homo sapiens

<400> SEQUENCE: 105
gugaggaggg gcuggcaggg ac 22

<210> SEQ ID NO 106
<211> LENGTH: 18
<212> TYPE: RNA
<213> ORGANISM: Homo sapiens

<400> SEQUENCE: 106
ggugggcuuc ccggaggg 18

<210> SEQ ID NO 107
<211> LENGTH: 18
<212> TYPE: RNA
<213> ORGANISM: Homo sapiens

<400> SEQUENCE: 107
agcaggugcg gggcggcg 18

<210> SEQ ID NO 108
<211> LENGTH: 19
<212> TYPE: RNA
<213> ORGANISM: Homo sapiens

<400> SEQUENCE: 108
aggcagguua ucugggcug 19

<210> SEQ ID NO 109
<211> LENGTH: 21
<212> TYPE: RNA
<213> ORGANISM: Homo sapiens

<400> SEQUENCE: 109
uggcuguugg agggggcagg c 21

<210> SEQ ID NO 110
<211> LENGTH: 21
<212> TYPE: RNA
<213> ORGANISM: Homo sapiens

<400> SEQUENCE: 110
cggcggggac ggcgauuggu c 21

<210> SEQ ID NO 111
<211> LENGTH: 21
<212> TYPE: RNA
<213> ORGANISM: Homo sapiens

<400> SEQUENCE: 111
auccaguucu cugagggggc u 21

<210> SEQ ID NO 112
<211> LENGTH: 17
<212> TYPE: RNA
<213> ORGANISM: Homo sapiens

<400> SEQUENCE: 112
accccacucc ugguacc 17

<210> SEQ ID NO 113
<211> LENGTH: 22
<212> TYPE: RNA
<213> ORGANISM: Homo sapiens

<400> SEQUENCE: 113
cuucccccca guaaucuuca uc 22

<210> SEQ ID NO 114
<211> LENGTH: 22
<212> TYPE: RNA
<213> ORGANISM: Homo sapiens

<400> SEQUENCE: 114
ccccuggggc ugggcaggcg ga 22

<210> SEQ ID NO 115
<211> LENGTH: 21
<212> TYPE: RNA
<213> ORGANISM: Homo sapiens

<400> SEQUENCE: 115
gugccagcug caguggggga g 21

<210> SEQ ID NO 116
<211> LENGTH: 17
<212> TYPE: RNA
<213> ORGANISM: Homo sapiens

<400> SEQUENCE: 116
ggcgggugcg ggggugg 17

<210> SEQ ID NO 117
<211> LENGTH: 21
<212> TYPE: RNA
<213> ORGANISM: Homo sapiens

<400> SEQUENCE: 117
agcggugcuc cugcgggccg a 21

<210> SEQ ID NO 118
<211> LENGTH: 24
<212> TYPE: RNA
<213> ORGANISM: Homo sapiens

<400> SEQUENCE: 118
ugaggggccu cagaccgagc uuuu 24

<210> SEQ ID NO 119
<211> LENGTH: 23
<212> TYPE: RNA
<213> ORGANISM: Homo sapiens

<400> SEQUENCE: 119
acaggcggcu guagcaaugg ggg 23

<210> SEQ ID NO 120
<211> LENGTH: 20
<212> TYPE: RNA
<213> ORGANISM: Homo sapiens

<400> SEQUENCE: 120
ucucuucauc uacccccag 20

<210> SEQ ID NO 121
<211> LENGTH: 19
<212> TYPE: RNA
<213> ORGANISM: Homo sapiens

<400> SEQUENCE: 121
agcagggcug gggauugca 19

<210> SEQ ID NO 122
<211> LENGTH: 22
<212> TYPE: RNA
<213> ORGANISM: Homo sapiens

<400> SEQUENCE: 122
ggcuacaaca caggacccgg gc 22

<210> SEQ ID NO 123
<211> LENGTH: 22
<212> TYPE: RNA
<213> ORGANISM: Homo sapiens

<400> SEQUENCE: 123
ugggggagga aggacaggcc au 22

<210> SEQ ID NO 124
<211> LENGTH: 20
<212> TYPE: RNA
<213> ORGANISM: Homo sapiens

<400> SEQUENCE: 124
gggcuggggc gcggggaggu 20

<210> SEQ ID NO 125
<211> LENGTH: 21
<212> TYPE: RNA
<213> ORGANISM: Homo sapiens

<400> SEQUENCE: 125
cugggagggg cuggguuugg c 21

<210> SEQ ID NO 126
<211> LENGTH: 22
<212> TYPE: RNA
<213> ORGANISM: Homo sapiens

<400> SEQUENCE: 126
caggcaggga ggugggacca ug 22

<210> SEQ ID NO 127
<211> LENGTH: 25
<212> TYPE: RNA
<213> ORGANISM: Homo sapiens

<400> SEQUENCE: 127
acuugggcag gagggacccu guaug 25

<210> SEQ ID NO 128
<211> LENGTH: 23
<212> TYPE: RNA
<213> ORGANISM: Homo sapiens

<400> SEQUENCE: 128
ugggcugagg gcaggaggcc ugu 23

<210> SEQ ID NO 129
<211> LENGTH: 24
<212> TYPE: RNA
<213> ORGANISM: Homo sapiens

<400> SEQUENCE: 129
uguaggcaug aggcagggcc cagg 24

<210> SEQ ID NO 130
<211> LENGTH: 22
<212> TYPE: RNA
<213> ORGANISM: Homo sapiens

<400> SEQUENCE: 130
agugggaggc cagggcacgg ca 22

<210> SEQ ID NO 131
<211> LENGTH: 23
<212> TYPE: RNA
<213> ORGANISM: Homo sapiens

<400> SEQUENCE: 131
gggggggcag gaggggcuca ggg 23

<210> SEQ ID NO 132
<211> LENGTH: 21
<212> TYPE: RNA
<213> ORGANISM: Homo sapiens

<400> SEQUENCE: 132
cugggcucgg gacgcgcggc u 21

<210> SEQ ID NO 133
<211> LENGTH: 22
<212> TYPE: RNA
<213> ORGANISM: Homo sapiens

<400> SEQUENCE: 133
uuggggaaac ggccgcugag ug 22

<210> SEQ ID NO 134
<211> LENGTH: 21
<212> TYPE: RNA
<213> ORGANISM: Homo sapiens

<400> SEQUENCE: 134
agcaugacag aggagaggug g 21

<210> SEQ ID NO 135
<211> LENGTH: 22
<212> TYPE: RNA
<213> ORGANISM: Homo sapiens

<400> SEQUENCE: 135
gggaccaucc ugccugcugu gg 22

<210> SEQ ID NO 136
<211> LENGTH: 22
<212> TYPE: RNA
<213> ORGANISM: Homo sapiens

<400> SEQUENCE: 136 gggugggau uuguugcauu ac 22

<210> SEQ ID NO 137
<211> LENGTH: 23
<212> TYPE: RNA
<213> ORGANISM: Homo sapiens

<400> SEQUENCE: 137
cggggccgua gcacugucug aga 23

<210> SEQ ID NO 138
<211> LENGTH: 25
<212> TYPE: RNA
<213> ORGANISM: Homo sapiens

<400> SEQUENCE: 138
agggaucgcg ggcggguggc ggccu 25

<210> SEQ ID NO 139
<211> LENGTH: 19
<212> TYPE: RNA
<213> ORGANISM: Homo sapiens

<400> SEQUENCE: 139
ggggccuggc ggugggcgg 19

<210> SEQ ID NO 140
<211> LENGTH: 20
<212> TYPE: RNA
<213> ORGANISM: Homo sapiens

<400> SEQUENCE: 140
acucaaacug ugggggcacu 20

<210> SEQ ID NO 141
<211> LENGTH: 21
<212> TYPE: RNA
<213> ORGANISM: Homo sapiens

<400> SEQUENCE: 141
gcagggacag caaaggggug c 21

<210> SEQ ID NO 142
<211> LENGTH: 21
<212> TYPE: RNA
<213> ORGANISM: Homo sapiens

<400> SEQUENCE: 142
accacugcac uccagccuga g 21

<210> SEQ ID NO 143
<211> LENGTH: 21
<212> TYPE: RNA
<213> ORGANISM: Homo sapiens

<400> SEQUENCE: 143
cccggagcca ggaugcagcu c 21

<210> SEQ ID NO 144
<211> LENGTH: 22
<212> TYPE: RNA
<213> ORGANISM: Homo sapiens

<400> SEQUENCE: 144
uggaguguga caaugguguu ug 22

<210> SEQ ID NO 145
<211> LENGTH: 17
<212> TYPE: RNA
<213> ORGANISM: Homo sapiens

<400> SEQUENCE: 145
ccccgccacc gccuugg 17

<210> SEQ ID NO 146
<211> LENGTH: 20
<212> TYPE: RNA
<213> ORGANISM: Homo sapiens

<400> SEQUENCE: 146
aaaaggcggg agaagcccca 20

<210> SEQ ID NO 147
<211> LENGTH: 20
<212> TYPE: RNA
<213> ORGANISM: Homo sapiens

<400> SEQUENCE: 147
ugugggacug caaaugggag 20

<210> SEQ ID NO 148
<211> LENGTH: 23
<212> TYPE: RNA
<213> ORGANISM: Homo sapiens

<400> SEQUENCE: 148
uggggaaggc uuggcaggga aga 23

<210> SEQ ID NO 149
<211> LENGTH: 86
<212> TYPE: RNA
<213> ORGANISM: Homo sapiens

<400> SEQUENCE: 149
ugccagucuc uaggucccug agacccuuua accugugagg acauccaggg ucacagguga 60
gguucuuggg agccuggcgu cuggcc 86

<210> SEQ ID NO 150
<211> LENGTH: 69
<212> TYPE: RNA
<213> ORGANISM: Homo sapiens

<400> SEQUENCE: 150
ccgggcaggc agguguaggg uggagcccac uguggcuccu gacucagccc ugcugccuuc 60
accugccag 69

<210> SEQ ID NO 151
<211> LENGTH: 110
<212> TYPE: RNA
<213> ORGANISM: Homo sapiens

<400> SEQUENCE: 151
ggcuacaguc uuucuucaug ugacucgugg acuucccuuu gucauccuau gccugagaau 60
auaugaagga ggcugggaag gcaaagggac guucaauugu caucacuggc 110

<210> SEQ ID NO 152
<211> LENGTH: 70
<212> TYPE: RNA
<213> ORGANISM: Homo sapiens

<400> SEQUENCE: 152
aaaagccugu cccuaagucc cucccagccu uccagaguug gugccaggaa ggauuuaggg 60
acaggcuuug 70

<210> SEQ ID NO 153
<211> LENGTH: 76
<212> TYPE: RNA
<213> ORGANISM: Homo sapiens

<400> SEQUENCE: 153
ccgaugccuc gggagucuac agcagggcca ugucugugag ggcccaaggg ugcauguguc 60
ucccagguuu cggugc 76

<210> SEQ ID NO 154
<211> LENGTH: 84
<212> TYPE: RNA
<213> ORGANISM: Homo sapiens

<400> SEQUENCE: 154
cuccccaugg cccugucucc caacccuugu accagugcug ggcucagacc cugguacagg 60
ccugggggac agggaccugg ggac 84

<210> SEQ ID NO 155
<211> LENGTH: 65
<212> TYPE: RNA
<213> ORGANISM: Homo sapiens

<400> SEQUENCE: 155
gagggugggc gagggcggcu gagcggcucc aucccccggc cugcucaucc cccucgcccu 60
cucag 65

<210> SEQ ID NO 156
<211> LENGTH: 61
<212> TYPE: RNA
<213> ORGANISM: Homo sapiens

<400> SEQUENCE: 156
ucucguuuga ucucggaagc uaagcagggu ugggccuggu uaguacuugg augggaaacu 60
u 61

<210> SEQ ID NO 157
<211> LENGTH: 53
<212> TYPE: RNA
<213> ORGANISM: Homo sapiens

<400> SEQUENCE: 157
guuugaucuc ggaagcuaag cagggucggg ccugguuagu acuuggaugg gag 53

<210> SEQ ID NO 158
<211> LENGTH: 87
<212> TYPE: RNA
<213> ORGANISM: Homo sapiens

<400> SEQUENCE: 158
gugaggcggg gccaggaggg ugugugggcgu gggugcugcg gggccgucag ggugccugcg 60
ggacgcucac cuggcuggcc cgcccag 87

<210> SEQ ID NO 159
<211> LENGTH: 62
<212> TYPE: RNA
<213> ORGANISM: Homo sapiens

<400> SEQUENCE: 159
ccuucugcgg cagagcuggg gucaccagcc cucauguacu ugugacuucu ccccugccac 60
ag 62

<210> SEQ ID NO 160
<211> LENGTH: 94
<212> TYPE: RNA
<213> ORGANISM: Homo sapiens

<400> SEQUENCE: 160
aauucagccc ugccacuggc uuaugucaug accuugggcu acucaggcug ucugcacaau 60
gagccaguug gacaggagca gugccacuca acuc 94

<210> SEQ ID NO 161
<211> LENGTH: 63
<212> TYPE: RNA
<213> ORGANISM: Homo sapiens

<400> SEQUENCE: 161
ggcuccgcag ggcccuggcg caggcaucca gacagcgggc gaaugccucc cccggccccg 60
cag 63

<210> SEQ ID NO 162
<211> LENGTH: 47
<212> TYPE: RNA
<213> ORGANISM: Homo sapiens

<400> SEQUENCE: 162
cucggcgcgg ggcgcgggcu ccggguuggg gcgagccaac gccgggg 47

<210> SEQ ID NO 163
<211> LENGTH: 93
<212> TYPE: RNA
<213> ORGANISM: Homo sapiens

<400> SEQUENCE: 163
ccuuccggcg ucccaggcgg ggcgccgcgg gaccgcccuc gugucugugg cggugggauc 60
ccgcggccgu guuuuccugg uggcccggcc aug 93

<210> SEQ ID NO 164
<211> LENGTH: 95
<212> TYPE: RNA
<213> ORGANISM: Homo sapiens

<400> SEQUENCE: 164
gacaccacau gcuccuccag gccugccugc ccuccagguc auguuccagu gucccacaga 60
ugcagcacca cggcccaggc ggcauuggug ucacc 95

<210> SEQ ID NO 165
<211> LENGTH: 54
<212> TYPE: RNA
<213> ORGANISM: Homo sapiens

<400> SEQUENCE: 165
ggacaagggc ggcgcgaccg gcccggggcu cuugggcggc cgcguuuccc cucc 54

<210> SEQ ID NO 166
<211> LENGTH: 94
<212> TYPE: RNA
<213> ORGANISM: Homo sapiens

<400> SEQUENCE: 166
auaaaggaag uuaggcugag gggcagagag cgagacuuuu cuauuuucca aaagcucggu 60
cugaggcccc ucagucuugc uuccuaaccc gcgc 94

<210> SEQ ID NO 167
<211> LENGTH: 55
<212> TYPE: RNA
<213> ORGANISM: Homo sapiens

<400> SEQUENCE: 167
ccggauccga gucacggcac caaauuucau gcguguccgu gugaagagac cacca 55

<210> SEQ ID NO 168
<211> LENGTH: 65
<212> TYPE: RNA
<213> ORGANISM: Homo sapiens

<400> SEQUENCE: 168
gucuccuggg gggaggagac ccugcucucc cuggcagcaa gccucuccug cccuuccaga 60
uuagc 65

<210> SEQ ID NO 169
<211> LENGTH: 98
<212> TYPE: RNA
<213> ORGANISM: Homo sapiens

<400> SEQUENCE: 169
cgagguaggg gcgucccggg cgcgcgggcg ggucccaggc ugggccccuc ggaggccggg 60
ugcucacugc ccguccccgg cgcccguguc uccuccag 98

<210> SEQ ID NO 170
<211> LENGTH: 64
<212> TYPE: RNA
<213> ORGANISM: Homo sapiens

<400> SEQUENCE: 170
aguucagggc cgaagggugg aagcugcugg ugcucaucuc agccucugcc cuuggccucc 60
ccag 64

<210> SEQ ID NO 171
<211> LENGTH: 74
<212> TYPE: RNA
<213> ORGANISM: Homo sapiens

<400> SEQUENCE: 171
gcagcccggu gagcgcucgc uggccuggca gugcgucgga agaacagggc gggugggggcc 60 gcgcacaucu cugc 74

<210> SEQ ID NO 172
<211> LENGTH: 56
<212> TYPE: RNA
<213> ORGANISM: Homo sapiens

<400> SEQUENCE: 172
cgaccgcacc cgcccgaagc ugggucaagg agcccagcag gacgggagcg cggcgc 56

<210> SEQ ID NO 173
<211> LENGTH: 68
<212> TYPE: RNA
<213> ORGANISM: Homo sapiens

<400> SEQUENCE: 173
gugcaaagag caggaggaca ggggauuuau cucccaaggg agguccccug auccuaguca 60
cggcacca 68

<210> SEQ ID NO 174
<211> LENGTH: 92
<212> TYPE: RNA
<213> ORGANISM: Homo sapiens

<400> SEQUENCE: 174
cgcugcgcuu cugggcccgc ggcgggcgug ggcugcccg ggccggucga ccagcgcgcc 60
guagcucccg aggcccgagc cgcgacccgc gg 92

<210> SEQ ID NO 175
<211> LENGTH: 72
<212> TYPE: RNA
<213> ORGANISM: Homo sapiens

<400> SEQUENCE: 175
gauuucagug accuggcagc agggagcguc gucaguguuu gacuguuuau gguaugucag 60
ggagcugguu cc 72

<210> SEQ ID NO 176
<211> LENGTH: 49
<212> TYPE: RNA
<213> ORGANISM: Homo sapiens

<400> SEQUENCE: 176
uucccagcca acgcaccaaa aaugauaugg gucuguuguc uggagaaac 49

<210> SEQ ID NO 177
<211> LENGTH: 92
<212> TYPE: RNA
<213> ORGANISM: Homo sapiens

<400> SEQUENCE: 177
gucagugucu gggcggacag cugcaggaaa gggaagacca aggcuugcug ucuguccagu 60
cugccacccu acccugucug uucuugccac ag 92

<210> SEQ ID NO 178
<211> LENGTH: 69
<212> TYPE: RNA
<213> ORGANISM: Homo sapiens

<400> SEQUENCE: 178
gaggagggga ggugugcagg gcugggguca cugacucugc uuccccugcc cugcauggug 60
uccccacag 69

<210> SEQ ID NO 179
<211> LENGTH: 96
<212> TYPE: RNA
<213> ORGANISM: Homo sapiens

<400> SEQUENCE: 179
cucgggaggg gcgggagggg gguccccggu gcucggaucu cgagggugcu uauuguucgg 60
uccgagccug ggucucccuc uucccccaa cccccc 96

<210> SEQ ID NO 180
<211> LENGTH: 65
<212> TYPE: RNA
<213> ORGANISM: Homo sapiens

<400> SEQUENCE: 180
ugucugggga uuuggagaag uggugagcgc aggucuuugg caccaucucc ccuggucccu 60
uggcu 65

<210> SEQ ID NO 181
<211> LENGTH: 61
<212> TYPE: RNA
<213> ORGANISM: Homo sapiens

<400> SEQUENCE: 181
gggggcggga gcuggggucu gcagguucgc acugaugccu gcucgcccug ucucccgcua 60
g 61

<210> SEQ ID NO 182
<211> LENGTH: 72
<212> TYPE: RNA
<213> ORGANISM: Homo sapiens

<400> SEQUENCE: 182
gagucugagg gacccaggac aggagaaggc cuauggugau uugcauucuu ccugcccugg 60
cuccauccuc ag 72

<210> SEQ ID NO 183
<211> LENGTH: 70
<212> TYPE: RNA
<213> ORGANISM: Homo sapiens

<400> SEQUENCE: 183
cucgggcccg accgcgccgg cccgcaccuc ccggcccgga gcugcgggcu gcggucaggg 60
cgaucccggg 70

<210> SEQ ID NO 184
<211> LENGTH: 89
<212> TYPE: RNA
<213> ORGANISM: Homo sapiens

<400> SEQUENCE: 184
gucagcagug ccuuagcagc acguaaauau uggcguuaag auucuaaaau uaucuccagu 60
auuaacugug cugcugaagu aagguugac 89

<210> SEQ ID NO 185
<211> LENGTH: 81
<212> TYPE: RNA
<213> ORGANISM: Homo sapiens

<400> SEQUENCE: 185
guuccacucu agcagcacgu aaauauuggc guagugaaau auauauuaaa caccaauauu 60
acugugcugc uuuaguguga c 81

<210> SEQ ID NO 186
<211> LENGTH: 98
<212> TYPE: RNA
<213> ORGANISM: Homo sapiens

<400> SEQUENCE: 186
uucucacccc cgccugacac gggcgacagc ugcggcccgc uguguucacu cgggccgagu 60
gcgucuccug ucaggcaagg gagagcagag ccccccug 98

<210> SEQ ID NO 187
<211> LENGTH: 73
<212> TYPE: RNA
<213> ORGANISM: Homo sapiens

<400> SEQUENCE: 187
cggcgacggc ggggugggug aggucgggcc ccaagacucg ggguuugccg ggcgccucag 60
uucaccgcgg ccg 73

<210> SEQ ID NO 188
<211> LENGTH: 86
<212> TYPE: RNA
<213> ORGANISM: Homo sapiens

<400> SEQUENCE: 188
cgccugagcg ugcagcagga caucuuccug accugguaau aauuagguga gaaggauggu 60
ugggggcggu cggcguaacu caggga 86

<210> SEQ ID NO 189
<211> LENGTH: 83
<212> TYPE: RNA
<213> ORGANISM: Homo sapiens

<400> SEQUENCE: 189
gugaguggga gccccagugu gugguugggg ccauggcggg ugggcagccc agccucugag 60
ccuuccucgu cugucugccc cag 83

<210> SEQ ID NO 190
<211> LENGTH: 62
<212> TYPE: RNA
<213> ORGANISM: Homo sapiens

<400> SEQUENCE: 190
gaggguggug gaggaagagg gcagcuccca ugacugccug accgccuucu cuccuccccc 60
ag 62

<210> SEQ ID NO 191
<211> LENGTH: 80
<212> TYPE: RNA
<213> ORGANISM: Homo sapiens

<400> SEQUENCE: 191
gcgucaagau ggcggcgggg agguaggcag agcaggacgc cgcugcugcc gccgccaccg 60
ccgccuccgc uccagucgcc 80

<210> SEQ ID NO 192
<211> LENGTH: 81
<212> TYPE: RNA
<213> ORGANISM: Homo sapiens

<400> SEQUENCE: 192 aguuggugggg ggagccauga gauaagagca ccuccuagag aauguugaac uaaaggugcc 60
cucucuggcu ccuccccaaa g 81

<210> SEQ ID NO 193
<211> LENGTH: 76
<212> TYPE: RNA
<213> ORGANISM: Homo sapiens

<400> SEQUENCE: 193
gagggagcug uagagcaggg agcaggaagc ugugugugc cagcccugac cuguccuguu 60
cugcccccag ccccuc 76

<210> SEQ ID NO 194
<211> LENGTH: 96
<212> TYPE: RNA
<213> ORGANISM: Homo sapiens

<400> SEQUENCE: 194
gcucuggggc gugccgccgc cgucgcugcc accuccccua ccgcuagugg aagaagaugg 60
cggaaggcgg agcggcggau cuggacaccc agcggu 96

<210> SEQ ID NO 195
<211> LENGTH: 60
<212> TYPE: RNA
<213> ORGANISM: Homo sapiens

<400> SEQUENCE: 195 cgcuggguce gcgcgcccug ggccgggcga uguccgcuug ggggagcgag gggcggggcg 60

<210> SEQ ID NO 196
<211> LENGTH: 61
<212> TYPE: RNA
<213> ORGANISM: Homo sapiens

<400> SEQUENCE: 196
uccgcucugu ggaguggggu gccuguccce ugccacuggg ugacccaccc cucuccacca 60
g 61

<210> SEQ ID NO 197
<211> LENGTH: 94
<212> TYPE: RNA
<213> ORGANISM: Homo sapiens

<400> SEQUENCE: 197
cgggcagcgg gugccaggca cggugucagc aggcaacaug gccgagaggc cggggccucc 60
gggcggcgcc guguccgcga ccgcguaccc ugac 94

<210> SEQ ID NO 198
<211> LENGTH: 72
<212> TYPE: RNA
<213> ORGANISM: Homo sapiens

<400> SEQUENCE: 198
cuugggaaug gcaaggaaac cguuaccauu acugaguuua guaaugguaa ugguucucuu 60
gcuauaccca ga 72

<210> SEQ ID NO 199
<211> LENGTH: 68
<212> TYPE: RNA
<213> ORGANISM: Homo sapiens

<400> SEQUENCE: 199
ugcccaggcu ggagcgagug caguggugca gucaguccua gcucacugca gccucgaacu 60
ccugggcu 68

<210> SEQ ID NO 200
<211> LENGTH: 89
<212> TYPE: RNA
<213> ORGANISM: Homo sapiens

<400> SEQUENCE: 200
accuccggga cggcugggcg ccggcggccg ggagauccgc gcuuccugaa ucccggccgg 60
cccgcccggc gcccguccgc ccgcggguc 89

<210> SEQ ID NO 201
<211> LENGTH: 79
<212> TYPE: RNA
<213> ORGANISM: Homo sapiens

<400> SEQUENCE: 201
cucgaggugc ugggggacgc gugagcgcga gccgcuuccu cacggcucgg ccgcggcgcg 60
uagcccccgc cacaucggg 79

<210> SEQ ID NO 202
<211> LENGTH: 83
<212> TYPE: RNA
<213> ORGANISM: Homo sapiens

<400> SEQUENCE: 202
aauagagggu gcacaggcac gggagcucag gugaggcagg gagcugagcu caccugaccu 60
cccaugccug ugcacccucu auu 83

<210> SEQ ID NO 203
<211> LENGTH: 61
<212> TYPE: RNA
<213> ORGANISM: Homo sapiens

<400> SEQUENCE: 203
gugcggaacg cuggccgggg cgggaggga agggacgccc ggccggaacg ccgcacucac 60
g 61

<210> SEQ ID NO 204
<211> LENGTH: 74
<212> TYPE: RNA
<213> ORGANISM: Homo sapiens

<400> SEQUENCE: 204
gugcguggug gcucgaggcg ggggugggggg ccucgcccug cuugggcccu cccugaccuc 60
uccgcuccgc acag 74

<210> SEQ ID NO 205
<211> LENGTH: 119
<212> TYPE: RNA
<213> ORGANISM: Homo sapiens

<400> SEQUENCE: 205
ccaugaggag cuggcagugg gauggccugg ggguaggagc guggcuucug gagcuagacc 60 acaugguuc agaucccagc ggugccucua acuggccaca ggaccuuggg cagucagcu 119

<210> SEQ ID NO 206
<211> LENGTH: 62
<212> TYPE: RNA
<213> ORGANISM: Homo sapiens

<400> SEQUENCE: 206
gugggucucg caucaggagg caaggccagg acccgcugac ccaugccucc ugccgcgguc 60
ag 62

<210> SEQ ID NO 207
<211> LENGTH: 81
<212> TYPE: RNA
<213> ORGANISM: Homo sapiens

<400> SEQUENCE: 207
cauccuccuu acgucccacc ccccacuccu guuucuggug aaauauucaa acaggagugg 60
gggugggaca uaaggaggau a 81

<210> SEQ ID NO 208
<211> LENGTH: 88
<212> TYPE: RNA
<213> ORGANISM: Homo sapiens

<400> SEQUENCE: 208
guggggccag gcgguggugg gcacugcugg ggugggcaca gcagccaugc agagcgggca 60
uuugaccccg ugccacccuu uuccccag 88

<210> SEQ ID NO 209
<211> LENGTH: 85
<212> TYPE: RNA
<213> ORGANISM: Homo sapiens

<400> SEQUENCE: 209
ggcgccuccu gcucugcugu gccgccaggg ccucccccuag cgcgccuucu ggagaggcuu 60
ugugcggaua cggggcugga ggccu 85

<210> SEQ ID NO 210
<211> LENGTH: 59
<212> TYPE: RNA
<213> ORGANISM: Homo sapiens

<400> SEQUENCE: 210
cggggucggc ggcgacgugc ucagcuuggc acccaaguuc ugccgcuccg acgcccggc 59

<210> SEQ ID NO 211
<211> LENGTH: 68
<212> TYPE: RNA
<213> ORGANISM: Homo sapiens

<400> SEQUENCE: 211
gaauggaaga agaaggcggu cggucugcgg gagccaggcc gcagagccau ccgccuucug 60
uccauguc 68

<210> SEQ ID NO 212
<211> LENGTH: 80
<212> TYPE: RNA
<213> ORGANISM: Homo sapiens

<400> SEQUENCE: 212
cgggaaugcc gcggcgggga cggcgauugg uccguaugug uggugccacc ggccgccggc 60
uccgccccgg cccccgcccc 80

<210> SEQ ID NO 213
<211> LENGTH: 64
<212> TYPE: RNA
<213> ORGANISM: Homo sapiens

<400> SEQUENCE: 213
aaccccgggc cggaggucaa gggcgucgcu ucucccuaau guugccucuu uuccacggcc 60
ucag 64

<210> SEQ ID NO 214
<211> LENGTH: 62
<212> TYPE: RNA
<213> ORGANISM: Homo sapiens

<400> SEQUENCE: 214
uggccuaggg ggcggcuugu ggaguguaug ggcugagccu ugcucugcuc ccccgccccc 60
ag 62

<210> SEQ ID NO 215
<211> LENGTH: 82
<212> TYPE: RNA
<213> ORGANISM: Homo sapiens

<400> SEQUENCE: 215
aaggagcacu cacuccaauu ucccuggacu gggggcaggc ugccaccucc uggggacagg 60
ggauuggggc aggauguucc ag 82

<210> SEQ ID NO 216
<211> LENGTH: 72
<212> TYPE: RNA
<213> ORGANISM: Homo sapiens

<400> SEQUENCE: 216
ucuccucgag ggucucugc cucuacccag gacucuuuca ugaccaggag gcugaggccc 60
cucacaggcg gc 72

<210> SEQ ID NO 217
<211> LENGTH: 63
<212> TYPE: RNA
<213> ORGANISM: Homo sapiens

<400> SEQUENCE: 217
gcaugcuggg cgaggcuggc aucuagcaca ggcgguagau gcuugcucuu gccauugcaa 60
uga 63

<210> SEQ ID NO 218
<211> LENGTH: 78
<212> TYPE: RNA
<213> ORGANISM: Homo sapiens

<400> SEQUENCE: 218
ggccucaggc aggcgcaccc gaccacaugc auggcuggug gcggcgugca ggggucgggu 60
gggccaggcu guggggcg 78

<210> SEQ ID NO 219
<211> LENGTH: 73
<212> TYPE: RNA
<213> ORGANISM: Homo sapiens

<400> SEQUENCE: 219
accuuuccag cucaucccac cucugccacc aaaacacuca ucgcggggguc agagggagug 60 ccaaaaaagg uaa 73

<210> SEQ ID NO 220
<211> LENGTH: 80
<212> TYPE: RNA
<213> ORGANISM: Homo sapiens

<400> SEQUENCE: 220
gguuccggag ccccggcgcg ggcggguucu ggggguguaga cgcugcuggc cagcccgccc 60
cagccgaggu ucucggcacc 80

<210> SEQ ID NO 221
<211> LENGTH: 63
<212> TYPE: RNA
<213> ORGANISM: Homo sapiens

<400> SEQUENCE: 221 aaugggggugg ugcugguggg agccgugccc uggccacuca uucggcucuc ucccucaccc 60
uag 63

<210> SEQ ID NO 222
<211> LENGTH: 89
<212> TYPE: RNA
<213> ORGANISM: Homo sapiens

<400> SEQUENCE: 222
ucuccguuua ucccaccacu gccaccauua uugcuacugu ucagcaggug cugcuggugg 60
ugauggugau agucuggugg gggcggugg 89

<210> SEQ ID NO 223
<211> LENGTH: 73
<212> TYPE: RNA
<213> ORGANISM: Homo sapiens

<400> SEQUENCE: 223
uguauccuug aauggauuuu uggagcagga guggacaccu gacccaaagg aaaucaaucc 60
auaggcuagc aau 73

<210> SEQ ID NO 224
<211> LENGTH: 61
<212> TYPE: RNA
<213> ORGANISM: Homo sapiens

<400> SEQUENCE: 224
aacugcgggg ccagagcaga gagcccuugc acaccaccag ccucuccucc cugugcccca 60
g 61

<210> SEQ ID NO 225
<211> LENGTH: 68
<212> TYPE: RNA
<213> ORGANISM: Homo sapiens

<400> SEQUENCE: 225
gacucggcug cgguggacaa guccggcucc agaaccugga caccgcucag ccggccgcgg 60
caggggguc 68

<210> SEQ ID NO 226
<211> LENGTH: 110
<212> TYPE: RNA
<213> ORGANISM: Homo sapiens

<400> SEQUENCE: 226
gucuaccagg ugugggccca gcuuuacaua guucaugcug aggccgggau uucaugcaga 60
aaacugguug caaaaggugc ugaaggggcu gggggagcac aagggagaag 110

<210> SEQ ID NO 227
<211> LENGTH: 73
<212> TYPE: RNA
<213> ORGANISM: Homo sapiens

<400> SEQUENCE: 227
gugggcgggg gcaggugugu ggugggugu ggccugcggu gagcagggcc cucacaccug 60
ccucgccccc cag 73

<210> SEQ ID NO 228
<211> LENGTH: 60
<212> TYPE: RNA
<213> ORGANISM: Homo sapiens

<400> SEQUENCE: 228
ugugaaugac ccccuuccag agccaaaauc accagggaug gaggaggggu cuuggguacu 60

<210> SEQ ID NO 229
<211> LENGTH: 59
<212> TYPE: RNA
<213> ORGANISM: Homo sapiens

<400> SEQUENCE: 229
ugaaguacca gcuacucgag aggucagagg auugcuccug aauagcuggg acuacaggu 59

<210> SEQ ID NO 230
<211> LENGTH: 90
<212> TYPE: RNA
<213> ORGANISM: Homo sapiens

<400> SEQUENCE: 230
cgggcggggc ggguccggcc gccuccgagc ccggccggca gcccccggcc uuaaagcgcg 60
ggcuguccgg aggggucggc uuucccaccg 90

<210> SEQ ID NO 231
<211> LENGTH: 102
<212> TYPE: RNA
<213> ORGANISM: Homo sapiens

<400> SEQUENCE: 231
uguguucccu auccuccuua ugucccaccc ccacuccugu uugaauauuu caccagaaac 60 aggaguggggg ggugggacgu aaggaggaug ggggaaagaa ca 102

<210> SEQ ID NO 232
<211> LENGTH: 75
<212> TYPE: RNA
<213> ORGANISM: Homo sapiens

<400> SEQUENCE: 232
ggcugugccg gguagagagg gcagugggag guaagagcuc uucacccuuc accaccuucu 60
ccacccagca uggcc 75

<210> SEQ ID NO 233
<211> LENGTH: 70
<212> TYPE: RNA
<213> ORGANISM: Homo sapiens

<400> SEQUENCE: 233
ggccgcggcg cgcaagaugg cggcgggccc gggcaccgcc ccuuccgccc cgccgggcgu 60
cgcacgaggc 70

<210> SEQ ID NO 234
<211> LENGTH: 86
<212> TYPE: RNA
<213> ORGANISM: Homo sapiens

<400> SEQUENCE: 234
auucuaggug gggagacuga cggcuggagg cccauaagcu gucuaaaacu ucggccccca 60
gauuucuggu cuccccacuu cagaac 86

<210> SEQ ID NO 235
<211> LENGTH: 67
<212> TYPE: RNA
<213> ORGANISM: Homo sapiens

<400> SEQUENCE: 235
cugguccauu ucccugccau ucccuuggcu ucaauuuacu cccagggcug gcagugacau 60
gggucaa 67

<210> SEQ ID NO 236
<211> LENGTH: 99
<212> TYPE: RNA
<213> ORGANISM: Homo sapiens

<400> SEQUENCE: 236
cgcccaccuc agccucccaa aaugcuggga uuacaggcau gagccacugc ggucgaccau 60
gaccuggaca uguuugugcc caguacuguc aguuugcag 99

<210> SEQ ID NO 237
<211> LENGTH: 66
<212> TYPE: RNA
<213> ORGANISM: Homo sapiens

<400> SEQUENCE: 237
ccgagugggg cggggcaggu cccugcaggg acugugacac ugaaggaccu gcaccuucgc 60
ccacag 66

<210> SEQ ID NO 238
<211> LENGTH: 73
<212> TYPE: RNA
<213> ORGANISM: Homo sapiens

<400> SEQUENCE: 238
guucaagugg gaggacagga ggcaggugug guuggaggaa gcagccugaa ccugccuccc 60
ugacauucca cag 73

<210> SEQ ID NO 239
<211> LENGTH: 68
<212> TYPE: RNA
<213> ORGANISM: Homo sapiens

<400> SEQUENCE: 239
cuccggugcc uacugagcug auaucaguuc ucauuuuaca cacuggcuca guucagcagg 60
aacaggag 68

<210> SEQ ID NO 240
<211> LENGTH: 73
<212> TYPE: RNA
<213> ORGANISM: Homo sapiens

<400> SEQUENCE: 240
cucugccucc cgugccuacu gagcugaaac acaguugguu uguguacacu ggcucaguuc 60
agcaggaaca ggg 73

<210> SEQ ID NO 241
<211> LENGTH: 80
<212> TYPE: RNA
<213> ORGANISM: Homo sapiens

<400> SEQUENCE: 241
ugagaggccg caccuugccu ugcugcccgg gccgugcacc cgugggcccc agggcgacgc 60
ggcgggggcg gcccuagcga 80

<210> SEQ ID NO 242
<211> LENGTH: 66
<212> TYPE: RNA
<213> ORGANISM: Homo sapiens

<400> SEQUENCE: 242
agcagcccuc ggcggcccgg ggggcgggcg gcggugcccg ucccggggcu gcgcgaggca 60
caggcg 66

<210> SEQ ID NO 243
<211> LENGTH: 59
<212> TYPE: RNA
<213> ORGANISM: Homo sapiens

<400> SEQUENCE: 243
cugugucggg gagucugggg uccggaauuc uccagagccu cugugccccu acuucccag 59

<210> SEQ ID NO 244
<211> LENGTH: 68
<212> TYPE: RNA
<213> ORGANISM: Homo sapiens

<400> SEQUENCE: 244
gcauccugua cugagcugcc ccgaggcccu ucaugcugcc cagcucgggg cagcucagua 60
caggauac 68

<210> SEQ ID NO 245
<211> LENGTH: 64
<212> TYPE: RNA
<213> ORGANISM: Homo sapiens

<400> SEQUENCE: 245
uccuguacug agcugccccg agcugggcag caugaagggc cucggggcag cucaguacag 60
gaug 64

<210> SEQ ID NO 246
<211> LENGTH: 59
<212> TYPE: RNA
<213> ORGANISM: Homo sapiens

<400> SEQUENCE: 246
cuccagggag acagugugug aggccucuug ccauggccuc ccugcccgcc ucucugcag 59

<210> SEQ ID NO 247
<211> LENGTH: 97
<212> TYPE: RNA
<213> ORGANISM: Homo sapiens

<400> SEQUENCE: 247
aucugaguug ggagggaccc ucuccaaaug ugucuugggg ugggggauca agacacauuu 60
ggagagggaa ccucccaacu cggccucugc caucauu 97

<210> SEQ ID NO 248
<211> LENGTH: 103
<212> TYPE: RNA
<213> ORGANISM: Homo sapiens

<400> SEQUENCE: 248
gugucggcug uggcgugacu gucccucugu gucccccacu aggcccacug cucaguggag 60
cguggaggac gaggaggagg ccguccacga gcaaugccag cau 103

<210> SEQ ID NO 249
<211> LENGTH: 72
<212> TYPE: RNA
<213> ORGANISM: Homo sapiens

<400> SEQUENCE: 249
ccaggcacac aggaaaagcg gggcccuggg uucggcugcu accccaaagg ccacauucuc 60
cugugcacac ag 72

<210> SEQ ID NO 250
<211> LENGTH: 78
<212> TYPE: RNA
<213> ORGANISM: Homo sapiens

<400> SEQUENCE: 250
gagcgucacg uugacacuca aaaaguuuca gauuuuggaa cauuucggau uuuggauuuu 60
uggaucaggg augcucaa 78

<210> SEQ ID NO 251
<211> LENGTH: 87
<212> TYPE: RNA
<213> ORGANISM: Homo sapiens

<400> SEQUENCE: 251
guguggccgg caggcgggug ggcgggggcg gccgguggga accccgcccc gccccgcgcc 60
cgcacucacc cgcccgucuc cccacag 87

<210> SEQ ID NO 252
<211> LENGTH: 96
<212> TYPE: RNA
<213> ORGANISM: Homo sapiens

<400> SEQUENCE: 252
cgggccccgg gcgggcggga gggacgggac gcggugcagu guuguuuuuu cccccgccaa 60
uauugcacuc gucccggccu ccggcccccc cggccc 96

<210> SEQ ID NO 253
<211> LENGTH: 115
<212> TYPE: RNA
<213> ORGANISM: Homo sapiens

<400> SEQUENCE: 253
ggugccgagg gccguccggc auccuaggcg ggucgcugcg guaccucccu ccugucugug 60
gcggugggau cccguggccg uguuuuccug guggcccggc cgugccugag guuuc 115

<210> SEQ ID NO 254
<211> LENGTH: 102
<212> TYPE: RNA
<213> ORGANISM: Homo sapiens

<400> SEQUENCE: 254
gcuuaucgag gaaaagaucg agguggguug gggcgggcuc uggggauuug gucucacagc 60
ccggauccca gcccacuuac cuugguuacu cuccuuccuu cu 102

<210> SEQ ID NO 255
<211> LENGTH: 63
<212> TYPE: RNA
<213> ORGANISM: Homo sapiens

<400> SEQUENCE: 255
ugguggcggc gguaguuaug ggcuucucuu ucucaccagc agccccuggg ccgccgccuc 60
ccu 63

<210> SEQ ID NO 256
<211> LENGTH: 67
<212> TYPE: RNA
<213> ORGANISM: Homo sapiens

<400> SEQUENCE: 256
gugaggaggg gcuggcaggg accccuccaa guuggggacg gcagccagcc ccugcucacc 60
ccucgcc 67

<210> SEQ ID NO 257
<211> LENGTH: 73
<212> TYPE: RNA
<213> ORGANISM: Homo sapiens

<400> SEQUENCE: 257
gaaaacaacc aggugggcuu cccggagggc ggaacaccca gccccagcau ccagggcuca 60
ccuaccacgu uug 73

<210> SEQ ID NO 258
<211> LENGTH: 105
<212> TYPE: RNA
<213> ORGANISM: Homo sapiens

<400> SEQUENCE: 258
gcgggcggcg gcggcggcag cagcagcagg ugcggggcgg cggccgcgcu ggccgcucga 60
cuccgcagcu gcucguucug cuucuccagc uugcgcacca gcucc 105

<210> SEQ ID NO 259
<211> LENGTH: 47
<212> TYPE: RNA
<213> ORGANISM: Homo sapiens

<400> SEQUENCE: 259
aggcagguua ucugggcugc caucucccac uggcugcuug ccugccu 47

<210> SEQ ID NO 260
<211> LENGTH: 80
<212> TYPE: RNA
<213> ORGANISM: Homo sapiens

<400> SEQUENCE: 260
accugaggag ccagcccucc ucccgcaccc aaacuuggag cacuugaccu uuggcuguug 60
gagggggcag gcucgcgggu 80

<210> SEQ ID NO 261
<211> LENGTH: 115
<212> TYPE: RNA
<213> ORGANISM: Homo sapiens

<400> SEQUENCE: 261
gagcaaaaac cagagaacaa caugggagcg uuccuaaccc cuaaggcaac uggaugggag 60
accugaccca uccaguucuc ugagggggcu cuugugugguu cuacaagguu guuca 115

<210> SEQ ID NO 262
<211> LENGTH: 93
<212> TYPE: RNA
<213> ORGANISM: Homo sapiens

<400> SEQUENCE: 262
uacuuauggc accccacucc ugguaccaua gucauaaguu aggagauguu agagcuguga 60
guaccaugac uuaagugugg uggcuuaaac aug 93

<210> SEQ ID NO 263
<211> LENGTH: 68
<212> TYPE: RNA
<213> ORGANISM: Homo sapiens

<400> SEQUENCE: 263
cguggugagg auauggcagg gaaggggagu uucccucuau ucccuucccc ccaguaaucu 60
ucaucaug 68

<210> SEQ ID NO 264
<211> LENGTH: 67
<212> TYPE: RNA
<213> ORGANISM: Homo sapiens

<400> SEQUENCE: 264
ccagaccccu ggggcugggc aggcggaaag aggucugaac ugccucugcc uccuuggucu 60
ccggcag 67

<210> SEQ ID NO 265
<211> LENGTH: 83
<212> TYPE: RNA
<213> ORGANISM: Homo sapiens

<400> SEQUENCE: 265
ccugcugcag aggugccagc ugcagugggg gaggcacugc cagggcugcc cacucugcuu 60
agccagcagg ugccaagaac agg 83

<210> SEQ ID NO 266
<211> LENGTH: 69
<212> TYPE: RNA
<213> ORGANISM: Homo sapiens

<400> SEQUENCE: 266
cuuucggcca gcgggacggc auccgaggug ggcuaggcuc gggcccgugg cgggugcggg 60
ggugggagg 69

<210> SEQ ID NO 267
<211> LENGTH: 71
<212> TYPE: RNA
<213> ORGANISM: Homo sapiens

<400> SEQUENCE: 267
gugucugugc cggucccagg agaaccugca gaggcaucgg gucagcggug cuccugcggg 60
ccgacacuca c 71

<210> SEQ ID NO 268
<211> LENGTH: 75
<212> TYPE: RNA
<213> ORGANISM: Homo sapiens

<400> SEQUENCE: 268
aagcaagacu gaggggccuc agaccgagcu uuuggaaaau agaaaagucu cgcucucugc 60
cccucagccu aacuu 75

<210> SEQ ID NO 269
<211> LENGTH: 106
<212> TYPE: RNA
<213> ORGANISM: Homo sapiens

<400> SEQUENCE: 269
agaagaaugc ccaaccagcc cucaguugcu acaguucccu guuguuucag cucgacaaca 60
acaggcggcu guagcaaugg ggggcuggau gggcaucuca augugc 106

<210> SEQ ID NO 270
<211> LENGTH: 57
<212> TYPE: RNA
<213> ORGANISM: Homo sapiens

<400> SEQUENCE: 270
cauuggaggg uguggaagac aucugggcca acucugaucu cuucaucuac cccccag 57

<210> SEQ ID NO 271
<211> LENGTH: 109
<212> TYPE: RNA
<213> ORGANISM: Homo sapiens

<400> SEQUENCE: 271
ugcuauuguc uuacugcuac agcagggcug gggauugcag uauccgcugu ugcugcugcu 60
cccaguccug ccccugcugc uaccuagucc agccucaccg caucccaga 109

<210> SEQ ID NO 272
<211> LENGTH: 109
<212> TYPE: RNA
<213> ORGANISM: Homo sapiens

<400> SEQUENCE: 272
ggucgggcuc accaugacac agugugagac cucgggcuac aacacaggac ccgggcgcug 60
cucugacccc ucgugucuug uguugcagcc ggagggacgc agguccgca 109

<210> SEQ ID NO 273
<211> LENGTH: 72
<212> TYPE: RNA
<213> ORGANISM: Homo sapiens

<400> SEQUENCE: 273
cugggggagg aaggacaggc caucugcuau ucguccacca accugacuug auccucucuu 60
cccuccuccc ag 72

<210> SEQ ID NO 274
<211> LENGTH: 55
<212> TYPE: RNA
<213> ORGANISM: Homo sapiens

<400> SEQUENCE: 274
gggggcuggg gcgcggggag gugcuagguc ggccucggcu cccgcgccgc acccc 55

<210> SEQ ID NO 275
<211> LENGTH: 64
<212> TYPE: RNA
<213> ORGANISM: Homo sapiens

<400> SEQUENCE: 275
gagcucuggg aggggcuggg uuuggcagga caguuuccaa gcccugucuc cucccaucuu 60
ccag 64

<210> SEQ ID NO 276
<211> LENGTH: 59
<212> TYPE: RNA
<213> ORGANISM: Homo sapiens

<400> SEQUENCE: 276
ggggccaggc agggaggugg gaccaugggg gccuugcugu gugaccaccg uuccugcag 59

<210> SEQ ID NO 277
<211> LENGTH: 70
<212> TYPE: RNA
<213> ORGANISM: Homo sapiens

<400> SEQUENCE: 277
ugugcacuug ggcaggaggg acccuguaug ucuccccgca gcaccgucau cgugucccuc 60
uuguccacag 70

<210> SEQ ID NO 278
<211> LENGTH: 75
<212> TYPE: RNA
<213> ORGANISM: Homo sapiens

<400> SEQUENCE: 278
aggcuggcgu gggcugaggg caggaggccu guggccgguc ccaggccucc ugcuuccugg 60
gcucaggcuc gguuu 75

<210> SEQ ID NO 279
<211> LENGTH: 64
<212> TYPE: RNA
<213> ORGANISM: Homo sapiens

<400> SEQUENCE: 279
ugcucuguag gcaugaggca gggcccaggu uccaugugau gcugaagcuc ugacauuccu 60
gcag 64

<210> SEQ ID NO 280
<211> LENGTH: 82
<212> TYPE: RNA
<213> ORGANISM: Homo sapiens

<400> SEQUENCE: 280 gugagauggga ggccagggca cggcaggggg agcugcaggg cuaugggagg ggccccagcg 60
ucugagcccu guccucccgc ag 82

<210> SEQ ID NO 281
<211> LENGTH: 82
<212> TYPE: RNA
<213> ORGANISM: Homo sapiens

<400> SEQUENCE: 281 gugagauggga ggccagggca cggcaggggg agcugcaggg cuaugggagg ggccccagcg 60
ucugagcccu guccucccgc ag 82

<210> SEQ ID NO 282
<211> LENGTH: 75
<212> TYPE: RNA
<213> ORGANISM: Homo sapiens

<400> SEQUENCE: 282 uggaguggggg gggcaggagg ggcucaggga gaaagugcau acagccccug gcccucucug 60
cccuuccguc cccug 75

<210> SEQ ID NO 283
<211> LENGTH: 87
<212> TYPE: RNA
<213> ORGANISM: Homo sapiens

<400> SEQUENCE: 283
cccaggcgcc cgcucccgac ccacgccgcg ccgccggguc ccuccucccc ggagaggcug 60
ggcucgggac gcgcggcuca gcucggg 87

<210> SEQ ID NO 284
<211> LENGTH: 75
<212> TYPE: RNA
<213> ORGANISM: Homo sapiens

<400> SEQUENCE: 284 caggggguuug gggaaacggc cgcugaguga ggcgucggcu guguuucuca ccgcggucuu 60
uuccucccac ucuug 75

<210> SEQ ID NO 285
<211> LENGTH: 113
<212> TYPE: RNA
<213> ORGANISM: Homo sapiens

<400> SEQUENCE: 285
agcaugacag aggagaggug gagguaggcg agaguaauau aauuucucca ggagaacauc 60
ugagagggga aguugcuuuc cugcccuggc ccuuucaccc uccugaguuu ggg 113

<210> SEQ ID NO 286
<211> LENGTH: 83
<212> TYPE: RNA
<213> ORGANISM: Homo sapiens

<400> SEQUENCE: 286
acggcaucuu ugcacucagc aggcaggcug gugcagcccg ugguggggga ccauccugcc 60 ugcuguggg uaaggacggc ugu 83

<210> SEQ ID NO 287
<211> LENGTH: 75
<212> TYPE: RNA
<213> ORGANISM: Homo sapiens

<400> SEQUENCE: 287
ucaucccugg guggggauuu guugcauuac uuguguucua uauaaaguau ugcacuuguc 60
ccggccugug gaaga 75

<210> SEQ ID NO 288
<211> LENGTH: 82
<212> TYPE: RNA
<213> ORGANISM: Homo sapiens

<400> SEQUENCE: 288
ugagcuguug gauucggggc cguagcacug ucugagaggu uuacauuucu cacagugaac 60
cggucucuuu uucagcugcu uc 82

<210> SEQ ID NO 289
<211> LENGTH: 100
<212> TYPE: RNA
<213> ORGANISM: Homo sapiens

<400> SEQUENCE: 289
gugagcgggc gcggcaggga ucgcgggcgg guggcggccu agggcgcgga gggcggaccg 60
ggaauggcgc gccgugcgcc gccggcguaa cugcggcgcu 100

<210> SEQ ID NO 290
<211> LENGTH: 90
<212> TYPE: RNA
<213> ORGANISM: Homo sapiens

<400> SEQUENCE: 290
ggcgccucug cagcuccggc ucccccuggc cucucgggaa cuacaagucc caggggggccu 60 ggcggugggc ggcgggcgga agaggcgggg 90

<210> SEQ ID NO 291
<211> LENGTH: 67
<212> TYPE: RNA
<213> ORGANISM: Homo sapiens

<400> SEQUENCE: 291
guggcacuca aacugugggg gcacuuucug cucucuggug aaagugccgc caucuuuuga 60
guguuac 67

<210> SEQ ID NO 292
<211> LENGTH: 110
<212> TYPE: RNA
<213> ORGANISM: Homo sapiens

<400> SEQUENCE: 292
ucaccuggcc augugacuug ugggcuuccc uuugucaucc uucgccuagg gcucugagca 60
gggcagggac agcaaagggg ugcucaguug ucacuuccca cagcacggag 110

<210> SEQ ID NO 293
<211> LENGTH: 100
<212> TYPE: RNA
<213> ORGANISM: Homo sapiens

<400> SEQUENCE: 293
gaggugggag gauugcuuga gucagggugg uugaggcugc aguaaguugu gaucauacca 60
cugcacucca gccugaguga cagagcaaga ccuugucuca 100

<210> SEQ ID NO 294
<211> LENGTH: 85
<212> TYPE: RNA
<213> ORGANISM: Homo sapiens

<400> SEQUENCE: 294
uccuccccgg agccaggaug cagcucaagc cacagcaggg uguuuagcgc ucuucagugg 60
cuccagauug uggcgcuggu gcagg 85

<210> SEQ ID NO 295
<211> LENGTH: 85
<212> TYPE: RNA
<213> ORGANISM: Homo sapiens

<400> SEQUENCE: 295
ccuuagcaga gcuguggagu gugacaaugg uguuugugac uaaacuauca aacgccauua 60
ucacacuaaa uagcuacugc uaggc 85

<210> SEQ ID NO 296
<211> LENGTH: 91
<212> TYPE: RNA
<213> ORGANISM: Homo sapiens

<400> SEQUENCE: 296
acgccccccg ccccgccacc gccuuggagg cugaccucuu acuuucgguc ggucuucuuc 60
ccugggcuug guuugggggc gggggagugu c 91

<210> SEQ ID NO 297
<211> LENGTH: 83
<212> TYPE: RNA
<213> ORGANISM: Homo sapiens

<400> SEQUENCE: 297
ggguuuccuc ugccuuuuuu uccaaugaaa auaacgaaac cuguuauuuc ccauugaggg 60
ggaaaaaggc gggagaagcc cca 83

<210> SEQ ID NO 298
<211> LENGTH: 72
<212> TYPE: RNA
<213> ORGANISM: Homo sapiens

<400> SEQUENCE: 298
ugugggacug caaaugggag cucagcaccu gccugccacc cacgcagacc agccccugcu 60
cuguucccac ag 72

<210> SEQ ID NO 299
<211> LENGTH: 79
<212> TYPE: RNA
<213> ORGANISM: Homo sapiens

<400> SEQUENCE: 299
cagccugggg aaggcuuggc agggaagaca caugagcagu gccuccacuu cacgccucuc 60
ccuugucucc uuucccuag 79

<210> SEQ ID NO 300
<211> LENGTH: 23
<212> TYPE: RNA
<213> ORGANISM: Homo sapiens

<400> SEQUENCE: 300
cacaggugag guucuuggga gcc 23

<210> SEQ ID NO 301
<211> LENGTH: 15
<212> TYPE: RNA
<213> ORGANISM: Homo sapiens

<400> SEQUENCE: 301
acaggugagg uucuu 15

<210> SEQ ID NO 302
<211> LENGTH: 24
<212> TYPE: RNA
<213> ORGANISM: Homo sapiens

<400> SEQUENCE: 302
gaggcuggga aggcaaaggg acgu 24

<210> SEQ ID NO 303
<211> LENGTH: 15
<212> TYPE: RNA
<213> ORGANISM: Homo sapiens

<400> SEQUENCE: 303
gaaggaggcu gggaa 15

<210> SEQ ID NO 304
<211> LENGTH: 25
<212> TYPE: RNA
<213> ORGANISM: Homo sapiens

<400> SEQUENCE: 304
caggaaggau uuagggacag gcuuu 25

<210> SEQ ID NO 305
<211> LENGTH: 19
<212> TYPE: RNA
<213> ORGANISM: Homo sapiens

<400> SEQUENCE: 305
caggaaggau uuagggaca 19

<210> SEQ ID NO 306
<211> LENGTH: 24
<212> TYPE: RNA
<213> ORGANISM: Homo sapiens

<400> SEQUENCE: 306
cugguacagg ccugggggac aggg 24

<210> SEQ ID NO 307
<211> LENGTH: 18
<212> TYPE: RNA
<213> ORGANISM: Homo sapiens

<400> SEQUENCE: 307
cugguacagg ccuggggg 18

<210> SEQ ID NO 308
<211> LENGTH: 26
<212> TYPE: RNA
<213> ORGANISM: Homo sapiens

<400> SEQUENCE: 308
cggugggauc ccgcggccgu guuuuc 26

<210> SEQ ID NO 309
<211> LENGTH: 15
<212> TYPE: RNA
<213> ORGANISM: Homo sapiens

<400> SEQUENCE: 309
ggggcgccgc gggac 15

<210> SEQ ID NO 310
<211> LENGTH: 19
<212> TYPE: RNA
<213> ORGANISM: Homo sapiens

<400> SEQUENCE: 310
cggcgcgacc ggcccgggg 19

<210> SEQ ID NO 311
<211> LENGTH: 19
<212> TYPE: RNA
<213> ORGANISM: Homo sapiens

<400> SEQUENCE: 311
cggcgcgacc ggcccgggg 19

<210> SEQ ID NO 312
<211> LENGTH: 30
<212> TYPE: RNA
<213> ORGANISM: Homo sapiens

<400> SEQUENCE: 312
ugaggggcag agagcgagac uuuucuauuu 30

<210> SEQ ID NO 313
<211> LENGTH: 15
<212> TYPE: RNA
<213> ORGANISM: Homo sapiens

<400> SEQUENCE: 313
ugaggggcag agagc 15

<210> SEQ ID NO 314
<211> LENGTH: 21
<212> TYPE: RNA
<213> ORGANISM: Homo sapiens

<400> SEQUENCE: 314
cggauccgag ucacggcacc a 21

<210> SEQ ID NO 315
<211> LENGTH: 15
<212> TYPE: RNA
<213> ORGANISM: Homo sapiens

<400> SEQUENCE: 315
ggauccgagu cacgg 15

<210> SEQ ID NO 316
<211> LENGTH: 17
<212> TYPE: RNA
<213> ORGANISM: Homo sapiens

<400> SEQUENCE: 316
ggugagcgcu cgcuggc 17

<210> SEQ ID NO 317
<211> LENGTH: 15
<212> TYPE: RNA
<213> ORGANISM: Homo sapiens

<400> SEQUENCE: 317
cggugagcgc ucgcu 15

<210> SEQ ID NO 318
<211> LENGTH: 21
<212> TYPE: RNA
<213> ORGANISM: Homo sapiens

<400> SEQUENCE: 318
cccagcagga cgggagcgcg g 21

<210> SEQ ID NO 319
<211> LENGTH: 16
<212> TYPE: RNA
<213> ORGANISM: Homo sapiens

<400> SEQUENCE: 319
aagcuggguc aaggag 16

<210> SEQ ID NO 320
<211> LENGTH: 17
<212> TYPE: RNA
<213> ORGANISM: Homo sapiens

<400> SEQUENCE: 320
uccuagucac ggcacca 17

<210> SEQ ID NO 321
<211> LENGTH: 17
<212> TYPE: RNA
<213> ORGANISM: Homo sapiens

<400> SEQUENCE: 321
uccuagucac ggcacca 17

<210> SEQ ID NO 322
<211> LENGTH: 25
<212> TYPE: RNA
<213> ORGANISM: Homo sapiens

<400> SEQUENCE: 322
uucugggccc gcggcgggcg ugggg 25

<210> SEQ ID NO 323
<211> LENGTH: 15
<212> TYPE: RNA
<213> ORGANISM: Homo sapiens

<400> SEQUENCE: 323
cgcggcgggc guggg 15

<210> SEQ ID NO 324
<211> LENGTH: 23
<212> TYPE: RNA
<213> ORGANISM: Homo sapiens

<400> SEQUENCE: 324
gggggucccc ggugcucgga ucu 23

<210> SEQ ID NO 325
<211> LENGTH: 16
<212> TYPE: RNA
<213> ORGANISM: Homo sapiens

<400> SEQUENCE: 325
ucgggagggg cgggag 16

<210> SEQ ID NO 326
<211> LENGTH: 22
<212> TYPE: RNA
<213> ORGANISM: Homo sapiens

<400> SEQUENCE: 326
uggggauuug gagaagugguu ga 22

<210> SEQ ID NO 327
<211> LENGTH: 22
<212> TYPE: RNA
<213> ORGANISM: Homo sapiens

<400> SEQUENCE: 327
uggggauuug gagaagugguu ga 22

<210> SEQ ID NO 328
<211> LENGTH: 24
<212> TYPE: RNA
<213> ORGANISM: Homo sapiens

<400> SEQUENCE: 328
gcugcgggcu gcggucaggg cgau 24

<210> SEQ ID NO 329
<211> LENGTH: 20
<212> TYPE: RNA
<213> ORGANISM: Homo sapiens

<400> SEQUENCE: 329
gcugcgggcu gcggucaggg 20

<210> SEQ ID NO 330
<211> LENGTH: 27
<212> TYPE: RNA
<213> ORGANISM: Homo sapiens

<400> SEQUENCE: 330
uagcagcacg uaaauauugg cguuaag 27

<210> SEQ ID NO 331
<211> LENGTH: 15
<212> TYPE: RNA
<213> ORGANISM: Homo sapiens

<400> SEQUENCE: 331
uagcagcacg uaaau 15

<210> SEQ ID NO 332
<211> LENGTH: 23
<212> TYPE: RNA
<213> ORGANISM: Homo sapiens

<400> SEQUENCE: 332
ggugggugag gucgggcccc aag 23

<210> SEQ ID NO 333
<211> LENGTH: 20
<212> TYPE: RNA
<213> ORGANISM: Homo sapiens

<400> SEQUENCE: 333
cggggugggu gaggucgggc 20

<210> SEQ ID NO 334
<211> LENGTH: 25
<212> TYPE: RNA
<213> ORGANISM: Homo sapiens

<400> SEQUENCE: 334
gggggagcca ugagauaaga gcacc 25

<210> SEQ ID NO 335
<211> LENGTH: 20
<212> TYPE: RNA
<213> ORGANISM: Homo sapiens

<400> SEQUENCE: 335
ugggggagcc augagauaag 20

<210> SEQ ID NO 336
<211> LENGTH: 23
<212> TYPE: RNA
<213> ORGANISM: Homo sapiens

<400> SEQUENCE: 336
uguagagcag ggagcaggaa gcu 23

<210> SEQ ID NO 337
<211> LENGTH: 15
<212> TYPE: RNA
<213> ORGANISM: Homo sapiens

<400> SEQUENCE: 337
cagggagcag gaagc 15

<210> SEQ ID NO 338
<211> LENGTH: 23
<212> TYPE: RNA
<213> ORGANISM: Homo sapiens

<400> SEQUENCE: 338
cuaguggaag aagauggcgg aag 23

<210> SEQ ID NO 339
<211> LENGTH: 15
<212> TYPE: RNA
<213> ORGANISM: Homo sapiens

<400> SEQUENCE: 339
uaguggaaga agaug 15

<210> SEQ ID NO 340
<211> LENGTH: 18
<212> TYPE: RNA
<213> ORGANISM: Homo sapiens

<400> SEQUENCE: 340
cuccgggcgg cgccgugu 18

<210> SEQ ID NO 341
<211> LENGTH: 18
<212> TYPE: RNA
<213> ORGANISM: Homo sapiens

<400> SEQUENCE: 341
cuccgggcgg cgccgugu 18

<210> SEQ ID NO 342
<211> LENGTH: 27
<212> TYPE: RNA
<213> ORGANISM: Homo sapiens

<400> SEQUENCE: 342
aaaccguuac cauuacugag uuuagua 27

<210> SEQ ID NO 343
<211> LENGTH: 15
<212> TYPE: RNA
<213> ORGANISM: Homo sapiens

<400> SEQUENCE: 343
gaaaccguua ccauu 15

<210> SEQ ID NO 344
<211> LENGTH: 21
<212> TYPE: RNA
<213> ORGANISM: Homo sapiens

<400> SEQUENCE: 344
cccaggcugg agcgagugca g 21

<210> SEQ ID NO 345
<211> LENGTH: 15
<212> TYPE: RNA
<213> ORGANISM: Homo sapiens

<400> SEQUENCE: 345
agcucacugc agccu 15

<210> SEQ ID NO 346
<211> LENGTH: 17
<212> TYPE: RNA
<213> ORGANISM: Homo sapiens

<400> SEQUENCE: 346
ccuccgggac ggcuggg 17

<210> SEQ ID NO 347
<211> LENGTH: 15
<212> TYPE: RNA
<213> ORGANISM: Homo sapiens

<400> SEQUENCE: 347
cuccgggacg gcugg 15

<210> SEQ ID NO 348
<211> LENGTH: 23
<212> TYPE: RNA
<213> ORGANISM: Homo sapiens

<400> SEQUENCE: 348
cugggggacg cgugagcgcg agc 23

<210> SEQ ID NO 349
<211> LENGTH: 21
<212> TYPE: RNA
<213> ORGANISM: Homo sapiens

<400> SEQUENCE: 349
cugggggacg cgugagcgcg a 21

<210> SEQ ID NO 350
<211> LENGTH: 22
<212> TYPE: RNA
<213> ORGANISM: Homo sapiens

<400> SEQUENCE: 350
caggcacggg agcucaggug ag 22

<210> SEQ ID NO 351
<211> LENGTH: 17
<212> TYPE: RNA
<213> ORGANISM: Homo sapiens

<400> SEQUENCE: 351
caggcacggg agcucag 17

<210> SEQ ID NO 352
<211> LENGTH: 17
<212> TYPE: RNA
<213> ORGANISM: Homo sapiens

<400> SEQUENCE: 352
gaucccagcg gugccuc 17

<210> SEQ ID NO 353
<211> LENGTH: 15
<212> TYPE: RNA
<213> ORGANISM: Homo sapiens

<400> SEQUENCE: 353
gaucccagcg gugcc 15

<210> SEQ ID NO 354
<211> LENGTH: 23
<212> TYPE: RNA
<213> ORGANISM: Homo sapiens

<400> SEQUENCE: 354
acaggagugg gggugggaca uaa 23

<210> SEQ ID NO 355
<211> LENGTH: 20
<212> TYPE: RNA
<213> ORGANISM: Homo sapiens

<400> SEQUENCE: 355
acaggagugg gggugggaca 20

<210> SEQ ID NO 356
<211> LENGTH: 26
<212> TYPE: RNA
<213> ORGANISM: Homo sapiens

<400> SEQUENCE: 356
ccuucuggag aggcuuugug cggaua 26

<210> SEQ ID NO 357
<211> LENGTH: 15
<212> TYPE: RNA
<213> ORGANISM: Homo sapiens

<400> SEQUENCE: 357
ccuucuggag aggcu 15

<210> SEQ ID NO 358
<211> LENGTH: 23
<212> TYPE: RNA
<213> ORGANISM: Homo sapiens

<400> SEQUENCE: 358
agaagaaggc ggucggucug cgg 23

<210> SEQ ID NO 359
<211> LENGTH: 21
<212> TYPE: RNA
<213> ORGANISM: Homo sapiens

<400> SEQUENCE: 359
aagaaggcgg ucggucugcg g 21

<210> SEQ ID NO 360
<211> LENGTH: 21
<212> TYPE: RNA
<213> ORGANISM: Homo sapiens

<400> SEQUENCE: 360
ccggccgccg gcuccgcccc g 21

<210> SEQ ID NO 361
<211> LENGTH: 17
<212> TYPE: RNA
<213> ORGANISM: Homo sapiens

<400> SEQUENCE: 361
ccggccgccg gcuccgc 17

<210> SEQ ID NO 362
<211> LENGTH: 22
<212> TYPE: RNA
<213> ORGANISM: Homo sapiens

<400> SEQUENCE: 362
accaggaggc ugaggccccu ca 22

<210> SEQ ID NO 363
<211> LENGTH: 15
<212> TYPE: RNA
<213> ORGANISM: Homo sapiens

<400> SEQUENCE: 363
accaggaggc ugagg 15

<210> SEQ ID NO 364
<211> LENGTH: 19
<212> TYPE: RNA
<213> ORGANISM: Homo sapiens

<400> SEQUENCE: 364
gcugggcgag gcuggcauc 19

<210> SEQ ID NO 365
<211> LENGTH: 17
<212> TYPE: RNA
<213> ORGANISM: Homo sapiens

<400> SEQUENCE: 365
gcugggcgag gcuggca 17

<210> SEQ ID NO 366
<211> LENGTH: 20
<212> TYPE: RNA
<213> ORGANISM: Homo sapiens

<400> SEQUENCE: 366
aucccaccuc ugccaccaaa 20

<210> SEQ ID NO 367
<211> LENGTH: 15
<212> TYPE: RNA
<213> ORGANISM: Homo sapiens

<400> SEQUENCE: 367
aucccaccuc ugcca 15

<210> SEQ ID NO 368
<211> LENGTH: 23
<212> TYPE: RNA
<213> ORGANISM: Homo sapiens

<400> SEQUENCE: 368
gccccggcgc gggcggguuc ugg 23

<210> SEQ ID NO 369
<211> LENGTH: 16
<212> TYPE: RNA
<213> ORGANISM: Homo sapiens

<400> SEQUENCE: 369
ggagccccgg cgcggg 16

<210> SEQ ID NO 370
<211> LENGTH: 20
<212> TYPE: RNA
<213> ORGANISM: Homo sapiens

<400> SEQUENCE: 370
aucccaccac ugccaccauu 20

<210> SEQ ID NO 371
<211> LENGTH: 15
<212> TYPE: RNA
<213> ORGANISM: Homo sapiens

<400> SEQUENCE: 371
aucccaccac ugcca 15

<210> SEQ ID NO 372
<211> LENGTH: 21
<212> TYPE: RNA
<213> ORGANISM: Homo sapiens

<400> SEQUENCE: 372
gaauggauuu uuggagcagg a 21

<210> SEQ ID NO 373
<211> LENGTH: 15
<212> TYPE: RNA
<213> ORGANISM: Homo sapiens

<400> SEQUENCE: 373
gaauggauuu uugga 15

<210> SEQ ID NO 374
<211> LENGTH: 22
<212> TYPE: RNA
<213> ORGANISM: Homo sapiens

<400> SEQUENCE: 374
acucggcugc gguggacaag uc 22

<210> SEQ ID NO 375
<211> LENGTH: 20
<212> TYPE: RNA
<213> ORGANISM: Homo sapiens

<400> SEQUENCE: 375
acucggcugc gguggacaag 20

<210> SEQ ID NO 376
<211> LENGTH: 22
<212> TYPE: RNA
<213> ORGANISM: Homo sapiens

<400> SEQUENCE: 376
ccucacaccu gccucgcccc cc 22

<210> SEQ ID NO 377
<211> LENGTH: 15
<212> TYPE: RNA
<213> ORGANISM: Homo sapiens

<400> SEQUENCE: 377
ucacaccugc cucgc 15

<210> SEQ ID NO 378
<211> LENGTH: 22
<212> TYPE: RNA
<213> ORGANISM: Homo sapiens

<400> SEQUENCE: 378
cugaauagcu gggacuacag gu 22

<210> SEQ ID NO 379
<211> LENGTH: 15
<212> TYPE: RNA
<213> ORGANISM: Homo sapiens

<400> SEQUENCE: 379
ccugaauagc uggga 15

<210> SEQ ID NO 380
<211> LENGTH: 26
<212> TYPE: RNA
<213> ORGANISM: Homo sapiens

<400> SEQUENCE: 380
gcgggcuguc cggaggguc ggcuuu 26

<210> SEQ ID NO 381
<211> LENGTH: 16
<212> TYPE: RNA
<213> ORGANISM: Homo sapiens

<400> SEQUENCE: 381
gcuguccgga gggguc 16

<210> SEQ ID NO 382
<211> LENGTH: 26
<212> TYPE: RNA
<213> ORGANISM: Homo sapiens

<400> SEQUENCE: 382
cggguagaga gggcaguggg agguaa 26

<210> SEQ ID NO 383
<211> LENGTH: 15
<212> TYPE: RNA
<213> ORGANISM: Homo sapiens

<400> SEQUENCE: 383
cggguagaga gggca 15

<210> SEQ ID NO 384
<211> LENGTH: 15
<212> TYPE: RNA
<213> ORGANISM: Homo sapiens

<400> SEQUENCE: 384
ggcggcgggc ccggg 15

<210> SEQ ID NO 385
<211> LENGTH: 15
<212> TYPE: RNA
<213> ORGANISM: Homo sapiens

<400> SEQUENCE: 385
ggcggcgggc ccggg 15

<210> SEQ ID NO 386
<211> LENGTH: 18
<212> TYPE: RNA
<213> ORGANISM: Homo sapiens

<400> SEQUENCE: 386 ucuaggugg gagacuga 18

<210> SEQ ID NO 387
<211> LENGTH: 16
<212> TYPE: RNA
<213> ORGANISM: Homo sapiens

<400> SEQUENCE: 387
guggggagac ugacgg 16

<210> SEQ ID NO 388
<211> LENGTH: 23
<212> TYPE: RNA
<213> ORGANISM: Homo sapiens

<400> SEQUENCE: 388
ccagggcugg cagugacaug ggu 23

<210> SEQ ID NO 389
<211> LENGTH: 19
<212> TYPE: RNA
<213> ORGANISM: Homo sapiens

<400> SEQUENCE: 389
cagggcuggc agugacaug 19

<210> SEQ ID NO 390
<211> LENGTH: 24
<212> TYPE: RNA
<213> ORGANISM: Homo sapiens

<400> SEQUENCE: 390
cccaaaaugc ugggauuaca ggca 24

<210> SEQ ID NO 391
<211> LENGTH: 15
<212> TYPE: RNA
<213> ORGANISM: Homo sapiens

<400> SEQUENCE: 391
gcccaccuca gccuc 15

<210> SEQ ID NO 392
<211> LENGTH: 24
<212> TYPE: RNA
<213> ORGANISM: Homo sapiens

<400> SEQUENCE: 392
acuggcucag uucagcagga acag 24

<210> SEQ ID NO 393
<211> LENGTH: 15
<212> TYPE: RNA
<213> ORGANISM: Homo sapiens

<400> SEQUENCE: 393
uggcucaguu cagca 15

<210> SEQ ID NO 394
<211> LENGTH: 20
<212> TYPE: RNA
<213> ORGANISM: Homo sapiens

<400> SEQUENCE: 394
ccccagggcg acgcggcggg 20

<210> SEQ ID NO 395
<211> LENGTH: 15
<212> TYPE: RNA
<213> ORGANISM: Homo sapiens

<400> SEQUENCE: 395
cgcggcgggg gcggc 15

<210> SEQ ID NO 396
<211> LENGTH: 26
<212> TYPE: RNA
<213> ORGANISM: Homo sapiens

<400> SEQUENCE: 396
gucccggggc ugcgcgaggc acaggc 26

<210> SEQ ID NO 397
<211> LENGTH: 15
<212> TYPE: RNA
<213> ORGANISM: Homo sapiens

<400> SEQUENCE: 397
ggcccggggg gcggg 15

<210> SEQ ID NO 398
<211> LENGTH: 23
<212> TYPE: RNA
<213> ORGANISM: Homo sapiens

<400> SEQUENCE: 398
cggggcagcu caguacagga uac 23

<210> SEQ ID NO 399
<211> LENGTH: 15
<212> TYPE: RNA
<213> ORGANISM: Homo sapiens

<400> SEQUENCE: 399
agcucaguac aggau 15

<210> SEQ ID NO 400
<211> LENGTH: 24
<212> TYPE: RNA
<213> ORGANISM: Homo sapiens

<400> SEQUENCE: 400
agacacauuu ggagagggaa ccuc 24

<210> SEQ ID NO 401
<211> LENGTH: 16
<212> TYPE: RNA
<213> ORGANISM: Homo sapiens

<400> SEQUENCE: 401
agacacauuu ggagag 16

<210> SEQ ID NO 402
<211> LENGTH: 20
<212> TYPE: RNA
<213> ORGANISM: Homo sapiens

<400> SEQUENCE: 402
ggauuuuugg aucagggaug 20

<210> SEQ ID NO 403
<211> LENGTH: 15
<212> TYPE: RNA
<213> ORGANISM: Homo sapiens

<400> SEQUENCE: 403
auuuuuggau caggg 15

<210> SEQ ID NO 404
<211> LENGTH: 26
<212> TYPE: RNA
<213> ORGANISM: Homo sapiens

<400> SEQUENCE: 404
agggacggga cgcggugcag uguugu 26

<210> SEQ ID NO 405
<211> LENGTH: 15
<212> TYPE: RNA
<213> ORGANISM: Homo sapiens

<400> SEQUENCE: 405
ggcgggcggg aggga 15

<210> SEQ ID NO 406
<211> LENGTH: 23
<212> TYPE: RNA
<213> ORGANISM: Homo sapiens

<400> SEQUENCE: 406
ggcccggccg ugccugaggu uuc 23

<210> SEQ ID NO 407
<211> LENGTH: 15
<212> TYPE: RNA
<213> ORGANISM: Homo sapiens

<400> SEQUENCE: 407
ggcgguggga ucccg 15

<210> SEQ ID NO 408
<211> LENGTH: 19
<212> TYPE: RNA
<213> ORGANISM: Homo sapiens

<400> SEQUENCE: 408 gugguuggg gcgggcucu 19

<210> SEQ ID NO 409
<211> LENGTH: 19
<212> TYPE: RNA
<213> ORGANISM: Homo sapiens

<400> SEQUENCE: 409 gugguuggg gcgggcucu 19

<210> SEQ ID NO 410
<211> LENGTH: 25
<212> TYPE: RNA
<213> ORGANISM: Homo sapiens

<400> SEQUENCE: 410
uggcggcggu aguuaugggc uucuc 25

<210> SEQ ID NO 411
<211> LENGTH: 25
<212> TYPE: RNA
<213> ORGANISM: Homo sapiens

<400> SEQUENCE: 411
uggcggcggu aguuaugggc uucuc 25

<210> SEQ ID NO 412
<211> LENGTH: 18
<212> TYPE: RNA
<213> ORGANISM: Homo sapiens

<400> SEQUENCE: 412
ggugggcuuc ccggaggg 18

<210> SEQ ID NO 413
<211> LENGTH: 15
<212> TYPE: RNA
<213> ORGANISM: Homo sapiens

<400> SEQUENCE: 413
ggugggcuuc ccgga 15

<210> SEQ ID NO 414
<211> LENGTH: 18
<212> TYPE: RNA
<213> ORGANISM: Homo sapiens

<400> SEQUENCE: 414
gcggcggcgg cggcagca 18

<210> SEQ ID NO 415
<211> LENGTH: 15
<212> TYPE: RNA
<213> ORGANISM: Homo sapiens

<400> SEQUENCE: 415
gcgggcggcg gcggc 15

<210> SEQ ID NO 416
<211> LENGTH: 20
<212> TYPE: RNA
<213> ORGANISM: Homo sapiens

<400> SEQUENCE: 416
uggcuguugg agggggcagg 20

<210> SEQ ID NO 417
<211> LENGTH: 15
<212> TYPE: RNA
<213> ORGANISM: Homo sapiens

<400> SEQUENCE: 417
ggagggggca ggcuc 15

<210> SEQ ID NO 418
<211> LENGTH: 22
<212> TYPE: RNA
<213> ORGANISM: Homo sapiens

<400> SEQUENCE: 418
cgcggcgggg acggcgauug gu 22

<210> SEQ ID NO 419
<211> LENGTH: 17
<212> TYPE: RNA
<213> ORGANISM: Homo sapiens

<400> SEQUENCE: 419
cggcggggac ggcgauu 17

<210> SEQ ID NO 420
<211> LENGTH: 21
<212> TYPE: RNA
<213> ORGANISM: Homo sapiens

<400> SEQUENCE: 420
auccaguucu cugaggggc u 21

<210> SEQ ID NO 421
<211> LENGTH: 21
<212> TYPE: RNA
<213> ORGANISM: Homo sapiens

<400> SEQUENCE: 421
auccaguucu cugagggggc u 21

<210> SEQ ID NO 422
<211> LENGTH: 22
<212> TYPE: RNA
<213> ORGANISM: Homo sapiens

<400> SEQUENCE: 422
accccacucc ugguaccaua gu 22

<210> SEQ ID NO 423
<211> LENGTH: 15
<212> TYPE: RNA
<213> ORGANISM: Homo sapiens

<400> SEQUENCE: 423
accccacucc uggua 15

<210> SEQ ID NO 424
<211> LENGTH: 21
<212> TYPE: RNA
<213> ORGANISM: Homo sapiens

<400> SEQUENCE: 424 cuuccccca guaaucuuca u 21

<210> SEQ ID NO 425
<211> LENGTH: 21
<212> TYPE: RNA
<213> ORGANISM: Homo sapiens

<400> SEQUENCE: 425
cuucccccca guaaucuuca u 21

<210> SEQ ID NO 426
<211> LENGTH: 16
<212> TYPE: RNA
<213> ORGANISM: Homo sapiens

<400> SEQUENCE: 426
agcugcagug ggggag 16

<210> SEQ ID NO 427
<211> LENGTH: 15
<212> TYPE: RNA
<213> ORGANISM: Homo sapiens

<400> SEQUENCE: 427
gcugcagugg gggag 15

<210> SEQ ID NO 428
<211> LENGTH: 19
<212> TYPE: RNA
<213> ORGANISM: Homo sapiens

<400> SEQUENCE: 428
uggcgggugc gggggug gg 19

<210> SEQ ID NO 429
<211> LENGTH: 15
<212> TYPE: RNA
<213> ORGANISM: Homo sapiens

<400> SEQUENCE: 429
uggcgggugc ggggg 15

<210> SEQ ID NO 430
<211> LENGTH: 21
<212> TYPE: RNA
<213> ORGANISM: Homo sapiens

<400> SEQUENCE: 430
caacucugau cucuucaucu a 21

<210> SEQ ID NO 431
<211> LENGTH: 20
<212> TYPE: RNA
<213> ORGANISM: Homo sapiens

<400> SEQUENCE: 431
ucucuucauc uacccccccag 20

<210> SEQ ID NO 432
<211> LENGTH: 23
<212> TYPE: RNA
<213> ORGANISM: Homo sapiens

<400> SEQUENCE: 432
acagcagggc uggggauugc agu 23

<210> SEQ ID NO 433
<211> LENGTH: 19
<212> TYPE: RNA
<213> ORGANISM: Homo sapiens

<400> SEQUENCE: 433
ugcugcuccc aguccugcc 19

<210> SEQ ID NO 434
<211> LENGTH: 23
<212> TYPE: RNA
<213> ORGANISM: Homo sapiens

<400> SEQUENCE: 434
ggcuacaaca caggacccgg gcg 23

<210> SEQ ID NO 435
<211> LENGTH: 21
<212> TYPE: RNA
<213> ORGANISM: Homo sapiens

<400> SEQUENCE: 435
ggcuacaaca caggacccgg g 21

<210> SEQ ID NO 436
<211> LENGTH: 15
<212> TYPE: RNA
<213> ORGANISM: Homo sapiens

<400> SEQUENCE: 436
ggcgcgggga ggugc 15

<210> SEQ ID NO 437
<211> LENGTH: 15
<212> TYPE: RNA
<213> ORGANISM: Homo sapiens

<400> SEQUENCE: 437
ggcgcgggga ggugc 15

<210> SEQ ID NO 438
<211> LENGTH: 19
<212> TYPE: RNA
<213> ORGANISM: Homo sapiens

<400> SEQUENCE: 438
agugggaggc cagggcacg 19

<210> SEQ ID NO 439
<211> LENGTH: 15
<212> TYPE: RNA
<213> ORGANISM: Homo sapiens

<400> SEQUENCE: 439
agggggagcu gcagg 15

<210> SEQ ID NO 440
<211> LENGTH: 22
<212> TYPE: RNA
<213> ORGANISM: Homo sapiens

<400> SEQUENCE: 440
ggggggcagg aggggcucag gg 22

<210> SEQ ID NO 441
<211> LENGTH: 16
<212> TYPE: RNA
<213> ORGANISM: Homo sapiens

<400> SEQUENCE: 441
gugggggggc aggagg 16

<210> SEQ ID NO 442
<211> LENGTH: 22
<212> TYPE: RNA
<213> ORGANISM: Homo sapiens

<400> SEQUENCE: 442
cugggcucgg gacgcgcggc uc 22

<210> SEQ ID NO 443
<211> LENGTH: 19
<212> TYPE: RNA
<213> ORGANISM: Homo sapiens

<400> SEQUENCE: 443
cugggcucgg gacgcgcgg 19

<210> SEQ ID NO 444
<211> LENGTH: 28
<212> TYPE: RNA
<213> ORGANISM: Homo sapiens

<400> SEQUENCE: 444
uuggggaaac ggccgcugag ugaggcgu 28

<210> SEQ ID NO 445
<211> LENGTH: 15
<212> TYPE: RNA
<213> ORGANISM: Homo sapiens

<400> SEQUENCE: 445
ggggaaacgg ccgcu 15

<210> SEQ ID NO 446
<211> LENGTH: 25
<212> TYPE: RNA
<213> ORGANISM: Homo sapiens

<400> SEQUENCE: 446 gggugggau uuguugcauu acuug 25

<210> SEQ ID NO 447
<211> LENGTH: 20
<212> TYPE: RNA
<213> ORGANISM: Homo sapiens

<400> SEQUENCE: 447 gggugggau uuguugcauu 20

<210> SEQ ID NO 448
<211> LENGTH: 23
<212> TYPE: RNA
<213> ORGANISM: Homo sapiens

<400> SEQUENCE: 448
cggggccgua gcacugucug aga 23

<210> SEQ ID NO 449
<211> LENGTH: 20
<212> TYPE: RNA
<213> ORGANISM: Homo sapiens

<400> SEQUENCE: 449
cggggccgua gcacugucug 20

<210> SEQ ID NO 450
<211> LENGTH: 16
<212> TYPE: RNA
<213> ORGANISM: Homo sapiens

<400> SEQUENCE: 450
ggcgcggagg gcggac 16

<210> SEQ ID NO 451
<211> LENGTH: 15
<212> TYPE: RNA
<213> ORGANISM: Homo sapiens

<400> SEQUENCE: 451
ggcgcggagg gcgga 15

<210> SEQ ID NO 452
<211> LENGTH: 16
<212> TYPE: RNA
<213> ORGANISM: Homo sapiens

<400> SEQUENCE: 452
ggcggugggc ggcggg 16

<210> SEQ ID NO 453
<211> LENGTH: 15
<212> TYPE: RNA
<213> ORGANISM: Homo sapiens

<400> SEQUENCE: 453
ggccucucgg gaacu 15

<210> SEQ ID NO 454
<211> LENGTH: 22
<212> TYPE: RNA
<213> ORGANISM: Homo sapiens

<400> SEQUENCE: 454
acucaaacug ugggggcacu uu 22

<210> SEQ ID NO 455
<211> LENGTH: 19
<212> TYPE: RNA
<213> ORGANISM: Homo sapiens

<400> SEQUENCE: 455
acucaaacug ugggggcac 19

<210> SEQ ID NO 456
<211> LENGTH: 22
<212> TYPE: RNA
<213> ORGANISM: Homo sapiens

<400> SEQUENCE: 456
ggcagggaca gcaaaggggu gc 22

<210> SEQ ID NO 457
<211> LENGTH: 18
<212> TYPE: RNA
<213> ORGANISM: Homo sapiens

<400> SEQUENCE: 457
gcagggacag caaagggg 18

<210> SEQ ID NO 458
<211> LENGTH: 21
<212> TYPE: RNA
<213> ORGANISM: Homo sapiens

<400> SEQUENCE: 458
cagccugagu gacagagcaa g 21

<210> SEQ ID NO 459
<211> LENGTH: 15
<212> TYPE: RNA
<213> ORGANISM: Homo sapiens

<400> SEQUENCE: 459
acugcacucc agccu 15

<210> SEQ ID NO 460
<211> LENGTH: 24
<212> TYPE: RNA
<213> ORGANISM: Homo sapiens

<400> SEQUENCE: 460
guggagugug acaauggugu uugu 24

<210> SEQ ID NO 461
<211> LENGTH: 18
<212> TYPE: RNA
<213> ORGANISM: Homo sapiens

<400> SEQUENCE: 461
uggaguguga caauggug 18

<210> SEQ ID NO 462
<211> LENGTH: 22
<212> TYPE: RNA
<213> ORGANISM: Homo sapiens

<400> SEQUENCE: 462
gaaaaaggcg ggagaagccc ca 22

<210> SEQ ID NO 463
<211> LENGTH: 15
<212> TYPE: RNA
<213> ORGANISM: Homo sapiens

<400> SEQUENCE: 463
gaaaaaggcg ggaga 15

<210> SEQ ID NO 464
<211> LENGTH: 22
<212> TYPE: RNA
<213> ORGANISM: Homo sapiens

<400> SEQUENCE: 464
ugugggacug caaaugggag cu 22

<210> SEQ ID NO 465
<211> LENGTH: 22
<212> TYPE: RNA
<213> ORGANISM: Homo sapiens

<400> SEQUENCE: 465
ugugggacug caaaugggag cu 22

<210> SEQ ID NO 466
<211> LENGTH: 17
<212> TYPE: RNA
<213> ORGANISM: Homo sapiens

<400> SEQUENCE: 466
gggagaaggg ucggggc 17

<210> SEQ ID NO 467
<211> LENGTH: 24
<212> TYPE: RNA
<213> ORGANISM: Homo sapiens

<400> SEQUENCE: 467
ugggcgaggg gugggcucuc agag 24

<210> SEQ ID NO 468
<211> LENGTH: 20
<212> TYPE: RNA
<213> ORGANISM: Homo sapiens

<400> SEQUENCE: 468
cggcucuggg ucugugggga 20

<210> SEQ ID NO 469
<211> LENGTH: 23
<212> TYPE: RNA
<213> ORGANISM: Homo sapiens

<400> SEQUENCE: 469
uuagggagua gaaggguggg gag 23

<210> SEQ ID NO 470
<211> LENGTH: 17
<212> TYPE: RNA
<213> ORGANISM: Homo sapiens

<400> SEQUENCE: 470
ggggcgcggc cggaucg 17

<210> SEQ ID NO 471
<211> LENGTH: 21
<212> TYPE: RNA
<213> ORGANISM: Homo sapiens

<400> SEQUENCE: 471
aaggcagggc ccccgcuccc c 21

<210> SEQ ID NO 472
<211> LENGTH: 19
<212> TYPE: RNA
<213> ORGANISM: Homo sapiens

<400> SEQUENCE: 472
gggggaagaa aaggugggg 19

<210> SEQ ID NO 473
<211> LENGTH: 23
<212> TYPE: RNA
<213> ORGANISM: Homo sapiens

<400> SEQUENCE: 473
uggugggugg ggaggagaag ugc 23

<210> SEQ ID NO 474
<211> LENGTH: 17
<212> TYPE: RNA
<213> ORGANISM: Homo sapiens

<400> SEQUENCE: 474
gcggggcugg gcgcgcg 17

<210> SEQ ID NO 475
<211> LENGTH: 23
<212> TYPE: RNA
<213> ORGANISM: Homo sapiens

<400> SEQUENCE: 475
ucaauaggaa agagguggga ccu 23

<210> SEQ ID NO 476
<211> LENGTH: 22
<212> TYPE: RNA
<213> ORGANISM: Homo sapiens

<400> SEQUENCE: 476
uagggauggg aggccaggau ga 22

<210> SEQ ID NO 477
<211> LENGTH: 23
<212> TYPE: RNA
<213> ORGANISM: Homo sapiens

<400> SEQUENCE: 477
ucgaggacug guggaagggc cuu 23

<210> SEQ ID NO 478
<211> LENGTH: 22
<212> TYPE: RNA
<213> ORGANISM: Homo sapiens

<400> SEQUENCE: 478
cuccuggggc ccgcacucuc gc 22

<210> SEQ ID NO 479
<211> LENGTH: 86
<212> TYPE: RNA
<213> ORGANISM: Homo sapiens

<400> SEQUENCE: 479
agggagaagg gucggggcag ggagggcagg gcaggcucug gggugggggg ucugugaguc 60
agccacggcu cugcccacgu cucccc 86

<210> SEQ ID NO 480
<211> LENGTH: 64
<212> TYPE: RNA
<213> ORGANISM: Homo sapiens

<400> SEQUENCE: 480
ucugggcgag ggugggcuc ucagaggggc uggcaguacu gcucugaggc cugccucucc 60
ccag 64

<210> SEQ ID NO 481
<211> LENGTH: 80
<212> TYPE: RNA
<213> ORGANISM: Homo sapiens

<400> SEQUENCE: 481
ggcgcgucgc cccccucagu ccaccagagc ccggauaccu cagaaauucg gcucuggguc 60 ugugggggagc gaaaugcaac 80

<210> SEQ ID NO 482
<211> LENGTH: 82
<212> TYPE: RNA
<213> ORGANISM: Homo sapiens

<400> SEQUENCE: 482
cugacuuuuu uagggaguag aagggugggg agcaugaaca auguuucuca cucccuaccc 60
cuccacuccc caaaaaaguc ag 82

<210> SEQ ID NO 483
<211> LENGTH: 84
<212> TYPE: RNA
<213> ORGANISM: Homo sapiens

<400> SEQUENCE: 483
gaggcugggc ggggcgcggc cggaucgguc gagagcgucc uggcugauga cggucucccg 60
ugcccacgcc ccaaacgcag ucuc 84

<210> SEQ ID NO 484
<211> LENGTH: 94
<212> TYPE: RNA
<213> ORGANISM: Homo sapiens

<400> SEQUENCE: 484
gugaggugug ggcccggccc caggagcggg gccugggcag ccccgugugu ugaggaagga 60
aggcagggcc cccgcucccc gggccugacc ccac 94

<210> SEQ ID NO 485
<211> LENGTH: 67
<212> TYPE: RNA
<213> ORGANISM: Homo sapiens

<400> SEQUENCE: 485
aaaucucucu ccauaucuuu ccugcagccc ccaggugggg gggaagaaaa gguggggaau 60
uagauuc 67

<210> SEQ ID NO 486
<211> LENGTH: 62
<212> TYPE: RNA
<213> ORGANISM: Homo sapiens

<400> SEQUENCE: 486
cuuccuggug ggugggggagg agaagugccg uccucaugag ccccucucug ucccacccau 60
ag 62

<210> SEQ ID NO 487
<211> LENGTH: 70
<212> TYPE: RNA
<213> ORGANISM: Homo sapiens

<400> SEQUENCE: 487
aggacccagc ggggcugggc gcgcggagca gcgcugggug cagcgccugc gccggcagcu 60
gcaagggccg 70

<210> SEQ ID NO 488
<211> LENGTH: 98
<212> TYPE: RNA
<213> ORGANISM: Homo sapiens

<400> SEQUENCE: 488
cuuggucaau aggaaagagg ugggaccucc uggcuuuucc ucugcagcau ggcucggacc 60
uagugcaaug uuuaagcucc ccucucuuuc cuguucag 98

<210> SEQ ID NO 489
<211> LENGTH: 69
<212> TYPE: RNA
<213> ORGANISM: Homo sapiens

<400> SEQUENCE: 489
gggcuuaggg augggaggcc aggaugaaga uuaaucccua auccccaaca cuggccuugc 60
uauccccag 69

<210> SEQ ID NO 490
<211> LENGTH: 63
<212> TYPE: RNA
<213> ORGANISM: Homo sapiens

<400> SEQUENCE: 490
gagucgagga cugguggaag ggccuuuccc cucagaccaa ggcccuggcc ccagcuucuu 60
cuc 63

<210> SEQ ID NO 491
<211> LENGTH: 84
<212> TYPE: RNA
<213> ORGANISM: Homo sapiens

<400> SEQUENCE: 491
gcuggcgucg gugcugggga gcggcccccg ggugggccuc ugcucuggcc ccuccugggg 60
cccgcacucu cgcucugggc ccgc 84

<210> SEQ ID NO 492
<211> LENGTH: 23
<212> TYPE: RNA
<213> ORGANISM: Homo sapiens

<400> SEQUENCE: 492
agggucgggg cagggagggc agg 23

<210> SEQ ID NO 493
<211> LENGTH: 16
<212> TYPE: RNA
<213> ORGANISM: Homo sapiens

<400> SEQUENCE: 493 gagaagguc ggggca 16

<210> SEQ ID NO 494
<211> LENGTH: 25
<212> TYPE: RNA
<213> ORGANISM: Homo sapiens

<400> SEQUENCE: 494
ucugggcgag gggugggcuc ucaga 25

<210> SEQ ID NO 495
<211> LENGTH: 15
<212> TYPE: RNA
<213> ORGANISM: Homo sapiens

<400> SEQUENCE: 495
ucugggcgag gggug 15

<210> SEQ ID NO 496
<211> LENGTH: 23
<212> TYPE: RNA
<213> ORGANISM: Homo sapiens

<400> SEQUENCE: 496
ucggcucugg gucuguggggg agc 23

<210> SEQ ID NO 497
<211> LENGTH: 17
<212> TYPE: RNA
<213> ORGANISM: Homo sapiens

<400> SEQUENCE: 497
cggcucuggg ucugugg 17

<210> SEQ ID NO 498
<211> LENGTH: 23
<212> TYPE: RNA
<213> ORGANISM: Homo sapiens

<400> SEQUENCE: 498
agggaguaga aggguggga gca 23

<210> SEQ ID NO 499
<211> LENGTH: 16
<212> TYPE: RNA
<213> ORGANISM: Homo sapiens

<400> SEQUENCE: 499
uagggaguag aagggu 16

<210> SEQ ID NO 500
<211> LENGTH: 24
<212> TYPE: RNA
<213> ORGANISM: Homo sapiens

<400> SEQUENCE: 500
gaucggucga gagcguccug gcug 24

<210> SEQ ID NO 501
<211> LENGTH: 15
<212> TYPE: RNA
<213> ORGANISM: Homo sapiens

<400> SEQUENCE: 501
cggggcgcgg ccgga 15

<210> SEQ ID NO 502
<211> LENGTH: 23
<212> TYPE: RNA
<213> ORGANISM: Homo sapiens

<400> SEQUENCE: 502
aggaaggaag gcagggcccc cgc 23

<210> SEQ ID NO 503
<211> LENGTH: 15
<212> TYPE: RNA
<213> ORGANISM: Homo sapiens

<400> SEQUENCE: 503
gggcccccgc ucccc 15

<210> SEQ ID NO 504
<211> LENGTH: 18
<212> TYPE: RNA
<213> ORGANISM: Homo sapiens

<400> SEQUENCE: 504
agcggggcug ggcgcgcg 18

<210> SEQ ID NO 505
<211> LENGTH: 15
<212> TYPE: RNA
<213> ORGANISM: Homo sapiens

<400> SEQUENCE: 505
cggggcuggg cgcgc 15

<210> SEQ ID NO 506
<211> LENGTH: 24
<212> TYPE: RNA
<213> ORGANISM: Homo sapiens

<400> SEQUENCE: 506
ucgaggacug guggaagggc cuuu 24

<210> SEQ ID NO 507
<211> LENGTH: 16
<212> TYPE: RNA
<213> ORGANISM: Homo sapiens

<400> SEQUENCE: 507
ucgaggacug guggaa 16

<210> SEQ ID NO 508
<211> LENGTH: 23
<212> TYPE: RNA
<213> ORGANISM: Homo sapiens

<400> SEQUENCE: 508
cuccuggggc ccgcacucuc gcu 23

<210> SEQ ID NO 509
<211> LENGTH: 18
<212> TYPE: RNA
<213> ORGANISM: Homo sapiens

<400> SEQUENCE: 509
cuccuggggc ccgcacuc 18